US011534480B2

(12) United States Patent
Moustakas et al.

(10) Patent No.: US 11,534,480 B2
(45) Date of Patent: Dec. 27, 2022

(54) COMPOSITIONS AND METHODS FOR MODULATING IL-10 IMMUNOSTIMULATORY AND ANTI-INFLAMMATORY PROPERTIES

(71) Applicant: Alkermes, Inc., Waltham, MA (US)

(72) Inventors: Demetri T. Moustakas, Belmont, MA (US); Mark N. Namchuk, Arlington, MA (US); Heather C. Losey, Lexington, MA (US); Juan C. Alvarez, Lincoln, MA (US)

(73) Assignee: ALKERMES, INC., Waltham, MA (US)

( * ) Notice: Subject to any disclaimer, the term of this patent is extended or adjusted under 35 U.S.C. 154(b) by 0 days.

(21) Appl. No.: 16/414,223

(22) Filed: May 16, 2019

(65) Prior Publication Data
US 2019/0336582 A1 Nov. 7, 2019

Related U.S. Application Data

(62) Division of application No. 15/630,341, filed on Jun. 22, 2017, now Pat. No. 10,335,459.

(60) Provisional application No. 62/353,478, filed on Jun. 22, 2016.

(51) Int. Cl.
A61K 38/20 (2006.01)
C07K 14/54 (2006.01)
(52) U.S. Cl.
CPC ...... A61K 38/2066 (2013.01); C07K 14/5428 (2013.01); C07K 2319/30 (2013.01)
(58) Field of Classification Search
CPC .................................. A61K 38/2066
See application file for complete search history.

(56) References Cited

U.S. PATENT DOCUMENTS

| | | | |
|---|---|---|---|
| 6,428,985 | B1 | 8/2002 | Bromberg et al. |
| 7,696,322 | B2 | 4/2010 | Bleck et al. |
| 8,063,182 | B1 | 11/2011 | Brockhaus et al. |
| 8,163,522 | B1 | 4/2012 | Brockhaus et al. |
| 2002/0127227 | A1 | 9/2002 | Holmes et al. |
| 2005/0069552 | A1 | 3/2005 | Bleck et al. |
| 2010/0227394 | A1 | 9/2010 | Bleck et al. |
| 2010/0285014 | A1 | 11/2010 | Cox, III et al. |
| 2013/0217864 | A1 | 8/2013 | Cho et al. |
| 2013/0295084 | A1 | 11/2013 | Hunter et al. |
| 2013/0316404 | A1 | 11/2013 | Roers et al. |
| 2013/0336925 | A1 | 12/2013 | Alvarez et al. |
| 2014/0056895 | A1 | 2/2014 | Baurin et al. |
| 2014/0072581 | A1 | 3/2014 | Dixit et al. |
| 2014/0234962 | A1 | 8/2014 | Alvarez et al. |
| 2015/0071948 | A1 | 3/2015 | Lazar et al. |
| 2016/0068583 | A1 | 3/2016 | McCauley et al. |
| 2016/0175458 | A1 | 6/2016 | Alvarez et al. |
| 2018/0289825 | A1 | 10/2018 | Alvarez et al. |

FOREIGN PATENT DOCUMENTS

| | | |
|---|---|---|
| CN | 101962413 A | 2/2011 |
| JP | 2003508023 A | 3/2003 |
| WO | 0103737 A1 | 1/2001 |
| WO | 0158950 A1 | 8/2001 |
| WO | WO 2004/0044006 | 5/2004 |
| WO | 2004101740 A2 | 11/2004 |
| WO | 2008140595 A2 | 11/2008 |
| WO | 2011076781 A1 | 6/2011 |
| WO | 2011090762 A1 | 7/2011 |
| WO | 2011122923 A2 | 10/2011 |
| WO | 2012146628 A1 | 11/2012 |
| WO | 2012178137 A1 | 12/2012 |
| WO | 2013026833 A1 | 2/2013 |
| WO | 2013184942 A1 | 12/2013 |
| WO | 2014018572 A2 | 1/2014 |
| WO | 2014023673 A1 | 2/2014 |
| WO | 2014151910 A1 | 9/2014 |
| WO | 2015017548 A2 | 2/2015 |
| WO | 2015117930 A1 | 8/2015 |
| WO | 2016082677 A1 | 6/2016 |
| WO | 2016100788 A1 | 6/2016 |
| WO | 2017165464 A1 | 9/2017 |
| WO | 2018005226 A2 | 1/2018 |
| WO | 2018005226 A3 | 4/2018 |

OTHER PUBLICATIONS

Czajkowsky, D. M. et al., "Fc-fusion proteins: new developments and future perspectives", EMBO Molecular Medicine, vol. 4, No. 10, Jul. 26, 2012, 1015-1028.
Ding, Y. et al., "A Single Amino Acid Determines the Immunostimulatory Activity of Interleukin 10", J. Exp. Med., 191 (2), Jan. 2000, 213-223.
Linderholm, A. L. et al., "Immunoglobulin Fc-Fusion Proteins Part 2: Therapeutic Uses and Clinical Development", Bioprocess International, vol. 12(10), Nov. 1, 2014, 1-7.
Shimamoto, G. et al., "Peptibodies: A flexible alternative format to antibodies", MABS, vol. 4, No. 5, Sep. 1, 2012, 586-591.

(Continued)

Primary Examiner — Prema M Mertz
(74) Attorney, Agent, or Firm — Lathrop GPM LLP; Michael Spellberg, Esq.

(57) ABSTRACT

The invention provides compositions and methods for modulating the immunostimulatory properties and/or anti-inflammatory properties of IL-10. The present invention provides scIL-10 polypeptides of Formula 1. The polypeptides of the invention are optionally linked to a fusion partner. The polypeptides of Formula 1 are referred to herein as "scIL-10" polypeptides and comprise an amino acid sequence arrangement from N-terminus to C-terminus in accordance with Formula 1:

(first monomer subunit)-LINKER-(second monomer subunit)  Formula 1 wherein the first monomer subunit, the second monomer subunit or both the first and second monomer subunits may be independently selected from: an unsubstituted IL-10 monomer subunit; or a substituted IL-10 monomer subunit comprising at least one amino acid substitution; and wherein LINKER is any amino acid linker of at least 1-100 amino acids in length.

14 Claims, 7 Drawing Sheets
Specification includes a Sequence Listing.

(56) References Cited

OTHER PUBLICATIONS

Vallee, S. et al., "Pulmonary Administration of Interferon Beta-1 a-Fc Fusion Protein in Non-Human Primates Using an Immunoglobulin Transport Pathway", Journal of Interferon and Cytokine Research, vol. 32, No. 4, Apr. 1, 2012, 178-184.
Wu, B. et al., "Pharmacokinetics of Peptide-Fc Fusion Proteins", Journal of Pharmaceutical Sciences, vol. 103, No. 1, Jan. 27, 2014, 53-64.
Yoon, S. et al., "Conformational changes mediate interleukin-10 receptor 2 (IL-10R2) binding to IL-10 and assembly of the signaling complex", J Biol Chem., 281(46), 2006, 35088-96.
Zhao, L. et al., "Eradication of non-Hodgkin lymphoma through the induction of tumor-specific T-cell immunity by CD20-Flex BiFP", Blood, 122(26), 2013, 4230-6.
Zheng, X. X. et al., "Administration of noncytolytic IL-10/Fc in murine models of lipopolysaccharide-induced septic shock and allogeneic islet transplantation", The Journal of Immunology, The American Association of Immunologists, US, vol. 154, No. 10, May 15, 1995, 5590-5600.
Zheng, X. X. et al., "I L-2 receptor-targeted cytolytic IL-2/Fc fusion protein treatment blocks diabetogenic autoimmunity in nonobese diabetic mice", The Journal of Immunology, The American Association of Immunologists, US, vol. 163, No. 7, Oct. 1, 1999, 4041-4048.
Zheng, X. X. et al., "Noncytolytic IL-10/Fc fusion protein prevents diabetes, blocks autoimmunity, and promotes suppressor phenomena in NOD mice", The Journal of Immunology, The American Association of Immunologists, US, vol. 158, No. 9, May 1, 1997, 4507-4513.
U.S. Appl. No. 15/630,341 2017/0368144 U.S. Pat. No. 10/335,459, filed Jun. 22, 2017 Dec. 28, 2017 Jul. 2, 2019, Demetri T. Moustakas.
Supplementary European Search Report for European Patent Application No. 17820960.7, dated Jul. 7, 2020.

SEQUENCE LISTING

```
<160> NUMBER OF SEQ ID NOS: 54

<210> SEQ ID NO 1
<211> LENGTH: 160
<212> TYPE: PRT
<213> ORGANISM: Homo sapiens

<400> SEQUENCE: 1

Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
            20                  25                  30

Val Lys Thr Phe Phe Gln Met Lys Asp Gln Leu Asp Asn Leu Leu Leu
        35                  40                  45

Lys Glu Ser Leu Leu Glu Asp Phe Lys Gly Tyr Leu Gly Cys Gln Ala
    50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
                85                  90                  95

Asn Leu Lys Thr Leu Arg Leu Arg Leu Arg Arg Cys His Arg Phe Leu
            100                 105                 110

Pro Cys Glu Asn Lys Ser Lys Ala Val Glu Gln Val Lys Asn Ala Phe
        115                 120                 125

Asn Lys Leu Gln Glu Lys Gly Ile Tyr Lys Ala Met Ser Glu Phe Asp
    130                 135                 140

Ile Phe Ile Asn Tyr Ile Glu Ala Tyr Met Thr Met Lys Ile Arg Asn
145                 150                 155                 160

<210> SEQ ID NO 2
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
            20                  25                  30

Val Lys Thr Phe Phe Gln Met Lys Asp Gln Leu Asp Asn Leu Leu Leu
        35                  40                  45

Lys Glu Ser Leu Leu Glu Asp Phe Lys Gly Tyr Leu Gly Cys Gln Ala
    50                  55                  60
```

```
Leu Ser Glu Met Ile Gln Phe Tyr Leu Glu Glu Val Met Pro Gln Ala
 65                  70                  75                  80

Glu Asn Gln Asp Pro Asp Ile Lys Ala His Val Asn Ser Leu Gly Glu
                 85                  90                  95

Asn Leu Lys Thr Leu Arg Leu Arg Leu Arg Arg Cys His Arg Phe Leu
            100                 105                 110

Pro Cys Glu Asn Lys Ser Lys Ala Val Glu Gln Val Lys Asn Ala Phe
        115                 120                 125

Asn Lys Leu Gln Glu Lys Gly Ile Tyr Lys Ala Met Ser Glu Phe Asp
    130                 135                 140

Ile Phe Ile Asn Tyr Ile Glu Ala Tyr Met Thr Met Lys Ile Arg Asn
145                 150                 155                 160

Gly Gly Ser Gly Gly Gly Ser Gly Gly Ser Pro Gly Gln Gly Thr
                165                 170                 175

Gln Ser Glu Asn Ser Cys Thr His Phe Pro Gly Asn Leu Pro Asn Met
            180                 185                 190

Leu Arg Asp Leu Arg Asp Ala Phe Ser Arg Val Lys Thr Phe Phe Gln
        195                 200                 205

Met Lys Asp Gln Leu Asp Asn Leu Leu Leu Lys Glu Ser Leu Leu Glu
    210                 215                 220

Asp Phe Lys Gly Tyr Leu Gly Cys Gln Ala Leu Ser Glu Met Ile Gln
225                 230                 235                 240

Phe Tyr Leu Glu Glu Val Met Pro Gln Ala Glu Asn Gln Asp Pro Asp
                245                 250                 255

Ile Lys Ala His Val Asn Ser Leu Gly Glu Asn Leu Lys Thr Leu Arg
            260                 265                 270

Leu Arg Leu Arg Arg Cys His Arg Phe Leu Pro Cys Glu Asn Lys Ser
        275                 280                 285

Lys Ala Val Glu Gln Val Lys Asn Ala Phe Asn Lys Leu Gln Glu Lys
    290                 295                 300

Gly Ile Tyr Lys Ala Met Ser Glu Phe Asp Ile Phe Ile Asn Tyr Ile
305                 310                 315                 320

Glu Ala Tyr Met Thr Met Lys Ile Arg Asn
                325                 330

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Gly Ser Gly Gly Gly Ser Gly Gly
1               5                   10

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Gly Ser Gly Gly
1               5
```

```
<210> SEQ ID NO 5
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(40)
<223> OTHER INFORMATION: This sequence may encompass 1-10
      "Gly Gly Gly Ser" repeating units
<220> FEATURE:
<223> OTHER INFORMATION: See specification as filed for detailed
      description of substitutions and preferred embodiments

<400> SEQUENCE: 5

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
            20                  25                  30

Gly Gly Gly Ser Gly Gly Gly Ser
        35                  40

<210> SEQ ID NO 6
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(50)
<223> OTHER INFORMATION: This sequence may encompass 1-10
      "Gly Gly Gly Gly Ser" repeating units
<220> FEATURE:
<223> OTHER INFORMATION: See specification as filed for detailed
      description of substitutions and preferred embodiments

<400> SEQUENCE: 6

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser
    50

<210> SEQ ID NO 7
<211> LENGTH: 107
<212> TYPE: PRT
<213> ORGANISM: Homo sapiens

<400> SEQUENCE: 7

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60
```

```
Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Ser
            100                 105
```

<210> SEQ ID NO 8
<211> LENGTH: 98
<212> TYPE: PRT
<213> ORGANISM: Homo sapiens

<400> SEQUENCE: 8

```
Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
         50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Arg Val
```

<210> SEQ ID NO 9
<211> LENGTH: 330
<212> TYPE: PRT
<213> ORGANISM: Homo sapiens

<400> SEQUENCE: 9

```
Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
         50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175
```

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 10
<211> LENGTH: 232
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

```
Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 11
<211> LENGTH: 232
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Gln Val Lys Phe Asn Trp Tyr Val
50                  55                  60

Asp Gly Val Gln Val His Asn Ala Lys Thr Lys Pro Arg Glu Gln Gln
65                  70                  75                  80

Tyr Asn Ser Thr Tyr Arg Val Val Ser Val Leu Thr Val Leu His Gln
                85                  90                  95

Asn Trp Leu Asp Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 12
<211> LENGTH: 797
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
            20                  25                  30
```

```
Val Lys Thr Phe Phe Gln Met Lys Asp Gln Leu Asp Asn Leu Leu Leu
        35                  40                  45

Lys Glu Ser Leu Leu Glu Asp Phe Lys Gly Tyr Leu Gly Cys Gln Ala
    50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
                85                  90                  95

Asn Leu Lys Thr Leu Arg Leu Arg Leu Arg Arg Cys His Arg Phe Leu
            100                 105                 110

Pro Cys Glu Asn Lys Ser Lys Ala Val Glu Gln Val Lys Asn Ala Phe
            115                 120                 125

Asn Lys Leu Gln Glu Lys Gly Ile Tyr Lys Ala Met Ser Glu Phe Asp
            130                 135                 140

Ile Phe Ile Asn Tyr Ile Glu Ala Tyr Met Thr Met Lys Ile Arg Asn
145                 150                 155                 160

Gly Gly Ser Gly Gly Gly Ser Gly Gly Ser Pro Gly Gln Gly Thr
            165                 170                 175

Gln Ser Glu Asn Ser Cys Thr His Phe Pro Gly Asn Leu Pro Asn Met
            180                 185                 190

Leu Arg Asp Leu Arg Asp Ala Phe Ser Arg Val Lys Thr Phe Phe Gln
            195                 200                 205

Met Lys Asp Gln Leu Asp Asn Leu Leu Leu Lys Glu Ser Leu Leu Glu
    210                 215                 220

Asp Phe Lys Gly Tyr Leu Gly Cys Gln Ala Leu Ser Glu Met Ile Gln
225                 230                 235                 240

Phe Tyr Leu Glu Glu Val Met Pro Gln Ala Glu Asn Gln Asp Pro Asp
                245                 250                 255

Ile Lys Ala His Val Asn Ser Leu Gly Glu Asn Leu Lys Thr Leu Arg
            260                 265                 270

Leu Arg Leu Arg Arg Cys His Arg Phe Leu Pro Cys Glu Asn Lys Ser
        275                 280                 285

Lys Ala Val Glu Gln Val Lys Asn Ala Phe Asn Lys Leu Gln Glu Lys
        290                 295                 300

Gly Ile Tyr Lys Ala Met Ser Glu Phe Asp Ile Phe Ile Asn Tyr Ile
305                 310                 315                 320

Glu Ala Tyr Met Thr Met Lys Ile Arg Asn Gly Gly Gly Gly Ser Gly
                325                 330                 335

Gly Gly Gly Ser Arg Thr Val Ala Ala Pro Ser Val Phe Ile Phe Pro
            340                 345                 350

Pro Ser Asp Glu Gln Leu Lys Ser Gly Thr Ala Ser Val Val Cys Leu
            355                 360                 365

Leu Asn Asn Phe Tyr Pro Arg Glu Ala Lys Val Gln Trp Lys Val Asp
370                 375                 380

Asn Ala Leu Gln Ser Gly Asn Ser Gln Glu Ser Val Thr Glu Gln Asp
385                 390                 395                 400

Ser Lys Asp Ser Thr Tyr Ser Leu Ser Ser Thr Leu Thr Leu Ser Lys
            405                 410                 415

Ala Asp Tyr Glu Lys His Lys Val Tyr Ala Cys Glu Val Thr His Gln
            420                 425                 430

Gly Leu Ser Ser Pro Val Thr Lys Ser Phe Asn Arg Gly Glu Cys Gly
            435                 440                 445
```

```
Gly Gly Gly Ser Gly Gly Gly Ser Gly Gly Gly Ser Gly Gly
        450                 455                 460
Gly Gly Ser Ala Ser Thr Lys Gly Pro Ser Val Phe Pro Leu Ala Pro
465                 470                 475                 480
Ser Ser Lys Ser Thr Ser Gly Gly Thr Ala Ala Leu Gly Cys Leu Val
                485                 490                 495
Lys Asp Tyr Phe Pro Glu Pro Val Thr Val Ser Trp Asn Ser Gly Ala
            500                 505                 510
Leu Thr Ser Gly Val His Thr Phe Pro Ala Val Leu Gln Ser Ser Gly
        515                 520                 525
Leu Tyr Ser Leu Ser Ser Val Val Thr Val Pro Ser Ser Ser Leu Gly
530                 535                 540
Thr Gln Thr Tyr Ile Cys Asn Val Asn His Lys Pro Ser Asn Thr Lys
545                 550                 555                 560
Val Asp Lys Arg Val Glu Pro Lys Ser Cys Asp Lys Thr His Thr Cys
                565                 570                 575
Pro Pro Cys Pro Ala Pro Glu Leu Leu Gly Gly Pro Ser Val Phe Leu
            580                 585                 590
Phe Pro Pro Lys Pro Lys Asp Thr Leu Met Ile Ser Arg Thr Pro Glu
        595                 600                 605
Val Thr Cys Val Val Val Asp Val Ser His Glu Asp Pro Glu Val Lys
610                 615                 620
Phe Asn Trp Tyr Val Asp Gly Val Glu Val His Asn Ala Lys Thr Lys
625                 630                 635                 640
Pro Arg Glu Glu Gln Tyr Asn Ser Thr Tyr Arg Val Val Ser Val Leu
                645                 650                 655
Thr Val Leu His Gln Asp Trp Leu Asn Gly Lys Glu Tyr Lys Cys Lys
            660                 665                 670
Val Ser Asn Lys Ala Leu Pro Ala Pro Ile Glu Lys Thr Ile Ser Lys
        675                 680                 685
Ala Lys Gly Gln Pro Arg Glu Pro Gln Val Tyr Thr Leu Pro Pro Ser
690                 695                 700
Arg Glu Glu Met Thr Lys Asn Gln Val Ser Leu Thr Cys Leu Val Lys
705                 710                 715                 720
Gly Phe Tyr Pro Ser Asp Ile Ala Val Glu Trp Ser Asn Gly Gln
                725                 730                 735
Pro Glu Asn Asn Tyr Lys Thr Thr Pro Pro Val Leu Asp Ser Asp Gly
            740                 745                 750
Ser Phe Phe Leu Tyr Ser Lys Leu Thr Val Asp Lys Ser Arg Trp Gln
        755                 760                 765
Gln Gly Asn Val Phe Ser Cys Ser Val Met His Glu Ala Leu His Asn
770                 775                 780
His Tyr Thr Gln Lys Ser Leu Ser Leu Ser Pro Gly Lys
785                 790                 795

<210> SEQ ID NO 13
<211> LENGTH: 557
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Ser Pro Gly Gln Gly Thr Gln Ser Glu Asn Ser Cys Thr His Phe Pro
1               5                   10                  15
```

```
Gly Asn Leu Pro Asn Met Leu Arg Asp Leu Arg Asp Ala Phe Ser Arg
             20                  25                  30

Val Lys Thr Phe Phe Gln Met Lys Asp Gln Leu Asp Asn Leu Leu Leu
         35                  40                  45

Lys Glu Ser Leu Leu Glu Asp Phe Lys Gly Tyr Leu Gly Cys Gln Ala
 50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
                 85                  90                  95

Asn Leu Lys Thr Leu Arg Leu Arg Leu Arg Arg Cys His Arg Phe Leu
             100                 105                 110

Pro Cys Glu Asn Lys Ser Lys Ala Val Glu Gln Val Lys Asn Ala Phe
         115                 120                 125

Asn Lys Leu Gln Glu Lys Gly Ile Tyr Lys Ala Met Ser Glu Phe Asp
130                 135                 140

Ile Phe Ile Asn Tyr Ile Glu Ala Tyr Met Thr Met Lys Ile Arg Asn
145                 150                 155                 160

Gly Gly Ser Gly Gly Ser Pro Gly Gln Gly Thr Gln Ser Glu Asn Ser
                 165                 170                 175

Cys Thr His Phe Pro Gly Asn Leu Pro Asn Met Leu Arg Asp Leu Arg
             180                 185                 190

Asp Ala Phe Ser Arg Val Lys Thr Phe Phe Gln Met Lys Asp Gln Leu
         195                 200                 205

Asp Asn Leu Leu Leu Lys Glu Ser Leu Leu Glu Asp Phe Lys Gly Tyr
210                 215                 220

Leu Gly Cys Gln Ala Leu Ser Glu Met Ile Gln Phe Tyr Leu Glu Glu
225                 230                 235                 240

Val Met Pro Gln Ala Glu Asn Gln Asp Pro Asp Ile Lys Ala His Val
                 245                 250                 255

Asn Ser Leu Gly Glu Asn Leu Lys Thr Leu Arg Leu Arg Leu Arg Arg
             260                 265                 270

Cys His Arg Phe Leu Pro Cys Glu Asn Lys Ser Lys Ala Val Glu Gln
         275                 280                 285

Val Lys Asn Ala Phe Asn Lys Leu Gln Glu Lys Gly Ile Tyr Lys Ala
290                 295                 300

Met Ser Glu Phe Asp Ile Phe Ile Asn Tyr Ile Glu Ala Tyr Met Thr
305                 310                 315                 320

Met Lys Ile Arg Asn Glu Pro Lys Ser Ser Asp Lys Thr His Thr Cys
             325                 330                 335

Pro Pro Cys Pro Ala Pro Glu Leu Leu Gly Gly Pro Ser Val Phe Leu
         340                 345                 350

Phe Pro Pro Lys Pro Lys Asp Thr Leu Met Ile Ser Arg Thr Pro Glu
         355                 360                 365

Val Thr Cys Val Val Val Asp Val Ser His Glu Asp Pro Glu Val Lys
         370                 375                 380

Phe Asn Trp Tyr Val Asp Gly Val Glu Val His Asn Ala Lys Thr Lys
385                 390                 395                 400

Pro Arg Glu Glu Gln Tyr Asn Ser Thr Tyr Arg Val Val Ser Val Leu
             405                 410                 415

Thr Val Leu His Gln Asp Trp Leu Asn Gly Lys Glu Tyr Lys Cys Lys
             420                 425                 430
```

```
Val Ser Asn Lys Ala Leu Pro Ala Pro Ile Glu Lys Thr Ile Ser Lys
        435                 440                 445

Ala Lys Gly Gln Pro Arg Glu Pro Gln Val Tyr Thr Leu Pro Pro Ser
450                 455                 460

Arg Glu Glu Met Thr Lys Asn Gln Val Ser Leu Thr Cys Leu Val Lys
465                 470                 475                 480

Gly Phe Tyr Pro Ser Asp Ile Ala Val Glu Trp Glu Ser Asn Gly Gln
                485                 490                 495

Pro Glu Asn Asn Tyr Lys Thr Thr Pro Pro Val Leu Asp Ser Asp Gly
            500                 505                 510

Ser Phe Phe Leu Tyr Ser Lys Leu Thr Val Asp Lys Ser Arg Trp Gln
        515                 520                 525

Gln Gly Asn Val Phe Ser Cys Ser Val Met His Glu Ala Leu His Asn
    530                 535                 540

His Tyr Thr Gln Lys Ser Leu Ser Leu Ser Pro Gly Lys
545                 550                 555

<210> SEQ ID NO 14
<211> LENGTH: 553
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
            20                  25                  30

Val Lys Thr Phe Phe Gln Met Lys Asp Gln Leu Asp Asn Leu Leu Leu
        35                  40                  45

Lys Glu Ser Leu Leu Glu Asp Phe Lys Gly Tyr Leu Gly Cys Gln Ala
50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
                85                  90                  95

Asn Leu Lys Thr Leu Arg Leu Arg Leu Arg Arg Cys His Arg Phe Leu
            100                 105                 110

Pro Cys Glu Asn Lys Ser Lys Ala Val Glu Gln Val Lys Asn Ala Phe
        115                 120                 125

Asn Lys Leu Gln Glu Lys Gly Ile Tyr Lys Ala Met Ser Glu Phe Asp
    130                 135                 140

Ile Phe Ile Asn Tyr Ile Glu Ala Tyr Met Thr Met Lys Ile Arg Asn
145                 150                 155                 160

Gly Gly Ser Gly Gly Ser Pro Gly Gln Gly Thr Gln Ser Glu Asn Ser
                165                 170                 175

Cys Thr His Phe Pro Gly Asn Leu Pro Asn Met Leu Arg Asp Leu Arg
            180                 185                 190

Asp Ala Phe Ser Arg Val Lys Thr Phe Phe Gln Met Lys Asp Gln Leu
        195                 200                 205

Asp Asn Leu Leu Leu Lys Glu Ser Leu Leu Glu Asp Phe Lys Gly Tyr
    210                 215                 220

Leu Gly Cys Gln Ala Leu Ser Glu Met Ile Gln Phe Tyr Leu Glu Glu
225                 230                 235                 240
```

```
Val Met Pro Gln Ala Glu Asn Gln Asp Pro Asp Ile Lys Ala His Val
                245                 250                 255

Asn Ser Leu Gly Glu Asn Leu Lys Thr Leu Arg Leu Arg Leu Arg Arg
            260                 265                 270

Cys His Arg Phe Leu Pro Cys Glu Asn Lys Ser Lys Ala Val Glu Gln
        275                 280                 285

Val Lys Asn Ala Phe Asn Lys Leu Gln Glu Lys Gly Ile Tyr Lys Ala
    290                 295                 300

Met Ser Glu Phe Asp Ile Phe Ile Asn Tyr Ile Glu Ala Tyr Met Thr
305                 310                 315                 320

Met Lys Ile Arg Asn Ser Asp Lys Thr His Thr Cys Pro Pro Cys Pro
                325                 330                 335

Ala Pro Glu Leu Leu Gly Gly Pro Ser Val Phe Leu Phe Pro Pro Lys
            340                 345                 350

Pro Lys Asp Thr Leu Met Ile Ser Arg Thr Pro Glu Val Thr Cys Val
        355                 360                 365

Val Val Asp Val Ser His Glu Asp Pro Glu Val Lys Phe Asn Trp Tyr
    370                 375                 380

Val Asp Gly Val Glu Val His Asn Ala Lys Thr Lys Pro Arg Glu Glu
385                 390                 395                 400

Gln Tyr Asn Ser Thr Tyr Arg Val Val Ser Val Leu Thr Val Leu His
                405                 410                 415

Gln Asp Trp Leu Asn Gly Lys Glu Tyr Lys Cys Lys Val Ser Asn Lys
            420                 425                 430

Ala Leu Pro Ala Pro Ile Glu Lys Thr Ile Ser Lys Ala Lys Gly Gln
        435                 440                 445

Pro Arg Glu Pro Gln Val Tyr Thr Leu Pro Pro Ser Arg Glu Glu Met
    450                 455                 460

Thr Lys Asn Gln Val Ser Leu Thr Cys Leu Val Lys Gly Phe Tyr Pro
465                 470                 475                 480

Ser Asp Ile Ala Val Glu Trp Glu Ser Asn Gly Gln Pro Glu Asn Asn
                485                 490                 495

Tyr Lys Thr Thr Pro Pro Val Leu Asp Ser Asp Gly Ser Phe Phe Leu
            500                 505                 510

Tyr Ser Lys Leu Thr Val Asp Lys Ser Arg Trp Gln Gln Gly Asn Val
        515                 520                 525

Phe Ser Cys Ser Val Met His Glu Ala Leu His Asn His Tyr Thr Gln
    530                 535                 540

Lys Ser Leu Ser Leu Ser Pro Gly Lys
545                 550

<210> SEQ ID NO 15
<211> LENGTH: 550
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
            20                  25                  30

Val Lys Thr Phe Phe Gln Met Lys Asp Gln Leu Asp Asn Leu Leu Leu
```

```
                35                  40                  45
Lys Glu Ser Leu Leu Glu Asp Phe Lys Gly Tyr Leu Gly Cys Gln Ala
 50                  55                  60

Leu Ser Glu Met Ile Gln Phe Tyr Leu Glu Glu Val Met Pro Gln Ala
 65                  70                  75                  80

Glu Asn Gln Asp Pro Asp Ile Lys Ala His Val Asn Ser Leu Gly Glu
                 85                  90                  95

Asn Leu Lys Thr Leu Arg Leu Arg Leu Arg Arg Cys His Arg Phe Leu
                100                 105                 110

Pro Cys Glu Asn Lys Ser Lys Ala Val Glu Gln Val Lys Asn Ala Phe
                115                 120                 125

Asn Lys Leu Gln Glu Lys Gly Ile Tyr Lys Ala Met Ser Glu Phe Asp
                130                 135                 140

Ile Phe Ile Asn Tyr Ile Glu Ala Tyr Met Thr Met Lys Ile Arg Asn
145                 150                 155                 160

Gly Gly Ser Gly Gly Ser Pro Gly Gln Gly Thr Gln Ser Glu Asn Ser
                165                 170                 175

Cys Thr His Phe Pro Gly Asn Leu Pro Asn Met Leu Arg Asp Leu Arg
                180                 185                 190

Asp Ala Phe Ser Arg Val Lys Thr Phe Phe Gln Met Lys Asp Gln Leu
                195                 200                 205

Asp Asn Leu Leu Leu Lys Glu Ser Leu Leu Glu Asp Phe Lys Gly Tyr
                210                 215                 220

Leu Gly Cys Gln Ala Leu Ser Glu Met Ile Gln Phe Tyr Leu Glu Glu
225                 230                 235                 240

Val Met Pro Gln Ala Glu Asn Gln Asp Pro Asp Ile Lys Ala His Val
                245                 250                 255

Asn Ser Leu Gly Glu Asn Leu Lys Thr Leu Arg Leu Arg Leu Arg Arg
                260                 265                 270

Cys His Arg Phe Leu Pro Cys Glu Asn Lys Ser Lys Ala Val Glu Gln
                275                 280                 285

Val Lys Asn Ala Phe Asn Lys Leu Gln Glu Lys Gly Ile Tyr Lys Ala
                290                 295                 300

Met Ser Glu Phe Asp Ile Phe Ile Asn Tyr Ile Glu Ala Tyr Met Thr
305                 310                 315                 320

Met Lys Ile Arg Asn Thr His Thr Cys Pro Cys Pro Ala Pro Glu
                325                 330                 335

Leu Leu Gly Gly Pro Ser Val Phe Leu Phe Pro Pro Lys Pro Lys Asp
                340                 345                 350

Thr Leu Met Ile Ser Arg Thr Pro Glu Val Thr Cys Val Val Val Asp
                355                 360                 365

Val Ser His Glu Asp Pro Glu Val Lys Phe Asn Trp Tyr Val Asp Gly
                370                 375                 380

Val Glu Val His Asn Ala Lys Thr Lys Pro Arg Glu Glu Gln Tyr Asn
385                 390                 395                 400

Ser Thr Tyr Arg Val Val Ser Val Leu Thr Val Leu His Gln Asp Trp
                405                 410                 415

Leu Asn Gly Lys Glu Tyr Lys Cys Lys Val Ser Asn Lys Ala Leu Pro
                420                 425                 430

Ala Pro Ile Glu Lys Thr Ile Ser Lys Ala Lys Gly Gln Pro Arg Glu
                435                 440                 445

Pro Gln Val Tyr Thr Leu Pro Pro Ser Arg Glu Glu Met Thr Lys Asn
                450                 455                 460
```

-continued

```
Gln Val Ser Leu Thr Cys Leu Val Lys Gly Phe Tyr Pro Ser Asp Ile
465                 470                 475                 480

Ala Val Glu Trp Glu Ser Asn Gly Gln Pro Glu Asn Asn Tyr Lys Thr
            485                 490                 495

Thr Pro Pro Val Leu Asp Ser Asp Gly Ser Phe Phe Leu Tyr Ser Lys
        500                 505                 510

Leu Thr Val Asp Lys Ser Arg Trp Gln Gln Gly Asn Val Phe Ser Cys
            515                 520                 525

Ser Val Met His Glu Ala Leu His Asn His Tyr Thr Gln Lys Ser Leu
530                 535                 540

Ser Leu Ser Pro Gly Lys
545                 550

<210> SEQ ID NO 16
<211> LENGTH: 550
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
            20                  25                  30

Val Lys Thr Phe Phe Gln Met Lys Asp Gln Leu Asp Asn Leu Leu Leu
        35                  40                  45

Lys Glu Ser Leu Leu Glu Asp Phe Lys Gly Tyr Leu Gly Cys Gln Ala
    50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
                85                  90                  95

Asn Leu Lys Thr Leu Arg Leu Arg Leu Arg Arg Cys His Arg Phe Leu
            100                 105                 110

Pro Cys Glu Asn Lys Ser Lys Ala Val Glu Gln Val Lys Asn Ala Phe
        115                 120                 125

Asn Lys Leu Gln Glu Lys Gly Ile Tyr Lys Ala Met Ser Glu Phe Asp
    130                 135                 140

Ile Phe Ile Asn Tyr Ile Glu Ala Tyr Met Thr Met Lys Ile Arg Asn
145                 150                 155                 160

Gly Gly Ser Gly Gly Ser Pro Gly Gln Gly Thr Gln Ser Glu Asn Ser
                165                 170                 175

Cys Thr His Phe Pro Gly Asn Leu Pro Asn Met Leu Arg Asp Leu Arg
            180                 185                 190

Asp Ala Phe Ser Arg Val Lys Thr Phe Phe Gln Met Lys Asp Gln Leu
        195                 200                 205

Asp Asn Leu Leu Leu Lys Glu Ser Leu Leu Glu Asp Phe Lys Gly Tyr
    210                 215                 220

Leu Gly Cys Gln Ala Leu Ser Glu Met Ile Gln Phe Tyr Leu Glu Glu
225                 230                 235                 240

Val Met Pro Gln Ala Glu Asn Gln Asp Pro Asp Ile Lys Ala His Val
                245                 250                 255

Asn Ser Leu Gly Glu Asn Leu Lys Thr Leu Arg Leu Arg Leu Arg Arg
```

```
            260                 265                 270
Cys His Arg Phe Leu Pro Cys Glu Asn Lys Ser Lys Ala Val Glu Gln
            275                 280                 285

Val Lys Asn Ala Phe Asn Lys Leu Gln Glu Lys Gly Ile Tyr Lys Ala
290                 295                 300

Met Ser Glu Phe Asp Ile Phe Ile Asn Tyr Ile Glu Ala Tyr Met Thr
305                 310                 315                 320

Met Lys Ile Arg Asn Thr His Thr Cys Pro Pro Cys Pro Ala Pro Glu
            325                 330                 335

Leu Leu Gly Gly Pro Ser Val Phe Leu Phe Pro Pro Lys Pro Lys Asp
            340                 345                 350

Thr Leu Met Ile Ser Arg Thr Pro Glu Val Thr Cys Val Val Val Asp
            355                 360                 365

Val Ser His Glu Asp Pro Glu Val Lys Phe Asn Trp Tyr Val Asp Gly
            370                 375                 380

Val Glu Val His Asn Ala Lys Thr Lys Pro Arg Glu Glu Gln Tyr Asn
385                 390                 395                 400

Ser Thr Tyr Arg Val Val Ser Val Leu Thr Val Leu His Gln Asp Trp
            405                 410                 415

Leu Asn Gly Lys Glu Tyr Lys Cys Lys Val Ser Asn Lys Ala Leu Pro
            420                 425                 430

Ala Pro Ile Glu Lys Thr Ile Ser Lys Ala Lys Gly Gln Pro Arg Glu
            435                 440                 445

Pro Gln Val Tyr Thr Leu Pro Pro Ser Arg Glu Glu Met Thr Lys Asn
450                 455                 460

Gln Val Ser Leu Thr Cys Leu Val Lys Gly Phe Tyr Pro Ser Asp Ile
465                 470                 475                 480

Ala Val Glu Trp Glu Ser Asn Gly Gln Pro Glu Asn Asn Tyr Lys Thr
            485                 490                 495

Thr Pro Pro Val Leu Asp Ser Asp Gly Ser Phe Phe Leu Tyr Ser Lys
            500                 505                 510

Leu Thr Val Asp Lys Ser Arg Trp Gln Gln Gly Asn Val Phe Ser Cys
            515                 520                 525

Ser Val Met His Glu Ala Leu His Asn His Tyr Thr Gln Lys Ser Leu
            530                 535                 540

Ser Leu Ser Pro Gly Lys
545                 550

<210> SEQ ID NO 17
<211> LENGTH: 797
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
            20                  25                  30

Val Lys Thr Phe Phe Gln Met Lys Asp Gln Leu Asp Asn Leu Leu Leu
            35                  40                  45

Lys Glu Ser Leu Leu Glu Asp Phe Lys Gly Tyr Leu Gly Cys Gln Ala
        50                  55                  60
```

-continued

```
Leu Ser Glu Met Ile Gln Phe Tyr Leu Glu Val Met Pro Gln Ala
 65                  70                  75                  80

Glu Asn Gln Asp Pro Asp Ala Lys Ala His Val Asn Ser Leu Gly Glu
                 85                  90                  95

Asn Leu Lys Thr Leu Arg Leu Arg Leu Arg Arg Cys His Arg Phe Leu
            100                 105                 110

Pro Cys Glu Asn Lys Ser Lys Ala Val Glu Gln Val Lys Asn Ala Phe
        115                 120                 125

Asn Lys Leu Gln Glu Lys Gly Ile Tyr Lys Ala Met Ser Glu Phe Asp
    130                 135                 140

Ile Phe Ile Asn Tyr Ile Glu Ala Tyr Met Thr Met Lys Ile Arg Asn
145                 150                 155                 160

Gly Gly Ser Gly Gly Gly Ser Gly Gly Ser Pro Gly Gln Gly Thr
                165                 170                 175

Gln Ser Glu Asn Ser Cys Thr His Phe Pro Gly Asn Leu Pro Asn Met
                180                 185                 190

Leu Arg Asp Leu Arg Asp Ala Phe Ser Arg Val Lys Thr Phe Phe Gln
            195                 200                 205

Met Lys Asp Gln Leu Asp Asn Leu Leu Leu Lys Glu Ser Leu Leu Glu
        210                 215                 220

Asp Phe Lys Gly Tyr Leu Gly Cys Gln Ala Leu Ser Glu Met Ile Gln
225                 230                 235                 240

Phe Tyr Leu Glu Glu Val Met Pro Gln Ala Glu Asn Gln Asp Pro Asp
                245                 250                 255

Ala Lys Ala His Val Asn Ser Leu Gly Glu Asn Leu Lys Thr Leu Arg
            260                 265                 270

Leu Arg Leu Arg Arg Cys His Arg Phe Leu Pro Cys Glu Asn Lys Ser
        275                 280                 285

Lys Ala Val Glu Gln Val Lys Asn Ala Phe Asn Lys Leu Gln Glu Lys
    290                 295                 300

Gly Ile Tyr Lys Ala Met Ser Glu Phe Asp Ile Phe Ile Asn Tyr Ile
305                 310                 315                 320

Glu Ala Tyr Met Thr Met Lys Ile Arg Asn Gly Gly Gly Gly Ser Gly
                325                 330                 335

Gly Gly Gly Ser Arg Thr Val Ala Ala Pro Ser Val Phe Ile Phe Pro
            340                 345                 350

Pro Ser Asp Glu Gln Leu Lys Ser Gly Thr Ala Ser Val Val Cys Leu
        355                 360                 365

Leu Asn Asn Phe Tyr Pro Arg Glu Ala Lys Val Gln Trp Lys Val Asp
    370                 375                 380

Asn Ala Leu Gln Ser Gly Asn Ser Gln Glu Ser Val Thr Glu Gln Asp
385                 390                 395                 400

Ser Lys Asp Ser Thr Tyr Ser Leu Ser Ser Thr Leu Thr Leu Ser Lys
                405                 410                 415

Ala Asp Tyr Glu Lys His Lys Val Tyr Ala Cys Glu Val Thr His Gln
            420                 425                 430

Gly Leu Ser Ser Pro Val Thr Lys Ser Phe Asn Arg Gly Glu Cys Gly
        435                 440                 445

Gly Gly Gly Ser Gly Gly Gly Ser Gly Gly Gly Ser Gly Gly
    450                 455                 460

Gly Gly Ser Ala Ser Thr Lys Gly Pro Ser Val Phe Pro Leu Ala Pro
465                 470                 475                 480

Ser Ser Lys Ser Thr Ser Gly Gly Thr Ala Ala Leu Gly Cys Leu Val
```

```
            485                 490                 495
Lys Asp Tyr Phe Pro Glu Pro Val Thr Val Ser Trp Asn Ser Gly Ala
            500                 505                 510

Leu Thr Ser Gly Val His Thr Phe Pro Ala Val Leu Gln Ser Ser Gly
        515                 520                 525

Leu Tyr Ser Leu Ser Ser Val Val Thr Val Pro Ser Ser Ser Leu Gly
    530                 535                 540

Thr Gln Thr Tyr Ile Cys Asn Val Asn His Lys Pro Ser Asn Thr Lys
545                 550                 555                 560

Val Asp Lys Arg Val Glu Pro Lys Ser Cys Asp Lys Thr His Thr Cys
                565                 570                 575

Pro Pro Cys Pro Ala Pro Glu Leu Leu Gly Gly Pro Ser Val Phe Leu
            580                 585                 590

Phe Pro Pro Lys Pro Lys Asp Thr Leu Met Ile Ser Arg Thr Pro Glu
        595                 600                 605

Val Thr Cys Val Val Val Asp Val Ser His Glu Asp Pro Glu Val Lys
    610                 615                 620

Phe Asn Trp Tyr Val Asp Gly Val Glu Val His Asn Ala Lys Thr Lys
625                 630                 635                 640

Pro Arg Glu Glu Gln Tyr Asn Ser Thr Tyr Arg Val Val Ser Val Leu
                645                 650                 655

Thr Val Leu His Gln Asp Trp Leu Asn Gly Lys Glu Tyr Lys Cys Lys
            660                 665                 670

Val Ser Asn Lys Ala Leu Pro Ala Pro Ile Glu Lys Thr Ile Ser Lys
        675                 680                 685

Ala Lys Gly Gln Pro Arg Glu Pro Gln Val Tyr Thr Leu Pro Pro Ser
    690                 695                 700

Arg Glu Glu Met Thr Lys Asn Gln Val Ser Leu Thr Cys Leu Val Lys
705                 710                 715                 720

Gly Phe Tyr Pro Ser Asp Ile Ala Val Glu Trp Glu Ser Asn Gly Gln
                725                 730                 735

Pro Glu Asn Asn Tyr Lys Thr Thr Pro Pro Val Leu Asp Ser Asp Gly
            740                 745                 750

Ser Phe Phe Leu Tyr Ser Lys Leu Thr Val Asp Lys Ser Arg Trp Gln
        755                 760                 765

Gln Gly Asn Val Phe Ser Cys Ser Val Met His Glu Ala Leu His Asn
    770                 775                 780

His Tyr Thr Gln Lys Ser Leu Ser Leu Ser Pro Gly Lys
785                 790                 795

<210> SEQ ID NO 18
<211> LENGTH: 797
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
            20                  25                  30

Val Lys Thr Phe Phe Gln Met Lys Asp Gln Leu Asp Asn Leu Leu Leu
        35                  40                  45
```

```
Lys Glu Ser Leu Leu Glu Asp Phe Lys Gly Tyr Leu Gly Cys Gln Ala
 50                  55                  60

Leu Ser Glu Met Ile Gln Phe Tyr Leu Glu Glu Val Met Pro Gln Ala
 65                  70                  75                  80

Glu Asn Gln Asp Pro Asp Ala Lys Ala His Val Asn Ser Leu Gly Glu
                 85                  90                  95

Asn Leu Lys Thr Leu Arg Leu Arg Leu Arg Arg Cys His Arg Phe Leu
            100                 105                 110

Pro Cys Glu Asn Lys Ser Lys Ala Val Glu Gln Val Lys Asn Ala Phe
            115                 120                 125

Asn Lys Leu Gln Glu Lys Gly Ile Tyr Lys Ala Met Ser Glu Phe Asp
130                 135                 140

Ile Phe Ile Asn Tyr Ile Glu Ala Tyr Met Thr Met Lys Ile Arg Asn
145                 150                 155                 160

Gly Gly Ser Gly Gly Gly Ser Gly Gly Ser Pro Gly Gln Gly Thr
                165                 170                 175

Gln Ser Glu Asn Ser Cys Thr His Phe Pro Gly Asn Leu Pro Asn Met
            180                 185                 190

Leu Arg Asp Leu Arg Asp Ala Phe Ser Arg Val Lys Thr Phe Phe Gln
        195                 200                 205

Met Lys Asp Gln Leu Asp Asn Leu Leu Leu Lys Glu Ser Leu Leu Glu
    210                 215                 220

Asp Phe Lys Gly Tyr Leu Gly Cys Gln Ala Leu Ser Glu Met Ile Gln
225                 230                 235                 240

Phe Tyr Leu Glu Glu Val Met Pro Gln Ala Glu Asn Gln Asp Pro Asp
                245                 250                 255

Ile Lys Ala His Val Asn Ser Leu Gly Glu Asn Leu Lys Thr Leu Arg
            260                 265                 270

Leu Arg Leu Arg Arg Cys His Arg Phe Leu Pro Cys Glu Asn Lys Ser
        275                 280                 285

Lys Ala Val Glu Gln Val Lys Asn Ala Phe Asn Lys Leu Gln Glu Lys
    290                 295                 300

Gly Ile Tyr Lys Ala Met Ser Glu Phe Asp Ile Phe Ile Asn Tyr Ile
305                 310                 315                 320

Glu Ala Tyr Met Thr Met Lys Ile Arg Asn Gly Gly Gly Gly Ser Gly
                325                 330                 335

Gly Gly Gly Ser Arg Thr Val Ala Ala Pro Ser Val Phe Ile Phe Pro
            340                 345                 350

Pro Ser Asp Glu Gln Leu Lys Ser Gly Thr Ala Ser Val Val Cys Leu
            355                 360                 365

Leu Asn Asn Phe Tyr Pro Arg Glu Ala Lys Val Gln Trp Lys Val Asp
370                 375                 380

Asn Ala Leu Gln Ser Gly Asn Ser Gln Glu Ser Val Thr Glu Gln Asp
385                 390                 395                 400

Ser Lys Asp Ser Thr Tyr Ser Leu Ser Ser Thr Leu Thr Leu Ser Lys
                405                 410                 415

Ala Asp Tyr Glu Lys His Lys Val Tyr Ala Cys Glu Val Thr His Gln
            420                 425                 430

Gly Leu Ser Ser Pro Val Thr Lys Ser Phe Asn Arg Gly Glu Cys Gly
            435                 440                 445

Gly Gly Gly Ser Gly Gly Gly Gly Ser Gly Gly Gly Ser Gly Gly
    450                 455                 460

Gly Gly Ser Ala Ser Thr Lys Gly Pro Ser Val Phe Pro Leu Ala Pro
```

```
            465                 470                 475                 480
Ser Ser Lys Ser Thr Ser Gly Gly Thr Ala Ala Leu Gly Cys Leu Val
                    485                 490                 495

Lys Asp Tyr Phe Pro Glu Pro Val Thr Val Ser Trp Asn Ser Gly Ala
                500                 505                 510

Leu Thr Ser Gly Val His Thr Phe Pro Ala Val Leu Gln Ser Ser Gly
            515                 520                 525

Leu Tyr Ser Leu Ser Ser Val Val Thr Val Pro Ser Ser Ser Leu Gly
        530                 535                 540

Thr Gln Thr Tyr Ile Cys Asn Val Asn His Lys Pro Ser Asn Thr Lys
545                 550                 555                 560

Val Asp Lys Arg Val Glu Pro Lys Ser Cys Asp Lys Thr His Thr Cys
                565                 570                 575

Pro Pro Cys Pro Ala Pro Glu Leu Leu Gly Gly Pro Ser Val Phe Leu
                580                 585                 590

Phe Pro Pro Lys Pro Lys Asp Thr Leu Met Ile Ser Arg Thr Pro Glu
            595                 600                 605

Val Thr Cys Val Val Val Asp Val Ser His Glu Asp Pro Glu Val Lys
        610                 615                 620

Phe Asn Trp Tyr Val Asp Gly Val Glu Val His Asn Ala Lys Thr Lys
625                 630                 635                 640

Pro Arg Glu Glu Gln Tyr Asn Ser Thr Tyr Arg Val Val Ser Val Leu
                645                 650                 655

Thr Val Leu His Gln Asp Trp Leu Asn Gly Lys Glu Tyr Lys Cys Lys
            660                 665                 670

Val Ser Asn Lys Ala Leu Pro Ala Pro Ile Glu Lys Thr Ile Ser Lys
        675                 680                 685

Ala Lys Gly Gln Pro Arg Glu Pro Gln Val Tyr Thr Leu Pro Pro Ser
            690                 695                 700

Arg Glu Glu Met Thr Lys Asn Gln Val Ser Leu Thr Cys Leu Val Lys
705                 710                 715                 720

Gly Phe Tyr Pro Ser Asp Ile Ala Val Glu Trp Glu Ser Asn Gly Gln
                725                 730                 735

Pro Glu Asn Asn Tyr Lys Thr Thr Pro Pro Val Leu Asp Ser Asp Gly
            740                 745                 750

Ser Phe Phe Leu Tyr Ser Lys Leu Thr Val Asp Lys Ser Arg Trp Gln
        755                 760                 765

Gln Gly Asn Val Phe Ser Cys Ser Val Met His Glu Ala Leu His Asn
    770                 775                 780

His Tyr Thr Gln Lys Ser Leu Ser Leu Ser Pro Gly Lys
785                 790                 795

<210> SEQ ID NO 19
<211> LENGTH: 797
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
            20                  25                  30
```

```
Val Lys Thr Phe Phe Gln Met Lys Asp Gln Leu Asp Asn Leu Leu Leu
         35                  40                  45
Lys Glu Ser Leu Leu Glu Asp Phe Lys Gly Tyr Leu Gly Cys Gln Ala
 50                      55                  60
Leu Ser Glu Met Ile Gln Phe Tyr Leu Glu Glu Val Met Pro Gln Ala
 65                  70                  75                  80
Glu Asn Gln Asp Pro Asp Ile Lys Ala His Val Asn Ser Leu Gly Glu
                 85                  90                  95
Asn Leu Lys Thr Leu Arg Leu Arg Leu Arg Arg Cys His Arg Phe Leu
             100                 105                 110
Pro Cys Glu Asn Lys Ser Lys Ala Val Glu Gln Val Lys Asn Ala Phe
             115                 120                 125
Asn Lys Leu Gln Glu Lys Gly Ile Tyr Lys Ala Met Ser Glu Phe Asp
             130                 135                 140
Ile Phe Ile Asn Tyr Ile Glu Ala Tyr Met Thr Met Lys Ile Arg Asn
145                 150                 155                 160
Gly Gly Ser Gly Gly Gly Ser Gly Gly Ser Pro Gly Gln Gly Thr
             165                 170                 175
Gln Ser Glu Asn Ser Cys Thr His Phe Pro Gly Asn Leu Pro Asn Met
             180                 185                 190
Leu Arg Asp Leu Arg Asp Ala Phe Ser Arg Val Lys Thr Phe Phe Gln
             195                 200                 205
Met Lys Asp Gln Leu Asp Asn Leu Leu Leu Lys Glu Ser Leu Leu Glu
             210                 215                 220
Asp Phe Lys Gly Tyr Leu Gly Cys Gln Ala Leu Ser Glu Met Ile Gln
225                 230                 235                 240
Phe Tyr Leu Glu Glu Val Met Pro Gln Ala Glu Asn Gln Asp Pro Asp
                 245                 250                 255
Ala Lys Ala His Val Asn Ser Leu Gly Glu Asn Leu Lys Thr Leu Arg
             260                 265                 270
Leu Arg Leu Arg Arg Cys His Arg Phe Leu Pro Cys Glu Asn Lys Ser
             275                 280                 285
Lys Ala Val Glu Gln Val Lys Asn Ala Phe Asn Lys Leu Gln Glu Lys
             290                 295                 300
Gly Ile Tyr Lys Ala Met Ser Glu Phe Asp Ile Phe Ile Asn Tyr Ile
305                 310                 315                 320
Glu Ala Tyr Met Thr Met Lys Ile Arg Asn Gly Gly Gly Gly Ser Gly
                 325                 330                 335
Gly Gly Gly Ser Arg Thr Val Ala Ala Pro Ser Val Phe Ile Phe Pro
             340                 345                 350
Pro Ser Asp Glu Gln Leu Lys Ser Gly Thr Ala Ser Val Val Cys Leu
             355                 360                 365
Leu Asn Asn Phe Tyr Pro Arg Glu Ala Lys Val Gln Trp Lys Val Asp
             370                 375                 380
Asn Ala Leu Gln Ser Gly Asn Ser Gln Glu Ser Val Thr Glu Gln Asp
385                 390                 395                 400
Ser Lys Asp Ser Thr Tyr Ser Leu Ser Ser Thr Leu Thr Leu Ser Lys
                 405                 410                 415
Ala Asp Tyr Glu Lys His Lys Val Tyr Ala Cys Glu Val Thr His Gln
             420                 425                 430
Gly Leu Ser Ser Pro Val Thr Lys Ser Phe Asn Arg Gly Glu Cys Gly
             435                 440                 445
Gly Gly Gly Ser Gly Gly Gly Gly Ser Gly Gly Gly Gly Ser Gly Gly
```

```
            450                 455                 460
Gly Gly Ser Ala Ser Thr Lys Gly Pro Ser Val Phe Pro Leu Ala Pro
465                 470                 475                 480

Ser Ser Lys Ser Thr Ser Gly Gly Thr Ala Ala Leu Gly Cys Leu Val
                485                 490                 495

Lys Asp Tyr Phe Pro Glu Pro Val Thr Val Ser Trp Asn Ser Gly Ala
            500                 505                 510

Leu Thr Ser Gly Val His Thr Phe Pro Ala Val Leu Gln Ser Ser Gly
        515                 520                 525

Leu Tyr Ser Leu Ser Ser Val Val Thr Val Pro Ser Ser Ser Leu Gly
        530                 535                 540

Thr Gln Thr Tyr Ile Cys Asn Val Asn His Lys Pro Ser Asn Thr Lys
545                 550                 555                 560

Val Asp Lys Arg Val Glu Pro Lys Ser Cys Asp Lys Thr His Thr Cys
                565                 570                 575

Pro Pro Cys Pro Ala Pro Glu Leu Leu Gly Gly Pro Ser Val Phe Leu
            580                 585                 590

Phe Pro Pro Lys Pro Lys Asp Thr Leu Met Ile Ser Arg Thr Pro Glu
        595                 600                 605

Val Thr Cys Val Val Val Asp Val Ser His Glu Asp Pro Glu Val Lys
        610                 615                 620

Phe Asn Trp Tyr Val Asp Gly Val Glu Val His Asn Ala Lys Thr Lys
625                 630                 635                 640

Pro Arg Glu Glu Gln Tyr Asn Ser Thr Tyr Arg Val Val Ser Val Leu
                645                 650                 655

Thr Val Leu His Gln Asp Trp Leu Asn Gly Lys Glu Tyr Lys Cys Lys
            660                 665                 670

Val Ser Asn Lys Ala Leu Pro Ala Pro Ile Glu Lys Thr Ile Ser Lys
        675                 680                 685

Ala Lys Gly Gln Pro Arg Glu Pro Gln Val Tyr Thr Leu Pro Pro Ser
        690                 695                 700

Arg Glu Glu Met Thr Lys Asn Gln Val Ser Leu Thr Cys Leu Val Lys
705                 710                 715                 720

Gly Phe Tyr Pro Ser Asp Ile Ala Val Glu Trp Glu Ser Asn Gly Gln
                725                 730                 735

Pro Glu Asn Asn Tyr Lys Thr Thr Pro Pro Val Leu Asp Ser Asp Gly
            740                 745                 750

Ser Phe Phe Leu Tyr Ser Lys Leu Thr Val Asp Lys Ser Arg Trp Gln
        755                 760                 765

Gln Gly Asn Val Phe Ser Cys Ser Val Met His Glu Ala Leu His Asn
        770                 775                 780

His Tyr Thr Gln Lys Ser Leu Ser Leu Ser Pro Gly Lys
785                 790                 795
```

<210> SEQ ID NO 20
<211> LENGTH: 797
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

```
Ser Pro Gly Gln Gly Thr Gln Ser Glu Asn Ser Cys Thr His Phe Pro
1               5                   10                  15
```

-continued

```
Gly Asn Leu Pro Asn Met Leu Arg Asp Leu Arg Asp Ala Phe Ser Arg
             20                  25                  30

Val Lys Thr Phe Phe Gln Met Lys Phe Gln Leu Asp Asn Leu Leu Leu
         35                  40                  45

Lys Glu Ser Leu Leu Glu Asp Phe Lys Gly Tyr Leu Gly Cys Gln Ala
 50                  55                  60

Leu Ser Glu Met Ile Gln Phe Tyr Leu Glu Glu Val Met Pro Gln Ala
 65                  70                  75                  80

Glu Asn Gln Asp Pro Asp Ile Lys Ala His Val Asn Ser Leu Gly Glu
                 85                  90                  95

Asn Leu Lys Thr Leu Arg Leu Arg Leu Arg Arg Cys His Arg Phe Leu
             100                 105                 110

Pro Cys Glu Asn Lys Ser Lys Ala Val Glu Gln Val Lys Asn Ala Phe
         115                 120                 125

Asn Lys Leu Gln Glu Lys Gly Ile Tyr Lys Ala Met Ser Glu Phe Asp
         130                 135                 140

Ile Phe Ile Asn Tyr Ile Glu Ala Tyr Met Thr Met Lys Ile Arg Asn
145                 150                 155                 160

Gly Gly Ser Gly Gly Gly Ser Gly Gly Ser Pro Gly Gln Gly Thr
                 165                 170                 175

Gln Ser Glu Asn Ser Cys Thr His Phe Pro Gly Asn Leu Pro Asn Met
             180                 185                 190

Leu Arg Asp Leu Arg Asp Ala Phe Ser Arg Val Lys Thr Phe Phe Gln
         195                 200                 205

Met Lys Asp Gln Leu Asp Asn Leu Leu Leu Lys Glu Ser Leu Leu Glu
210                 215                 220

Asp Phe Lys Gly Tyr Leu Gly Cys Gln Ala Leu Ser Glu Met Ile Gln
225                 230                 235                 240

Phe Tyr Leu Glu Glu Val Met Pro Gln Ala Glu Asn Gln Asp Pro Asp
                 245                 250                 255

Ile Lys Ala His Val Asn Ser Leu Gly Glu Asn Leu Lys Thr Leu Arg
             260                 265                 270

Leu Arg Leu Arg Arg Cys His Arg Phe Leu Pro Cys Glu Asn Lys Ser
         275                 280                 285

Lys Ala Val Glu Gln Val Lys Asn Ala Phe Asn Lys Leu Gln Glu Lys
         290                 295                 300

Gly Ile Tyr Lys Ala Met Ser Glu Phe Asp Ile Phe Ile Asn Tyr Ile
305                 310                 315                 320

Glu Ala Tyr Met Thr Met Lys Ile Arg Asn Gly Gly Gly Gly Ser Gly
                 325                 330                 335

Gly Gly Gly Ser Arg Thr Val Ala Ala Pro Ser Val Phe Ile Phe Pro
             340                 345                 350

Pro Ser Asp Glu Gln Leu Lys Ser Gly Thr Ala Ser Val Val Cys Leu
         355                 360                 365

Leu Asn Asn Phe Tyr Pro Arg Glu Ala Lys Val Gln Trp Lys Val Asp
         370                 375                 380

Asn Ala Leu Gln Ser Gly Asn Ser Gln Glu Ser Val Thr Glu Gln Asp
385                 390                 395                 400

Ser Lys Asp Ser Thr Tyr Ser Leu Ser Ser Thr Leu Thr Leu Ser Lys
                 405                 410                 415

Ala Asp Tyr Glu Lys His Lys Val Tyr Ala Cys Glu Val Thr His Gln
             420                 425                 430

Gly Leu Ser Ser Pro Val Thr Lys Ser Phe Asn Arg Gly Glu Cys Gly
```

```
            435                 440                 445
Gly Gly Gly Ser Gly Gly Gly Ser Gly Gly Gly Ser Gly Gly
        450                 455                 460
Gly Gly Ser Ala Ser Thr Lys Gly Pro Ser Val Phe Pro Leu Ala Pro
465                 470                 475                 480
Ser Ser Lys Ser Thr Ser Gly Gly Thr Ala Ala Leu Gly Cys Leu Val
                485                 490                 495
Lys Asp Tyr Phe Pro Glu Pro Val Thr Val Ser Trp Asn Ser Gly Ala
            500                 505                 510
Leu Thr Ser Gly Val His Thr Phe Pro Ala Val Leu Gln Ser Ser Gly
        515                 520                 525
Leu Tyr Ser Leu Ser Ser Val Val Thr Val Pro Ser Ser Ser Leu Gly
    530                 535                 540
Thr Gln Thr Tyr Ile Cys Asn Val Asn His Lys Pro Ser Asn Thr Lys
545                 550                 555                 560
Val Asp Lys Arg Val Glu Pro Lys Ser Cys Asp Lys Thr His Thr Cys
                565                 570                 575
Pro Pro Cys Pro Ala Pro Glu Leu Leu Gly Gly Pro Ser Val Phe Leu
            580                 585                 590
Phe Pro Pro Lys Pro Lys Asp Thr Leu Met Ile Ser Arg Thr Pro Glu
        595                 600                 605
Val Thr Cys Val Val Val Asp Val Ser His Glu Asp Pro Glu Val Lys
    610                 615                 620
Phe Asn Trp Tyr Val Asp Gly Val Glu Val His Asn Ala Lys Thr Lys
625                 630                 635                 640
Pro Arg Glu Glu Gln Tyr Asn Ser Thr Tyr Arg Val Val Ser Val Leu
                645                 650                 655
Thr Val Leu His Gln Asp Trp Leu Asn Gly Lys Glu Tyr Lys Cys Lys
            660                 665                 670
Val Ser Asn Lys Ala Leu Pro Ala Pro Ile Glu Lys Thr Ile Ser Lys
        675                 680                 685
Ala Lys Gly Gln Pro Arg Glu Pro Gln Val Tyr Thr Leu Pro Pro Ser
    690                 695                 700
Arg Glu Glu Met Thr Lys Asn Gln Val Ser Leu Thr Cys Leu Val Lys
705                 710                 715                 720
Gly Phe Tyr Pro Ser Asp Ile Ala Val Glu Trp Glu Ser Asn Gly Gln
                725                 730                 735
Pro Glu Asn Asn Tyr Lys Thr Thr Pro Pro Val Leu Asp Ser Asp Gly
            740                 745                 750
Ser Phe Phe Leu Tyr Ser Lys Leu Thr Val Asp Lys Ser Arg Trp Gln
        755                 760                 765
Gln Gly Asn Val Phe Ser Cys Ser Val Met His Glu Ala Leu His Asn
    770                 775                 780
His Tyr Thr Gln Lys Ser Leu Ser Leu Ser Pro Gly Lys
785                 790                 795

<210> SEQ ID NO 21
<211> LENGTH: 797
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21
```

```
Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
            20                  25                  30

Val Lys Thr Phe Phe Gln Met Lys Asp Gln Leu Asp Asn Leu Leu Leu
        35                  40                  45

Lys Glu Ser Leu Leu Glu Asp Phe Lys Gly Tyr Leu Gly Cys Gln Ala
    50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
                85                  90                  95

Asn Leu Lys Thr Leu Arg Leu Arg Leu Arg Arg Cys His Arg Phe Leu
            100                 105                 110

Pro Cys Glu Asn Lys Ser Lys Ala Val Glu Gln Val Lys Asn Ala Phe
        115                 120                 125

Asn Lys Leu Gln Glu Lys Gly Ile Tyr Lys Ala Met Ser Glu Phe Asp
    130                 135                 140

Ile Phe Ile Asn Tyr Ile Glu Ala Tyr Met Thr Met Lys Ile Arg Asn
145                 150                 155                 160

Gly Gly Ser Gly Gly Gly Ser Gly Gly Ser Pro Gly Gln Gly Thr
                165                 170                 175

Gln Ser Glu Asn Ser Cys Thr His Phe Pro Gly Asn Leu Pro Asn Met
            180                 185                 190

Leu Arg Asp Leu Arg Asp Ala Phe Ser Arg Val Lys Thr Phe Phe Gln
    195                 200                 205

Met Lys Phe Gln Leu Asp Asn Leu Leu Leu Lys Glu Ser Leu Leu Glu
    210                 215                 220

Asp Phe Lys Gly Tyr Leu Gly Cys Gln Ala Leu Ser Glu Met Ile Gln
225                 230                 235                 240

Phe Tyr Leu Glu Glu Val Met Pro Gln Ala Glu Asn Gln Asp Pro Asp
                245                 250                 255

Ile Lys Ala His Val Asn Ser Leu Gly Glu Asn Leu Lys Thr Leu Arg
            260                 265                 270

Leu Arg Leu Arg Arg Cys His Arg Phe Leu Pro Cys Glu Asn Lys Ser
    275                 280                 285

Lys Ala Val Glu Gln Val Lys Asn Ala Phe Asn Lys Leu Gln Glu Lys
    290                 295                 300

Gly Ile Tyr Lys Ala Met Ser Glu Phe Asp Ile Phe Ile Asn Tyr Ile
305                 310                 315                 320

Glu Ala Tyr Met Thr Met Lys Ile Arg Asn Gly Gly Gly Gly Ser Gly
                325                 330                 335

Gly Gly Gly Ser Arg Thr Val Ala Ala Pro Ser Val Phe Ile Phe Pro
            340                 345                 350

Pro Ser Asp Glu Gln Leu Lys Ser Gly Thr Ala Ser Val Val Cys Leu
        355                 360                 365

Leu Asn Asn Phe Tyr Pro Arg Glu Ala Lys Val Gln Trp Lys Val Asp
    370                 375                 380

Asn Ala Leu Gln Ser Gly Asn Ser Gln Glu Ser Val Thr Glu Gln Asp
385                 390                 395                 400

Ser Lys Asp Ser Thr Tyr Ser Leu Ser Ser Thr Leu Thr Leu Ser Lys
                405                 410                 415

Ala Asp Tyr Glu Lys His Lys Val Tyr Ala Cys Glu Val Thr His Gln
```

```
            420             425             430
Gly Leu Ser Ser Pro Val Thr Lys Ser Phe Asn Arg Gly Glu Cys Gly
            435             440             445
Gly Gly Gly Ser Gly Gly Gly Ser Gly Gly Gly Ser Gly Gly
450             455             460
Gly Gly Ser Ala Ser Thr Lys Gly Pro Ser Val Phe Pro Leu Ala Pro
465             470             475             480
Ser Ser Lys Ser Thr Ser Gly Gly Thr Ala Ala Leu Gly Cys Leu Val
            485             490             495
Lys Asp Tyr Phe Pro Glu Pro Val Thr Val Ser Trp Asn Ser Gly Ala
            500             505             510
Leu Thr Ser Gly Val His Thr Phe Pro Ala Val Leu Gln Ser Ser Gly
            515             520             525
Leu Tyr Ser Leu Ser Ser Val Val Thr Val Pro Ser Ser Ser Leu Gly
            530             535             540
Thr Gln Thr Tyr Ile Cys Asn Val Asn His Lys Pro Ser Asn Thr Lys
545             550             555             560
Val Asp Lys Arg Val Glu Pro Lys Ser Cys Asp Lys Thr His Thr Cys
            565             570             575
Pro Pro Cys Pro Ala Pro Glu Leu Leu Gly Gly Pro Ser Val Phe Leu
            580             585             590
Phe Pro Pro Lys Pro Lys Asp Thr Leu Met Ile Ser Arg Thr Pro Glu
            595             600             605
Val Thr Cys Val Val Val Asp Val Ser His Glu Asp Pro Glu Val Lys
            610             615             620
Phe Asn Trp Tyr Val Asp Gly Val Glu Val His Asn Ala Lys Thr Lys
625             630             635             640
Pro Arg Glu Glu Gln Tyr Asn Ser Thr Tyr Arg Val Val Ser Val Leu
            645             650             655
Thr Val Leu His Gln Asp Trp Leu Asn Gly Lys Glu Tyr Lys Cys Lys
            660             665             670
Val Ser Asn Lys Ala Leu Pro Ala Pro Ile Glu Lys Thr Ile Ser Lys
            675             680             685
Ala Lys Gly Gln Pro Arg Glu Pro Gln Val Tyr Thr Leu Pro Pro Ser
            690             695             700
Arg Glu Glu Met Thr Lys Asn Gln Val Ser Leu Thr Cys Leu Val Lys
705             710             715             720
Gly Phe Tyr Pro Ser Asp Ile Ala Val Glu Trp Glu Ser Asn Gly Gln
            725             730             735
Pro Glu Asn Asn Tyr Lys Thr Thr Pro Pro Val Leu Asp Ser Asp Gly
            740             745             750
Ser Phe Phe Leu Tyr Ser Lys Leu Thr Val Asp Lys Ser Arg Trp Gln
            755             760             765
Gln Gly Asn Val Phe Ser Cys Ser Val Met His Glu Ala Leu His Asn
            770             775             780
His Tyr Thr Gln Lys Ser Leu Ser Leu Ser Pro Gly Lys
785             790             795
```

<210> SEQ ID NO 22
<211> LENGTH: 797
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 22

```
Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
            20                  25                  30

Val Lys Thr Phe Phe Gln Met Lys Phe Gln Leu Asp Asn Leu Leu Leu
        35                  40                  45

Lys Glu Ser Leu Leu Glu Asp Phe Lys Gly Tyr Leu Gly Cys Gln Ala
    50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
                85                  90                  95

Asn Leu Lys Thr Leu Arg Leu Arg Leu Arg Arg Cys His Arg Phe Leu
            100                 105                 110

Pro Cys Glu Asn Lys Ser Lys Ala Val Glu Gln Val Lys Asn Ala Phe
        115                 120                 125

Asn Lys Leu Gln Glu Lys Gly Ile Tyr Lys Ala Met Ser Glu Phe Asp
130                 135                 140

Ile Phe Ile Asn Tyr Ile Glu Ala Tyr Met Thr Met Lys Ile Arg Asn
145                 150                 155                 160

Gly Gly Ser Gly Gly Gly Ser Gly Gly Ser Pro Gly Gln Gly Thr
                165                 170                 175

Gln Ser Glu Asn Ser Cys Thr His Phe Pro Gly Asn Leu Pro Asn Met
            180                 185                 190

Leu Arg Asp Leu Arg Asp Ala Phe Ser Arg Val Lys Thr Phe Phe Gln
        195                 200                 205

Met Lys Phe Gln Leu Asp Asn Leu Leu Leu Lys Glu Ser Leu Leu Glu
    210                 215                 220

Asp Phe Lys Gly Tyr Leu Gly Cys Gln Ala Leu Ser Glu Met Ile Gln
225                 230                 235                 240

Phe Tyr Leu Glu Glu Val Met Pro Gln Ala Glu Asn Gln Asp Pro Asp
                245                 250                 255

Ile Lys Ala His Val Asn Ser Leu Gly Glu Asn Leu Lys Thr Leu Arg
            260                 265                 270

Leu Arg Leu Arg Arg Cys His Arg Phe Leu Pro Cys Glu Asn Lys Ser
        275                 280                 285

Lys Ala Val Glu Gln Val Lys Asn Ala Phe Asn Lys Leu Gln Glu Lys
    290                 295                 300

Gly Ile Tyr Lys Ala Met Ser Glu Phe Asp Ile Phe Ile Asn Tyr Ile
305                 310                 315                 320

Glu Ala Tyr Met Thr Met Lys Ile Arg Asn Gly Gly Gly Ser Gly
                325                 330                 335

Gly Gly Gly Ser Arg Thr Val Ala Ala Pro Ser Val Phe Ile Phe Pro
            340                 345                 350

Pro Ser Asp Glu Gln Leu Lys Ser Gly Thr Ala Ser Val Val Cys Leu
        355                 360                 365

Leu Asn Asn Phe Tyr Pro Arg Glu Ala Lys Val Gln Trp Lys Val Asp
    370                 375                 380

Asn Ala Leu Gln Ser Gly Asn Ser Gln Glu Ser Val Thr Glu Gln Asp
385                 390                 395                 400

Ser Lys Asp Ser Thr Tyr Ser Leu Ser Ser Thr Leu Thr Leu Ser Lys
```

```
                    405                 410                 415
Ala Asp Tyr Glu Lys His Lys Val Tyr Ala Cys Glu Val Thr His Gln
                420                 425                 430

Gly Leu Ser Ser Pro Val Thr Lys Ser Phe Asn Arg Gly Glu Cys Gly
            435                 440                 445

Gly Gly Gly Ser Gly Gly Gly Ser Gly Gly Gly Ser Gly Gly
        450                 455                 460

Gly Gly Ser Ala Ser Thr Lys Gly Pro Ser Val Phe Pro Leu Ala Pro
465                 470                 475                 480

Ser Ser Lys Ser Thr Ser Gly Gly Thr Ala Ala Leu Gly Cys Leu Val
                485                 490                 495

Lys Asp Tyr Phe Pro Glu Pro Val Thr Val Ser Trp Asn Ser Gly Ala
            500                 505                 510

Leu Thr Ser Gly Val His Thr Phe Pro Ala Val Leu Gln Ser Ser Gly
        515                 520                 525

Leu Tyr Ser Leu Ser Ser Val Val Thr Val Pro Ser Ser Ser Leu Gly
    530                 535                 540

Thr Gln Thr Tyr Ile Cys Asn Val Asn His Lys Pro Ser Asn Thr Lys
545                 550                 555                 560

Val Asp Lys Arg Val Glu Pro Lys Ser Cys Asp Lys Thr His Thr Cys
                565                 570                 575

Pro Pro Cys Pro Ala Pro Glu Leu Leu Gly Gly Pro Ser Val Phe Leu
            580                 585                 590

Phe Pro Pro Lys Pro Lys Asp Thr Leu Met Ile Ser Arg Thr Pro Glu
        595                 600                 605

Val Thr Cys Val Val Val Asp Val Ser His Glu Asp Pro Glu Val Lys
    610                 615                 620

Phe Asn Trp Tyr Val Asp Gly Val Glu Val His Asn Ala Lys Thr Lys
625                 630                 635                 640

Pro Arg Glu Glu Gln Tyr Asn Ser Thr Tyr Arg Val Val Ser Val Leu
                645                 650                 655

Thr Val Leu His Gln Asp Trp Leu Asn Gly Lys Glu Tyr Lys Cys Lys
            660                 665                 670

Val Ser Asn Lys Ala Leu Pro Ala Pro Ile Glu Lys Thr Ile Ser Lys
        675                 680                 685

Ala Lys Gly Gln Pro Arg Glu Pro Gln Val Tyr Thr Leu Pro Pro Ser
    690                 695                 700

Arg Glu Glu Met Thr Lys Asn Gln Val Ser Leu Thr Cys Leu Val Lys
705                 710                 715                 720

Gly Phe Tyr Pro Ser Asp Ile Ala Val Glu Trp Glu Ser Asn Gly Gln
                725                 730                 735

Pro Glu Asn Asn Tyr Lys Thr Thr Pro Pro Val Leu Asp Ser Asp Gly
            740                 745                 750

Ser Phe Phe Leu Tyr Ser Lys Leu Thr Val Asp Lys Ser Arg Trp Gln
        755                 760                 765

Gln Gly Asn Val Phe Ser Cys Ser Val Met His Glu Ala Leu His Asn
    770                 775                 780

His Tyr Thr Gln Lys Ser Leu Ser Leu Ser Pro Gly Lys
785                 790                 795

<210> SEQ ID NO 23
<211> LENGTH: 797
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 23

Ser Pro Gly Gln Gly Thr Gln Ser Glu Asn Ser Cys Thr His Phe Pro
1               5                   10                  15

Gly Asn Leu Pro Asn Ala Leu Arg Asp Leu Arg Asp Ala Phe Ser Arg
            20                  25                  30

Val Lys Thr Phe Phe Gln Met Lys Asp Gln Leu Asp Asn Leu Leu Leu
        35                  40                  45

Lys Glu Ser Leu Leu Glu Asp Phe Lys Gly Tyr Leu Gly Cys Gln Ala
    50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
                85                  90                  95

Asn Leu Lys Thr Leu Arg Leu Arg Leu Arg Arg Cys His Arg Phe Leu
            100                 105                 110

Pro Cys Glu Asn Lys Ser Lys Ala Val Glu Gln Val Lys Asn Ala Phe
        115                 120                 125

Asn Lys Leu Gln Glu Lys Gly Ile Tyr Lys Ala Met Ser Glu Phe Asp
    130                 135                 140

Ile Phe Ile Asn Tyr Ile Glu Ala Tyr Met Thr Met Lys Ile Arg Asn
145                 150                 155                 160

Gly Gly Ser Gly Gly Gly Ser Gly Gly Ser Pro Gly Gln Gly Thr
                165                 170                 175

Gln Ser Glu Asn Ser Cys Thr His Phe Pro Gly Asn Leu Pro Asn Met
                180                 185                 190

Leu Arg Asp Leu Arg Asp Ala Phe Ser Arg Val Lys Thr Phe Phe Gln
            195                 200                 205

Met Lys Asp Gln Leu Asp Asn Leu Leu Leu Lys Glu Ser Leu Leu Glu
        210                 215                 220

Asp Phe Lys Gly Tyr Leu Gly Cys Gln Ala Leu Ser Glu Met Ile Gln
225                 230                 235                 240

Phe Tyr Leu Glu Glu Val Met Pro Gln Ala Glu Asn Gln Asp Pro Asp
                245                 250                 255

Ile Lys Ala His Val Asn Ser Leu Gly Glu Asn Leu Lys Thr Leu Arg
            260                 265                 270

Leu Arg Leu Arg Arg Cys His Arg Phe Leu Pro Cys Glu Asn Lys Ser
        275                 280                 285

Lys Ala Val Glu Gln Val Lys Asn Ala Phe Asn Lys Leu Gln Glu Lys
    290                 295                 300

Gly Ile Tyr Lys Ala Met Ser Glu Phe Asp Ile Phe Ile Asn Tyr Ile
305                 310                 315                 320

Glu Ala Tyr Met Thr Met Lys Ile Arg Asn Gly Gly Gly Gly Ser Gly
                325                 330                 335

Gly Gly Gly Ser Arg Thr Val Ala Ala Pro Ser Val Phe Ile Phe Pro
            340                 345                 350

Pro Ser Asp Glu Gln Leu Lys Ser Gly Thr Ala Ser Val Val Cys Leu
        355                 360                 365

Leu Asn Asn Phe Tyr Pro Arg Glu Ala Lys Val Gln Trp Lys Val Asp
    370                 375                 380

Asn Ala Leu Gln Ser Gly Asn Ser Gln Glu Ser Val Thr Glu Gln Asp
```

```
            385                 390                 395                 400
        Ser Lys Asp Ser Thr Tyr Ser Leu Ser Ser Thr Leu Thr Leu Ser Lys
                        405                 410                 415

Ala Asp Tyr Glu Lys His Lys Val Tyr Ala Cys Glu Val Thr His Gln
                        420                 425                 430

Gly Leu Ser Ser Pro Val Thr Lys Ser Phe Asn Arg Gly Glu Cys Gly
                        435                 440                 445

Gly Gly Gly Ser Gly Gly Gly Gly Ser Gly Gly Gly Gly Ser Gly Gly
                        450                 455                 460

Gly Gly Ser Ala Ser Thr Lys Gly Pro Ser Val Phe Pro Leu Ala Pro
        465                 470                 475                 480

Ser Ser Lys Ser Thr Ser Gly Gly Thr Ala Ala Leu Gly Cys Leu Val
                        485                 490                 495

Lys Asp Tyr Phe Pro Glu Pro Val Thr Val Ser Trp Asn Ser Gly Ala
                        500                 505                 510

Leu Thr Ser Gly Val His Thr Phe Pro Ala Val Leu Gln Ser Ser Gly
                        515                 520                 525

Leu Tyr Ser Leu Ser Ser Val Val Thr Val Pro Ser Ser Ser Leu Gly
                        530                 535                 540

Thr Gln Thr Tyr Ile Cys Asn Val Asn His Lys Pro Ser Asn Thr Lys
        545                 550                 555                 560

Val Asp Lys Arg Val Glu Pro Lys Ser Cys Asp Lys Thr His Thr Cys
                        565                 570                 575

Pro Pro Cys Pro Ala Pro Glu Leu Leu Gly Gly Pro Ser Val Phe Leu
                        580                 585                 590

Phe Pro Pro Lys Pro Lys Asp Thr Leu Met Ile Ser Arg Thr Pro Glu
                        595                 600                 605

Val Thr Cys Val Val Val Asp Val Ser His Glu Asp Pro Glu Val Lys
                        610                 615                 620

Phe Asn Trp Tyr Val Asp Gly Val Glu Val His Asn Ala Lys Thr Lys
        625                 630                 635                 640

Pro Arg Glu Glu Gln Tyr Asn Ser Thr Tyr Arg Val Val Ser Val Leu
                        645                 650                 655

Thr Val Leu His Gln Asp Trp Leu Asn Gly Lys Glu Tyr Lys Cys Lys
                        660                 665                 670

Val Ser Asn Lys Ala Leu Pro Ala Pro Ile Glu Lys Thr Ile Ser Lys
                        675                 680                 685

Ala Lys Gly Gln Pro Arg Glu Pro Gln Val Tyr Thr Leu Pro Pro Ser
                        690                 695                 700

Arg Glu Glu Met Thr Lys Asn Gln Val Ser Leu Thr Cys Leu Val Lys
        705                 710                 715                 720

Gly Phe Tyr Pro Ser Asp Ile Ala Val Glu Trp Glu Ser Asn Gly Gln
                        725                 730                 735

Pro Glu Asn Asn Tyr Lys Thr Thr Pro Pro Val Leu Asp Ser Asp Gly
                        740                 745                 750

Ser Phe Phe Leu Tyr Ser Lys Leu Thr Val Asp Lys Ser Arg Trp Gln
                        755                 760                 765

Gln Gly Asn Val Phe Ser Cys Ser Val Met His Glu Ala Leu His Asn
                        770                 775                 780

His Tyr Thr Gln Lys Ser Leu Ser Leu Ser Pro Gly Lys
        785                 790                 795

<210> SEQ ID NO 24
```

<211> LENGTH: 797
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

```
Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
                20                  25                  30

Val Lys Thr Phe Phe Gln Met Lys Asp Gln Leu Asp Asn Leu Leu Leu
            35                  40                  45

Lys Glu Ser Leu Leu Glu Asp Phe Lys Gly Tyr Leu Gly Cys Gln Ala
    50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
                85                  90                  95

Asn Leu Lys Thr Leu Arg Leu Arg Leu Arg Arg Cys His Arg Phe Leu
                100                 105                 110

Pro Cys Glu Asn Lys Ser Lys Ala Val Glu Gln Val Lys Asn Ala Phe
            115                 120                 125

Asn Lys Leu Gln Glu Lys Gly Ile Tyr Lys Ala Met Ser Glu Phe Asp
    130                 135                 140

Ile Phe Ile Asn Tyr Ile Glu Ala Tyr Met Thr Met Lys Ile Arg Asn
145                 150                 155                 160

Gly Gly Ser Gly Gly Gly Ser Gly Gly Ser Pro Gly Gln Gly Thr
                165                 170                 175

Gln Ser Glu Asn Ser Cys Thr His Phe Pro Gly Asn Leu Pro Asn Ala
            180                 185                 190

Leu Arg Asp Leu Arg Asp Ala Phe Ser Arg Val Lys Thr Phe Phe Gln
    195                 200                 205

Met Lys Asp Gln Leu Asp Asn Leu Leu Leu Lys Glu Ser Leu Leu Glu
210                 215                 220

Asp Phe Lys Gly Tyr Leu Gly Cys Gln Ala Leu Ser Glu Met Ile Gln
225                 230                 235                 240

Phe Tyr Leu Glu Glu Val Met Pro Gln Ala Glu Asn Gln Asp Pro Asp
                245                 250                 255

Ile Lys Ala His Val Asn Ser Leu Gly Glu Asn Leu Lys Thr Leu Arg
            260                 265                 270

Leu Arg Leu Arg Arg Cys His Arg Phe Leu Pro Cys Glu Asn Lys Ser
    275                 280                 285

Lys Ala Val Glu Gln Val Lys Asn Ala Phe Asn Lys Leu Gln Glu Lys
290                 295                 300

Gly Ile Tyr Lys Ala Met Ser Glu Phe Asp Ile Phe Ile Asn Tyr Ile
305                 310                 315                 320

Glu Ala Tyr Met Thr Met Lys Ile Arg Asn Gly Gly Gly Ser Gly
                325                 330                 335

Gly Gly Gly Ser Arg Thr Val Ala Ala Pro Ser Val Phe Ile Phe Pro
            340                 345                 350

Pro Ser Asp Glu Gln Leu Lys Ser Gly Thr Ala Ser Val Val Cys Leu
    355                 360                 365

Leu Asn Asn Phe Tyr Pro Arg Glu Ala Lys Val Gln Trp Lys Val Asp
```

```
                370                 375                 380
Asn Ala Leu Gln Ser Gly Asn Ser Gln Glu Ser Val Thr Glu Gln Asp
385                 390                 395                 400

Ser Lys Asp Ser Thr Tyr Ser Leu Ser Ser Thr Leu Thr Leu Ser Lys
                405                 410                 415

Ala Asp Tyr Glu Lys His Lys Val Tyr Ala Cys Glu Val Thr His Gln
                420                 425                 430

Gly Leu Ser Ser Pro Val Thr Lys Ser Phe Asn Arg Gly Glu Cys Gly
                435                 440                 445

Gly Gly Gly Ser Gly Gly Gly Ser Gly Gly Gly Ser Gly Gly
                450                 455                 460

Gly Gly Ser Ala Ser Thr Lys Gly Pro Ser Val Phe Pro Leu Ala Pro
465                 470                 475                 480

Ser Ser Lys Ser Thr Ser Gly Gly Thr Ala Ala Leu Gly Cys Leu Val
                485                 490                 495

Lys Asp Tyr Phe Pro Glu Pro Val Thr Val Ser Trp Asn Ser Gly Ala
                500                 505                 510

Leu Thr Ser Gly Val His Thr Phe Pro Ala Val Leu Gln Ser Ser Gly
                515                 520                 525

Leu Tyr Ser Leu Ser Ser Val Val Thr Val Pro Ser Ser Ser Leu Gly
                530                 535                 540

Thr Gln Thr Tyr Ile Cys Asn Val Asn His Lys Pro Ser Asn Thr Lys
545                 550                 555                 560

Val Asp Lys Arg Val Glu Pro Lys Ser Cys Asp Lys Thr His Thr Cys
                565                 570                 575

Pro Pro Cys Pro Ala Pro Glu Leu Leu Gly Gly Pro Ser Val Phe Leu
                580                 585                 590

Phe Pro Pro Lys Pro Lys Asp Thr Leu Met Ile Ser Arg Thr Pro Glu
                595                 600                 605

Val Thr Cys Val Val Val Asp Val Ser His Glu Asp Pro Glu Val Lys
                610                 615                 620

Phe Asn Trp Tyr Val Asp Gly Val Glu Val His Asn Ala Lys Thr Lys
625                 630                 635                 640

Pro Arg Glu Glu Gln Tyr Asn Ser Thr Tyr Arg Val Val Ser Val Leu
                645                 650                 655

Thr Val Leu His Gln Asp Trp Leu Asn Gly Lys Glu Tyr Lys Cys Lys
                660                 665                 670

Val Ser Asn Lys Ala Leu Pro Ala Pro Ile Glu Lys Thr Ile Ser Lys
                675                 680                 685

Ala Lys Gly Gln Pro Arg Glu Pro Gln Val Tyr Thr Leu Pro Pro Ser
                690                 695                 700

Arg Glu Glu Met Thr Lys Asn Gln Val Ser Leu Thr Cys Leu Val Lys
705                 710                 715                 720

Gly Phe Tyr Pro Ser Asp Ile Ala Val Glu Trp Glu Ser Asn Gly Gln
                725                 730                 735

Pro Glu Asn Asn Tyr Lys Thr Thr Pro Pro Val Leu Asp Ser Asp Gly
                740                 745                 750

Ser Phe Phe Leu Tyr Ser Lys Leu Thr Val Asp Lys Ser Arg Trp Gln
                755                 760                 765

Gln Gly Asn Val Phe Ser Cys Ser Val Met His Glu Ala Leu His Asn
                770                 775                 780

His Tyr Thr Gln Lys Ser Leu Ser Leu Ser Pro Gly Lys
785                 790                 795
```

<210> SEQ ID NO 25
<211> LENGTH: 797
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

```
Ser Pro Gly Gln Gly Thr Gln Ser Glu Asn Ser Cys Thr His Phe Pro
1               5                   10                  15

Gly Asn Leu Pro Asn Ala Leu Arg Asp Leu Arg Asp Ala Phe Ser Arg
            20                  25                  30

Val Lys Thr Phe Phe Gln Met Lys Asp Gln Leu Asp Asn Leu Leu Leu
        35                  40                  45

Lys Glu Ser Leu Leu Glu Asp Phe Lys Gly Tyr Leu Gly Cys Gln Ala
    50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
                85                  90                  95

Asn Leu Lys Thr Leu Arg Leu Arg Leu Arg Arg Cys His Arg Phe Leu
            100                 105                 110

Pro Cys Glu Asn Lys Ser Lys Ala Val Glu Gln Val Lys Asn Ala Phe
        115                 120                 125

Asn Lys Leu Gln Glu Lys Gly Ile Tyr Lys Ala Met Ser Glu Phe Asp
    130                 135                 140

Ile Phe Ile Asn Tyr Ile Glu Ala Tyr Met Thr Met Lys Ile Arg Asn
145                 150                 155                 160

Gly Gly Ser Gly Gly Gly Ser Gly Gly Ser Pro Gly Gln Gly Thr
                165                 170                 175

Gln Ser Glu Asn Ser Cys Thr His Phe Pro Gly Asn Leu Pro Asn Ala
            180                 185                 190

Leu Arg Asp Leu Arg Asp Ala Phe Ser Arg Val Lys Thr Phe Phe Gln
        195                 200                 205

Met Lys Asp Gln Leu Asp Asn Leu Leu Leu Lys Glu Ser Leu Leu Glu
    210                 215                 220

Asp Phe Lys Gly Tyr Leu Gly Cys Gln Ala Leu Ser Glu Met Ile Gln
225                 230                 235                 240

Phe Tyr Leu Glu Glu Val Met Pro Gln Ala Glu Asn Gln Asp Pro Asp
                245                 250                 255

Ile Lys Ala His Val Asn Ser Leu Gly Glu Asn Leu Lys Thr Leu Arg
            260                 265                 270

Leu Arg Leu Arg Arg Cys His Arg Phe Leu Pro Cys Glu Asn Lys Ser
        275                 280                 285

Lys Ala Val Glu Gln Val Lys Asn Ala Phe Asn Lys Leu Gln Glu Lys
    290                 295                 300

Gly Ile Tyr Lys Ala Met Ser Glu Phe Asp Ile Phe Ile Asn Tyr Ile
305                 310                 315                 320

Glu Ala Tyr Met Thr Met Lys Ile Arg Asn Gly Gly Gly Gly Ser Gly
                325                 330                 335

Gly Gly Gly Ser Arg Thr Val Ala Ala Pro Ser Val Phe Ile Phe Pro
            340                 345                 350

Pro Ser Asp Glu Gln Leu Lys Ser Gly Thr Ala Ser Val Val Cys Leu
```

```
            355                 360                 365
Leu Asn Asn Phe Tyr Pro Arg Glu Ala Lys Val Gln Trp Lys Val Asp
370                 375                 380
Asn Ala Leu Gln Ser Gly Asn Ser Gln Glu Ser Val Thr Glu Gln Asp
385                 390                 395                 400
Ser Lys Asp Ser Thr Tyr Ser Leu Ser Ser Thr Leu Thr Leu Ser Lys
                    405                 410                 415
Ala Asp Tyr Glu Lys His Lys Val Tyr Ala Cys Glu Val Thr His Gln
            420                 425                 430
Gly Leu Ser Ser Pro Val Thr Lys Ser Phe Asn Arg Gly Glu Cys Gly
        435                 440                 445
Gly Gly Gly Ser Gly Gly Gly Gly Ser Gly Gly Gly Gly Ser Gly Gly
    450                 455                 460
Gly Gly Ser Ala Ser Thr Lys Gly Pro Ser Val Phe Pro Leu Ala Pro
465                 470                 475                 480
Ser Ser Lys Ser Thr Ser Gly Gly Thr Ala Ala Leu Gly Cys Leu Val
                    485                 490                 495
Lys Asp Tyr Phe Pro Glu Pro Val Thr Val Ser Trp Asn Ser Gly Ala
            500                 505                 510
Leu Thr Ser Gly Val His Thr Phe Pro Ala Val Leu Gln Ser Ser Gly
        515                 520                 525
Leu Tyr Ser Leu Ser Ser Val Val Thr Val Pro Ser Ser Ser Leu Gly
    530                 535                 540
Thr Gln Thr Tyr Ile Cys Asn Val Asn His Lys Pro Ser Asn Thr Lys
545                 550                 555                 560
Val Asp Lys Arg Val Glu Pro Lys Ser Cys Asp Lys Thr His Thr Cys
                    565                 570                 575
Pro Pro Cys Pro Ala Pro Glu Leu Leu Gly Gly Pro Ser Val Phe Leu
            580                 585                 590
Phe Pro Pro Lys Pro Lys Asp Thr Leu Met Ile Ser Arg Thr Pro Glu
        595                 600                 605
Val Thr Cys Val Val Val Asp Val Ser His Glu Asp Pro Glu Val Lys
    610                 615                 620
Phe Asn Trp Tyr Val Asp Gly Val Glu Val His Asn Ala Lys Thr Lys
625                 630                 635                 640
Pro Arg Glu Glu Gln Tyr Asn Ser Thr Tyr Arg Val Val Ser Val Leu
                    645                 650                 655
Thr Val Leu His Gln Asp Trp Leu Asn Gly Lys Glu Tyr Lys Cys Lys
            660                 665                 670
Val Ser Asn Lys Ala Leu Pro Ala Pro Ile Glu Lys Thr Ile Ser Lys
        675                 680                 685
Ala Lys Gly Gln Pro Arg Glu Pro Gln Val Tyr Thr Leu Pro Pro Ser
    690                 695                 700
Arg Glu Glu Met Thr Lys Asn Gln Val Ser Leu Thr Cys Leu Val Lys
705                 710                 715                 720
Gly Phe Tyr Pro Ser Asp Ile Ala Val Glu Trp Glu Ser Asn Gly Gln
                    725                 730                 735
Pro Glu Asn Asn Tyr Lys Thr Thr Pro Pro Val Leu Asp Ser Asp Gly
            740                 745                 750
Ser Phe Phe Leu Tyr Ser Lys Leu Thr Val Asp Lys Ser Arg Trp Gln
        755                 760                 765
Gln Gly Asn Val Phe Ser Cys Ser Val Met His Glu Ala Leu His Asn
    770                 775                 780
```

His Tyr Thr Gln Lys Ser Leu Ser Leu Ser Pro Gly Lys
785                 790                 795

<210> SEQ ID NO 26
<211> LENGTH: 797
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Ser Pro Gly Gln Gly Thr Gln Ser Glu Asn Ser Cys Thr His Phe Pro
1               5                   10                  15

Gly Asn Leu Pro Asn Ala Leu Arg Asp Leu Arg Asp Ala Phe Ser Arg
            20                  25                  30

Val Lys Thr Phe Phe Gln Met Lys Phe Gln Leu Asp Asn Leu Leu Leu
        35                  40                  45

Lys Glu Ser Leu Leu Glu Asp Phe Lys Gly Tyr Leu Gly Cys Gln Ala
    50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
                85                  90                  95

Asn Leu Lys Thr Leu Arg Leu Arg Leu Arg Arg Cys His Arg Phe Leu
            100                 105                 110

Pro Cys Glu Asn Lys Ser Lys Ala Val Glu Gln Val Lys Asn Ala Phe
        115                 120                 125

Asn Lys Leu Gln Glu Lys Gly Ile Tyr Lys Ala Met Ser Glu Phe Asp
    130                 135                 140

Ile Phe Ile Asn Tyr Ile Glu Ala Tyr Met Thr Met Lys Ile Arg Asn
145                 150                 155                 160

Gly Gly Ser Gly Gly Gly Gly Ser Gly Gly Ser Pro Gly Gln Gly Thr
                165                 170                 175

Gln Ser Glu Asn Ser Cys Thr His Phe Pro Gly Asn Leu Pro Asn Met
            180                 185                 190

Leu Arg Asp Leu Arg Asp Ala Phe Ser Arg Val Lys Thr Phe Phe Gln
        195                 200                 205

Met Lys Asp Gln Leu Asp Asn Leu Leu Leu Lys Glu Ser Leu Leu Glu
    210                 215                 220

Asp Phe Lys Gly Tyr Leu Gly Cys Gln Ala Leu Ser Glu Met Ile Gln
225                 230                 235                 240

Phe Tyr Leu Glu Glu Val Met Pro Gln Ala Glu Asn Gln Asp Pro Asp
                245                 250                 255

Ile Lys Ala His Val Asn Ser Leu Gly Glu Asn Leu Lys Thr Leu Arg
            260                 265                 270

Leu Arg Leu Arg Arg Cys His Arg Phe Leu Pro Cys Glu Asn Lys Ser
        275                 280                 285

Lys Ala Val Glu Gln Val Lys Asn Ala Phe Asn Lys Leu Gln Glu Lys
    290                 295                 300

Gly Ile Tyr Lys Ala Met Ser Glu Phe Asp Ile Phe Ile Asn Tyr Ile
305                 310                 315                 320

Glu Ala Tyr Met Thr Met Lys Ile Arg Asn Gly Gly Gly Gly Ser Gly
                325                 330                 335

Gly Gly Gly Ser Arg Thr Val Ala Ala Pro Ser Val Phe Ile Phe Pro

```
                340             345             350
Pro Ser Asp Glu Gln Leu Lys Ser Gly Thr Ala Ser Val Val Cys Leu
            355             360             365

Leu Asn Asn Phe Tyr Pro Arg Glu Ala Lys Val Gln Trp Lys Val Asp
370             375             380

Asn Ala Leu Gln Ser Gly Asn Ser Gln Glu Ser Val Thr Glu Gln Asp
385             390             395             400

Ser Lys Asp Ser Thr Tyr Ser Leu Ser Ser Thr Leu Thr Leu Ser Lys
            405             410             415

Ala Asp Tyr Glu Lys His Lys Val Tyr Ala Cys Glu Val Thr His Gln
            420             425             430

Gly Leu Ser Ser Pro Val Thr Lys Ser Phe Asn Arg Gly Glu Cys Gly
            435             440             445

Gly Gly Gly Ser Gly Gly Gly Ser Gly Gly Gly Ser Gly Gly
            450             455             460

Gly Gly Ser Ala Ser Thr Lys Gly Pro Ser Val Phe Pro Leu Ala Pro
465             470             475             480

Ser Ser Lys Ser Thr Ser Gly Gly Thr Ala Ala Leu Gly Cys Leu Val
            485             490             495

Lys Asp Tyr Phe Pro Glu Pro Val Thr Val Ser Trp Asn Ser Gly Ala
            500             505             510

Leu Thr Ser Gly Val His Thr Phe Pro Ala Val Leu Gln Ser Ser Gly
            515             520             525

Leu Tyr Ser Leu Ser Ser Val Val Thr Val Pro Ser Ser Ser Leu Gly
            530             535             540

Thr Gln Thr Tyr Ile Cys Asn Val Asn His Lys Pro Ser Asn Thr Lys
545             550             555             560

Val Asp Lys Arg Val Glu Pro Lys Ser Cys Asp Lys Thr His Thr Cys
            565             570             575

Pro Pro Cys Pro Ala Pro Glu Leu Leu Gly Gly Pro Ser Val Phe Leu
            580             585             590

Phe Pro Pro Lys Pro Lys Asp Thr Leu Met Ile Ser Arg Thr Pro Glu
            595             600             605

Val Thr Cys Val Val Val Asp Val Ser His Glu Asp Pro Glu Val Lys
            610             615             620

Phe Asn Trp Tyr Val Asp Gly Val Glu Val His Asn Ala Lys Thr Lys
625             630             635             640

Pro Arg Glu Glu Gln Tyr Asn Ser Thr Tyr Arg Val Val Ser Val Leu
            645             650             655

Thr Val Leu His Gln Asp Trp Leu Asn Gly Lys Glu Tyr Lys Cys Lys
            660             665             670

Val Ser Asn Lys Ala Leu Pro Ala Pro Ile Glu Lys Thr Ile Ser Lys
            675             680             685

Ala Lys Gly Gln Pro Arg Glu Pro Gln Val Tyr Thr Leu Pro Pro Ser
            690             695             700

Arg Glu Glu Met Thr Lys Asn Gln Val Ser Leu Thr Cys Leu Val Lys
705             710             715             720

Gly Phe Tyr Pro Ser Asp Ile Ala Val Glu Trp Glu Ser Asn Gly Gln
            725             730             735

Pro Glu Asn Asn Tyr Lys Thr Thr Pro Pro Val Leu Asp Ser Asp Gly
            740             745             750

Ser Phe Phe Leu Tyr Ser Lys Leu Thr Val Asp Lys Ser Arg Trp Gln
            755             760             765
```

```
Gln Gly Asn Val Phe Ser Cys Ser Val Met His Glu Ala Leu His Asn
        770                 775                 780

His Tyr Thr Gln Lys Ser Leu Ser Leu Ser Pro Gly Lys
785                 790                 795

<210> SEQ ID NO 27
<211> LENGTH: 797
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
            20                  25                  30

Val Lys Thr Phe Phe Gln Met Lys Asp Gln Leu Asp Asn Leu Leu Leu
        35                  40                  45

Lys Glu Ser Leu Leu Glu Asp Phe Lys Gly Tyr Leu Gly Cys Gln Ala
50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
                85                  90                  95

Asn Leu Lys Thr Leu Arg Leu Arg Leu Arg Arg Cys His Arg Phe Leu
            100                 105                 110

Pro Cys Glu Asn Lys Ser Lys Ala Val Glu Gln Val Lys Asn Ala Phe
        115                 120                 125

Asn Lys Leu Gln Glu Lys Gly Ile Tyr Lys Ala Met Ser Glu Phe Asp
130                 135                 140

Ile Phe Ile Asn Tyr Ile Glu Ala Tyr Met Thr Met Lys Ile Arg Asn
145                 150                 155                 160

Gly Gly Ser Gly Gly Gly Ser Gly Gly Ser Pro Gly Gln Gly Thr
            165                 170                 175

Gln Ser Glu Asn Ser Cys Thr His Phe Pro Gly Asn Leu Pro Asn Ala
        180                 185                 190

Leu Arg Asp Leu Arg Asp Ala Phe Ser Arg Val Lys Thr Phe Phe Gln
195                 200                 205

Met Lys Phe Gln Leu Asp Asn Leu Leu Leu Lys Glu Ser Leu Leu Glu
        210                 215                 220

Asp Phe Lys Gly Tyr Leu Gly Cys Gln Ala Leu Ser Glu Met Ile Gln
225                 230                 235                 240

Phe Tyr Leu Glu Glu Val Met Pro Gln Ala Glu Asn Gln Asp Pro Asp
                245                 250                 255

Ile Lys Ala His Val Asn Ser Leu Gly Glu Asn Leu Lys Thr Leu Arg
            260                 265                 270

Leu Arg Leu Arg Arg Cys His Arg Phe Leu Pro Cys Glu Asn Lys Ser
        275                 280                 285

Lys Ala Val Glu Gln Val Lys Asn Ala Phe Asn Lys Leu Gln Glu Lys
290                 295                 300

Gly Ile Tyr Lys Ala Met Ser Glu Phe Asp Ile Phe Ile Asn Tyr Ile
305                 310                 315                 320

Glu Ala Tyr Met Thr Met Lys Ile Arg Asn Gly Gly Gly Gly Ser Gly
```

```
                        325                 330                 335
        Gly Gly Gly Ser Arg Thr Val Ala Ala Pro Ser Val Phe Ile Phe Pro
                        340                 345                 350
        Pro Ser Asp Glu Gln Leu Lys Ser Gly Thr Ala Ser Val Val Cys Leu
                        355                 360                 365
        Leu Asn Asn Phe Tyr Pro Arg Glu Ala Lys Val Gln Trp Lys Val Asp
                        370                 375                 380
        Asn Ala Leu Gln Ser Gly Asn Ser Gln Glu Ser Val Thr Glu Gln Asp
        385                 390                 395                 400
        Ser Lys Asp Ser Thr Tyr Ser Leu Ser Ser Thr Leu Thr Leu Ser Lys
                        405                 410                 415
        Ala Asp Tyr Glu Lys His Lys Val Tyr Ala Cys Glu Val Thr His Gln
                        420                 425                 430
        Gly Leu Ser Ser Pro Val Thr Lys Ser Phe Asn Arg Gly Glu Cys Gly
                        435                 440                 445
        Gly Gly Gly Ser Gly Gly Gly Gly Ser Gly Gly Gly Gly Ser Gly Gly
                        450                 455                 460
        Gly Gly Ser Ala Ser Thr Lys Gly Pro Ser Val Phe Pro Leu Ala Pro
        465                 470                 475                 480
        Ser Ser Lys Ser Thr Ser Gly Gly Thr Ala Ala Leu Gly Cys Leu Val
                        485                 490                 495
        Lys Asp Tyr Phe Pro Glu Pro Val Thr Val Ser Trp Asn Ser Gly Ala
                        500                 505                 510
        Leu Thr Ser Gly Val His Thr Phe Pro Ala Val Leu Gln Ser Ser Gly
                        515                 520                 525
        Leu Tyr Ser Leu Ser Ser Val Val Thr Val Pro Ser Ser Ser Leu Gly
                        530                 535                 540
        Thr Gln Thr Tyr Ile Cys Asn Val Asn His Lys Pro Ser Asn Thr Lys
        545                 550                 555                 560
        Val Asp Lys Arg Val Glu Pro Lys Ser Cys Asp Lys Thr His Thr Cys
                        565                 570                 575
        Pro Pro Cys Pro Ala Pro Glu Leu Leu Gly Gly Pro Ser Val Phe Leu
                        580                 585                 590
        Phe Pro Pro Lys Pro Lys Asp Thr Leu Met Ile Ser Arg Thr Pro Glu
                        595                 600                 605
        Val Thr Cys Val Val Val Asp Val Ser His Glu Asp Pro Glu Val Lys
                        610                 615                 620
        Phe Asn Trp Tyr Val Asp Gly Val Glu Val His Asn Ala Lys Thr Lys
        625                 630                 635                 640
        Pro Arg Glu Glu Gln Tyr Asn Ser Thr Tyr Arg Val Val Ser Val Leu
                        645                 650                 655
        Thr Val Leu His Gln Asp Trp Leu Asn Gly Lys Glu Tyr Lys Cys Lys
                        660                 665                 670
        Val Ser Asn Lys Ala Leu Pro Ala Pro Ile Glu Lys Thr Ile Ser Lys
                        675                 680                 685
        Ala Lys Gly Gln Pro Arg Glu Pro Gln Val Tyr Thr Leu Pro Pro Ser
                        690                 695                 700
        Arg Glu Glu Met Thr Lys Asn Gln Val Ser Leu Thr Cys Leu Val Lys
        705                 710                 715                 720
        Gly Phe Tyr Pro Ser Asp Ile Ala Val Glu Trp Glu Ser Asn Gly Gln
                        725                 730                 735
        Pro Glu Asn Asn Tyr Lys Thr Thr Pro Pro Val Leu Asp Ser Asp Gly
                        740                 745                 750
```

```
Ser Phe Phe Leu Tyr Ser Lys Leu Thr Val Asp Lys Ser Arg Trp Gln
        755                 760                 765

Gln Gly Asn Val Phe Ser Cys Ser Val Met His Glu Ala Leu His Asn
    770                 775                 780

His Tyr Thr Gln Lys Ser Leu Ser Leu Ser Pro Gly Lys
785                 790                 795

<210> SEQ ID NO 28
<211> LENGTH: 797
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
            20                  25                  30

Val Lys Thr Phe Phe Gln Met Lys Phe Gln Leu Asp Asn Leu Leu Leu
        35                  40                  45

Lys Glu Ser Leu Leu Glu Asp Phe Lys Gly Tyr Leu Gly Cys Gln Ala
    50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
                85                  90                  95

Asn Leu Lys Thr Leu Arg Leu Arg Leu Arg Arg Cys His Arg Phe Leu
            100                 105                 110

Pro Cys Glu Asn Lys Ser Lys Ala Val Glu Gln Val Lys Asn Ala Phe
        115                 120                 125

Asn Lys Leu Gln Glu Lys Gly Ile Tyr Lys Ala Met Ser Glu Phe Asp
    130                 135                 140

Ile Phe Ile Asn Tyr Ile Glu Ala Tyr Met Thr Met Lys Ile Arg Asn
145                 150                 155                 160

Gly Gly Ser Gly Gly Gly Ser Gly Gly Ser Pro Gly Gln Gly Thr
                165                 170                 175

Gln Ser Glu Asn Ser Cys Thr His Phe Pro Gly Asn Leu Pro Asn Ala
            180                 185                 190

Leu Arg Asp Leu Arg Asp Ala Phe Ser Arg Val Lys Thr Phe Phe Gln
        195                 200                 205

Met Lys Asp Gln Leu Asp Asn Leu Leu Leu Lys Glu Ser Leu Leu Glu
    210                 215                 220

Asp Phe Lys Gly Tyr Leu Gly Cys Gln Ala Leu Ser Glu Met Ile Gln
225                 230                 235                 240

Phe Tyr Leu Glu Glu Val Met Pro Gln Ala Glu Asn Gln Asp Pro Asp
                245                 250                 255

Ile Lys Ala His Val Asn Ser Leu Gly Glu Asn Leu Lys Thr Leu Arg
            260                 265                 270

Leu Arg Leu Arg Arg Cys His Arg Phe Leu Pro Cys Glu Asn Lys Ser
        275                 280                 285

Lys Ala Val Glu Gln Val Lys Asn Ala Phe Asn Lys Leu Gln Glu Lys
    290                 295                 300

Gly Ile Tyr Lys Ala Met Ser Glu Phe Asp Ile Phe Ile Asn Tyr Ile
```

```
            305                 310                 315                 320
        Glu Ala Tyr Met Thr Met Lys Ile Arg Asn Gly Gly Gly Ser Gly
                        325                 330                 335
        Gly Gly Gly Ser Arg Thr Val Ala Ala Pro Ser Val Phe Ile Phe Pro
                        340                 345                 350
        Pro Ser Asp Glu Gln Leu Lys Ser Gly Thr Ala Ser Val Val Cys Leu
                        355                 360                 365
        Leu Asn Asn Phe Tyr Pro Arg Glu Ala Lys Val Gln Trp Lys Val Asp
                370                 375                 380
        Asn Ala Leu Gln Ser Gly Asn Ser Gln Glu Ser Val Thr Glu Gln Asp
        385                 390                 395                 400
        Ser Lys Asp Ser Thr Tyr Ser Leu Ser Ser Thr Leu Thr Leu Ser Lys
                        405                 410                 415
        Ala Asp Tyr Glu Lys His Lys Val Tyr Ala Cys Glu Val Thr His Gln
                        420                 425                 430
        Gly Leu Ser Ser Pro Val Thr Lys Ser Phe Asn Arg Gly Glu Cys Gly
                        435                 440                 445
        Gly Gly Gly Ser Gly Gly Gly Ser Gly Gly Gly Ser Gly Gly
                        450                 455                 460
        Gly Gly Ser Ala Ser Thr Lys Gly Pro Ser Val Phe Pro Leu Ala Pro
        465                 470                 475                 480
        Ser Ser Lys Ser Thr Ser Gly Gly Thr Ala Ala Leu Gly Cys Leu Val
                        485                 490                 495
        Lys Asp Tyr Phe Pro Glu Pro Val Thr Val Ser Trp Asn Ser Gly Ala
                        500                 505                 510
        Leu Thr Ser Gly Val His Thr Phe Pro Ala Val Leu Gln Ser Ser Gly
                        515                 520                 525
        Leu Tyr Ser Leu Ser Ser Val Val Thr Val Pro Ser Ser Ser Leu Gly
                        530                 535                 540
        Thr Gln Thr Tyr Ile Cys Asn Val Asn His Lys Pro Ser Asn Thr Lys
        545                 550                 555                 560
        Val Asp Lys Arg Val Glu Pro Lys Ser Cys Asp Lys Thr His Thr Cys
                        565                 570                 575
        Pro Pro Cys Pro Ala Pro Glu Leu Leu Gly Gly Pro Ser Val Phe Leu
                        580                 585                 590
        Phe Pro Pro Lys Pro Lys Asp Thr Leu Met Ile Ser Arg Thr Pro Glu
                        595                 600                 605
        Val Thr Cys Val Val Val Asp Val Ser His Glu Asp Pro Glu Val Lys
                        610                 615                 620
        Phe Asn Trp Tyr Val Asp Gly Val Glu Val His Asn Ala Lys Thr Lys
        625                 630                 635                 640
        Pro Arg Glu Glu Gln Tyr Asn Ser Thr Tyr Arg Val Val Ser Val Leu
                        645                 650                 655
        Thr Val Leu His Gln Asp Trp Leu Asn Gly Lys Glu Tyr Lys Cys Lys
                        660                 665                 670
        Val Ser Asn Lys Ala Leu Pro Ala Pro Ile Glu Lys Thr Ile Ser Lys
                        675                 680                 685
        Ala Lys Gly Gln Pro Arg Glu Pro Gln Val Tyr Thr Leu Pro Pro Ser
                        690                 695                 700
        Arg Glu Glu Met Thr Lys Asn Gln Val Ser Leu Thr Cys Leu Val Lys
        705                 710                 715                 720
        Gly Phe Tyr Pro Ser Asp Ile Ala Val Glu Trp Glu Ser Asn Gly Gln
                        725                 730                 735
```

```
Pro Glu Asn Asn Tyr Lys Thr Thr Pro Val Leu Asp Ser Asp Gly
            740                 745                 750

Ser Phe Phe Leu Tyr Ser Lys Leu Thr Val Asp Lys Ser Arg Trp Gln
        755                 760                 765

Gln Gly Asn Val Phe Ser Cys Ser Val Met His Glu Ala Leu His Asn
770                 775                 780

His Tyr Thr Gln Lys Ser Leu Ser Leu Ser Pro Gly Lys
785                 790                 795

<210> SEQ ID NO 29
<211> LENGTH: 797
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Ser Pro Gly Gln Gly Thr Gln Ser Glu Asn Ser Cys Thr His Phe Pro
1               5                   10                  15

Gly Asn Leu Pro Asn Ala Leu Arg Asp Leu Arg Asp Ala Phe Ser Arg
            20                  25                  30

Val Lys Thr Phe Phe Gln Met Lys Asp Gln Leu Asp Asn Leu Leu Leu
        35                  40                  45

Lys Glu Ser Leu Leu Glu Asp Phe Lys Gly Tyr Leu Gly Cys Gln Ala
    50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
                85                  90                  95

Asn Leu Lys Thr Leu Arg Leu Arg Leu Arg Arg Cys His Arg Phe Leu
            100                 105                 110

Pro Cys Glu Asn Lys Ser Lys Ala Val Glu Gln Val Lys Asn Ala Phe
        115                 120                 125

Asn Lys Leu Gln Glu Lys Gly Ile Tyr Lys Ala Met Ser Glu Phe Asp
130                 135                 140

Ile Phe Ile Asn Tyr Ile Glu Ala Tyr Met Thr Met Lys Ile Arg Asn
145                 150                 155                 160

Gly Gly Ser Gly Gly Gly Gly Ser Gly Gly Ser Pro Gly Gln Gly Thr
                165                 170                 175

Gln Ser Glu Asn Ser Cys Thr His Phe Pro Gly Asn Leu Pro Asn Met
            180                 185                 190

Leu Arg Asp Leu Arg Asp Ala Phe Ser Arg Val Lys Thr Phe Phe Gln
        195                 200                 205

Met Lys Phe Gln Leu Asp Asn Leu Leu Leu Lys Glu Ser Leu Leu Glu
210                 215                 220

Asp Phe Lys Gly Tyr Leu Gly Cys Gln Ala Leu Ser Glu Met Ile Gln
225                 230                 235                 240

Phe Tyr Leu Glu Glu Val Met Pro Gln Ala Glu Asn Gln Asp Pro Asp
                245                 250                 255

Ile Lys Ala His Val Asn Ser Leu Gly Glu Asn Leu Lys Thr Leu Arg
            260                 265                 270

Leu Arg Leu Arg Arg Cys His Arg Phe Leu Pro Cys Glu Asn Lys Ser
        275                 280                 285

Lys Ala Val Glu Gln Val Lys Asn Ala Phe Asn Lys Leu Gln Glu Lys
```

```
            290                 295                 300
Gly Ile Tyr Lys Ala Met Ser Glu Phe Asp Ile Phe Ile Asn Tyr Ile
305                 310                 315                 320

Glu Ala Tyr Met Thr Met Lys Ile Arg Asn Gly Gly Gly Ser Gly
                    325                 330                 335

Gly Gly Gly Ser Arg Thr Val Ala Ala Pro Ser Val Phe Ile Phe Pro
                340                 345                 350

Pro Ser Asp Glu Gln Leu Lys Ser Gly Thr Ala Ser Val Val Cys Leu
            355                 360                 365

Leu Asn Asn Phe Tyr Pro Arg Glu Ala Lys Val Gln Trp Lys Val Asp
        370                 375                 380

Asn Ala Leu Gln Ser Gly Asn Ser Gln Glu Ser Val Thr Glu Gln Asp
385                 390                 395                 400

Ser Lys Asp Ser Thr Tyr Ser Leu Ser Ser Thr Leu Thr Leu Ser Lys
                405                 410                 415

Ala Asp Tyr Glu Lys His Lys Val Tyr Ala Cys Glu Val Thr His Gln
                420                 425                 430

Gly Leu Ser Ser Pro Val Thr Lys Ser Phe Asn Arg Gly Glu Cys Gly
            435                 440                 445

Gly Gly Gly Ser Gly Gly Gly Gly Ser Gly Gly Gly Gly Ser Gly Gly
            450                 455                 460

Gly Gly Ser Ala Ser Thr Lys Gly Pro Ser Val Phe Pro Leu Ala Pro
465                 470                 475                 480

Ser Ser Lys Ser Thr Ser Gly Gly Thr Ala Ala Leu Gly Cys Leu Val
                485                 490                 495

Lys Asp Tyr Phe Pro Glu Pro Val Thr Val Ser Trp Asn Ser Gly Ala
                500                 505                 510

Leu Thr Ser Gly Val His Thr Phe Pro Ala Val Leu Gln Ser Ser Gly
            515                 520                 525

Leu Tyr Ser Leu Ser Ser Val Val Thr Val Pro Ser Ser Ser Leu Gly
        530                 535                 540

Thr Gln Thr Tyr Ile Cys Asn Val Asn His Lys Pro Ser Asn Thr Lys
545                 550                 555                 560

Val Asp Lys Arg Val Glu Pro Lys Ser Cys Asp Lys Thr His Thr Cys
                565                 570                 575

Pro Pro Cys Pro Ala Pro Glu Leu Leu Gly Gly Pro Ser Val Phe Leu
            580                 585                 590

Phe Pro Pro Lys Pro Lys Asp Thr Leu Met Ile Ser Arg Thr Pro Glu
        595                 600                 605

Val Thr Cys Val Val Val Asp Val Ser His Glu Asp Pro Glu Val Lys
610                 615                 620

Phe Asn Trp Tyr Val Asp Gly Val Glu Val His Asn Ala Lys Thr Lys
625                 630                 635                 640

Pro Arg Glu Glu Gln Tyr Asn Ser Thr Tyr Arg Val Val Ser Val Leu
                645                 650                 655

Thr Val Leu His Gln Asp Trp Leu Asn Gly Lys Glu Tyr Lys Cys Lys
                660                 665                 670

Val Ser Asn Lys Ala Leu Pro Ala Pro Ile Glu Lys Thr Ile Ser Lys
            675                 680                 685

Ala Lys Gly Gln Pro Arg Glu Pro Gln Val Tyr Thr Leu Pro Pro Ser
        690                 695                 700

Arg Glu Glu Met Thr Lys Asn Gln Val Ser Leu Thr Cys Leu Val Lys
705                 710                 715                 720
```

```
Gly Phe Tyr Pro Ser Asp Ile Ala Val Glu Trp Glu Ser Asn Gly Gln
                725                 730                 735

Pro Glu Asn Asn Tyr Lys Thr Thr Pro Pro Val Leu Asp Ser Asp Gly
            740                 745                 750

Ser Phe Phe Leu Tyr Ser Lys Leu Thr Val Asp Lys Ser Arg Trp Gln
        755                 760                 765

Gln Gly Asn Val Phe Ser Cys Ser Val Met His Glu Ala Leu His Asn
770                 775                 780

His Tyr Thr Gln Lys Ser Leu Ser Leu Ser Pro Gly Lys
785                 790                 795

<210> SEQ ID NO 30
<211> LENGTH: 797
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Ser Pro Gly Gln Gly Thr Gln Ser Glu Asn Ser Cys Thr His Phe Pro
1               5                   10                  15

Gly Asn Leu Pro Asn Ala Leu Arg Asp Leu Arg Asp Ala Phe Ser Arg
            20                  25                  30

Val Lys Thr Phe Phe Gln Met Lys Phe Gln Leu Asp Asn Leu Leu Leu
        35                  40                  45

Lys Glu Ser Leu Leu Glu Asp Phe Lys Gly Tyr Leu Gly Cys Gln Ala
50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
                85                  90                  95

Asn Leu Lys Thr Leu Arg Leu Arg Leu Arg Arg Cys His Arg Phe Leu
            100                 105                 110

Pro Cys Glu Asn Lys Ser Lys Ala Val Glu Gln Val Lys Asn Ala Phe
        115                 120                 125

Asn Lys Leu Gln Glu Lys Gly Ile Tyr Lys Ala Met Ser Glu Phe Asp
130                 135                 140

Ile Phe Ile Asn Tyr Ile Glu Ala Tyr Met Thr Met Lys Ile Arg Asn
145                 150                 155                 160

Gly Gly Ser Gly Gly Gly Ser Gly Gly Ser Pro Gly Gln Gly Thr
                165                 170                 175

Gln Ser Glu Asn Ser Cys Thr His Phe Pro Gly Asn Leu Pro Asn Ala
            180                 185                 190

Leu Arg Asp Leu Arg Asp Ala Phe Ser Arg Val Lys Thr Phe Phe Gln
        195                 200                 205

Met Lys Phe Gln Leu Asp Asn Leu Leu Leu Lys Glu Ser Leu Leu Glu
210                 215                 220

Asp Phe Lys Gly Tyr Leu Gly Cys Gln Ala Leu Ser Glu Met Ile Gln
225                 230                 235                 240

Phe Tyr Leu Glu Glu Val Met Pro Gln Ala Glu Asn Gln Asp Pro Asp
                245                 250                 255

Ile Lys Ala His Val Asn Ser Leu Gly Glu Asn Leu Lys Thr Leu Arg
            260                 265                 270

Leu Arg Leu Arg Arg Cys His Arg Phe Leu Pro Cys Glu Asn Lys Ser
```

```
            275                 280                 285
Lys Ala Val Glu Gln Val Lys Asn Ala Phe Asn Lys Leu Gln Glu Lys
290                 295                 300
Gly Ile Tyr Lys Ala Met Ser Glu Phe Asp Ile Phe Ile Asn Tyr Ile
305                 310                 315                 320
Glu Ala Tyr Met Thr Met Lys Ile Arg Asn Gly Gly Gly Ser Gly
                    325                 330                 335
Gly Gly Gly Ser Arg Thr Val Ala Ala Pro Ser Val Phe Ile Phe Pro
                340                 345                 350
Pro Ser Asp Glu Gln Leu Lys Ser Gly Thr Ala Ser Val Val Cys Leu
            355                 360                 365
Leu Asn Asn Phe Tyr Pro Arg Glu Ala Lys Val Gln Trp Lys Val Asp
370                 375                 380
Asn Ala Leu Gln Ser Gly Asn Ser Gln Glu Ser Val Thr Glu Gln Asp
385                 390                 395                 400
Ser Lys Asp Ser Thr Tyr Ser Leu Ser Ser Thr Leu Thr Leu Ser Lys
                    405                 410                 415
Ala Asp Tyr Glu Lys His Lys Val Tyr Ala Cys Glu Val Thr His Gln
                420                 425                 430
Gly Leu Ser Ser Pro Val Thr Lys Ser Phe Asn Arg Gly Glu Cys Gly
            435                 440                 445
Gly Gly Gly Ser Gly Gly Gly Ser Gly Gly Gly Gly Ser Gly Gly
450                 455                 460
Gly Gly Ser Ala Ser Thr Lys Gly Pro Ser Val Phe Pro Leu Ala Pro
465                 470                 475                 480
Ser Ser Lys Ser Thr Ser Gly Gly Thr Ala Ala Leu Gly Cys Leu Val
                    485                 490                 495
Lys Asp Tyr Phe Pro Glu Pro Val Thr Val Ser Trp Asn Ser Gly Ala
                500                 505                 510
Leu Thr Ser Gly Val His Thr Phe Pro Ala Val Leu Gln Ser Ser Gly
            515                 520                 525
Leu Tyr Ser Leu Ser Ser Val Val Thr Val Pro Ser Ser Ser Leu Gly
530                 535                 540
Thr Gln Thr Tyr Ile Cys Asn Val Asn His Lys Pro Ser Asn Thr Lys
545                 550                 555                 560
Val Asp Lys Arg Val Glu Pro Lys Ser Cys Asp Lys Thr His Thr Cys
                    565                 570                 575
Pro Pro Cys Pro Ala Pro Glu Leu Leu Gly Gly Pro Ser Val Phe Leu
                580                 585                 590
Phe Pro Pro Lys Pro Lys Asp Thr Leu Met Ile Ser Arg Thr Pro Glu
            595                 600                 605
Val Thr Cys Val Val Val Asp Val Ser His Glu Asp Pro Glu Val Lys
            610                 615                 620
Phe Asn Trp Tyr Val Asp Gly Val Glu Val His Asn Ala Lys Thr Lys
625                 630                 635                 640
Pro Arg Glu Glu Gln Tyr Asn Ser Thr Tyr Arg Val Val Ser Val Leu
                    645                 650                 655
Thr Val Leu His Gln Asp Trp Leu Asn Gly Lys Glu Tyr Lys Cys Lys
                660                 665                 670
Val Ser Asn Lys Ala Leu Pro Ala Pro Ile Glu Lys Thr Ile Ser Lys
            675                 680                 685
Ala Lys Gly Gln Pro Arg Glu Pro Gln Val Tyr Thr Leu Pro Pro Ser
690                 695                 700
```

```
Arg Glu Glu Met Thr Lys Asn Gln Val Ser Leu Thr Cys Leu Val Lys
705                 710                 715                 720

Gly Phe Tyr Pro Ser Asp Ile Ala Val Glu Trp Glu Ser Asn Gly Gln
                725                 730                 735

Pro Glu Asn Asn Tyr Lys Thr Thr Pro Pro Val Leu Asp Ser Asp Gly
            740                 745                 750

Ser Phe Phe Leu Tyr Ser Lys Leu Thr Val Asp Lys Ser Arg Trp Gln
        755                 760                 765

Gln Gly Asn Val Phe Ser Cys Ser Val Met His Glu Ala Leu His Asn
    770                 775                 780

His Tyr Thr Gln Lys Ser Leu Ser Leu Ser Pro Gly Lys
785                 790                 795

<210> SEQ ID NO 31
<211> LENGTH: 797
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Ser Pro Gly Gln Gly Thr Gln Ser Glu Asn Ser Cys Thr His Phe Pro
1               5                   10                  15

Gly Asn Leu Pro Asn Ala Leu Arg Asp Leu Arg Asp Ala Phe Ser Arg
            20                  25                  30

Val Lys Thr Phe Phe Gln Met Lys Phe Gln Leu Asp Asn Leu Leu Leu
        35                  40                  45

Lys Glu Ser Leu Leu Glu Asp Phe Lys Gly Tyr Leu Gly Cys Gln Ala
    50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
                85                  90                  95

Asn Leu Lys Thr Leu Arg Leu Arg Leu Arg Arg Cys His Arg Phe Leu
            100                 105                 110

Pro Cys Glu Asn Lys Ser Lys Ala Val Glu Gln Val Lys Asn Ala Phe
        115                 120                 125

Asn Lys Leu Gln Glu Lys Gly Ile Tyr Lys Ala Met Ser Glu Phe Asp
    130                 135                 140

Ile Phe Ile Asn Tyr Ile Glu Ala Tyr Met Thr Met Lys Ile Arg Asn
145                 150                 155                 160

Gly Gly Ser Gly Gly Gly Ser Gly Gly Ser Pro Gly Gln Gly Thr
                165                 170                 175

Gln Ser Glu Asn Ser Cys Thr His Phe Pro Gly Asn Leu Pro Asn Ala
                180                 185                 190

Leu Arg Asp Leu Arg Asp Ala Phe Ser Arg Val Lys Thr Phe Phe Gln
            195                 200                 205

Met Lys Asp Gln Leu Asp Asn Leu Leu Leu Lys Glu Ser Leu Leu Glu
        210                 215                 220

Asp Phe Lys Gly Tyr Leu Gly Cys Gln Ala Leu Ser Glu Met Ile Gln
225                 230                 235                 240

Phe Tyr Leu Glu Glu Val Met Pro Gln Ala Glu Asn Gln Asp Pro Asp
                245                 250                 255

Ile Lys Ala His Val Asn Ser Leu Gly Glu Asn Leu Lys Thr Leu Arg
```

```
                    260                 265                 270
Leu Arg Leu Arg Arg Cys His Arg Phe Leu Pro Cys Glu Asn Lys Ser
                275                 280                 285
Lys Ala Val Glu Gln Val Lys Asn Ala Phe Asn Lys Leu Gln Glu Lys
            290                 295                 300
Gly Ile Tyr Lys Ala Met Ser Glu Phe Asp Ile Phe Ile Asn Tyr Ile
305                 310                 315                 320
Glu Ala Tyr Met Thr Met Lys Ile Arg Asn Gly Gly Gly Ser Gly
                325                 330                 335
Gly Gly Gly Ser Arg Thr Val Ala Ala Pro Ser Val Phe Ile Phe Pro
            340                 345                 350
Pro Ser Asp Glu Gln Leu Lys Ser Gly Thr Ala Ser Val Val Cys Leu
            355                 360                 365
Leu Asn Asn Phe Tyr Pro Arg Glu Ala Lys Val Gln Trp Lys Val Asp
            370                 375                 380
Asn Ala Leu Gln Ser Gly Asn Ser Gln Glu Ser Val Thr Glu Gln Asp
385                 390                 395                 400
Ser Lys Asp Ser Thr Tyr Ser Leu Ser Ser Thr Leu Thr Leu Ser Lys
                405                 410                 415
Ala Asp Tyr Glu Lys His Lys Val Tyr Ala Cys Glu Val Thr His Gln
                420                 425                 430
Gly Leu Ser Ser Pro Val Thr Lys Ser Phe Asn Arg Gly Glu Cys Gly
            435                 440                 445
Gly Gly Gly Ser Gly Gly Gly Gly Ser Gly Gly Gly Gly Ser Gly Gly
            450                 455                 460
Gly Gly Ser Ala Ser Thr Lys Gly Pro Ser Val Phe Pro Leu Ala Pro
465                 470                 475                 480
Ser Ser Lys Ser Thr Ser Gly Gly Thr Ala Ala Leu Gly Cys Leu Val
                485                 490                 495
Lys Asp Tyr Phe Pro Glu Pro Val Thr Val Ser Trp Asn Ser Gly Ala
                500                 505                 510
Leu Thr Ser Gly Val His Thr Phe Pro Ala Val Leu Gln Ser Ser Gly
            515                 520                 525
Leu Tyr Ser Leu Ser Ser Val Val Thr Val Pro Ser Ser Ser Leu Gly
            530                 535                 540
Thr Gln Thr Tyr Ile Cys Asn Val Asn His Lys Pro Ser Asn Thr Lys
545                 550                 555                 560
Val Asp Lys Arg Val Glu Pro Lys Ser Cys Asp Lys Thr His Thr Cys
                565                 570                 575
Pro Pro Cys Pro Ala Pro Glu Leu Leu Gly Gly Pro Ser Val Phe Leu
            580                 585                 590
Phe Pro Pro Lys Pro Lys Asp Thr Leu Met Ile Ser Arg Thr Pro Glu
            595                 600                 605
Val Thr Cys Val Val Val Asp Val Ser His Glu Asp Pro Glu Val Lys
            610                 615                 620
Phe Asn Trp Tyr Val Asp Gly Val Glu Val His Asn Ala Lys Thr Lys
625                 630                 635                 640
Pro Arg Glu Glu Gln Tyr Asn Ser Thr Tyr Arg Val Val Ser Val Leu
                645                 650                 655
Thr Val Leu His Gln Asp Trp Leu Asn Gly Lys Glu Tyr Lys Cys Lys
                660                 665                 670
Val Ser Asn Lys Ala Leu Pro Ala Pro Ile Glu Lys Thr Ile Ser Lys
            675                 680                 685
```

```
Ala Lys Gly Gln Pro Arg Glu Pro Gln Val Tyr Thr Leu Pro Pro Ser
    690                 695                 700

Arg Glu Glu Met Thr Lys Asn Gln Val Ser Leu Thr Cys Leu Val Lys
705                 710                 715                 720

Gly Phe Tyr Pro Ser Asp Ile Ala Val Glu Trp Glu Ser Asn Gly Gln
                725                 730                 735

Pro Glu Asn Asn Tyr Lys Thr Thr Pro Pro Val Leu Asp Ser Asp Gly
            740                 745                 750

Ser Phe Phe Leu Tyr Ser Lys Leu Thr Val Asp Lys Ser Arg Trp Gln
        755                 760                 765

Gln Gly Asn Val Phe Ser Cys Ser Val Met His Glu Ala Leu His Asn
    770                 775                 780

His Tyr Thr Gln Lys Ser Leu Ser Leu Ser Pro Gly Lys
785                 790                 795
```

<210> SEQ ID NO 32
<211> LENGTH: 797
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 32

```
Ser Pro Gly Gln Gly Thr Gln Ser Glu Asn Ser Cys Thr His Phe Pro
1               5                   10                  15

Gly Asn Leu Pro Asn Ala Leu Arg Asp Leu Arg Asp Ala Phe Ser Arg
            20                  25                  30

Val Lys Thr Phe Phe Gln Met Lys Phe Gln Leu Asp Asn Leu Leu Leu
        35                  40                  45

Lys Glu Ser Leu Leu Glu Asp Phe Lys Gly Tyr Leu Gly Cys Gln Ala
50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
                85                  90                  95

Asn Leu Lys Thr Leu Arg Leu Arg Leu Arg Arg Cys His Arg Phe Leu
            100                 105                 110

Pro Cys Glu Asn Lys Ser Lys Ala Val Glu Gln Val Lys Asn Ala Phe
        115                 120                 125

Asn Lys Leu Gln Glu Lys Gly Ile Tyr Lys Ala Met Ser Glu Phe Asp
    130                 135                 140

Ile Phe Ile Asn Tyr Ile Glu Ala Tyr Met Thr Met Lys Ile Arg Asn
145                 150                 155                 160

Gly Gly Ser Gly Gly Gly Ser Gly Gly Ser Pro Gly Gln Gly Thr
                165                 170                 175

Gln Ser Glu Asn Ser Cys Thr His Phe Pro Gly Asn Leu Pro Asn Met
            180                 185                 190

Leu Arg Asp Leu Arg Asp Ala Phe Ser Arg Val Lys Thr Phe Phe Gln
        195                 200                 205

Met Lys Phe Gln Leu Asp Asn Leu Leu Leu Lys Glu Ser Leu Leu Glu
    210                 215                 220

Asp Phe Lys Gly Tyr Leu Gly Cys Gln Ala Leu Ser Glu Met Ile Gln
225                 230                 235                 240

Phe Tyr Leu Glu Glu Val Met Pro Gln Ala Glu Asn Gln Asp Pro Asp
```

-continued

```
                245                 250                 255
Ile Lys Ala His Val Asn Ser Leu Gly Glu Asn Leu Lys Thr Leu Arg
            260                 265                 270

Leu Arg Leu Arg Arg Cys His Arg Phe Leu Pro Cys Glu Asn Lys Ser
        275                 280                 285

Lys Ala Val Glu Gln Val Lys Asn Ala Phe Asn Lys Leu Gln Glu Lys
    290                 295                 300

Gly Ile Tyr Lys Ala Met Ser Glu Phe Asp Ile Phe Ile Asn Tyr Ile
305                 310                 315                 320

Glu Ala Tyr Met Thr Met Lys Ile Arg Asn Gly Gly Gly Ser Gly
                325                 330                 335

Gly Gly Gly Ser Arg Thr Val Ala Ala Pro Ser Val Phe Ile Phe Pro
            340                 345                 350

Pro Ser Asp Glu Gln Leu Lys Ser Gly Thr Ala Ser Val Val Cys Leu
        355                 360                 365

Leu Asn Asn Phe Tyr Pro Arg Glu Ala Lys Val Gln Trp Lys Val Asp
    370                 375                 380

Asn Ala Leu Gln Ser Gly Asn Ser Gln Glu Ser Val Thr Glu Gln Asp
385                 390                 395                 400

Ser Lys Asp Ser Thr Tyr Ser Leu Ser Ser Thr Leu Thr Leu Ser Lys
                405                 410                 415

Ala Asp Tyr Glu Lys His Lys Val Tyr Ala Cys Glu Val Thr His Gln
            420                 425                 430

Gly Leu Ser Ser Pro Val Thr Lys Ser Phe Asn Arg Gly Glu Cys Gly
        435                 440                 445

Gly Gly Gly Ser Gly Gly Gly Gly Ser Gly Gly Gly Gly Ser Gly Gly
    450                 455                 460

Gly Gly Ser Ala Ser Thr Lys Gly Pro Ser Val Phe Pro Leu Ala Pro
465                 470                 475                 480

Ser Ser Lys Ser Thr Ser Gly Gly Thr Ala Ala Leu Gly Cys Leu Val
                485                 490                 495

Lys Asp Tyr Phe Pro Glu Pro Val Thr Val Ser Trp Asn Ser Gly Ala
            500                 505                 510

Leu Thr Ser Gly Val His Thr Phe Pro Ala Val Leu Gln Ser Ser Gly
        515                 520                 525

Leu Tyr Ser Leu Ser Ser Val Val Thr Val Pro Ser Ser Ser Leu Gly
    530                 535                 540

Thr Gln Thr Tyr Ile Cys Asn Val Asn His Lys Pro Ser Asn Thr Lys
545                 550                 555                 560

Val Asp Lys Arg Val Glu Pro Lys Ser Cys Asp Lys Thr His Thr Cys
                565                 570                 575

Pro Pro Cys Pro Ala Pro Glu Leu Leu Gly Gly Pro Ser Val Phe Leu
            580                 585                 590

Phe Pro Pro Lys Pro Lys Asp Thr Leu Met Ile Ser Arg Thr Pro Glu
        595                 600                 605

Val Thr Cys Val Val Val Asp Val Ser His Glu Asp Pro Glu Val Lys
    610                 615                 620

Phe Asn Trp Tyr Val Asp Gly Val Glu Val His Asn Ala Lys Thr Lys
625                 630                 635                 640

Pro Arg Glu Glu Gln Tyr Asn Ser Thr Tyr Arg Val Val Ser Val Leu
                645                 650                 655

Thr Val Leu His Gln Asp Trp Leu Asn Gly Lys Glu Tyr Lys Cys Lys
            660                 665                 670
```

```
Val Ser Asn Lys Ala Leu Pro Ala Pro Ile Glu Lys Thr Ile Ser Lys
        675                 680                 685

Ala Lys Gly Gln Pro Arg Glu Pro Gln Val Tyr Thr Leu Pro Pro Ser
    690                 695                 700

Arg Glu Glu Met Thr Lys Asn Gln Val Ser Leu Thr Cys Leu Val Lys
705                 710                 715                 720

Gly Phe Tyr Pro Ser Asp Ile Ala Val Glu Trp Glu Ser Asn Gly Gln
                725                 730                 735

Pro Glu Asn Asn Tyr Lys Thr Thr Pro Pro Val Leu Asp Ser Asp Gly
            740                 745                 750

Ser Phe Phe Leu Tyr Ser Lys Leu Thr Val Asp Lys Ser Arg Trp Gln
        755                 760                 765

Gln Gly Asn Val Phe Ser Cys Ser Val Met His Glu Ala Leu His Asn
    770                 775                 780

His Tyr Thr Gln Lys Ser Leu Ser Leu Ser Pro Gly Lys
785                 790                 795

<210> SEQ ID NO 33
<211> LENGTH: 797
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Ser Pro Gly Gln Gly Thr Gln Ser Glu Asn Ser Cys Thr His Phe Pro
1               5                   10                  15

Gly Asn Leu Pro Asn Ala Leu Arg Asp Leu Arg Asp Ala Phe Ser Arg
            20                  25                  30

Val Lys Thr Phe Phe Gln Met Lys Asp Gln Leu Asp Asn Leu Leu Leu
        35                  40                  45

Lys Glu Ser Leu Leu Glu Asp Phe Lys Gly Tyr Leu Gly Cys Gln Ala
    50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
                85                  90                  95

Asn Leu Lys Thr Leu Arg Leu Arg Leu Arg Arg Cys His Arg Phe Leu
            100                 105                 110

Pro Cys Glu Asn Lys Ser Lys Ala Val Glu Gln Val Lys Asn Ala Phe
        115                 120                 125

Asn Lys Leu Gln Glu Lys Gly Ile Tyr Lys Ala Met Ser Glu Phe Asp
    130                 135                 140

Ile Phe Ile Asn Tyr Ile Glu Ala Tyr Met Thr Met Lys Ile Arg Asn
145                 150                 155                 160

Gly Gly Ser Gly Gly Gly Ser Gly Gly Ser Pro Gly Gln Gly Thr
                165                 170                 175

Gln Ser Glu Asn Ser Cys Thr His Phe Pro Gly Asn Leu Pro Asn Ala
            180                 185                 190

Leu Arg Asp Leu Arg Asp Ala Phe Ser Arg Val Lys Thr Phe Phe Gln
        195                 200                 205

Met Lys Phe Gln Leu Asp Asn Leu Leu Leu Lys Glu Ser Leu Leu Glu
    210                 215                 220

Asp Phe Lys Gly Tyr Leu Gly Cys Gln Ala Leu Ser Glu Met Ile Gln
```

-continued

```
              225                 230                 235                 240
        Phe Tyr Leu Glu Glu Val Met Pro Gln Ala Glu Asn Gln Asp Pro Asp
                        245                 250                 255

Ile Lys Ala His Val Asn Ser Leu Gly Glu Asn Leu Lys Thr Leu Arg
                        260                 265                 270

Leu Arg Leu Arg Arg Cys His Arg Phe Leu Pro Cys Glu Asn Lys Ser
                        275                 280                 285

Lys Ala Val Glu Gln Val Lys Asn Ala Phe Asn Lys Leu Gln Glu Lys
                        290                 295                 300

Gly Ile Tyr Lys Ala Met Ser Glu Phe Asp Ile Phe Ile Asn Tyr Ile
        305                 310                 315                 320

Glu Ala Tyr Met Thr Met Lys Ile Arg Asn Gly Gly Gly Ser Gly
                            325                 330                 335

Gly Gly Gly Ser Arg Thr Val Ala Ala Pro Ser Val Phe Ile Phe Pro
                        340                 345                 350

Pro Ser Asp Glu Gln Leu Lys Ser Gly Thr Ala Ser Val Val Cys Leu
                        355                 360                 365

Leu Asn Asn Phe Tyr Pro Arg Glu Ala Lys Val Gln Trp Lys Val Asp
                        370                 375                 380

Asn Ala Leu Gln Ser Gly Asn Ser Gln Glu Ser Val Thr Glu Gln Asp
        385                 390                 395                 400

Ser Lys Asp Ser Thr Tyr Ser Leu Ser Ser Thr Leu Thr Leu Ser Lys
                        405                 410                 415

Ala Asp Tyr Glu Lys His Lys Val Tyr Ala Cys Glu Val Thr His Gln
                        420                 425                 430

Gly Leu Ser Ser Pro Val Thr Lys Ser Phe Asn Arg Gly Glu Cys Gly
                        435                 440                 445

Gly Gly Gly Ser Gly Gly Gly Ser Gly Gly Gly Ser Gly
                        450                 455                 460

Gly Gly Ser Ala Ser Thr Lys Gly Pro Ser Val Phe Pro Leu Ala Pro
        465                 470                 475                 480

Ser Ser Lys Ser Thr Ser Gly Gly Thr Ala Ala Leu Gly Cys Leu Val
                        485                 490                 495

Lys Asp Tyr Phe Pro Glu Pro Val Thr Val Ser Trp Asn Ser Gly Ala
                        500                 505                 510

Leu Thr Ser Gly Val His Thr Phe Pro Ala Val Leu Gln Ser Ser Gly
                        515                 520                 525

Leu Tyr Ser Leu Ser Ser Val Val Thr Val Pro Ser Ser Ser Leu Gly
                        530                 535                 540

Thr Gln Thr Tyr Ile Cys Asn Val Asn His Lys Pro Ser Asn Thr Lys
        545                 550                 555                 560

Val Asp Lys Arg Val Glu Pro Lys Ser Cys Asp Lys Thr His Thr Cys
                        565                 570                 575

Pro Pro Cys Pro Ala Pro Glu Leu Leu Gly Gly Pro Ser Val Phe Leu
                        580                 585                 590

Phe Pro Pro Lys Pro Lys Asp Thr Leu Met Ile Ser Arg Thr Pro Glu
                        595                 600                 605

Val Thr Cys Val Val Val Asp Val Ser His Glu Asp Pro Glu Val Lys
                        610                 615                 620

Phe Asn Trp Tyr Val Asp Gly Val Glu Val His Asn Ala Lys Thr Lys
        625                 630                 635                 640

Pro Arg Glu Glu Gln Tyr Asn Ser Thr Tyr Arg Val Val Ser Val Leu
                        645                 650                 655
```

```
Thr Val Leu His Gln Asp Trp Leu Asn Gly Lys Glu Tyr Lys Cys Lys
            660                 665                 670

Val Ser Asn Lys Ala Leu Pro Ala Pro Ile Glu Lys Thr Ile Ser Lys
            675                 680                 685

Ala Lys Gly Gln Pro Arg Glu Pro Gln Val Tyr Thr Leu Pro Pro Ser
            690                 695                 700

Arg Glu Glu Met Thr Lys Asn Gln Val Ser Leu Thr Cys Leu Val Lys
705                 710                 715                 720

Gly Phe Tyr Pro Ser Asp Ile Ala Val Glu Trp Glu Ser Asn Gly Gln
                725                 730                 735

Pro Glu Asn Asn Tyr Lys Thr Thr Pro Pro Val Leu Asp Ser Asp Gly
            740                 745                 750

Ser Phe Phe Leu Tyr Ser Lys Leu Thr Val Asp Lys Ser Arg Trp Gln
            755                 760                 765

Gln Gly Asn Val Phe Ser Cys Ser Val Met His Glu Ala Leu His Asn
            770                 775                 780

His Tyr Thr Gln Lys Ser Leu Ser Leu Ser Pro Gly Lys
785                 790                 795

<210> SEQ ID NO 34
<211> LENGTH: 797
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
            20                  25                  30

Val Lys Thr Phe Phe Gln Met Lys Phe Gln Leu Asp Asn Leu Leu Leu
            35                  40                  45

Lys Glu Ser Leu Leu Glu Asp Phe Lys Gly Tyr Leu Gly Cys Gln Ala
        50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
                85                  90                  95

Asn Leu Lys Thr Leu Arg Leu Arg Leu Arg Arg Cys His Arg Phe Leu
            100                 105                 110

Pro Cys Glu Asn Lys Ser Lys Ala Val Glu Gln Val Lys Asn Ala Phe
            115                 120                 125

Asn Lys Leu Gln Glu Lys Gly Ile Tyr Lys Ala Met Ser Glu Phe Asp
        130                 135                 140

Ile Phe Ile Asn Tyr Ile Glu Ala Tyr Met Thr Met Lys Ile Arg Asn
145                 150                 155                 160

Gly Gly Ser Gly Gly Gly Gly Ser Gly Gly Ser Pro Gly Gln Gly Thr
                165                 170                 175

Gln Ser Glu Asn Ser Cys Thr His Phe Pro Gly Asn Leu Pro Asn Ala
            180                 185                 190

Leu Arg Asp Leu Arg Asp Ala Phe Ser Arg Val Lys Thr Phe Phe Gln
            195                 200                 205

Met Lys Phe Gln Leu Asp Asn Leu Leu Leu Lys Glu Ser Leu Leu Glu
```

-continued

```
                210                 215                 220
Asp Phe Lys Gly Tyr Leu Gly Cys Gln Ala Leu Ser Glu Met Ile Gln
225                 230                 235                 240

Phe Tyr Leu Glu Glu Val Met Pro Gln Ala Glu Asn Gln Asp Pro Asp
                245                 250                 255

Ile Lys Ala His Val Asn Ser Leu Gly Glu Asn Leu Lys Thr Leu Arg
                260                 265                 270

Leu Arg Leu Arg Arg Cys His Arg Phe Leu Pro Cys Glu Asn Lys Ser
                275                 280                 285

Lys Ala Val Glu Gln Val Lys Asn Ala Phe Asn Lys Leu Gln Glu Lys
                290                 295                 300

Gly Ile Tyr Lys Ala Met Ser Glu Phe Asp Ile Phe Ile Asn Tyr Ile
305                 310                 315                 320

Glu Ala Tyr Met Thr Met Lys Ile Arg Asn Gly Gly Gly Ser Gly
                325                 330                 335

Gly Gly Gly Ser Arg Thr Val Ala Ala Pro Ser Val Phe Ile Phe Pro
                340                 345                 350

Pro Ser Asp Glu Gln Leu Lys Ser Gly Thr Ala Ser Val Val Cys Leu
                355                 360                 365

Leu Asn Asn Phe Tyr Pro Arg Glu Ala Lys Val Gln Trp Lys Val Asp
                370                 375                 380

Asn Ala Leu Gln Ser Gly Asn Ser Gln Glu Ser Val Thr Glu Gln Asp
385                 390                 395                 400

Ser Lys Asp Ser Thr Tyr Ser Leu Ser Ser Thr Leu Thr Leu Ser Lys
                405                 410                 415

Ala Asp Tyr Glu Lys His Lys Val Tyr Ala Cys Glu Val Thr His Gln
                420                 425                 430

Gly Leu Ser Ser Pro Val Thr Lys Ser Phe Asn Arg Gly Glu Cys Gly
                435                 440                 445

Gly Gly Gly Ser Gly Gly Gly Gly Ser Gly Gly Gly Gly Ser Gly Gly
                450                 455                 460

Gly Gly Ser Ala Ser Thr Lys Gly Pro Ser Val Phe Pro Leu Ala Pro
465                 470                 475                 480

Ser Ser Lys Ser Thr Ser Gly Gly Thr Ala Ala Leu Gly Cys Leu Val
                485                 490                 495

Lys Asp Tyr Phe Pro Glu Pro Val Thr Val Ser Trp Asn Ser Gly Ala
                500                 505                 510

Leu Thr Ser Gly Val His Thr Phe Pro Ala Val Leu Gln Ser Ser Gly
                515                 520                 525

Leu Tyr Ser Leu Ser Ser Val Val Thr Val Pro Ser Ser Ser Leu Gly
                530                 535                 540

Thr Gln Thr Tyr Ile Cys Asn Val Asn His Lys Pro Ser Asn Thr Lys
545                 550                 555                 560

Val Asp Lys Arg Val Glu Pro Lys Ser Cys Asp Lys Thr His Thr Cys
                565                 570                 575

Pro Pro Cys Pro Ala Pro Glu Leu Leu Gly Gly Pro Ser Val Phe Leu
                580                 585                 590

Phe Pro Pro Lys Pro Lys Asp Thr Leu Met Ile Ser Arg Thr Pro Glu
                595                 600                 605

Val Thr Cys Val Val Val Asp Val Ser His Glu Asp Pro Glu Val Lys
                610                 615                 620

Phe Asn Trp Tyr Val Asp Gly Val Glu Val His Asn Ala Lys Thr Lys
625                 630                 635                 640
```

-continued

Pro Arg Glu Glu Gln Tyr Asn Ser Thr Tyr Arg Val Ser Val Leu
                645                 650                 655

Thr Val Leu His Gln Asp Trp Leu Asn Gly Lys Glu Tyr Lys Cys Lys
            660                 665                 670

Val Ser Asn Lys Ala Leu Pro Ala Pro Ile Glu Lys Thr Ile Ser Lys
        675                 680                 685

Ala Lys Gly Gln Pro Arg Glu Pro Gln Val Tyr Thr Leu Pro Pro Ser
690                 695                 700

Arg Glu Glu Met Thr Lys Asn Gln Val Ser Leu Thr Cys Leu Val Lys
705                 710                 715                 720

Gly Phe Tyr Pro Ser Asp Ile Ala Val Glu Trp Glu Ser Asn Gly Gln
                725                 730                 735

Pro Glu Asn Asn Tyr Lys Thr Thr Pro Pro Val Leu Asp Ser Asp Gly
            740                 745                 750

Ser Phe Phe Leu Tyr Ser Lys Leu Thr Val Asp Lys Ser Arg Trp Gln
        755                 760                 765

Gln Gly Asn Val Phe Ser Cys Ser Val Met His Glu Ala Leu His Asn
770                 775                 780

His Tyr Thr Gln Lys Ser Leu Ser Leu Ser Pro Gly Lys
785                 790                 795

<210> SEQ ID NO 35
<211> LENGTH: 792
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
                20                  25                  30

Val Lys Thr Phe Phe Gln Met Lys Asp Gln Leu Asp Asn Leu Leu Leu
            35                  40                  45

Lys Glu Ser Leu Leu Glu Asp Phe Lys Gly Tyr Leu Gly Cys Gln Ala
        50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
                85                  90                  95

Asn Leu Lys Thr Leu Arg Leu Arg Leu Arg Arg Cys His Arg Phe Leu
            100                 105                 110

Pro Cys Glu Asn Lys Ser Lys Ala Val Glu Gln Val Lys Asn Ala Phe
        115                 120                 125

Asn Lys Leu Gln Glu Lys Gly Ile Tyr Lys Ala Met Ser Glu Phe Asp
    130                 135                 140

Ile Phe Ile Asn Tyr Ile Glu Ala Tyr Met Thr Met Lys Ile Arg Asn
145                 150                 155                 160

Gly Gly Ser Gly Gly Ser Pro Gly Gln Gly Thr Gln Ser Glu Asn Ser
                165                 170                 175

Cys Thr His Phe Pro Gly Asn Leu Pro Asn Met Leu Arg Asp Leu Arg
            180                 185                 190

Asp Ala Phe Ser Arg Val Lys Thr Phe Phe Gln Met Lys Asp Gln Leu

```
            195                 200                 205
Asp Asn Leu Leu Leu Lys Glu Ser Leu Leu Glu Asp Phe Lys Gly Tyr
    210                 215                 220

Leu Gly Cys Gln Ala Leu Ser Glu Met Ile Gln Phe Tyr Leu Glu Glu
225                 230                 235                 240

Val Met Pro Gln Ala Glu Asn Gln Asp Pro Asp Ile Lys Ala His Val
                245                 250                 255

Asn Ser Leu Gly Glu Asn Leu Lys Thr Leu Arg Leu Arg Leu Arg Arg
            260                 265                 270

Cys His Arg Phe Leu Pro Cys Glu Asn Lys Ser Lys Ala Val Glu Gln
                275                 280                 285

Val Lys Asn Ala Phe Asn Lys Leu Gln Glu Lys Gly Ile Tyr Lys Ala
    290                 295                 300

Met Ser Glu Phe Asp Ile Phe Ile Asn Tyr Ile Glu Ala Tyr Met Thr
305                 310                 315                 320

Met Lys Ile Arg Asn Gly Gly Gly Ser Gly Gly Gly Ser Arg
                325                 330                 335

Thr Val Ala Ala Pro Ser Val Phe Ile Phe Pro Pro Ser Asp Glu Gln
                340                 345                 350

Leu Lys Ser Gly Thr Ala Ser Val Val Cys Leu Leu Asn Asn Phe Tyr
            355                 360                 365

Pro Arg Glu Ala Lys Val Gln Trp Lys Val Asp Asn Ala Leu Gln Ser
    370                 375                 380

Gly Asn Ser Gln Glu Ser Val Thr Glu Gln Asp Ser Lys Asp Ser Thr
385                 390                 395                 400

Tyr Ser Leu Ser Ser Thr Leu Thr Leu Ser Lys Ala Asp Tyr Glu Lys
                405                 410                 415

His Lys Val Tyr Ala Cys Glu Val Thr His Gln Gly Leu Ser Ser Pro
            420                 425                 430

Val Thr Lys Ser Phe Asn Arg Gly Glu Cys Gly Gly Gly Gly Ser Gly
    435                 440                 445

Gly Gly Ser Gly Gly Gly Gly Ser Gly Gly Gly Gly Ser Ala Ser
    450                 455                 460

Thr Lys Gly Pro Ser Val Phe Pro Leu Ala Pro Ser Ser Lys Ser Thr
465                 470                 475                 480

Ser Gly Gly Thr Ala Ala Leu Gly Cys Leu Val Lys Asp Tyr Phe Pro
                485                 490                 495

Glu Pro Val Thr Val Ser Trp Asn Ser Gly Ala Leu Thr Ser Gly Val
                500                 505                 510

His Thr Phe Pro Ala Val Leu Gln Ser Ser Gly Leu Tyr Ser Leu Ser
            515                 520                 525

Ser Val Val Thr Val Pro Ser Ser Leu Gly Thr Gln Thr Tyr Ile
    530                 535                 540

Cys Asn Val Asn His Lys Pro Ser Asn Thr Lys Val Asp Lys Arg Val
545                 550                 555                 560

Glu Pro Lys Ser Cys Asp Lys Thr His Thr Cys Pro Pro Cys Pro Ala
                565                 570                 575

Pro Glu Leu Leu Gly Gly Pro Ser Val Phe Leu Phe Pro Pro Lys Pro
            580                 585                 590

Lys Asp Thr Leu Met Ile Ser Arg Thr Pro Glu Val Thr Cys Val Val
    595                 600                 605

Val Asp Val Ser His Glu Asp Pro Glu Val Lys Phe Asn Trp Tyr Val
610                 615                 620
```

```
Asp Gly Val Glu Val His Asn Ala Lys Thr Lys Pro Arg Glu Glu Gln
625                 630                 635                 640

Tyr Asn Ser Thr Tyr Arg Val Val Ser Val Leu Thr Val Leu His Gln
                645                 650                 655

Asp Trp Leu Asn Gly Lys Glu Tyr Lys Cys Lys Val Ser Asn Lys Ala
            660                 665                 670

Leu Pro Ala Pro Ile Glu Lys Thr Ile Ser Lys Ala Lys Gly Gln Pro
        675                 680                 685

Arg Glu Pro Gln Val Tyr Thr Leu Pro Pro Ser Arg Glu Glu Met Thr
    690                 695                 700

Lys Asn Gln Val Ser Leu Thr Cys Leu Val Lys Gly Phe Tyr Pro Ser
705                 710                 715                 720

Asp Ile Ala Val Glu Trp Glu Ser Asn Gly Gln Pro Glu Asn Asn Tyr
                725                 730                 735

Lys Thr Thr Pro Pro Val Leu Asp Ser Asp Gly Ser Phe Phe Leu Tyr
            740                 745                 750

Ser Lys Leu Thr Val Asp Lys Ser Arg Trp Gln Gln Gly Asn Val Phe
        755                 760                 765

Ser Cys Ser Val Met His Glu Ala Leu His Asn His Tyr Thr Gln Lys
    770                 775                 780

Ser Leu Ser Leu Ser Pro Gly Lys
785                 790

<210> SEQ ID NO 36
<211> LENGTH: 790
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
            20                  25                  30

Val Lys Thr Phe Phe Gln Met Lys Asp Gln Leu Asp Asn Leu Leu Leu
        35                  40                  45

Lys Glu Ser Leu Leu Glu Asp Phe Lys Gly Tyr Leu Gly Cys Gln Ala
    50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
                85                  90                  95

Asn Leu Lys Thr Leu Arg Leu Arg Leu Arg Arg Cys His Arg Phe Leu
            100                 105                 110

Pro Cys Glu Asn Lys Ser Lys Ala Val Glu Gln Val Lys Asn Ala Phe
        115                 120                 125

Asn Lys Leu Gln Glu Lys Gly Ile Tyr Lys Ala Met Ser Glu Phe Asp
    130                 135                 140

Ile Phe Ile Asn Tyr Ile Glu Ala Tyr Met Thr Met Lys Ile Arg Asn
145                 150                 155                 160

Gly Gly Gly Ser Pro Gly Gln Gly Thr Gln Ser Glu Asn Ser Cys Thr
                165                 170                 175

His Phe Pro Gly Asn Leu Pro Asn Met Leu Arg Asp Leu Arg Asp Ala
```

```
                180             185             190
Phe Ser Arg Val Lys Thr Phe Phe Gln Met Lys Asp Gln Leu Asp Asn
            195             200             205
Leu Leu Leu Lys Glu Ser Leu Glu Asp Phe Lys Gly Tyr Leu Gly
        210             215             220
Cys Gln Ala Leu Ser Glu Met Ile Gln Phe Tyr Leu Glu Glu Val Met
225             230             235             240
Pro Gln Ala Glu Asn Gln Asp Pro Asp Ile Lys Ala His Val Asn Ser
            245             250             255
Leu Gly Glu Asn Leu Lys Thr Leu Arg Leu Arg Leu Arg Arg Cys His
        260             265             270
Arg Phe Leu Pro Cys Glu Asn Lys Ser Lys Ala Val Glu Gln Val Lys
        275             280             285
Asn Ala Phe Asn Lys Leu Gln Glu Lys Gly Ile Tyr Lys Ala Met Ser
        290             295             300
Glu Phe Asp Ile Phe Ile Asn Tyr Ile Glu Ala Tyr Met Thr Met Lys
305             310             315             320
Ile Arg Asn Gly Gly Gly Gly Ser Gly Gly Gly Ser Arg Thr Val
            325             330             335
Ala Ala Pro Ser Val Phe Ile Phe Pro Ser Asp Glu Gln Leu Lys
        340             345             350
Ser Gly Thr Ala Ser Val Val Cys Leu Leu Asn Asn Phe Tyr Pro Arg
        355             360             365
Glu Ala Lys Val Gln Trp Lys Val Asp Asn Ala Leu Gln Ser Gly Asn
        370             375             380
Ser Gln Glu Ser Val Thr Glu Gln Asp Ser Lys Asp Ser Thr Tyr Ser
385             390             395             400
Leu Ser Ser Thr Leu Thr Leu Ser Lys Ala Asp Tyr Glu Lys His Lys
            405             410             415
Val Tyr Ala Cys Glu Val Thr His Gln Gly Leu Ser Ser Pro Val Thr
            420             425             430
Lys Ser Phe Asn Arg Gly Glu Cys Gly Gly Gly Gly Ser Gly Gly Gly
        435             440             445
Gly Ser Gly Gly Gly Gly Ser Gly Gly Gly Ser Ala Ser Thr Lys
        450             455             460
Gly Pro Ser Val Phe Pro Leu Ala Pro Ser Ser Lys Ser Thr Ser Gly
465             470             475             480
Gly Thr Ala Ala Leu Gly Cys Leu Val Lys Asp Tyr Phe Pro Glu Pro
            485             490             495
Val Thr Val Ser Trp Asn Ser Gly Ala Leu Thr Ser Gly Val His Thr
            500             505             510
Phe Pro Ala Val Leu Gln Ser Ser Gly Leu Tyr Ser Leu Ser Ser Val
        515             520             525
Val Thr Val Pro Ser Ser Ser Leu Gly Thr Gln Thr Tyr Ile Cys Asn
        530             535             540
Val Asn His Lys Pro Ser Asn Thr Lys Val Asp Lys Arg Val Glu Pro
545             550             555             560
Lys Ser Cys Asp Lys Thr His Thr Cys Pro Pro Cys Pro Ala Pro Glu
            565             570             575
Leu Leu Gly Gly Pro Ser Val Phe Leu Phe Pro Pro Lys Pro Lys Asp
        580             585             590
Thr Leu Met Ile Ser Arg Thr Pro Glu Val Thr Cys Val Val Val Asp
        595             600             605
```

```
Val Ser His Glu Asp Pro Glu Val Lys Phe Asn Trp Tyr Val Asp Gly
    610                 615                 620

Val Glu Val His Asn Ala Lys Thr Lys Pro Arg Glu Glu Gln Tyr Asn
625                 630                 635                 640

Ser Thr Tyr Arg Val Val Ser Val Leu Thr Val Leu His Gln Asp Trp
                645                 650                 655

Leu Asn Gly Lys Glu Tyr Lys Cys Lys Val Ser Asn Lys Ala Leu Pro
            660                 665                 670

Ala Pro Ile Glu Lys Thr Ile Ser Lys Ala Lys Gly Gln Pro Arg Glu
        675                 680                 685

Pro Gln Val Tyr Thr Leu Pro Pro Ser Arg Glu Glu Met Thr Lys Asn
    690                 695                 700

Gln Val Ser Leu Thr Cys Leu Val Lys Gly Phe Tyr Pro Ser Asp Ile
705                 710                 715                 720

Ala Val Glu Trp Glu Ser Asn Gly Gln Pro Glu Asn Asn Tyr Lys Thr
                725                 730                 735

Thr Pro Pro Val Leu Asp Ser Asp Gly Ser Phe Phe Leu Tyr Ser Lys
            740                 745                 750

Leu Thr Val Asp Lys Ser Arg Trp Gln Gln Gly Asn Val Phe Ser Cys
        755                 760                 765

Ser Val Met His Glu Ala Leu His Asn His Tyr Thr Gln Lys Ser Leu
    770                 775                 780

Ser Leu Ser Pro Gly Lys
785                 790

<210> SEQ ID NO 37
<211> LENGTH: 797
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
            20                  25                  30

Val Lys Thr Phe Phe Gln Met Lys Asp Gln Leu Asp Asn Leu Leu Leu
        35                  40                  45

Lys Glu Ser Leu Leu Glu Asp Phe Lys Gly Tyr Leu Gly Cys Gln Ala
50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
                85                  90                  95

Asn Leu Lys Thr Leu Arg Leu Arg Leu Arg Arg Cys His Arg Phe Leu
            100                 105                 110

Pro Cys Glu Asn Lys Ser Lys Ala Val Glu Gln Val Lys Asn Ala Phe
        115                 120                 125

Asn Lys Leu Gln Glu Lys Gly Ile Tyr Lys Ala Met Ser Glu Phe Asp
    130                 135                 140

Ile Phe Ile Asn Tyr Ile Glu Ala Tyr Met Thr Met Lys Ile Arg Asn
145                 150                 155                 160

Gly Gly Ser Gly Gly Gly Gly Ser Gly Gly Ser Pro Gly Gln Gly Thr
```

```
              165                 170                 175
Gln Ser Glu Asn Ser Cys Thr His Phe Pro Gly Asn Leu Pro Asn Met
            180                 185                 190

Leu Arg Asp Leu Arg Asp Ala Phe Ser Arg Val Lys Thr Phe Phe Gln
            195                 200                 205

Met Lys Ala Gln Leu Asp Asn Leu Leu Leu Lys Glu Ser Leu Leu Glu
            210                 215                 220

Asp Phe Lys Gly Tyr Leu Gly Cys Gln Ala Leu Ser Glu Met Ile Gln
225                 230                 235                 240

Phe Tyr Leu Glu Glu Val Met Pro Gln Ala Glu Asn Gln Asp Pro Asp
                245                 250                 255

Ile Lys Ala His Val Asn Ser Leu Gly Glu Asn Leu Lys Thr Leu Arg
                260                 265                 270

Leu Arg Leu Arg Arg Cys His Arg Phe Leu Pro Cys Glu Asn Lys Ser
                275                 280                 285

Lys Ala Val Glu Gln Val Lys Asn Ala Phe Asn Lys Leu Gln Glu Lys
            290                 295                 300

Gly Ile Tyr Lys Ala Met Ser Glu Phe Asp Ile Phe Ile Asn Tyr Ile
305                 310                 315                 320

Glu Ala Tyr Met Thr Met Lys Ile Arg Asn Gly Gly Gly Ser Gly
                325                 330                 335

Gly Gly Gly Ser Arg Thr Val Ala Ala Pro Ser Val Phe Ile Phe Pro
            340                 345                 350

Pro Ser Asp Glu Gln Leu Lys Ser Gly Thr Ala Ser Val Val Cys Leu
            355                 360                 365

Leu Asn Asn Phe Tyr Pro Arg Glu Ala Lys Val Gln Trp Lys Val Asp
370                 375                 380

Asn Ala Leu Gln Ser Gly Asn Ser Gln Glu Ser Val Thr Glu Gln Asp
385                 390                 395                 400

Ser Lys Asp Ser Thr Tyr Ser Leu Ser Ser Thr Leu Thr Leu Ser Lys
                405                 410                 415

Ala Asp Tyr Glu Lys His Lys Val Tyr Ala Cys Glu Val Thr His Gln
                420                 425                 430

Gly Leu Ser Ser Pro Val Thr Lys Ser Phe Asn Arg Gly Glu Cys Gly
            435                 440                 445

Gly Gly Gly Ser Gly Gly Gly Ser Gly Gly Gly Ser Gly
            450                 455                 460

Gly Gly Ser Ala Ser Thr Lys Gly Pro Ser Val Phe Pro Leu Ala Pro
465                 470                 475                 480

Ser Ser Lys Ser Thr Ser Gly Gly Thr Ala Ala Leu Gly Cys Leu Val
                485                 490                 495

Lys Asp Tyr Phe Pro Glu Pro Val Thr Val Ser Trp Asn Ser Gly Ala
            500                 505                 510

Leu Thr Ser Gly Val His Thr Phe Pro Ala Val Leu Gln Ser Ser Gly
            515                 520                 525

Leu Tyr Ser Leu Ser Ser Val Val Thr Val Pro Ser Ser Ser Leu Gly
            530                 535                 540

Thr Gln Thr Tyr Ile Cys Asn Val Asn His Lys Pro Ser Asn Thr Lys
545                 550                 555                 560

Val Asp Lys Arg Val Glu Pro Lys Ser Cys Asp Lys Thr His Thr Cys
                565                 570                 575

Pro Pro Cys Pro Ala Pro Glu Leu Leu Gly Gly Pro Ser Val Phe Leu
            580                 585                 590
```

```
Phe Pro Pro Lys Pro Lys Asp Thr Leu Met Ile Ser Arg Thr Pro Glu
            595                 600                 605

Val Thr Cys Val Val Asp Val Ser His Glu Asp Pro Glu Val Lys
    610                 615                 620

Phe Asn Trp Tyr Val Asp Gly Val Glu Val His Asn Ala Lys Thr Lys
625                 630                 635                 640

Pro Arg Glu Glu Gln Tyr Asn Ser Thr Tyr Arg Val Val Ser Val Leu
                645                 650                 655

Thr Val Leu His Gln Asp Trp Leu Asn Gly Lys Glu Tyr Lys Cys Lys
            660                 665                 670

Val Ser Asn Lys Ala Leu Pro Ala Pro Ile Glu Lys Thr Ile Ser Lys
            675                 680                 685

Ala Lys Gly Gln Pro Arg Glu Pro Gln Val Tyr Thr Leu Pro Pro Ser
            690                 695                 700

Arg Glu Glu Met Thr Lys Asn Gln Val Ser Leu Thr Cys Leu Val Lys
705                 710                 715                 720

Gly Phe Tyr Pro Ser Asp Ile Ala Val Glu Trp Glu Ser Asn Gly Gln
                725                 730                 735

Pro Glu Asn Asn Tyr Lys Thr Thr Pro Pro Val Leu Asp Ser Asp Gly
            740                 745                 750

Ser Phe Phe Leu Tyr Ser Lys Leu Thr Val Asp Lys Ser Arg Trp Gln
            755                 760                 765

Gln Gly Asn Val Phe Ser Cys Ser Val Met His Glu Ala Leu His Asn
770                 775                 780

His Tyr Thr Gln Lys Ser Leu Ser Leu Ser Pro Gly Lys
785                 790                 795

<210> SEQ ID NO 38
<211> LENGTH: 797
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
            20                  25                  30

Val Lys Thr Phe Phe Gln Met Lys Asp Gln Leu Asp Asn Leu Leu Leu
        35                  40                  45

Lys Glu Ser Leu Leu Glu Asp Phe Lys Gly Tyr Leu Gly Cys Gln Ala
    50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
                85                  90                  95

Asn Leu Lys Thr Leu Arg Leu Arg Leu Arg Arg Cys His Arg Phe Leu
            100                 105                 110

Pro Cys Glu Asn Lys Ser Lys Ala Val Glu Gln Val Lys Asn Ala Phe
        115                 120                 125

Asn Lys Leu Gln Glu Lys Gly Ile Tyr Lys Ala Met Ser Glu Phe Asp
    130                 135                 140

Ile Phe Ile Asn Tyr Ile Glu Ala Tyr Met Thr Met Lys Ile Arg Asn
```

-continued

```
            145                 150                 155                 160
Gly Gly Ser Gly Gly Gly Ser Gly Gly Ser Pro Gly Gln Gly Thr
                165                 170                 175

Gln Ser Glu Asn Ser Cys Thr His Phe Pro Gly Asn Leu Pro Asn Ala
                180                 185                 190

Leu Arg Asp Leu Arg Asp Ala Phe Ser Arg Val Lys Thr Phe Phe Gln
                195                 200                 205

Met Lys Ala Gln Leu Asp Asn Leu Leu Leu Lys Glu Ser Leu Leu Glu
    210                 215                 220

Asp Phe Lys Gly Tyr Leu Gly Cys Gln Ala Leu Ser Glu Met Ile Gln
225                 230                 235                 240

Phe Tyr Leu Glu Glu Val Met Pro Gln Ala Glu Asn Gln Asp Pro Asp
                245                 250                 255

Ile Lys Ala His Val Asn Ser Leu Gly Glu Asn Leu Lys Thr Leu Arg
                260                 265                 270

Leu Arg Leu Arg Arg Cys His Arg Phe Leu Pro Cys Glu Asn Lys Ser
                275                 280                 285

Lys Ala Val Glu Gln Val Lys Asn Ala Phe Asn Lys Leu Gln Glu Lys
    290                 295                 300

Gly Ile Tyr Lys Ala Met Ser Glu Phe Asp Ile Phe Ile Asn Tyr Ile
305                 310                 315                 320

Glu Ala Tyr Met Thr Met Lys Ile Arg Asn Gly Gly Gly Gly Ser Gly
                325                 330                 335

Gly Gly Gly Ser Arg Thr Val Ala Ala Pro Ser Val Phe Ile Phe Pro
                340                 345                 350

Pro Ser Asp Glu Gln Leu Lys Ser Gly Thr Ala Ser Val Val Cys Leu
                355                 360                 365

Leu Asn Asn Phe Tyr Pro Arg Glu Ala Lys Val Gln Trp Lys Val Asp
                370                 375                 380

Asn Ala Leu Gln Ser Gly Asn Ser Gln Glu Ser Val Thr Glu Gln Asp
385                 390                 395                 400

Ser Lys Asp Ser Thr Tyr Ser Leu Ser Ser Thr Leu Thr Leu Ser Lys
                405                 410                 415

Ala Asp Tyr Glu Lys His Lys Val Tyr Ala Cys Glu Val Thr His Gln
                420                 425                 430

Gly Leu Ser Ser Pro Val Thr Lys Ser Phe Asn Arg Gly Glu Cys Gly
                435                 440                 445

Gly Gly Gly Ser Gly Gly Gly Gly Ser Gly Gly Gly Gly Ser Gly Gly
                450                 455                 460

Gly Gly Ser Ala Ser Thr Lys Gly Pro Ser Val Phe Pro Leu Ala Pro
465                 470                 475                 480

Ser Ser Lys Ser Thr Ser Gly Gly Thr Ala Ala Leu Gly Cys Leu Val
                485                 490                 495

Lys Asp Tyr Phe Pro Glu Pro Val Thr Val Ser Trp Asn Ser Gly Ala
                500                 505                 510

Leu Thr Ser Gly Val His Thr Phe Pro Ala Val Leu Gln Ser Ser Gly
                515                 520                 525

Leu Tyr Ser Leu Ser Ser Val Val Thr Val Pro Ser Ser Ser Leu Gly
                530                 535                 540

Thr Gln Thr Tyr Ile Cys Asn Val Asn His Lys Pro Ser Asn Thr Lys
545                 550                 555                 560

Val Asp Lys Arg Val Glu Pro Lys Ser Cys Asp Lys Thr His Thr Cys
                565                 570                 575
```

Pro Pro Cys Pro Ala Pro Glu Leu Leu Gly Gly Pro Ser Val Phe Leu
            580                 585                 590

Phe Pro Pro Lys Pro Lys Asp Thr Leu Met Ile Ser Arg Thr Pro Glu
            595                 600                 605

Val Thr Cys Val Val Val Asp Val Ser His Glu Asp Pro Glu Val Lys
610                 615                 620

Phe Asn Trp Tyr Val Asp Gly Val Glu Val His Asn Ala Lys Thr Lys
625                 630                 635                 640

Pro Arg Glu Glu Gln Tyr Asn Ser Thr Tyr Arg Val Val Ser Val Leu
                645                 650                 655

Thr Val Leu His Gln Asp Trp Leu Asn Gly Lys Glu Tyr Lys Cys Lys
            660                 665                 670

Val Ser Asn Lys Ala Leu Pro Ala Pro Ile Glu Lys Thr Ile Ser Lys
            675                 680                 685

Ala Lys Gly Gln Pro Arg Glu Pro Gln Val Tyr Thr Leu Pro Pro Ser
        690                 695                 700

Arg Glu Glu Met Thr Lys Asn Gln Val Ser Leu Thr Cys Leu Val Lys
705                 710                 715                 720

Gly Phe Tyr Pro Ser Asp Ile Ala Val Glu Trp Glu Ser Asn Gly Gln
                725                 730                 735

Pro Glu Asn Asn Tyr Lys Thr Thr Pro Pro Val Leu Asp Ser Asp Gly
            740                 745                 750

Ser Phe Phe Leu Tyr Ser Lys Leu Thr Val Asp Lys Ser Arg Trp Gln
            755                 760                 765

Gln Gly Asn Val Phe Ser Cys Ser Val Met His Glu Ala Leu His Asn
        770                 775                 780

His Tyr Thr Gln Lys Ser Leu Ser Leu Ser Pro Gly Lys
785                 790                 795

<210> SEQ ID NO 39
<211> LENGTH: 797
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
            20                  25                  30

Val Lys Thr Phe Phe Gln Met Lys Ala Gln Leu Asp Asn Leu Leu Leu
        35                  40                  45

Lys Glu Ser Leu Leu Glu Asp Phe Lys Gly Tyr Leu Gly Cys Gln Ala
    50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
                85                  90                  95

Asn Leu Lys Thr Leu Arg Leu Arg Leu Arg Arg Cys His Arg Phe Leu
            100                 105                 110

Pro Cys Glu Asn Lys Ser Lys Ala Val Glu Gln Val Lys Asn Ala Phe
        115                 120                 125

Asn Lys Leu Gln Glu Lys Gly Ile Tyr Lys Ala Met Ser Glu Phe Asp

-continued

```
            130                 135                 140
Ile Phe Ile Asn Tyr Ile Glu Ala Tyr Met Thr Met Lys Ile Arg Asn
145                 150                 155                 160

Gly Gly Ser Gly Gly Gly Ser Gly Gly Ser Pro Gly Gln Gly Thr
                165                 170                 175

Gln Ser Glu Asn Ser Cys Thr His Phe Pro Gly Asn Leu Pro Asn Ala
                180                 185                 190

Leu Arg Asp Leu Arg Asp Ala Phe Ser Arg Val Lys Thr Phe Phe Gln
                195                 200                 205

Met Lys Asp Gln Leu Asp Asn Leu Leu Leu Lys Glu Ser Leu Leu Glu
                210                 215                 220

Asp Phe Lys Gly Tyr Leu Gly Cys Gln Ala Leu Ser Glu Met Ile Gln
225                 230                 235                 240

Phe Tyr Leu Glu Glu Val Met Pro Gln Ala Glu Asn Gln Asp Pro Asp
                245                 250                 255

Ile Lys Ala His Val Asn Ser Leu Gly Glu Asn Leu Lys Thr Leu Arg
                260                 265                 270

Leu Arg Leu Arg Arg Cys His Arg Phe Leu Pro Cys Glu Asn Lys Ser
                275                 280                 285

Lys Ala Val Glu Gln Val Lys Asn Ala Phe Asn Lys Leu Gln Glu Lys
                290                 295                 300

Gly Ile Tyr Lys Ala Met Ser Glu Phe Asp Ile Phe Ile Asn Tyr Ile
305                 310                 315                 320

Glu Ala Tyr Met Thr Met Lys Ile Arg Asn Gly Gly Gly Gly Ser Gly
                325                 330                 335

Gly Gly Gly Ser Arg Thr Val Ala Ala Pro Ser Val Phe Ile Phe Pro
                340                 345                 350

Pro Ser Asp Glu Gln Leu Lys Ser Gly Thr Ala Ser Val Val Cys Leu
                355                 360                 365

Leu Asn Asn Phe Tyr Pro Arg Glu Ala Lys Val Gln Trp Lys Val Asp
                370                 375                 380

Asn Ala Leu Gln Ser Gly Asn Ser Gln Glu Ser Val Thr Glu Gln Asp
385                 390                 395                 400

Ser Lys Asp Ser Thr Tyr Ser Leu Ser Ser Thr Leu Thr Leu Ser Lys
                405                 410                 415

Ala Asp Tyr Glu Lys His Lys Val Tyr Ala Cys Glu Val Thr His Gln
                420                 425                 430

Gly Leu Ser Ser Pro Val Thr Lys Ser Phe Asn Arg Gly Glu Cys Gly
                435                 440                 445

Gly Gly Gly Ser Gly Gly Gly Ser Gly Gly Gly Ser Gly Gly
                450                 455                 460

Gly Gly Ser Ala Ser Thr Lys Gly Pro Ser Val Phe Pro Leu Ala Pro
465                 470                 475                 480

Ser Ser Lys Ser Thr Ser Gly Gly Thr Ala Ala Leu Gly Cys Leu Val
                485                 490                 495

Lys Asp Tyr Phe Pro Glu Pro Val Thr Val Ser Trp Asn Ser Gly Ala
                500                 505                 510

Leu Thr Ser Gly Val His Thr Phe Pro Ala Val Leu Gln Ser Ser Gly
                515                 520                 525

Leu Tyr Ser Leu Ser Ser Val Val Thr Val Pro Ser Ser Ser Leu Gly
                530                 535                 540

Thr Gln Thr Tyr Ile Cys Asn Val Asn His Lys Pro Ser Asn Thr Lys
545                 550                 555                 560
```

```
Val Asp Lys Arg Val Glu Pro Lys Ser Cys Asp Lys Thr His Thr Cys
                565                 570                 575

Pro Pro Cys Pro Ala Pro Glu Leu Leu Gly Gly Pro Ser Val Phe Leu
            580                 585                 590

Phe Pro Pro Lys Pro Lys Asp Thr Leu Met Ile Ser Arg Thr Pro Glu
        595                 600                 605

Val Thr Cys Val Val Val Asp Val Ser His Glu Asp Pro Glu Val Lys
    610                 615                 620

Phe Asn Trp Tyr Val Asp Gly Val Glu Val His Asn Ala Lys Thr Lys
625                 630                 635                 640

Pro Arg Glu Glu Gln Tyr Asn Ser Thr Tyr Arg Val Val Ser Val Leu
                645                 650                 655

Thr Val Leu His Gln Asp Trp Leu Asn Gly Lys Glu Tyr Lys Cys Lys
            660                 665                 670

Val Ser Asn Lys Ala Leu Pro Ala Pro Ile Glu Lys Thr Ile Ser Lys
        675                 680                 685

Ala Lys Gly Gln Pro Arg Glu Pro Gln Val Tyr Thr Leu Pro Pro Ser
    690                 695                 700

Arg Glu Glu Met Thr Lys Asn Gln Val Ser Leu Thr Cys Leu Val Lys
705                 710                 715                 720

Gly Phe Tyr Pro Ser Asp Ile Ala Val Glu Trp Glu Ser Asn Gly Gln
                725                 730                 735

Pro Glu Asn Asn Tyr Lys Thr Thr Pro Pro Val Leu Asp Ser Asp Gly
            740                 745                 750

Ser Phe Phe Leu Tyr Ser Lys Leu Thr Val Asp Lys Ser Arg Trp Gln
        755                 760                 765

Gln Gly Asn Val Phe Ser Cys Ser Val Met His Glu Ala Leu His Asn
    770                 775                 780

His Tyr Thr Gln Lys Ser Leu Ser Leu Ser Pro Gly Lys
785                 790                 795

<210> SEQ ID NO 40
<211> LENGTH: 797
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Ser Pro Gly Gln Gly Thr Gln Ser Glu Asn Ser Cys Thr His Phe Pro
1               5                   10                  15

Gly Asn Leu Pro Asn Ala Leu Arg Asp Leu Arg Asp Ala Phe Ser Arg
            20                  25                  30

Val Lys Thr Phe Phe Gln Met Lys Asp Gln Leu Asp Asn Leu Leu Leu
        35                  40                  45

Lys Glu Ser Leu Leu Glu Asp Phe Lys Gly Tyr Leu Gly Cys Gln Ala
    50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
                85                  90                  95

Asn Leu Lys Thr Leu Arg Leu Arg Leu Arg Arg Cys His Arg Phe Leu
            100                 105                 110

Pro Cys Glu Asn Lys Ser Lys Ala Val Glu Gln Val Lys Asn Ala Phe
```

```
            115                 120                 125
Asn Lys Leu Gln Glu Lys Gly Ile Tyr Lys Ala Met Ser Glu Phe Asp
            130                 135                 140
Ile Phe Ile Asn Tyr Ile Glu Ala Tyr Met Thr Met Lys Ile Arg Asn
145                 150                 155                 160
Gly Gly Ser Gly Gly Gly Ser Gly Gly Ser Pro Gly Gln Gly Thr
                165                 170                 175
Gln Ser Glu Asn Ser Cys Thr His Phe Pro Gly Asn Leu Pro Asn Met
            180                 185                 190
Leu Arg Asp Leu Arg Asp Ala Phe Ser Arg Val Lys Thr Phe Phe Gln
            195                 200                 205
Met Lys Ala Gln Leu Asp Asn Leu Leu Leu Lys Glu Ser Leu Leu Glu
            210                 215                 220
Asp Phe Lys Gly Tyr Leu Gly Cys Gln Ala Leu Ser Glu Met Ile Gln
225                 230                 235                 240
Phe Tyr Leu Glu Glu Val Met Pro Gln Ala Glu Asn Gln Asp Pro Asp
                245                 250                 255
Ile Lys Ala His Val Asn Ser Leu Gly Glu Asn Leu Lys Thr Leu Arg
            260                 265                 270
Leu Arg Leu Arg Arg Cys His Arg Phe Leu Pro Cys Glu Asn Lys Ser
            275                 280                 285
Lys Ala Val Glu Gln Val Lys Asn Ala Phe Asn Lys Leu Gln Glu Lys
            290                 295                 300
Gly Ile Tyr Lys Ala Met Ser Glu Phe Asp Ile Phe Ile Asn Tyr Ile
305                 310                 315                 320
Glu Ala Tyr Met Thr Met Lys Ile Arg Asn Gly Gly Gly Ser Gly
                325                 330                 335
Gly Gly Gly Ser Arg Thr Val Ala Ala Pro Ser Val Phe Ile Phe Pro
            340                 345                 350
Pro Ser Asp Glu Gln Leu Lys Ser Gly Thr Ala Ser Val Val Cys Leu
            355                 360                 365
Leu Asn Asn Phe Tyr Pro Arg Glu Ala Lys Val Gln Trp Lys Val Asp
            370                 375                 380
Asn Ala Leu Gln Ser Gly Asn Ser Gln Glu Ser Val Thr Glu Gln Asp
385                 390                 395                 400
Ser Lys Asp Ser Thr Tyr Ser Leu Ser Ser Thr Leu Thr Leu Ser Lys
                405                 410                 415
Ala Asp Tyr Glu Lys His Lys Val Tyr Ala Cys Glu Val Thr His Gln
            420                 425                 430
Gly Leu Ser Ser Pro Val Thr Lys Ser Phe Asn Arg Gly Glu Cys Gly
            435                 440                 445
Gly Gly Gly Ser Gly Gly Gly Ser Gly Gly Gly Ser Gly Gly
            450                 455                 460
Gly Gly Ser Ala Ser Thr Lys Gly Pro Ser Val Phe Pro Leu Ala Pro
465                 470                 475                 480
Ser Ser Lys Ser Thr Ser Gly Gly Thr Ala Ala Leu Gly Cys Leu Val
                485                 490                 495
Lys Asp Tyr Phe Pro Glu Pro Val Thr Val Ser Trp Asn Ser Gly Ala
            500                 505                 510
Leu Thr Ser Gly Val His Thr Phe Pro Ala Val Leu Gln Ser Ser Gly
            515                 520                 525
Leu Tyr Ser Leu Ser Ser Val Val Thr Val Pro Ser Ser Leu Gly
            530                 535                 540
```

```
Thr Gln Thr Tyr Ile Cys Asn Val Asn His Lys Pro Ser Asn Thr Lys
545                 550                 555                 560

Val Asp Lys Arg Val Glu Pro Lys Ser Cys Asp Lys Thr His Thr Cys
                565                 570                 575

Pro Pro Cys Pro Ala Pro Glu Leu Leu Gly Gly Pro Ser Val Phe Leu
            580                 585                 590

Phe Pro Pro Lys Pro Lys Asp Thr Leu Met Ile Ser Arg Thr Pro Glu
                595                 600                 605

Val Thr Cys Val Val Val Asp Val Ser His Glu Asp Pro Glu Val Lys
            610                 615                 620

Phe Asn Trp Tyr Val Asp Gly Val Glu Val His Asn Ala Lys Thr Lys
625                 630                 635                 640

Pro Arg Glu Glu Gln Tyr Asn Ser Thr Tyr Arg Val Val Ser Val Leu
                645                 650                 655

Thr Val Leu His Gln Asp Trp Leu Asn Gly Lys Glu Tyr Lys Cys Lys
            660                 665                 670

Val Ser Asn Lys Ala Leu Pro Ala Pro Ile Glu Lys Thr Ile Ser Lys
                675                 680                 685

Ala Lys Gly Gln Pro Arg Glu Pro Gln Val Tyr Thr Leu Pro Pro Ser
690                 695                 700

Arg Glu Glu Met Thr Lys Asn Gln Val Ser Leu Thr Cys Leu Val Lys
705                 710                 715                 720

Gly Phe Tyr Pro Ser Asp Ile Ala Val Glu Trp Glu Ser Asn Gly Gln
                725                 730                 735

Pro Glu Asn Asn Tyr Lys Thr Thr Pro Pro Val Leu Asp Ser Asp Gly
            740                 745                 750

Ser Phe Phe Leu Tyr Ser Lys Leu Thr Val Asp Lys Ser Arg Trp Gln
                755                 760                 765

Gln Gly Asn Val Phe Ser Cys Ser Val Met His Glu Ala Leu His Asn
            770                 775                 780

His Tyr Thr Gln Lys Ser Leu Ser Leu Ser Pro Gly Lys
785                 790                 795

<210> SEQ ID NO 41
<211> LENGTH: 797
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
                20                  25                  30

Val Lys Thr Phe Phe Gln Met Lys Asp Gln Leu Asp Asn Leu Leu Leu
            35                  40                  45

Lys Glu Ser Leu Leu Glu Asp Phe Lys Gly Tyr Leu Gly Cys Gln Ala
50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
                85                  90                  95

Asn Leu Lys Thr Leu Arg Leu Arg Leu Arg Arg Cys His Arg Phe Leu
```

```
                100               105                110
Pro Cys Glu Asn Lys Ser Lys Ala Val Glu Gln Val Lys Asn Ala Phe
            115                 120                 125
Asn Lys Leu Gln Glu Lys Gly Ile Tyr Lys Ala Met Ser Glu Phe Asp
130                 135                 140
Ile Phe Ile Asn Tyr Ile Glu Ala Tyr Met Thr Met Lys Ile Arg Asn
145                 150                 155                 160
Gly Gly Ser Gly Gly Gly Ser Gly Gly Ser Pro Gly Gln Gly Thr
                165                 170                 175
Gln Ser Glu Asn Ser Cys Thr His Phe Pro Gly Asn Leu Pro Asn Met
            180                 185                 190
Leu Arg Asp Leu Arg Asp Ala Phe Ser Arg Val Lys Thr Phe Phe Gln
            195                 200                 205
Met Lys Asn Gln Leu Asp Asn Leu Leu Leu Lys Glu Ser Leu Leu Glu
    210                 215                 220
Asp Phe Lys Gly Tyr Leu Gly Cys Gln Ala Leu Ser Glu Met Ile Gln
225                 230                 235                 240
Phe Tyr Leu Glu Glu Val Met Pro Gln Ala Glu Asn Gln Asp Pro Asp
                245                 250                 255
Ile Lys Ala His Val Asn Ser Leu Gly Glu Asn Leu Lys Thr Leu Arg
            260                 265                 270
Leu Arg Leu Arg Arg Cys His Arg Phe Leu Pro Cys Glu Asn Lys Ser
            275                 280                 285
Lys Ala Val Glu Gln Val Lys Asn Ala Phe Asn Lys Leu Gln Glu Lys
    290                 295                 300
Gly Ile Tyr Lys Ala Met Ser Glu Phe Asp Ile Phe Ile Asn Tyr Ile
305                 310                 315                 320
Glu Ala Tyr Met Thr Met Lys Ile Arg Asn Gly Gly Gly Gly Ser Gly
                325                 330                 335
Gly Gly Gly Ser Arg Thr Val Ala Ala Pro Ser Val Phe Ile Phe Pro
            340                 345                 350
Pro Ser Asp Glu Gln Leu Lys Ser Gly Thr Ala Ser Val Val Cys Leu
            355                 360                 365
Leu Asn Asn Phe Tyr Pro Arg Glu Ala Lys Val Gln Trp Lys Val Asp
    370                 375                 380
Asn Ala Leu Gln Ser Gly Asn Ser Gln Glu Ser Val Thr Glu Gln Asp
385                 390                 395                 400
Ser Lys Asp Ser Thr Tyr Ser Leu Ser Ser Thr Leu Thr Leu Ser Lys
                405                 410                 415
Ala Asp Tyr Glu Lys His Lys Val Tyr Ala Cys Glu Val Thr His Gln
            420                 425                 430
Gly Leu Ser Ser Pro Val Thr Lys Ser Phe Asn Arg Gly Glu Cys Gly
            435                 440                 445
Gly Gly Gly Ser Gly Gly Gly Gly Ser Gly Gly Gly Gly Ser Gly Gly
    450                 455                 460
Gly Gly Ser Ala Ser Thr Lys Gly Pro Ser Val Phe Pro Leu Ala Pro
465                 470                 475                 480
Ser Ser Lys Ser Thr Ser Gly Gly Thr Ala Ala Leu Gly Cys Leu Val
                485                 490                 495
Lys Asp Tyr Phe Pro Glu Pro Val Thr Val Ser Trp Asn Ser Gly Ala
            500                 505                 510
Leu Thr Ser Gly Val His Thr Phe Pro Ala Val Leu Gln Ser Ser Gly
            515                 520                 525
```

Leu Tyr Ser Leu Ser Ser Val Thr Val Pro Ser Ser Leu Gly
            530                 535                 540

Thr Gln Thr Tyr Ile Cys Asn Val Asn His Lys Pro Ser Asn Thr Lys
545                 550                 555                 560

Val Asp Lys Arg Val Glu Pro Lys Ser Cys Asp Lys Thr His Thr Cys
                565                 570                 575

Pro Pro Cys Pro Ala Pro Glu Leu Leu Gly Gly Pro Ser Val Phe Leu
            580                 585                 590

Phe Pro Pro Lys Pro Lys Asp Thr Leu Met Ile Ser Arg Thr Pro Glu
        595                 600                 605

Val Thr Cys Val Val Val Asp Val Ser His Glu Asp Pro Glu Val Lys
            610                 615                 620

Phe Asn Trp Tyr Val Asp Gly Val Glu Val His Asn Ala Lys Thr Lys
625                 630                 635                 640

Pro Arg Glu Glu Gln Tyr Asn Ser Thr Tyr Arg Val Val Ser Val Leu
                645                 650                 655

Thr Val Leu His Gln Asp Trp Leu Asn Gly Lys Glu Tyr Lys Cys Lys
            660                 665                 670

Val Ser Asn Lys Ala Leu Pro Ala Pro Ile Glu Lys Thr Ile Ser Lys
        675                 680                 685

Ala Lys Gly Gln Pro Arg Glu Pro Gln Val Tyr Thr Leu Pro Pro Ser
690                 695                 700

Arg Glu Glu Met Thr Lys Asn Gln Val Ser Leu Thr Cys Leu Val Lys
705                 710                 715                 720

Gly Phe Tyr Pro Ser Asp Ile Ala Val Glu Trp Glu Ser Asn Gly Gln
                725                 730                 735

Pro Glu Asn Asn Tyr Lys Thr Thr Pro Pro Val Leu Asp Ser Asp Gly
            740                 745                 750

Ser Phe Phe Leu Tyr Ser Lys Leu Thr Val Asp Lys Ser Arg Trp Gln
        755                 760                 765

Gln Gly Asn Val Phe Ser Cys Ser Val Met His Glu Ala Leu His Asn
770                 775                 780

His Tyr Thr Gln Lys Ser Leu Ser Leu Ser Pro Gly Lys
785                 790                 795

<210> SEQ ID NO 42
<211> LENGTH: 797
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
            20                  25                  30

Val Lys Thr Phe Phe Gln Met Lys Asp Gln Leu Asp Asn Leu Leu Leu
        35                  40                  45

Lys Glu Ser Leu Leu Glu Asp Phe Lys Gly Tyr Leu Gly Cys Gln Ala
    50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu

```
                85                  90                  95
Asn Leu Lys Thr Leu Arg Leu Arg Leu Arg Arg Cys His Arg Phe Leu
            100                 105                 110
Pro Cys Glu Asn Lys Ser Lys Ala Val Glu Gln Val Lys Asn Ala Phe
            115                 120                 125
Asn Lys Leu Gln Glu Lys Gly Ile Tyr Lys Ala Met Ser Glu Phe Asp
            130                 135                 140
Ile Phe Ile Asn Tyr Ile Glu Ala Tyr Met Thr Met Lys Ile Arg Asn
145                 150                 155                 160
Gly Gly Ser Gly Gly Gly Ser Gly Gly Ser Pro Gly Gln Gly Thr
                165                 170                 175
Gln Ser Glu Asn Ser Cys Thr His Phe Pro Gly Asn Leu Pro Asn Ala
            180                 185                 190
Leu Arg Asp Leu Arg Asp Ala Phe Ser Arg Val Lys Thr Phe Phe Gln
            195                 200                 205
Met Lys Asn Gln Leu Asp Asn Leu Leu Leu Lys Glu Ser Leu Leu Glu
            210                 215                 220
Asp Phe Lys Gly Tyr Leu Gly Cys Gln Ala Leu Ser Glu Met Ile Gln
225                 230                 235                 240
Phe Tyr Leu Glu Glu Val Met Pro Gln Ala Glu Asn Gln Asp Pro Asp
                245                 250                 255
Ile Lys Ala His Val Asn Ser Leu Gly Glu Asn Leu Lys Thr Leu Arg
            260                 265                 270
Leu Arg Leu Arg Arg Cys His Arg Phe Leu Pro Cys Glu Asn Lys Ser
            275                 280                 285
Lys Ala Val Glu Gln Val Lys Asn Ala Phe Asn Lys Leu Gln Glu Lys
            290                 295                 300
Gly Ile Tyr Lys Ala Met Ser Glu Phe Asp Ile Phe Ile Asn Tyr Ile
305                 310                 315                 320
Glu Ala Tyr Met Thr Met Lys Ile Arg Asn Gly Gly Gly Gly Ser Gly
                325                 330                 335
Gly Gly Gly Ser Arg Thr Val Ala Ala Pro Ser Val Phe Ile Phe Pro
            340                 345                 350
Pro Ser Asp Glu Gln Leu Lys Ser Gly Thr Ala Ser Val Val Cys Leu
            355                 360                 365
Leu Asn Asn Phe Tyr Pro Arg Glu Ala Lys Val Gln Trp Lys Val Asp
            370                 375                 380
Asn Ala Leu Gln Ser Gly Asn Ser Gln Glu Ser Val Thr Glu Gln Asp
385                 390                 395                 400
Ser Lys Asp Ser Thr Tyr Ser Leu Ser Ser Thr Leu Thr Leu Ser Lys
                405                 410                 415
Ala Asp Tyr Glu Lys His Lys Val Tyr Ala Cys Glu Val Thr His Gln
            420                 425                 430
Gly Leu Ser Ser Pro Val Thr Lys Ser Phe Asn Arg Gly Glu Cys Gly
            435                 440                 445
Gly Gly Gly Ser Gly Gly Gly Gly Ser Gly Gly Gly Gly Ser Gly Gly
            450                 455                 460
Gly Gly Ser Ala Ser Thr Lys Gly Pro Ser Val Phe Pro Leu Ala Pro
465                 470                 475                 480
Ser Ser Lys Ser Thr Ser Gly Gly Thr Ala Ala Leu Gly Cys Leu Val
                485                 490                 495
Lys Asp Tyr Phe Pro Glu Pro Val Thr Val Ser Trp Asn Ser Gly Ala
            500                 505                 510
```

```
Leu Thr Ser Gly Val His Thr Phe Pro Ala Val Leu Gln Ser Ser Gly
            515                 520                 525

Leu Tyr Ser Leu Ser Ser Val Val Thr Val Pro Ser Ser Ser Leu Gly
            530                 535                 540

Thr Gln Thr Tyr Ile Cys Asn Val Asn His Lys Pro Ser Asn Thr Lys
545                 550                 555                 560

Val Asp Lys Arg Val Glu Pro Lys Ser Cys Asp Lys Thr His Thr Cys
                565                 570                 575

Pro Pro Cys Pro Ala Pro Glu Leu Leu Gly Gly Pro Ser Val Phe Leu
            580                 585                 590

Phe Pro Pro Lys Pro Lys Asp Thr Leu Met Ile Ser Arg Thr Pro Glu
            595                 600                 605

Val Thr Cys Val Val Val Asp Val Ser His Glu Asp Pro Glu Val Lys
            610                 615                 620

Phe Asn Trp Tyr Val Asp Gly Val Glu Val His Asn Ala Lys Thr Lys
625                 630                 635                 640

Pro Arg Glu Glu Gln Tyr Asn Ser Thr Tyr Arg Val Val Ser Val Leu
                645                 650                 655

Thr Val Leu His Gln Asp Trp Leu Asn Gly Lys Glu Tyr Lys Cys Lys
            660                 665                 670

Val Ser Asn Lys Ala Leu Pro Ala Pro Ile Glu Lys Thr Ile Ser Lys
            675                 680                 685

Ala Lys Gly Gln Pro Arg Glu Pro Gln Val Tyr Thr Leu Pro Pro Ser
            690                 695                 700

Arg Glu Glu Met Thr Lys Asn Gln Val Ser Leu Thr Cys Leu Val Lys
705                 710                 715                 720

Gly Phe Tyr Pro Ser Asp Ile Ala Val Glu Trp Glu Ser Asn Gly Gln
                725                 730                 735

Pro Glu Asn Asn Tyr Lys Thr Thr Pro Pro Val Leu Asp Ser Asp Gly
            740                 745                 750

Ser Phe Phe Leu Tyr Ser Lys Leu Thr Val Asp Lys Ser Arg Trp Gln
            755                 760                 765

Gln Gly Asn Val Phe Ser Cys Ser Val Met His Glu Ala Leu His Asn
            770                 775                 780

His Tyr Thr Gln Lys Ser Leu Ser Leu Ser Pro Gly Lys
785                 790                 795

<210> SEQ ID NO 43
<211> LENGTH: 797
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
            20                  25                  30

Val Lys Thr Phe Phe Gln Met Lys Asn Gln Leu Asp Asn Leu Leu Leu
            35                  40                  45

Lys Glu Ser Leu Leu Glu Asp Phe Lys Gly Tyr Leu Gly Cys Gln Ala
        50                  55                  60

Leu Ser Glu Met Ile Gln Phe Tyr Leu Glu Glu Val Met Pro Gln Ala
```

-continued

```
                65                  70                  75                  80
            Glu Asn Gln Asp Pro Asp Ile Lys Ala His Val Asn Ser Leu Gly Glu
                            85                  90                  95

Asn Leu Lys Thr Leu Arg Leu Arg Leu Arg Cys His Arg Phe Leu
                        100                 105                 110

Pro Cys Glu Asn Lys Ser Lys Ala Val Glu Gln Val Lys Asn Ala Phe
                        115                 120                 125

Asn Lys Leu Gln Glu Lys Gly Ile Tyr Lys Ala Met Ser Glu Phe Asp
            130                 135                 140

Ile Phe Ile Asn Tyr Ile Glu Ala Tyr Met Thr Met Lys Ile Arg Asn
            145                 150                 155                 160

Gly Gly Ser Gly Gly Gly Ser Gly Gly Ser Pro Gly Gln Gly Thr
                            165                 170                 175

Gln Ser Glu Asn Ser Cys Thr His Phe Pro Gly Asn Leu Pro Asn Ala
                        180                 185                 190

Leu Arg Asp Leu Arg Asp Ala Phe Ser Arg Val Lys Thr Phe Phe Gln
                        195                 200                 205

Met Lys Asp Gln Leu Asp Asn Leu Leu Leu Lys Glu Ser Leu Leu Glu
                        210                 215                 220

Asp Phe Lys Gly Tyr Leu Gly Cys Gln Ala Leu Ser Glu Met Ile Gln
            225                 230                 235                 240

Phe Tyr Leu Glu Glu Val Met Pro Gln Ala Glu Asn Gln Asp Pro Asp
                        245                 250                 255

Ile Lys Ala His Val Asn Ser Leu Gly Glu Asn Leu Lys Thr Leu Arg
                        260                 265                 270

Leu Arg Leu Arg Arg Cys His Arg Phe Leu Pro Cys Glu Asn Lys Ser
                    275                 280                 285

Lys Ala Val Glu Gln Val Lys Asn Ala Phe Asn Lys Leu Gln Glu Lys
                    290                 295                 300

Gly Ile Tyr Lys Ala Met Ser Glu Phe Asp Ile Phe Ile Asn Tyr Ile
            305                 310                 315                 320

Glu Ala Tyr Met Thr Met Lys Ile Arg Asn Gly Gly Gly Ser Gly
                            325                 330                 335

Gly Gly Gly Ser Arg Thr Val Ala Ala Pro Ser Val Phe Ile Phe Pro
                        340                 345                 350

Pro Ser Asp Glu Gln Leu Lys Ser Gly Thr Ala Ser Val Val Cys Leu
                        355                 360                 365

Leu Asn Asn Phe Tyr Pro Arg Glu Ala Lys Val Gln Trp Lys Val Asp
                        370                 375                 380

Asn Ala Leu Gln Ser Gly Asn Ser Gln Glu Ser Val Thr Glu Gln Asp
            385                 390                 395                 400

Ser Lys Asp Ser Thr Tyr Ser Leu Ser Ser Thr Leu Thr Leu Ser Lys
                        405                 410                 415

Ala Asp Tyr Glu Lys His Lys Val Tyr Ala Cys Glu Val Thr His Gln
                        420                 425                 430

Gly Leu Ser Ser Pro Val Thr Lys Ser Phe Asn Arg Gly Glu Cys Gly
                        435                 440                 445

Gly Gly Gly Ser Gly Gly Gly Gly Ser Gly Gly Gly Gly Ser Gly Gly
                        450                 455                 460

Gly Gly Ser Ala Ser Thr Lys Gly Pro Ser Val Phe Pro Leu Ala Pro
            465                 470                 475                 480

Ser Ser Lys Ser Thr Ser Gly Gly Thr Ala Ala Leu Gly Cys Leu Val
                        485                 490                 495
```

```
Lys Asp Tyr Phe Pro Glu Pro Val Thr Val Ser Trp Asn Ser Gly Ala
                500                 505                 510

Leu Thr Ser Gly Val His Thr Phe Pro Ala Val Leu Gln Ser Ser Gly
            515                 520                 525

Leu Tyr Ser Leu Ser Ser Val Val Thr Val Pro Ser Ser Ser Leu Gly
        530                 535                 540

Thr Gln Thr Tyr Ile Cys Asn Val Asn His Lys Pro Ser Asn Thr Lys
545                 550                 555                 560

Val Asp Lys Arg Val Glu Pro Lys Ser Cys Asp Lys Thr His Thr Cys
                565                 570                 575

Pro Pro Cys Pro Ala Pro Glu Leu Leu Gly Gly Pro Ser Val Phe Leu
            580                 585                 590

Phe Pro Pro Lys Pro Lys Asp Thr Leu Met Ile Ser Arg Thr Pro Glu
        595                 600                 605

Val Thr Cys Val Val Val Asp Val Ser His Glu Asp Pro Glu Val Lys
    610                 615                 620

Phe Asn Trp Tyr Val Asp Gly Val Glu Val His Asn Ala Lys Thr Lys
625                 630                 635                 640

Pro Arg Glu Glu Gln Tyr Asn Ser Thr Tyr Arg Val Val Ser Val Leu
                645                 650                 655

Thr Val Leu His Gln Asp Trp Leu Asn Gly Lys Glu Tyr Lys Cys Lys
            660                 665                 670

Val Ser Asn Lys Ala Leu Pro Ala Pro Ile Glu Lys Thr Ile Ser Lys
        675                 680                 685

Ala Lys Gly Gln Pro Arg Glu Pro Gln Val Tyr Thr Leu Pro Pro Ser
    690                 695                 700

Arg Glu Glu Met Thr Lys Asn Gln Val Ser Leu Thr Cys Leu Val Lys
705                 710                 715                 720

Gly Phe Tyr Pro Ser Asp Ile Ala Val Glu Trp Glu Ser Asn Gly Gln
                725                 730                 735

Pro Glu Asn Asn Tyr Lys Thr Thr Pro Pro Val Leu Asp Ser Asp Gly
            740                 745                 750

Ser Phe Phe Leu Tyr Ser Lys Leu Thr Val Asp Lys Ser Arg Trp Gln
        755                 760                 765

Gln Gly Asn Val Phe Ser Cys Ser Val Met His Glu Ala Leu His Asn
    770                 775                 780

His Tyr Thr Gln Lys Ser Leu Ser Leu Ser Pro Gly Lys
785                 790                 795

<210> SEQ ID NO 44
<211> LENGTH: 797
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Ser Pro Gly Gln Gly Thr Gln Ser Glu Asn Ser Cys Thr His Phe Pro
1               5                   10                  15

Gly Asn Leu Pro Asn Ala Leu Arg Asp Leu Arg Asp Ala Phe Ser Arg
            20                  25                  30

Val Lys Thr Phe Phe Gln Met Lys Asp Gln Leu Asp Asn Leu Leu Leu
        35                  40                  45

Lys Glu Ser Leu Leu Glu Asp Phe Lys Gly Tyr Leu Gly Cys Gln Ala
```

-continued

```
               50                  55                  60
Leu Ser Glu Met Ile Gln Phe Tyr Leu Glu Glu Val Met Pro Gln Ala
 65                  70                  75                  80

Glu Asn Gln Asp Pro Asp Ile Lys Ala His Val Asn Ser Leu Gly Glu
                     85                  90                  95

Asn Leu Lys Thr Leu Arg Leu Arg Leu Arg Arg Cys His Arg Phe Leu
                100                 105                 110

Pro Cys Glu Asn Lys Ser Lys Ala Val Glu Gln Val Lys Asn Ala Phe
                115                 120                 125

Asn Lys Leu Gln Glu Lys Gly Ile Tyr Lys Ala Met Ser Glu Phe Asp
                130                 135                 140

Ile Phe Ile Asn Tyr Ile Glu Ala Tyr Met Thr Met Lys Ile Arg Asn
145                 150                 155                 160

Gly Gly Ser Gly Gly Gly Ser Gly Gly Ser Pro Gly Gln Gly Thr
                165                 170                 175

Gln Ser Glu Asn Ser Cys Thr His Phe Pro Gly Asn Leu Pro Asn Met
                180                 185                 190

Leu Arg Asp Leu Arg Asp Ala Phe Ser Arg Val Lys Thr Phe Phe Gln
                195                 200                 205

Met Lys Asn Gln Leu Asp Asn Leu Leu Leu Lys Glu Ser Leu Leu Glu
                210                 215                 220

Asp Phe Lys Gly Tyr Leu Gly Cys Gln Ala Leu Ser Glu Met Ile Gln
225                 230                 235                 240

Phe Tyr Leu Glu Glu Val Met Pro Gln Ala Glu Asn Gln Asp Pro Asp
                245                 250                 255

Ile Lys Ala His Val Asn Ser Leu Gly Glu Asn Leu Lys Thr Leu Arg
                260                 265                 270

Leu Arg Leu Arg Arg Cys His Arg Phe Leu Pro Cys Glu Asn Lys Ser
                275                 280                 285

Lys Ala Val Glu Gln Val Lys Asn Ala Phe Asn Lys Leu Gln Glu Lys
                290                 295                 300

Gly Ile Tyr Lys Ala Met Ser Glu Phe Asp Ile Phe Ile Asn Tyr Ile
305                 310                 315                 320

Glu Ala Tyr Met Thr Met Lys Ile Arg Asn Gly Gly Gly Gly Ser Gly
                325                 330                 335

Gly Gly Gly Ser Arg Thr Val Ala Ala Pro Ser Val Phe Ile Phe Pro
                340                 345                 350

Pro Ser Asp Glu Gln Leu Lys Ser Gly Thr Ala Ser Val Val Cys Leu
                355                 360                 365

Leu Asn Asn Phe Tyr Pro Arg Glu Ala Lys Val Gln Trp Lys Val Asp
370                 375                 380

Asn Ala Leu Gln Ser Gly Asn Ser Gln Glu Ser Val Thr Glu Gln Asp
385                 390                 395                 400

Ser Lys Asp Ser Thr Tyr Ser Leu Ser Ser Thr Leu Thr Leu Ser Lys
                405                 410                 415

Ala Asp Tyr Glu Lys His Lys Val Tyr Ala Cys Glu Val Thr His Gln
                420                 425                 430

Gly Leu Ser Ser Pro Val Thr Lys Ser Phe Asn Arg Gly Glu Cys Gly
                435                 440                 445

Gly Gly Gly Ser Gly Gly Gly Gly Ser Gly Gly Gly Gly Ser Gly Gly
                450                 455                 460

Gly Gly Ser Ala Ser Thr Lys Gly Pro Ser Val Phe Pro Leu Ala Pro
465                 470                 475                 480
```

```
Ser Ser Lys Ser Thr Ser Gly Gly Thr Ala Ala Leu Gly Cys Leu Val
            485                 490                 495

Lys Asp Tyr Phe Pro Glu Pro Val Thr Val Ser Trp Asn Ser Gly Ala
            500                 505                 510

Leu Thr Ser Gly Val His Thr Phe Pro Ala Val Leu Gln Ser Ser Gly
            515                 520                 525

Leu Tyr Ser Leu Ser Ser Val Val Thr Val Pro Ser Ser Ser Leu Gly
            530                 535                 540

Thr Gln Thr Tyr Ile Cys Asn Val Asn His Lys Pro Ser Asn Thr Lys
545                 550                 555                 560

Val Asp Lys Arg Val Glu Pro Lys Ser Cys Asp Lys Thr His Thr Cys
            565                 570                 575

Pro Pro Cys Pro Ala Pro Glu Leu Leu Gly Gly Pro Ser Val Phe Leu
            580                 585                 590

Phe Pro Pro Lys Pro Lys Asp Thr Leu Met Ile Ser Arg Thr Pro Glu
            595                 600                 605

Val Thr Cys Val Val Val Asp Val Ser His Glu Asp Pro Glu Val Lys
            610                 615                 620

Phe Asn Trp Tyr Val Asp Gly Val Glu Val His Asn Ala Lys Thr Lys
625                 630                 635                 640

Pro Arg Glu Glu Gln Tyr Asn Ser Thr Tyr Arg Val Val Ser Val Leu
            645                 650                 655

Thr Val Leu His Gln Asp Trp Leu Asn Gly Lys Glu Tyr Lys Cys Lys
            660                 665                 670

Val Ser Asn Lys Ala Leu Pro Ala Pro Ile Glu Lys Thr Ile Ser Lys
            675                 680                 685

Ala Lys Gly Gln Pro Arg Glu Pro Gln Val Tyr Thr Leu Pro Pro Ser
            690                 695                 700

Arg Glu Glu Met Thr Lys Asn Gln Val Ser Leu Thr Cys Leu Val Lys
705                 710                 715                 720

Gly Phe Tyr Pro Ser Asp Ile Ala Val Glu Trp Glu Ser Asn Gly Gln
            725                 730                 735

Pro Glu Asn Asn Tyr Lys Thr Thr Pro Pro Val Leu Asp Ser Asp Gly
            740                 745                 750

Ser Phe Phe Leu Tyr Ser Lys Leu Thr Val Asp Lys Ser Arg Trp Gln
            755                 760                 765

Gln Gly Asn Val Phe Ser Cys Ser Val Met His Glu Ala Leu His Asn
            770                 775                 780

His Tyr Thr Gln Lys Ser Leu Ser Leu Ser Pro Gly Lys
785                 790                 795

<210> SEQ ID NO 45
<211> LENGTH: 325
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
            20                  25                  30

Val Lys Thr Phe Phe Gln Met Lys Asp Gln Leu Asp Asn Leu Leu Leu
```

```
                35                  40                  45
Lys Glu Ser Leu Leu Glu Asp Phe Lys Gly Tyr Leu Gly Cys Gln Ala
             50                  55                  60

Leu Ser Glu Met Ile Gln Phe Tyr Leu Glu Glu Val Met Pro Gln Ala
 65                  70                  75                  80

Glu Asn Gln Asp Pro Asp Ile Lys Ala His Val Asn Ser Leu Gly Glu
                 85                  90                  95

Asn Leu Lys Thr Leu Arg Leu Arg Leu Arg Arg Cys His Arg Phe Leu
            100                 105                 110

Pro Cys Glu Asn Lys Ser Lys Ala Val Glu Gln Val Lys Asn Ala Phe
        115                 120                 125

Asn Lys Leu Gln Glu Lys Gly Ile Tyr Lys Ala Met Ser Glu Phe Asp
    130                 135                 140

Ile Phe Ile Asn Tyr Ile Glu Ala Tyr Met Thr Met Lys Ile Arg Asn
145                 150                 155                 160

Gly Gly Ser Gly Gly Ser Pro Gly Gln Gly Thr Gln Ser Glu Asn Ser
                165                 170                 175

Cys Thr His Phe Pro Gly Asn Leu Pro Asn Met Leu Arg Asp Leu Arg
            180                 185                 190

Asp Ala Phe Ser Arg Val Lys Thr Phe Phe Gln Met Lys Asp Gln Leu
        195                 200                 205

Asp Asn Leu Leu Leu Lys Glu Ser Leu Leu Glu Asp Phe Lys Gly Tyr
    210                 215                 220

Leu Gly Cys Gln Ala Leu Ser Glu Met Ile Gln Phe Tyr Leu Glu Glu
225                 230                 235                 240

Val Met Pro Gln Ala Glu Asn Gln Asp Pro Asp Ile Lys Ala His Val
                245                 250                 255

Asn Ser Leu Gly Glu Asn Leu Lys Thr Leu Arg Leu Arg Leu Arg Arg
            260                 265                 270

Cys His Arg Phe Leu Pro Cys Glu Asn Lys Ser Lys Ala Val Glu Gln
        275                 280                 285

Val Lys Asn Ala Phe Asn Lys Leu Gln Glu Lys Gly Ile Tyr Lys Ala
    290                 295                 300

Met Ser Glu Phe Asp Ile Phe Ile Asn Tyr Ile Glu Ala Tyr Met Thr
305                 310                 315                 320

Met Lys Ile Arg Asn
            325

<210> SEQ ID NO 46
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Ser Pro Gly Gln Gly Thr Gln Ser Glu Asn Ser Cys Thr His Phe Pro
  1               5                  10                  15

Gly Asn Leu Pro Asn Met Leu Arg Asp Leu Arg Asp Ala Phe Ser Arg
             20                  25                  30

Val Lys Thr Phe Phe Gln Met Lys Asp Gln Leu Asp Asn Leu Leu Leu
         35                  40                  45

Lys Glu Ser Leu Leu Glu Asp Phe Lys Gly Tyr Leu Gly Cys Gln Ala
     50                  55                  60
```

```
Leu Ser Glu Met Ile Gln Phe Tyr Leu Glu Val Met Pro Gln Ala
 65                  70                  75                  80

Glu Asn Gln Asp Pro Asp Ile Lys Ala His Val Asn Ser Leu Gly Glu
             85                  90                  95

Asn Leu Lys Thr Leu Arg Leu Arg Leu Arg Arg Cys His Arg Phe Leu
            100                 105                 110

Pro Cys Glu Asn Lys Ser Lys Ala Val Glu Gln Val Lys Asn Ala Phe
        115                 120                 125

Asn Lys Leu Gln Glu Lys Gly Ile Tyr Lys Ala Met Ser Glu Phe Asp
    130                 135                 140

Ile Phe Ile Asn Tyr Ile Glu Ala Tyr Met Thr Met Lys Ile Arg Asn
145                 150                 155                 160

Gly Gly Ser Gly Gly Gly Ser Gly Gly Ser Pro Gly Gln Gly Thr
                165                 170                 175

Gln Ser Glu Asn Ser Cys Thr His Phe Pro Gly Asn Leu Pro Asn Met
                180                 185                 190

Leu Arg Asp Leu Arg Asp Ala Phe Ser Arg Val Lys Thr Phe Phe Gln
                195                 200                 205

Met Lys Asp Gln Leu Asp Asn Leu Leu Leu Lys Glu Ser Leu Leu Glu
            210                 215                 220

Asp Phe Lys Gly Tyr Leu Gly Cys Gln Ala Leu Ser Glu Met Ile Gln
225                 230                 235                 240

Phe Tyr Leu Glu Glu Val Met Pro Gln Ala Glu Asn Gln Asp Pro Asp
                245                 250                 255

Ile Lys Ala His Val Asn Ser Leu Gly Glu Asn Leu Lys Thr Leu Arg
            260                 265                 270

Leu Arg Leu Arg Arg Cys His Arg Phe Leu Pro Cys Glu Asn Lys Ser
        275                 280                 285

Lys Ala Val Glu Gln Val Lys Asn Ala Phe Asn Lys Leu Gln Glu Lys
    290                 295                 300

Gly Ile Tyr Lys Ala Met Ser Glu Phe Asp Ile Phe Ile Asn Tyr Ile
305                 310                 315                 320

Glu Ala Tyr Met Thr Met Lys Ile Arg Asn
                325                 330

<210> SEQ ID NO 47

<400> SEQUENCE: 47

000

<210> SEQ ID NO 48
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Met Tyr Arg Met Gln Leu Leu Ser Cys Ile Ala Leu Ser Leu Ala Leu
 1               5                  10                  15

Val Thr Asn Ser
            20

<210> SEQ ID NO 49
<211> LENGTH: 6
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: a, c, t, g, unknown or other

<400> SEQUENCE: 49 cncaat                                                                        6

<210> SEQ ID NO 50
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50 aataaa                                                                        6

<210> SEQ ID NO 51
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Glu Pro Lys Ser Ser Asp Lys Thr His Thr Cys Pro Pro Cys Pro
1               5                   10                  15

<210> SEQ ID NO 52
<211> LENGTH: 622
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Met Tyr Arg Met Gln Leu Leu Ser Cys Ile Ala Leu Ser Leu Ala Leu
1               5                   10                  15

Val Thr Asn Ser Ser Pro Gly Gln Gly Thr Gln Ser Glu Asn Ser Cys
                20                  25                  30

Thr His Phe Pro Gly Asn Leu Pro Asn Met Leu Arg Asp Leu Arg Asp
            35                  40                  45

Ala Phe Ser Arg Val Lys Thr Phe Phe Gln Met Lys Asp Gln Leu Asp
        50                  55                  60

Asn Leu Leu Leu Lys Glu Ser Leu Leu Glu Asp Phe Lys Gly Tyr Leu
65                  70                  75                  80

Gly Cys Gln Ala Leu Ser Glu Met Ile Gln Phe Tyr Leu Glu Glu Val
                85                  90                  95

Met Pro Gln Ala Glu Asn Gln Asp Pro Asp Ile Lys Ala His Val Asn
            100                 105                 110

Ser Leu Gly Glu Asn Leu Lys Thr Leu Arg Leu Arg Leu Arg Arg Cys
        115                 120                 125

His Arg Phe Leu Pro Cys Glu Asn Lys Ser Lys Ala Val Glu Gln Val
    130                 135                 140

Lys Asn Ala Phe Asn Lys Leu Gln Glu Lys Gly Ile Tyr Lys Ala Met
```

-continued

```
            145                 150                 155                 160
Ser Glu Phe Asp Ile Phe Ile Asn Tyr Ile Glu Ala Tyr Met Thr Met
                    165                 170                 175
Lys Ile Arg Asn Gly Ser Gly Ser Pro Gly Gln Gly Thr Gln
                180                 185                 190
Ser Glu Asn Ser Cys Thr His Phe Pro Gly Asn Leu Pro Asn Met Leu
                    195                 200                 205
Arg Asp Leu Arg Asp Ala Phe Ser Arg Val Lys Thr Phe Phe Gln Met
        210                 215                 220
Lys Asp Gln Leu Asp Asn Leu Leu Lys Glu Ser Leu Leu Glu Asp
225                 230                 235                 240
Phe Lys Gly Tyr Leu Gly Cys Gln Ala Leu Ser Glu Met Ile Gln Phe
                    245                 250                 255
Tyr Leu Glu Glu Val Met Pro Gln Ala Glu Asn Gln Asp Pro Asp Ile
                260                 265                 270
Lys Ala His Val Asn Ser Leu Gly Glu Asn Leu Lys Thr Leu Arg Leu
                275                 280                 285
Arg Leu Arg Arg Cys His Arg Phe Leu Pro Cys Glu Asn Lys Ser Lys
        290                 295                 300
Ala Val Glu Gln Val Lys Asn Ala Phe Asn Lys Leu Gln Glu Lys Gly
305                 310                 315                 320
Ile Tyr Lys Ala Met Ser Glu Phe Asp Ile Phe Ile Asn Tyr Ile Glu
                    325                 330                 335
Ala Tyr Met Thr Met Lys Ile Arg Asn Ser Gly Ser Gly Ala Ser
                340                 345                 350
Ser Glu Ser Ser Ala Ser Ser Asp Gly Pro His Pro Val Ile Thr Glu
            355                 360                 365
Ser Arg Ala Ser Ser Glu Ser Ala Ser Ser Asp Gly Pro His Pro
        370                 375                 380
Val Ile Thr Glu Ser Arg Glu Pro Lys Ser Ser Asp Lys Thr His Thr
385                 390                 395                 400
Cys Pro Pro Cys Pro Ala Pro Glu Leu Leu Gly Gly Pro Ser Val Phe
                405                 410                 415
Leu Phe Pro Pro Lys Pro Lys Asp Thr Leu Met Ile Ser Arg Thr Pro
                420                 425                 430
Glu Val Thr Cys Val Val Val Asp Val Ser His Glu Asp Pro Glu Val
                435                 440                 445
Lys Phe Asn Trp Tyr Val Asp Gly Val Glu Val His Asn Ala Lys Thr
        450                 455                 460
Lys Pro Arg Glu Glu Gln Tyr Asn Ser Thr Tyr Arg Val Val Ser Val
465                 470                 475                 480
Leu Thr Val Leu His Gln Asp Trp Leu Asn Gly Lys Glu Tyr Lys Cys
                    485                 490                 495
Lys Val Ser Asn Lys Ala Leu Pro Ala Pro Ile Glu Lys Thr Ile Ser
                500                 505                 510
Lys Ala Lys Gly Gln Pro Arg Glu Pro Gln Val Tyr Thr Leu Pro Pro
            515                 520                 525
Ser Arg Glu Glu Met Thr Lys Asn Gln Val Ser Leu Thr Cys Leu Val
        530                 535                 540
Lys Gly Phe Tyr Pro Ser Asp Ile Ala Val Glu Trp Glu Ser Asn Gly
545                 550                 555                 560
Gln Pro Glu Asn Asn Tyr Lys Thr Thr Pro Pro Val Leu Asp Ser Asp
                565                 570                 575
```

```
Gly Ser Phe Phe Leu Tyr Ser Lys Leu Thr Val Asp Lys Ser Arg Trp
            580                 585                 590

Gln Gln Gly Asn Val Phe Ser Cys Ser Val Met His Glu Ala Leu His
        595                 600                 605

Asn His Tyr Thr Gln Lys Ser Leu Ser Leu Ser Pro Gly Lys
        610                 615                 620

<210> SEQ ID NO 53
<211> LENGTH: 802
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
            20                  25                  30

Val Lys Thr Phe Phe Gln Met Lys Asp Gln Leu Asp Asn Leu Leu Leu
        35                  40                  45

Lys Glu Ser Leu Leu Glu Asp Phe Lys Gly Tyr Leu Gly Cys Gln Ala
    50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
                85                  90                  95

Asn Leu Lys Thr Leu Arg Leu Arg Leu Arg Arg Cys His Arg Phe Leu
            100                 105                 110

Pro Cys Glu Asn Lys Ser Lys Ala Val Glu Gln Val Lys Asn Ala Phe
        115                 120                 125

Asn Lys Leu Gln Glu Lys Gly Ile Tyr Lys Ala Met Ser Glu Phe Asp
    130                 135                 140

Ile Phe Ile Asn Tyr Ile Glu Ala Tyr Met Thr Met Lys Ile Arg Asn
145                 150                 155                 160

Gly Gly Ser Gly Gly Gly Ser Gly Gly Ser Pro Gly Gln Gly Thr
                165                 170                 175

Gln Ser Glu Asn Ser Cys Thr His Phe Pro Gly Asn Leu Pro Asn Met
            180                 185                 190

Leu Arg Asp Leu Arg Asp Ala Phe Ser Arg Val Lys Thr Phe Phe Gln
        195                 200                 205

Met Lys Asp Gln Leu Asp Asn Leu Leu Leu Lys Glu Ser Leu Leu Glu
    210                 215                 220

Asp Phe Lys Gly Tyr Leu Gly Cys Gln Ala Leu Ser Glu Met Ile Gln
225                 230                 235                 240

Phe Tyr Leu Glu Glu Val Met Pro Gln Ala Glu Asn Gln Asp Pro Asp
                245                 250                 255

Ile Lys Ala His Val Asn Ser Leu Gly Glu Asn Leu Lys Thr Leu Arg
            260                 265                 270

Leu Arg Leu Arg Arg Cys His Arg Phe Leu Pro Cys Glu Asn Lys Ser
        275                 280                 285

Lys Ala Val Glu Gln Val Lys Asn Ala Phe Asn Lys Leu Gln Glu Lys
    290                 295                 300

Gly Ile Tyr Lys Ala Met Ser Glu Phe Asp Ile Phe Ile Asn Tyr Ile
```

```
              305                 310                 315                 320
        Glu Ala Tyr Met Thr Met Lys Ile Arg Asn Gly Gly Gly Ser Gly
                            325                 330                 335
        Gly Gly Gly Ser Ala Ser Thr Lys Gly Pro Ser Val Phe Pro Leu Ala
                        340                 345                 350
        Pro Ser Ser Lys Ser Thr Ser Gly Gly Thr Ala Ala Leu Gly Cys Leu
                        355                 360                 365
        Val Lys Asp Tyr Phe Pro Glu Pro Val Thr Val Ser Trp Asn Ser Gly
            370                 375                 380
        Ala Leu Thr Ser Gly Val His Thr Phe Pro Ala Val Leu Gln Ser Ser
        385                 390                 395                 400
        Gly Leu Tyr Ser Leu Ser Ser Val Val Thr Val Pro Ser Ser Ser Leu
                        405                 410                 415
        Gly Thr Gln Thr Tyr Ile Cys Asn Val Asn His Lys Pro Ser Asn Thr
                        420                 425                 430
        Lys Val Asp Lys Arg Val Gly Gly Gly Ser Gly Gly Gly Gly Ser
            435                 440                 445
        Gly Gly Gly Gly Ser Gly Gly Gly Ser Arg Thr Val Ala Ala Pro
            450                 455                 460
        Ser Val Phe Ile Phe Pro Pro Ser Asp Glu Gln Leu Lys Ser Gly Thr
        465                 470                 475                 480
        Ala Ser Val Val Cys Leu Leu Asn Asn Phe Tyr Pro Arg Glu Ala Lys
                        485                 490                 495
        Val Gln Trp Lys Val Asp Asn Ala Leu Gln Ser Gly Asn Ser Gln Glu
                        500                 505                 510
        Ser Val Thr Glu Gln Asp Ser Lys Asp Ser Thr Tyr Ser Leu Ser Ser
                        515                 520                 525
        Thr Leu Thr Leu Ser Lys Ala Asp Tyr Glu Lys His Lys Val Tyr Ala
                        530                 535                 540
        Cys Glu Val Thr His Gln Gly Leu Ser Ser Pro Val Thr Lys Ser Phe
        545                 550                 555                 560
        Asn Arg Gly Glu Cys Gly Gly Ser Gly Gly Glu Pro Lys Ser Cys Asp
                        565                 570                 575
        Lys Thr His Thr Cys Pro Pro Cys Pro Ala Pro Glu Leu Leu Gly Gly
                        580                 585                 590
        Pro Ser Val Phe Leu Phe Pro Pro Lys Pro Lys Asp Thr Leu Met Ile
                        595                 600                 605
        Ser Arg Thr Pro Glu Val Thr Cys Val Val Val Asp Val Ser His Glu
                        610                 615                 620
        Asp Pro Glu Val Lys Phe Asn Trp Tyr Val Asp Gly Val Glu Val His
        625                 630                 635                 640
        Asn Ala Lys Thr Lys Pro Arg Glu Glu Gln Tyr Asn Ser Thr Tyr Arg
                        645                 650                 655
        Val Val Ser Val Leu Thr Val Leu His Gln Asp Trp Leu Asn Gly Lys
                        660                 665                 670
        Glu Tyr Lys Cys Lys Val Ser Asn Lys Ala Leu Pro Ala Pro Ile Glu
                        675                 680                 685
        Lys Thr Ile Ser Lys Ala Lys Gly Gln Pro Arg Glu Pro Gln Val Tyr
                        690                 695                 700
        Thr Leu Pro Pro Ser Arg Glu Glu Met Thr Lys Asn Gln Val Ser Leu
        705                 710                 715                 720
        Thr Cys Leu Val Lys Gly Phe Tyr Pro Ser Asp Ile Ala Val Glu Trp
                        725                 730                 735
```

```
Glu Ser Asn Gly Gln Pro Glu Asn Asn Tyr Lys Thr Pro Pro Val
            740                 745                 750

Leu Asp Ser Asp Gly Ser Phe Phe Leu Tyr Ser Lys Leu Thr Val Asp
        755                 760                 765

Lys Ser Arg Trp Gln Gln Gly Asn Val Phe Ser Cys Ser Val Met His
    770                 775                 780

Glu Ala Leu His Asn His Tyr Thr Gln Lys Ser Leu Ser Leu Ser Pro
785                 790                 795                 800

Gly Lys

<210> SEQ ID NO 54
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(25)
<223> OTHER INFORMATION: This sequence may encompass 1-5
      "Gly Gly Gly Gly Ser" repeating units
<220> FEATURE:
<223> OTHER INFORMATION: See specification as filed for detailed
      description of substitutions and preferred embodiments

<400> SEQUENCE: 54

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25
```

COMPOSITIONS AND METHODS FOR MODULATING IL-10 IMMUNOSTIMULATORY AND ANTI-INFLAMMATORY PROPERTIES

RELATED APPLICATIONS

This application is a division of U.S. application Ser. No. 15/630,341, filed Jun. 22, 2017, which claims the benefit of U.S. Provisional Application No. 62/353,478, filed Jun. 22, 2016. The entire teachings of the above applications are incorporated herein by reference.

BACKGROUND OF THE INVENTION

IL-10 is considered a potent anti-inflammatory cytokine that strongly inhibits the production of inflammatory mediators. However, recent studies have suggested that IL-10 also has immunostimulatory properties on $CD4^+$, $CD8^+$ T cells, and/or NK cells, resulting in increased IFN-γ production which in turn may lead to related inflammatory responses in humans.

Despite encouraging pre-clinical data suggesting this cytokine as therapeutically valuable biological, results of clinical trials evaluating the merit of IL-10 administration in chronic inflammation have been preponderantly disappointing. Bulk of pre-clinical data and analysis of patients with IL-10 or IL-10 receptor defects clearly point to endogenously produced IL-10 as potent and significant anti-inflammatory determinant. However, thorough analysis further suggests that IL-10 has the potential to acquire sharply contrasting properties in an inflammatory environment in vivo. In recent years several studies have been performed in order to verify the human response upon IL-10 administration, particularly in view of its anti-inflammatory potential. Those clinically important studies disclosed perplexing pro-inflammatory functions of IL-10. However, the basis of IL-10 immunostimulatory action remains unclear.

On the other hand, IL-10 has been explored for use in the treatment of proliferative disorders, e.g., cancer, tumors, etc. IL-10 induces cytotoxic activity of CD8 T-cells, antibody production of B-cell and suppresses macrophage activity and tumor promoting inflammation. IL-10 appears to increase the infiltration of CD8+ T cells to a tumor, as well as increasing the expression of inflammatory cytokines that play a role in tumor immunity. Treatment with IL-10 may provide a significant improvement for tumor treatment.

One drawback of using IL-10 and particularly any form of recombinant IL-10 in therapy is its short serum half-life. One strategy for increasing serum half-life of a therapeutic protein such as IL-10 is to attach the protein to an Fc (fragment crystallizable) domain of an antibody. Many such fusion proteins are capable of forming homodimers or heterodimers thereby forming antibody-like fusion protein molecules.

Depending on the therapeutic application, the ability to selectively enhance either the anti-inflammatory activity or the immunostimulatory activity of IL-10 would be desired. It would also be desirable to increase the half-life of recombinant IL-10.

SUMMARY OF THE INVENTION

The invention provides compositions and methods for modulating the immunostimulatory properties and/or anti-inflammatory properties of IL-10. The present invention provides scIL-10 polypeptides of Formula 1. The polypeptides of the invention are optionally linked to a fusion partner. The polypeptides of Formula 1 are referred to herein as "scIL-10" polypeptides and comprise an amino acid sequence arrangement from N-terminus to C-terminus in accordance with Formula 1:

(first monomer subunit)-LINKER-(second monomer subunit)  Formula 1 wherein the first monomer subunit, the second monomer subunit or both the first and second monomer subunits may be independently selected from: an unsubstituted IL-10 monomer subunit; or a substituted IL-10 monomer subunit comprising at least one amino acid substitution; and wherein LINKER is any amino acid linker of at least 1-100 amino acids in length.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale emphasis instead being placed upon illustrating the principles of the invention.

DETAILED DESCRIPTION OF THE INVENTION

Definitions

Figure 1:
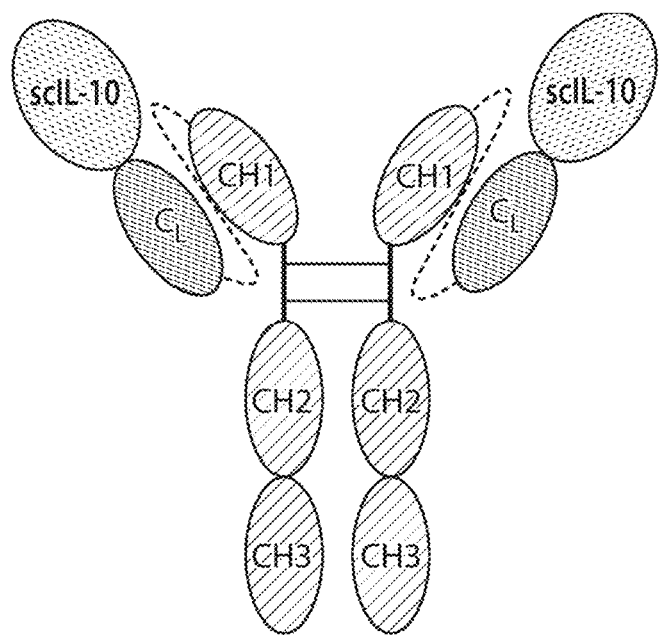
FIG. 1 is a diagram of an Fc fusion protein homodimer of two polypeptide chains, wherein in each polypeptide chain comprises as X, scIL-10 which is then fused to the Fc region of an IgG1 antibody via an scCLCH1 linker.

By "polypeptide" is meant any sequence of two or more amino acids, regardless of length, post-translation modification, or function. "Polypeptide," "peptide," and "protein"

are used interchangeably herein. Polypeptides can include natural amino acids and non-natural amino acids. Polypeptides can also be modified in any of a variety of standard chemical ways (e.g., an amino acid can be modified with a protecting group; the carboxy-terminal amino acid can be made into a terminal amide group; the amino-terminal residue can be modified with groups to, e.g., enhance lipophilicity; or the polypeptide can be chemically glycosylated or otherwise modified to increase stability or in vivo half-life). Polypeptide modifications can include the attachment of another structure such as a cyclic compound or other molecule to the polypeptide and can also include polypeptides that contain one or more amino acids in an altered configuration (i.e., R or S; or, L or D).

As used herein, "antibody" and "immunoglobulin" are used interchangeably and refer to a polypeptide substantially encoded by an immunoglobulin gene or immunoglobulin genes, or fragments thereof, which specifically bind and recognize an antigen. Identified immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD, and IgE, respectively. Terms understood by those in the art of antibody technology are each given the meaning acquired in the art, unless expressly defined differently herein. Antibodies are known to have variable regions, a hinge region, and constant domains. Immunoglobulin structure and function are reviewed, for example, in Harlow et al, Eds., Antibodies: A Laboratory Manual, Chapter 14 (Cold Spring Harbor Laboratory, Cold Spring Harbor, 1988).

The invention provides functional variants of the fusion proteins of Formulas 1 and 2 and functional portions thereof. A "functional variant" of a fusion protein of Formulas 1 and 2 as used herein refers to a polypeptide or protein having substantial or significant sequence identity to a polypeptide or protein of Formula 1 or Formula 2, which functional variant retains the biological activity of the polypeptide of Formula 1 or Formula 2 of which it is a variant. Functional variants encompass for example, those variants of Formulas 1 and 2 that retain the ability to recognize target cells and target receptors to a similar extent or the same extent, or a higher extent as compared to the peptide of Formula 1 or 2. For example an amino acid sequence encoding a functional variant of a peptide of Formula 1 or Formula 2 can be about 50% identical, about 60% identical, about 70% identical, about 80% identical about 90% identical, about 95% identical, about 98% identical, about 99% identical to the amino acid sequence of a peptide of Formula 1 or 2.

The term "functional portion" of the peptides of Formulas 1 and 2 refers to any part or fragment of the peptides of Formulas 1 and 2 which retains the biological activity of a peptide of Formulas 1 or 2 from which the functional portion is derived. For example, a functional portion of a peptide of Formula 1 or Formula 2 may comprise an amino acid sequence comprising about 10%, 25%, 30%, 50%, 60%, 70%, 80%, 90% or more of the parent peptide of Formula 1 or Formula 2. A functional portion of a peptide of Formula 1 or Formula 1 may comprise additional amino acids at the amino or carboxy terminus portion, or at both termini, which additional amino acids are not found in the amino acid sequence of the parent protein of Formula 1 or Formula 2. Preferably, the additional amino acids do not interfere with the biological function of the functional portion.

Sequences similar or homologous (e.g., at least about 70% sequence identity) to the sequences disclosed herein are also part of the invention. In some embodiments, the sequence identity at the amino acid level can be about 70%, 80%, 85%, 90%, 91%, 92%, 93%, 94%, 95%, 96%, 97%, 98%, 99% or higher. At the nucleic acid level, the sequence identity can be about 70%, 75%, 80%, 85%, 90%, 91%, 92%, 93%, 94%, 95%, 96%, 97%, 98%, 99% or higher. Alternatively, substantial identity exists when the nucleic acid segments will hybridize under selective hybridization conditions (e.g., very high stringency hybridization conditions), to the complement of the strand. The nucleic acids may be present in whole cells, in a cell lysate, or in a partially purified or substantially pure form.

Calculations of "homology" or "sequence identity" or "similarity" between two sequences (the terms are used interchangeably herein) are performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "homology" is equivalent to amino acid or nucleic acid "identity"). The percent identity between the two sequences is a function of the number of identical positions shared by the sequences, taking into account the number of gaps, and the length of each gap, which need to be introduced for optimal alignment of the two sequences. In the case of circularly related proteins, the sequence of one of the partners needs to be appropriately split and aligned in two sections to achieve optimal alignment of the functionally equivalent residues necessary to calculate the percent identity.

Amino acid and nucleotide sequence alignments and homology, similarity or identity, as defined herein are preferably prepared and determined using the algorithm BLAST 2 Sequences, using default parameters (Tatusova, T. A. et al., FEMS Microbiol Lett, 174:187-188 (1999)). Alternatively, the BLAST algorithm (version 2.0) is employed for sequence alignment, with parameters set to default values. BLAST (Basic Local Alignment Search Tool) is the heuristic search algorithm employed by the programs blastp, blastn, blastx, tblastn, and tblastx; these programs ascribe significance to their findings using the statistical methods of Karlin and Altschul, 1990, Proc. Natl. Acad. Sci. USA 87(6):2264-8.

The notations "mg/kg", or "mg per kg" refer to milligrams per kilogram. All notations are used interchangeably throughout the present disclosure.

The "half-life" of a polypeptide can generally be defined as the time taken for the serum concentration of the polypeptide to be reduced by 50%, in vivo, for example due to degradation of the polypeptide and/or clearance or sequestration of the polypeptide by natural mechanisms. The half-life can be determined in any manner known per se, such as by pharmacokinetic analysis. Suitable techniques will be clear to the person skilled in the art, and may, for example, generally involve the steps of administering a suitable dose of a polypeptide to a rodent or primate; collecting blood samples or other samples from a rodent or primate at regular intervals; determining the level or concentration of the polypeptide in said blood sample; and calculating, from (a plot of) the data thus obtained, the time until the level or concentration of the polypeptide has been reduced by 50% compared to the initial level upon dosing. Methods for determining half-life may be found, for example, in Kenneth et al., Chemical Stability of Pharmaceuticals: A Handbook for Pharmacists (1986); Peters et al, Pharmacokinete analysis: A Practical Approach (1996); and "Pharmacokinetics", M Gibaldi & D Perron, published by Marcel Dekker, 2nd Rev. edition (1982).

The half-life of a fusion polypeptide is increased if presence in a biological matrix (blood, serum, plasma, tissue) persists, in vivo, for a longer period as compared to an appropriate control. Half-life may be increased by 10%, 20%, 30%, 40%, 50% or more as compared to an appropriate control.

Half-life can be expressed using parameters such as the $t_{1/2\text{-}alpha}$, $t_{1/2\text{-}beta}$, and HL_Lambda_z. In the present specification, an "increase in half-life" refers to an increase in any one of these parameters, any two of these parameters, or all three of these parameters. An "increase in half-life" in particular refers to an increase in the $t_{1/2}$-beta and/or HL_Lambda_z, either with or without an increase in the $t_{1/2}$-alpha. Other PK parameters that can be assessed include volume of distribution (VD), clearance (CL), and mean residence time (MRT), and the area under the curve (AUC). In the present specification, a "change in pharmacokinetics" refers to changes in any one of these parameters, any two of these parameters, any three of these parameters, or all four of these parameters, in the presence or absence of changes in the half-life parameters listed above.

"Activity" for the purposes herein refers to an action or effect of a component of a fusion protein consistent with, but not necessarily identical to, that of the corresponding native active protein, wherein "biological activity" or "bioactivity" refers to an in vitro or in vivo biological function or effect, including but not limited to receptor binding, antagonist activity, agonist activity, or a cellular or physiologic response.

As used herein, a "dimer complex" comprises two single chains of sc-IL-10, or sc-IL-10 fused to an appropriate fusion partner such as, for example, the scIL-10-L1-HINGE-Fc fusion proteins of the invention, wherein the two single chain polypeptides are associated together under appropriate conditions via either non-covalent binding or covalent binding, for example, by a disulfide bridge. A "heterodimeric protein", "heterodimerized complex", or "heterodimer" as used interchangeably herein refers to a protein that is made of two single chain scIL-10-L1-HINGE-Fc polypeptides forming a dimer complex, wherein said two single chain polypeptides have different amino acid sequences. For example, one single chain peptide of the heterodimer has an scIL-10 based on Formula 1 with at least one amino acid substitution and the other single chain peptide of the heterodimer has an scIL-10 sequence based on Formula 1 with no amino acid substitutions. A "homodimeric protein" "homodimerized complex" or "homodimer" as used interchangeably herein, refers to a protein that is made of two identical or substantially identical polypeptides forming the dimer complex, wherein said two single chain polypeptides preferably share 100% identity. There are circumstances, especially with regard to larger polypeptides wherein a homodimer comprises two substantially identical polypeptides having at least about 95% or at least about 99% identity, wherein any amino acid differences between the two polypeptide chains comprise amino acid substitutions, additions or deletions which do not affect the functional and physical properties of the polypeptide compared to its partner polypeptide of the homodimer such as, for example, conservative amino acid substitutions.

As used herein, a protein is "soluble" when it lacks any transmembrane domain or protein domain that anchors or integrates the polypeptide into the membrane of a cell expressing such polypeptide.

As used herein, "Fc domain", "Fc region" or "Fc portion" as those terms may be used interchangeably herein to describe an scIL-10-L1-HINGE-Fc fusion protein of the invention, encompasses domains derived from the constant region of an immunoglobulin, preferably a human immunoglobulin, including a fragment, analog, variant, mutant or derivative of the constant region. Suitable immunoglobulins include IgG1, IgG2, IgG3, IgG4, and other classes such as IgA, IgD, IgE and IgM. The constant region of an immunoglobulin is defined as a naturally-occurring or synthetically-produced polypeptide homologous to the immunoglobulin C-terminal region, and can include a CH1 domain, a hinge, a CH2 domain, a CH3 domain, or a CH4 domain, separately or in combination.

As used herein, "treatment" or "treating," or "palliating" or "ameliorating" is used interchangeably herein. These terms refer to an approach for obtaining beneficial or desired results including but not limited to a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the subject, notwithstanding that the subject may still be afflicted with the underlying disorder.

For prophylactic benefit, the compositions may be administered to a subject at risk of developing a particular disease, or to a subject reporting one or more of the physiological symptoms of a disease, even though a diagnosis of this disease may not have been made.

A "therapeutic effect", as used herein, refers to a physiologic effect, including but not limited to the cure, mitigation, amelioration, or prevention of disease in humans or other animals, or to otherwise enhance physical or mental well-being of humans or animals, caused by a fusion protein of the invention.

The terms "therapeutically effective amount" and "therapeutically effective dose", as used herein, refers to an amount of an active protein, either alone or as a part of a fusion protein composition, that is capable of having any detectable, beneficial effect on any symptom, aspect, measured parameter or characteristics of a disease state or condition when administered in one or repeated doses to a subject. Such effect need not be absolute to be beneficial.

The term "therapeutically effective dose regimen", as used herein, refers to a schedule for consecutively administered doses of an active protein, either alone or as a part of a fusion protein composition, wherein the doses are given in therapeutically effective amounts to result in sustained beneficial effect on any symptom, aspect, measured parameter or characteristics of a disease state or condition.

As used herein the "anti-inflammatory window" is defined as the range of scIL-10 concentrations that produce anti-inflammatory effects on PBMCs/macrophages, while not inducing immunostimulatory effects (on CD8 T cells, NK cells, etc. . . . ). For example, two assays are used in the Examples to define the potencies of those two bioactivities:
1) PBMC cytokine release assay: yields an IC50 value (usually in the low picomolar range) for the concentration at which anti-inflammatory effects occur as measured by inhibition of release of TNF-alpha (TNFα); and
2) MC/9 proliferation assay: yields an EC50 value (usually in the high picomolar to nanomolar range) for the concentration at which immunostimulation effects occur.

The ratio in Tables 11 and 12 is the ratio of (MC/9 EC50)/(PBMC IC50) values. These two assays represent an approximation of the two types of activities. IL-10 targets cell populations within PBMCs to suppress their release of pro-inflammatory cytokines upon LPS stimulation, and IL-10 drives the proliferation of MC/9 cells at concentrations relevant to its immunostimulatory effects. There are many other potential assays that may be used to address the anti-inflammatory window size of the molecules of the invention. However, it is understood that both the immunostimulatory and anti-inflammatory effects of scIL-10 occur in a wider number of cell types.

scIL-10

Human wild-type IL-10 (wtIL-10) is a non-covalently linked dimer protein comprising two identical monomer subunits. Each identical monomer subunit of human wild type IL-10 (wtIL-10) has the following amino acid sequence (absent the leader sequence):

(SEQ ID NO: 1)
SPGQGTQSENSCTHFPGNLPNMLRDLRDAFSRVKTFFQMKDQLDNLLLKE

SLLEDFKGYLGCQALSEMIQFYLEEVMPQAENQDPDIKAHVNSLGENLKT

LRLRLRRCHRFLPCENKSKAVEQVKNAFNKLQEKGIYKAMSEFDIFINYI

EAYMTMKIRN (UniProtKB-P22301[chain 19-178] of IL 10, Interleukin-10, Homosapiens). SEQ ID NO: 1 is also referred to herein as an "unsubstituted IL-10 monomer subunit". Amino Acid sequences based on SEQ ID NO: 1 that comprise at least one amino acid substitution are referred to herein as "substituted IL-10 monomer subunits". The invention also provides sequences that are functional variants of portions of SEQ ID NO: 1 and sequences that are preferably at least 70% or more identical to SEQ ID NO: 1.

The polypeptides of Formula 1 are referred to herein as "scIL-10" polypeptides and comprise an amino acid sequence arrangement from N-terminus to C-terminus in accordance with Formula 1:

(first monomer subunit)-LINKER-(second monomer subunit)    Formula 1 wherein the first monomer subunit, the second monomer subunit or both the first and second monomer subunits may be independently selected from: an unsubstituted IL-10 monomer subunit; or a substituted IL-10 monomer subunit comprising at least one amino acid substitution; and wherein LINKER is any amino acid linker of at least 1-100 amino acids in length.

Preferably, LINKER has a length of between at least 2 amino acids and less than 100 amino acids, such as for example between at least 2 amino acids and less than 75 amino acids, more preferably between at least 3 amino acids and less than 50 amino acids, such as for example between at least 4 amino acids and less than 25 amino acids, such as for example between at least 5 amino acids and less than 20 amino acids and even more preferably between at least 6 amino acids and less than 15 amino acids. More preferably, the linker has a length of between at least 3 amino acids and less than 10 amino acids. Most preferably, the linker has a length of 2, 3, 4, 5, 6, 7, 8, 9, 10, 11, 12, 13, 14 or 15 amino acids. Preferably, the linker is a flexible linker. Preferably, the flexible linker comprises or consists of the amino acids glycine, asparagine and/or serine. More preferably, the flexible linker comprises or consists of the amino acids glycine and serine.

Preferably the first monomer subunit and the second monomer subunit of Formula 1 are both unsubstituted IL-10 monomer subunits and each have the amino acid sequence of SEQ ID NO: 1. These peptides are also referred to herein as "unsubstituted seIl-10".

Preferably, scIL-10 peptides of Formula 1 comprise at least one amino acid substitution in either the first monomer subunit of Formula 1, the second monomer subunit of Formula 1, or in both the first and second monomer subunits of Formula 1. These scIl-10 proteins comprising substituted monomer subunits as compared to human wtscIL-10 of SEQ ID NO: 1 are also referred to herein as "scIL-10 variants".

A preferred scIL-10 peptide of the invention is referred to herein as "unsubstituted scIL-10 (10aa linker)" and has the following amino acid sequence:

(SEQ ID NO: 2)
SPGQGTQSENSCTHFPGNLPNMLRDLRDAFSRVKTFFQMKDQLDNLLLKE

SLLEDFKGYLGCQALSEMIQFYLEEVMPQAENQDPDIKAHVNSLGENLKT

LRLRLRRCHRFLPCENKSKAVEQVKNAFNKLQEKGIYKAMSEFDIFINYI

EAYMTMKIRN<u>GGSGGGGSGGS</u>PGQGTQSENSCTHFPGNLPNMLRDLRDAF

SRVKTFFQMKDQLDNLLLKESLLEDFKGYLGCQALSEMIQFYLEEVMPQA

ENQDPDIKAHVNSLGENLKTLRLRLRRCHRFLPCENKSKAVEQVKNAFNK

LQEKGIYKANISEFDIFINYIEAYMTMKIRN or a sequence that is 50%, 60%, 75%, 80%, 85%, 90%, 95%, 96%, 97%, 98%, or 99% identical to (SEQ ID NO: 2). The ten amino acid linker between the two IL-10 subunits at amino acids 179-188 is indicated by underlining. It is understood that other covalently linked IL-10 dimer proteins may include any suitable flexible peptide linker and may also be longer or shorter than the underlined sequence of SEQ ID NO: 2.

scIL-10 (10aa linker) as represented by SEQ ID NO: 2 comprises two unsubstituted scIL-10 monomer subunits each comprising the amino acid sequence of SEQ ID NO: 1 and as per Formula 1, a LINKER, wherein LINKER is 10 amino acids in length having the sequence: GGSGGGGSGG (SEQ ID NO: 3). Preferably LINKER of scIL-10 is not SEQ ID NO: 3 when the scIL-10 peptide of the invention comprises two unsubstituted scIL-10 monomer subunits of SEQ ID NO: 1.

Other preferred unsubstituted scIL-10 peptides of Formula 1 include peptides wherein LINKER is a 5 amino acid linker also referred to herein as "unsubstituted sc-IL10 (5aa linker)". One preferred five, amino acid linker is the sequence: GGSGG (SEQ ID NO: 4).

Other preferred unsubstituted scIL-10 peptides of Formula 1 include peptides wherein LINKER is a three amino acid linker also referred to herein as "unsubstituted sc-IL10

(3aa linker)". One preferred three, amino acid linker is the sequence is the sequence GGG.

The present invention is based in part on the discovery that fusion proteins comprising unsubstituted scIL-10 and scIL-10 comprising at least one amino acid substitution ("scIL-10 variants, possess a broad anti-inflammatory window. The present invention is also based in part on the discovery that certain amino acid substitutions of unsubstituted scIL-10 further increase the immunostimulatory $EC_{50}$. The ability to increase the immunostimulatory $EC_{50}$ while maintaining a low anti-inflammatory $IC_{50}$ provides several orders of magnitude increase in the anti-inflammatory window size as compared to, for example, wild-type IL-10 or other fusion proteins comprising IL-10 that are not modified in accordance with the invention.

Without being limited to any theory, it is believed that amino acid substitutions at the interface of scIL-10 with the IL-10R1 and/or IL-10 R2 receptor resulted in modulation of IL-10's immunostimulatory properties, anti-inflammatory properties or both.

It was found that an amino acid substitution at aspartic acid at position 41 (based on SEQ ID NO: 1) in the first monomer subunit or at aspartic acid at position 41 (based on SEQ ID NO: 1) of the second monomer subunit of scIL-10 of Formula 1 disrupts at least one of the scIL-10 interfaces with its IL-10R1 receptor thereby slightly weakening the anti-inflammatory potency while significantly weakening the immunostimulatory potency of scIL-10 resulting in an increase in the anti-inflammatory window. It was also found that mutations that disrupt scIL-10 at one interface with IL-10R1 on one of either the first or second monomer subunit and also disrupts scIL-10 at one interface with IL-10R2, (for example at the methionine at position 22 of SEQ ID NO: 1) on either the first or second monomer subunit that is not the same as the mutation that disrupts the IL-10 R1 interface provides an extremely large anti-inflammatory window.

It was also discovered that an amino acid substitution of isoleucine at position 87 (based on SEQ ID NO: 1) and which is believed to affect the binding to both IL-10R1 and IL-10R2 appears to have a similar effect as when scIL-10 is designed to disrupt IL-10R1 in one subunit and disrupt IL-10R2 in the other subunit. Without being limited to any theory, it is believed that the isoleucine at position 87 in human wtIL-10 modulates the interaction with both IL-10 receptors. See also, Ding et al, (2000) *J. Exp. Med.* 191(2): 213.

Preferably, the invention provides scIL-10 variants wherein at least one amino acid substitution (as compared to human wild type IL-10 of SEQ ID NO: 1) is introduced in the first and/or second monomer subunit of Formula 1. Preferably scIL-10 comprises at least one amino acid substitution at the interface of the IL-10R1 interface on only one of the first or second monomer subunits of Formula 1 but not both of the first or second monomer subunits of Formula 1. Even more preferably scIL-10 comprises at least one amino acid substitution at the interface of the IL-10R1 interface of only one of the first or second monomer subunits of Formula 1 and also comprises at least one amino acid substitution at an IL-10R2 interface on only one of the first or second monomer subunits of Formula that is not the same monomer subunit as the amino acid substitution at the IL-1-R1 interface.

Preferred amino acid substitutions for scIL-10 variants are based on the numbering of amino acids of SEQ ID NO: 1 and include the following mutations: methionine at position 22 and aspartic acid at position 41.

Preferably the invention provides scIL-10 variants wherein at least one amino acid is substituted at position 41 in the first or second monomer subunit of Formula 1 and at least one amino acid is substituted at position 22 in the first or second monomer subunit that is not the same subunit that comprises the amino acid substitution at position 41.

Preferably the invention provides scIL-10 variants wherein at least one amino acid is substituted at the isoleucine at position 87 of only the first monomer subunit or the second monomer subunit of Formula 1 but not at both monomer subunits.

Amino acid substitutions of methionine at position 22, aspartic acid at position 41 and isoleucine at position 87 may include substitution with any other amino acid. Either conservative or non-conservative amino acid substitutions can be made at one or more amino acid residues. Both conservative and non-conservative substitutions can be made. Conservative replacements are those that take place within a family of amino acids that are related in their side chains. Genetically encoded amino acids can be divided into four families: (1) acidic=aspartate, glutamate; (2) basic=lysine, arginine, histidine; (3) nonpolar (hydrophobic)=cysteine, alanine, valine, leucine, isoleucine, proline, phenylalanine, methionine, tryptophan, glycine, tyrosine; and (4) uncharged polar=asparagine, glutamine, serine, threonine. Non-polar may be subdivided into: strongly hydrophobic=alanine, valine, leucine, isoleucine, methionine, phenylalanine and moderately hydrophobic=glycine, proline, cysteine, tyrosine, tryptophan. In alternative fashion, the amino acid repertoire can be grouped as (1) acidic=aspartate, glutamate; (2) basic=lysine, arginine, histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide=asparagine, glutamine; and (6) sulfur-containing=cysteine and methionine.

Preferred amino acid substitutions for the first monomer subunit and/or the second monomer subunit in accordance with Formula 1 include the following substitutions: the methionine at position 22 to alanine (M22A); aspartic acid at position 41 to asparagine (D41N); aspartic acid at position 41 to alanine (D41A); aspartic acid at position 41 to phenylalanine (D41F); isoleucine at position 87 to alanine (I87A).

The invention is also based in part on the discovery that the immunostimulatory or anti-inflammatory activities of scIL-10 and scIL-10 variants can be further modulated by fusing scIL-10 or scIL-10 variants to fusion partners including, but not limited to, Fc polypeptides and modified Fc polypeptides such as single chain Fc fusion proteins, mucin linker Fc fusions, Fc polypeptides with truncated hinge regions. Other fusion partners include, but are not limited to: mucin domain polypeptides, albumin fusion proteins, transferrin proteins and other fusion partners not comprising an Fc domain.

Single Chain Fc Fusion Proteins of sc-IL10

Single chain Fc fusion proteins of the invention have the following arrangement from amino-terminus (N-terminus) to carboxy-terminus (C-terminus) as shown in Formula 2:

(scIL-10)-L1-HINGE:Fc  (Formula 2)

wherein, scIL-10 has the amino acid sequence of Formula 1; L1 is a linker having the following arrangement from amino-terminus to carboxy-terminus:

L2-CL-L3-CH1-L4  (Formula 3)

wherein,

L2 and L4 are independently polypeptide linkers or are independently absent,

L3 is a polypeptide linker;

CL is a constant region polypeptide from an immunoglobulin light chain; and

CH1 a constant region polypeptide from a CH1 domain of an immunoglobulin heavy chain;

HINGE is a hinge sequence of an immunoglobulin or is absent with the proviso that if HINGE is absent, L4 is present; and Fc is the carboxy-terminus of an immunoglobulin or any active fragment or derivative thereof.

In accordance with the invention, an scIL-10 of Formula 1 is fused to the N-terminal region of an immunoglobulin Fc region via a novel linker (L1) that is derived from the CL and CH1 domains of an immunoglobulin arranged as a single chain (sc) also referred to herein as "scCLCH1 linkers" (Formula 3).

The C-terminus of the CL region may be linked to the N-terminal region of a CH1 region via polypeptide linker L3. The N-terminus of the CL region may be fused to the C-terminus of scIL-10 of Formula 1 via an optional polypeptide linker L2. The C-terminus of the CH1 domain is linked to the Fc domain via an immunoglobulin hinge region (HINGE) or a polypeptide linker (L4) or both a hinge (HINGE) and a polypeptide linker (L4).

The C-terminus of the CH1 domain may also be linked to the N-terminus of a CL region via polypeptide linker L3. The N-terminus of the CH1 region may be fused to the C-terminus of scIL-10 of Formula 1 via an optional polypeptide linker L2. The C-terminus of the CL region is linked to the Fc region via an immunoglobulin hinge region (HINGE) or a polypeptide linker (L4) or both a hinge (HINGE) and a polypeptide linker (L4).

Preferably, L3 is selected from artificial flexible domains comprising amino acids selected from Gly (G), and/or Ser (S). Preferably, the linker is comprised of polypeptide of the general formula (Gly-Gly-Gly-Ser)n (SEQ ID NO: 5) or (Gly-Gly-Gly-Gly-Ser)n (SEQ ID NO: 6) wherein n is an integer from 1 to 10. Preferably, each linker is a polypeptide comprising from about 1 to about 100 amino acids, preferably about 1-50 amino acids, preferably about 1-25 amino acids, preferably about 1-15 amino acids preferably about 1-10 amino acids, preferably about 4-24 amino acids, preferably about 5-20 amino acids preferably about 5-15 amino acids and preferably about 5-10 amino acids. Preferably, the linker is (Gly-Gly-Gly-Gly-Ser) n (SEQ ID NO: 6) wherein n is 2 or 4.

L2 and L4 are independently selected from artificial flexible domains comprising amino acids selected from, for example, Gly (G), and Ser (S). Preferably, the linker is comprised of polypeptide of the general formula (Gly-Gly-Gly-Ser)n (SEQ ID NO: 5) or (Gly-Gly-Gly-Gly-Ser)n (SEQ ID NO: 6) wherein n is an integer from 1 to 10. Preferably, each linker is a polypeptide comprising from about 1 to about 100 amino acids, preferably about 1-50 amino acids, preferably about 1-25 amino acids, preferably about 1-15 amino acids preferably about 1-10 amino acids, preferably about 4-24 amino acids, preferably about 5-20 amino acids preferably about 5-15 amino acids and preferably about 5-10 amino acids. Preferably, the linker is (Gly-Gly-Gly-Gly-Ser)n (SEQ ID NO: 6) wherein n is 2 or 4.

L2, L3 and L4, may further comprise amino acids such as, for example, Lys (K), Thr (T), Glu (E), and Asp (D).

The CL region of the novel scCLCH1 linker (L1) may be substantially identical to the corresponding CL region of native immunoglobulins belonging to any of the immunoglobulin classes, i.e., IgA, IgD, IgE, IgG, or IgM or any of the IgG antibody subclasses, i.e., IgG1, IgG2, IgG3, and IgG4. The CL region (L1) may have amino acid sequence that is at least 50%, 60%, 75%, 80%, 85%, 90%, 95%, 96%, 97%, 98%, or 99% identical to the corresponding CL region of native immunoglobulins belonging to any of the immunoglobulin classes, i.e., IgA, IgD, IgE, IgG, or IgM or any of the IgG antibody subclasses, i.e., IgG1, IgG2, IgG3, and IgG4. If the CL region of L1 is a modified derivative or variant of a native CL region such modifications include, but are not limited to, amino acid insertions, deletions, substitutions and rearrangements. Preferably, the amino acid sequence of the CL region in accordance with the invention, is at least 80%, more preferably at least 85%, more preferably at least 90%, and more preferably at least 95% identical to the corresponding CL region of native immunoglobulins belonging to any of the immunoglobulin classes, i.e., IgA, IgD, IgE, IgG, or IgM or any of the IgG antibody subclasses, i.e., IgG1, IgG2, IgG3, and IgG4.

The CH1 region of the novel scCLCH1 linker (L1) may be substantially identical to the corresponding CH1 region of native immunoglobulins belonging to any of the immunoglobulin classes, i.e., IgA, IgD, IgE, IgG, or IgM or any of the IgG antibody subclasses, i.e., IgG1, IgG2, IgG3, and IgG4. The CH1 region of L1 may have amino acid sequence that is at least 50%, 60%, 75%, 80%, 85%, 90%, 95%, 96%, 97%, 98%, or 99% identical to the corresponding CH1 region of native immunoglobulins belonging to any of the immunoglobulin classes, i.e., IgA, IgD, IgE, IgG, or IgM or any of the IgG antibody subclasses, i.e., IgG1, IgG2, IgG3, and IgG4. If the CH1 region of the L1 linker is a modified derivative or variant of a native CH1 immunoglobulin region such modifications include, but are not limited to, amino acid insertions, deletions, substitutions and rearrangements. Preferably, the amino acid sequence of the CH1 region is at least 80%, more preferably at least 85%, more preferably at least 90%, and more preferably at least 95% identical to the corresponding CH1 region of native immunoglobulins belonging to any of the immunoglobulin classes, i.e., IgA, IgD, IgE, IgG, or IgM or any of the IgG antibody subclasses, i.e., IgG1, IgG2, IgG3, and IgG4.

The CH1 region and CL regions of L1 do not need to be identical to or a variant of, the corresponding regions of the same immunoglobulin class. For example, the CL region may be derived from the corresponding region of IgE and the CH1 region may be derived from the corresponding region of IgG.

Preferably, CL and CH1 of the scCLCH1 linker are derived from the corresponding CL and CH1 regions of IgG1, preferably human IgG1.

An exemplary CL region corresponding to the CL region of a human IgG1 (hIgG1) includes:

(SEQ ID NO: 7)
RTVAAPSVFIFPPSDEQLKSGTASVVCLLNNFYPREAKVQWKVDNALQSG

NSQESVTEQDSKDSTYSLSSTLTLSKADYEKHKVYACEVTHQGLSSPVTK

SFNRGES.

An exemplary CH1 region corresponding to the CH1 region of hIgG1 includes:

(SEQ ID NO: 8)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKRV.

The single chain Fc fusion proteins disclosed herein comprise an Fc region that includes at least a portion of the carboxy-terminus of an immunoglobulin heavy chain. For example, the Fc portion may comprise: a CH2 domain, a CH3 domain, a CH4 domain, a CH2-CH3 domain, a CH2-CH4 domain, a CH2-CH3-CH4 domain, a hinge-CH2 domain, a hinge-CH2-CH3 domain, a hinge-CH2-CH4 domain, or a hinge-CH2-CH3-CH4 domain. The Fc domain may be derived from antibodies belonging any of the immunoglobulin classes, i.e., IgA, IgD, IgE, IgG, or IgM or any of the IgG antibody subclasses, i.e., IgG1, IgG2, IgG3, and IgG4. Preferably, the Fc region is derived from IgG1 preferably human IgG1.

The Fc domain may be a naturally occurring Fc sequence belonging any of the immunoglobulin classes, i.e., IgA, IgD, IgE, IgG, or IgM or any of the IgG antibody subclasses, i.e., IgG1, IgG2, IgG3, and IgG4, including natural allelic or splice variants. Alternatively, the Fc domain may be a hybrid domain comprising a portion of an Fc domain from two or more different Ig isotypes, for example, an IgG2/IgG4 hybrid Fc domain. Preferably, the Fc domain is derived from a human immunoglobulin molecule. Alternatively, the Fc domain may be a humanized or deimmunized (removal of T cell epitopes which can activate helper T cells) version of an Fc domain from a non-human animal, including but not limited to mouse, rat, rabbit, and monkey.

The Fc domain may be a variant Fc sequence, e.g., an Fc sequence that has been modified (e.g., by amino acid substitution, deletion and/or insertion) relative to a parent Fc sequence (e.g., an unmodified Fc polypeptide that is subsequently modified to generate a variant), to provide desirable structural features and/or biological activity. For example, one may make modifications in the Fc region in order to generate an Fc variant that (a) has increased or decreased antibody-dependent cell-mediated cytotoxicity (ADCC), (b) increased or decreased complement mediated cytotoxicity (CDC), (c) has increased or decreased affinity for C1q and/or (d) has increased or decreased affinity for a Fc receptor relative to the parent Fc. Such Fc region variants will generally comprise at least one amino acid modification in the Fc region. Combining amino acid modifications is thought to be particularly desirable. For example, the variant Fc region may include two, three, four, five, etc. substitutions therein, e.g. of the specific Fc region positions identified herein.

The hinge region of the Fc fusion proteins of the invention may be derived from antibodies belonging to any of the immunoglobulin classes, i.e., IgA, IgD, IgE, IgG, or IgM. The hinge region may be derived from any of the IgG antibody subclasses, i.e., IgG1, IgG2, IgG3, and IgG4. The hinge region may naturally contain a cysteine residue or may be engineered to contain one or more cysteine residues.

Preferably, the hinge region may have an amino acid sequence that is at least 50%, 60%, 75%, 80%, 85%, 90%, 95%, 96%, 97%, 98%, or 99% identical to the corresponding hinge region of native immunoglobulins belonging to any of the immunoglobulin classes, i.e., IgA, IgD, IgE, IgG, or IgM or any of the IgG antibody subclasses, i.e., IgG1, IgG2, IgG3, and IgG4. Preferably, the amino acid sequence of the hinge region is at least 80%, more preferably at least 85%, more preferably at least 90%, and more preferably at least 95% identical to the corresponding hinge region of human IgG1.

Shown below is the sequence of a human IgG1 immunoglobulin constant region, and the relative position of the hinge region is indicated by solid underlining:

(SEQ ID NO: 9)

ASTKGPSVFPLAPSSKSTSGGTAALGCLVKDYFPEPVTVSWNSGALTSGVHTFPAVLQSS

GLYSLSSVVTVPSSSLGTQTYICNVNHKPSNTKVDKKVEPKSCDKTHTCPPCPAPELLG

GPSVFLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQVYTLPPSRDEL
TKNQVSLTCLVKGFYPSDIAVEWESNGQPENNYKTTPPVLDSDGSFFLYSKLTVDKSRWQQ
GNVFSCSVMHEALHNHYTQKSLSLSPGK

The CH1 region is indicated by underlining with a dotted line, and the CH2 and CH3 regions are indicated by bold lettering. The C-terminal lysine of an IgG sequence may be removed or replaced with a non-lysine amino acid, such as alanine, to further increase the serum half-life of the Fc fusion protein.

The hinge sequence may include substitutions that confer desirable pharmacokinetic, biophysical, and/or biological properties. An exemplary hinge region of the invention comprises an amino acid sequence that is at least 50%, 60%, 75%, 80%, 85%, 90%, 95%, 96%, 97%, 98%, or 99% identical to the following: EPKSSDKTHTCPPCP (SEQ ID NO: 51).

The Fc domain and the hinge region may be derived from one antibody class or subclass. For example, the hinge region and the Fc domain may be derived from IgG1. The Fc domain and hinge region may correspond to different antibody classes or subclasses. For example, the Fc domain may correspond to the Fc region of IgG2 or IgG4 and the hinge region may correspond to IgG1.

Preferably, all immunoglobulin domains of the Fc fusion proteins of the invention are derived from IgG1, preferably human IgG1. Preferably, the combined hinge region and Fc region of the fusion proteins of the invention comprise an amino acid sequence that is at least 50%, 60%, 75%, 80%, 85%, 90%, 95%, 96%, 97%, 98%, or 99% identical to:

(SEQ ID NO: 10)
EPKSSDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSREEMTKNQVSL

TCLVKGFYPSDIAVEWESNGQPENNYKTTPPVLDSDGSFFLYSKLTVDKS

RWQQGNVFSCSVMHEALHNHYTQKSLSLSPGK.

Preferably, the combined hinge region and Fc region of the fusion proteins of the invention comprise an amino acid sequence that is at least 50%, 60%, 75%, 80%, 85%, 90%, 95%, 96%, 97%, 98%, or 99% identical to:

(SEQ ID NO: 11)
EPKSCDKTHTCPPCPAPELLGGPSVFLFPPKPKDTLMISRTPEVTCVVVD

VSHEDPQVKFNWYVDGVQVHNAKTKPREQQYNSTYRVVSVLTVLHQNWLD

-continued

GKEYKCKVSNKALPAPIEKTISKAKGQPREPQVYTLPPSREEMTKNQVSL

TCLVKGFYPSDIAVEWESNGQPENNYKTTPPVLDSDGSFFLYSKLTVDKS

RWQQGNVFSCSVMHEALHNHYTQKSLSLSPGK.

It may be desirable to have a hinge sequence and/or Fc region of the single chain fusion proteins of the invention comprising a free cysteine residue in order to permit the formation of a disulfide bond between the hinge and or Fc regions thereby forming dimers of the Fc fusion proteins of the invention. It may be desirable to alter the hinge and/or Fc region sequences to remove free cysteine residues, e.g., by mutating one or more cysteine residues in a linker to another residue, such as a serine, alanine or glycine. The hinge region of the single chain fusion proteins of the invention may comprise one or more free cysteine residues capable of forming one or more disulfide bonds with a second single chain fusion protein of the invention thereby forming a dimer complex.

Preferably, the (scIL-10)-L1-HINGE-Fc fusion proteins of the invention are dimer complexes comprising two monomeric single chain (scIL-10)-L1-HINGE-Fc fusion proteins of the invention linked via a disulfide bond to the hinge region or in the Fc region of the other monomer. The dimer complexes may be homodimeric (e.g., both monomeric fusion proteins are identical) or heterodimeric (e.g., scIL-10 may be different for each monomeric fusion protein). Preferably, the dimer complexes are homodimers thereby forming a homodimeric complex that provides an antibody configuration that resembles that of a native antibody.

Without being limited to any one theory, it is believed that the homodimeric fusion proteins of the invention increase half-life due to the presence of a dimerized Fc region which more closely resembles the native antibody structure as compared to traditional Fc fusion proteins. This is particularly true when the fusion protein has the configuration of Formula 3. A more native Fc domain antibody configuration is believed to enable better binding to the FcRn receptor and therefore increase the circulating half-life of the of the scIL-10-L1-HINGE-Fc dimer complex.

Another improved property associated with scIL-10-L1-HINGE-Fc dimer complexes is that bioactivity is increased versus a traditional Fc fusion proteins based on the use of the scCLCH1 linker which imparts flexibility to relieve steric hindrance caused by the dimerization through the Fc in the hinge region.

Preferably the invention provides (scIL-10)-L1-HINGE-Fc fusion wherein scIL-10 of Formula 1 is unsubstituted scIL-10 (10aa linker). Preferably the invention provides (scIL-10)-L1-HINGE-Fc fusion wherein the scIL-10 of Formula 1 is an sc-IL-10 variant comprising at least one amino acid substitution in the first monomer subunit or the second monomer subunit as per Formula 1 selected from the methionine at position 22, the aspartic acid at position 41, and the isoleucine at position 87 or any combination thereof. Preferably there is at least one amino acid substitution at position 41 in the first or second monomer subunit of Formula 1 and at least one amino acid is substituted at position 22 in the first or second monomer subunit that is not the same subunit that comprises the amino acid substitution at position 41.

A preferred scIL10-L1-HINGE-Fc fusion protein of the invention comprises an amino acid sequence that is 50%, 60%, 75%, 80%, 85%, 90%, 95%, 96%, 97%, 98%, or 99% identical to SEQ ID NO: 12 wherein scIL-10 is unsubstituted scIL-10 (10aa linker).

Preferred scIL-10-L1-HINGE-Fc fusion proteins of the invention comprise an amino acid sequence that is 50%, 60%, 75%, 80%, 85%, 90%, 95%, 96%, 97%, 98%, or 99% identical to SEQ ID NOs: 20-21 and 37-44 all as shown in Table 4.

Preferred scIL-10-L1-HINGE-Fc fusion proteins of the invention comprise an amino acid sequence that is 50%, 60%, 75%, 80%, 85%, 90%, 95%, 96%, 97%, 98%, or 99% identical to SEQ ID NOs: 17-19 as shown in Table 4 wherein scIL-10 is an scIL-10 variant.

The invention also provides nucleic acids encoding any of the various fusion proteins disclosed herein. Codon usage may be selected so as to improve expression in a cell. Such codon usage will depend on the cell type selected. Specialized codon usage patterns have been developed for *E. coli* and other bacteria, as well as mammalian cells, plant cells, yeast cells and insect cells. See for example: Mayfield et al., *Proc. Natl. Acad. Sci. USA,* 100(2):438-442 (Jan. 21, 2003); Sinclair et al., *Protein Expr. Purif.,* 26(I):96-105 (October 2002); Connell, N. D., *Curr. Opin. Biotechnol.,* 12(5):446-449 (October 2001); Makrides et al., *Microbiol Rev.,* 60(3): 512-538 (September 1996); and Sharp et al., *Yeast,* 7(7): 657-678 (October 1991).

General techniques for nucleic acid manipulation are described for example in Sambrook et al., *Molecular Cloning: A Laboratory Manual,* 2nd Edition, Vols. 1-3, Cold Spring Harbor Laboratory Press (1989), or Ausubel, F. et al., *Current Protocols in Molecular Biology,* Green Publishing and Wiley-Interscience, New York (1987) and periodic updates, herein incorporated by reference. Generally, the DNA encoding the polypeptide is operably linked to suitable transcriptional or translational regulatory elements derived from mammalian, viral, or insect genes. Such regulatory elements include a transcriptional promoter, an optional operator sequence to control transcription, a sequence encoding suitable mRNA ribosomal binding sites, and sequences that control the termination of transcription and translation. The ability to replicate in a host, usually conferred by an origin of replication, and a selection gene to facilitate recognition of transformants is additionally incorporated.

The fusion proteins described herein may be produced recombinantly not only directly, but also as a fusion polypeptide with a heterologous polypeptide, which is preferably a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell. An exemplary N-terminal leader sequence for production of polypeptides in a mammalian system is MYRMQLLSCIALSLALVTNS (SEQ ID NO: 48), which is removed by the host cell following expression.

For prokaryotic host cells that do not recognize and process a native signal sequence, the signal sequence is substituted by a prokaryotic signal sequence selected, for example, from the group of the alkaline phosphatase, penicillinase, or heat-stable enterotoxin II leaders.

For yeast secretion the native signal sequence may be substituted by, e.g., the yeast invertase leader, a factor leader (including *Saccharomyces* and *Kluyveromyces* alpha-factor leaders), or acid phosphatase leader, the *C. albicans* glucoamylase leader, or the signal described in U.S. Pat. No. 5,631,144. In mammalian cell expression, mammalian signal sequences as well as viral secretory leaders, for example, the herpes simplex gD signal, are available. The DNA for such precursor regions may be ligated in reading frame to DNA encoding the protein.

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2 micron plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

Expression and cloning vectors may contain a selection gene, also termed a selectable marker. Typical selection genes encode proteins that (a) confer resistance to antibiotics or other toxins, e.g., ampicillin, neomycin, methotrexate, or tracycline, (b) complement auxotrophic deficiencies, or (c) supply critical nutrients not available from complex media, e.g., the gene encoding D-alanine racemase for Bacilli.

Expression and cloning vectors usually contain a promoter that is recognized by the host organism and is operably linked to the nucleic acid encoding the protein disclosed herein, e.g., a fibronectin-based scaffold protein. Promoters suitable for use with prokaryotic hosts include the phoA promoter, beta-lactamase and lactose promoter systems, alkaline phosphatase, a tryptophan (trp) promoter system, and hybrid promoters such as the tan promoter. However, other known bacterial promoters are suitable. Promoters for use in bacterial systems also will contain a Shine-Dalgarno (S.D.) sequence operably linked to the DNA encoding the protein disclosed herein. Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT (SEQ ID NO: 49) region where N may be any nucleotide. At the 3' end of most eukaryotic genes is an AATAAA (SEQ ID NO: 50) sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Transcription from vectors in mammalian host cells can be controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heat-shock promoters, provided such promoters are compatible with the host cell systems.

Transcription of a DNA encoding proteins disclosed herein by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, *Nature*, 297:17-18 (1982) on enhancing elements for activation of eukaryotic promoters. The enhancer may be spliced into the vector at a position 5' or 3' to the peptide-encoding sequence, but is preferably located at a site 5' from the promoter.

Expression vectors used in eukaryotic host cells (e.g., yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of mRNA encoding the protein disclosed herein. One useful transcription termination component is the bovine growth hormone polyadenylation region. See WO 94/11026 and the expression vector disclosed therein.

The recombinant DNA can also include any type of protein tag sequence that may be useful for purifying the protein. Examples of protein tags include but are not limited to a histidine tag, a FLAG tag, a myc tag, an HA tag, or a GST tag. Appropriate cloning and expression vectors for use with bacterial, fungal, yeast, and mammalian cellular hosts can be found in *Cloning Vectors: A Laboratory Manual*, (Elsevier, New York (1985)), the relevant disclosure of which is hereby incorporated by reference.

The expression construct is introduced into the host cell using a method appropriate to the host cell, as will be apparent to one of skill in the art. A variety of methods for introducing nucleic acids into host cells are known in the art, including, but not limited to, electroporation; transfection employing calcium chloride, rubidium chloride, calcium phosphate, DEAE-dextran, or other substances; microprojectile bombardment; lipofection; and infection (where the vector is an infectious agent).

Suitable host cells include prokaryotes, yeast, mammalian cells, or bacterial cells. Suitable bacteria include gram negative or gram positive organisms, for example, *E. coli* or *Bacillus* spp. Yeast, preferably from the *Saccharomyces* species, such as *S. cerevisiae*, may also be used for production of polypeptides. Various mammalian or insect cell culture systems can also be employed to express recombinant proteins. Baculovirus systems for production of heterologous proteins in insect cells are reviewed by Luckow et al. (*Bio/Technology*, 6:47 (1988)). Examples of suitable mammalian host cell lines include endothelial cells, COS-7 monkey kidney cells, CV-1, L cells, C127, 3T3, Chinese hamster ovary (CHO), human embryonic kidney cells, HeLa, 293, 293T, and BHK cell lines. Purified polypeptides are prepared by culturing suitable host/vector systems to express the recombinant proteins. For many applications, the small size of many of the polypeptides disclosed herein would make expression in *E. coli* as the preferred method for expression. The protein is then purified from culture media or cell extracts.

In other aspects, the invention provides host cells containing vectors encoding the fusion proteins described herein, as well as methods for producing the fusion proteins described herein. Host cells may be transformed with the herein-described expression or cloning vectors for protein production and cultured in conventional nutrient media modified as appropriate for inducing promoters, selecting transformants, or amplifying the genes encoding the desired sequences. Host cells useful for high-throughput protein production (HTPP) and mid-scale production include the HMS 174-bacterial strain. The host cells used to produce the proteins disclosed herein may be cultured in a variety of media. Commercially available media such as Ham's F10 (Sigma), Minimal Essential Medium ((MEM), (Sigma)), RPMI-1640 (Sigma), and Dulbecco's Modified Eagle's Medium ((DMEM), Sigma)) are suitable for culturing the host cells. In addition, many of the media described in various scientific literature may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as Gentamycin drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

The fusion proteins provided herein can also be produced using cell-translation systems. For such purposes the nucleic acids encoding the fusion protein must be modified to allow in vitro transcription to produce mRNA and to allow cell-free translation of the mRNA in the particular cell-free system being utilized (eukaryotic such as a mammalian or yeast cell-free translation system or prokaryotic such as a bacterial cell-free translation system).

The fusion proteins disclosed herein can also be produced by chemical synthesis (e.g., by the methods described in *Solid Phase Peptide Synthesis,* 2nd Edition, The Pierce Chemical Co., Rockford, Ill. (1984)). Modifications to the fusion proteins can also be produced by chemical synthesis.

The fusion proteins disclosed herein can be purified by isolation/purification methods for proteins generally known in the field of protein chemistry. Non-limiting examples include extraction, recrystallization, salting out (e.g., with ammonium sulfate or sodium sulfate), centrifugation, dialysis, ultrafiltration, adsorption chromatography, ion exchange chromatography, hydrophobic chromatography, normal phase chromatography, reversed-phase chromatography, get filtration, gel permeation chromatography, affinity chromatography, electrophoresis, countercurrent distribution or any combinations of these. After purification, polypeptides may be exchanged into different buffers and/or concentrated by any of a variety of methods known to the art, including, but not limited to, filtration and dialysis.

The purified fusion protein is preferably at least 85% pure, or preferably at least 95% pure, and most preferably at least 98% pure. Regardless of the exact numerical value of the purity, the fusion protein is sufficiently pure for use as a pharmaceutical product.

Other Fusion Partners

Other appropriate fusion partners for scIL-10 proteins of the invention include but are not limited to proteins comprising an Fc region of all other types.

For example, scIL-10 proteins may be fused directly to the hinge region of a native immunoglobulin containing an Fc region, for example IgG1. SEQ ID NO: 13 is an example of unsubstituted scIL-10 (5aa linker) fused to the hinge region of an IgG1 molecule. The IgG1 molecule may be modified, by, for example, by shortening the hinge region of IgG1. SEQ ID NO: 14 is an example of scIL-10 (5aa linker) fused to the hinge region of IgG1 wherein in the hinge region of the native IgG1 has been shortened by 4 amino acids. SEQ ID NO: 15 is an example of scIL-10 fused to the hinge region of IgG1 wherein in the hinge region of the native IgG1 has been shortened by 7 amino acids. SEQ ID NO: 16 is an example of scIL-10 fused to the hinge region of IgG1 wherein in the hinge region of the native IgG1 has been shortened by 10 amino acids.

A preferred fusion partner comprises an Fc region further comprising a mucin-domain polypeptide linker as is described in WO 2013/184938 incorporated herein by reference. A "mucin-domain polypeptide linker" is defined herein as any protein comprising a "mucin domain" capable of being linked to one or more fusion polypeptide partners. A mucin domain is rich in potential glycosylation sites, and has a high content of serine and/or threonine and proline, which can represent greater than 40% of the amino acids within the mucin domain. A mucin domain is heavily glycosylated with predominantly O-linked glycans. A mucin-domain polypeptide has at least about 60%, at least 70%. at least 80%, or at least 90% of its mass due to the glycans. Mucin domains may comprise tandem amino acid repeat units (also referred to herein as TR) that may vary in length from about 8 amino acids to 150 amino acids per each tandem repeat unit. The number of tandem repeat units may vary between 1 and 25 in a mucin-domain polypeptide of the invention.

Mucin-domain polypeptide linkers of the invention include, but are not limited to, all or a portion of a mucin protein. A "portion thereof" is meant that the mucin polypeptide linker comprises at least one mucin domain of a mucin protein. Mucin proteins include any protein encoded for by a MUC gene (e.g., MUC1, MUC2, MUC3A, MUC3B, MUC4, MUC5AC, MUC5B, MUC6, MUC7, MUC8, MUC9, MUC11, MUC12, MUC13, MUC15, MUC16, MUC17, MUC19, MUC20, MUC21). The mucin domain of a mucin protein is typically flanked on either side by non-repeating amino acid regions. A mucin-domain polypeptide may comprise all or a portion of a mucin protein (e.g. MUC20). A mucin-domain polypeptide may comprise all or a portion of a mucin protein of a soluble mucin protein. Preferably the mucin-domain polypeptide comprises the extracellular portion of a mucin protein.

Preferably, an scIL-10 protein of Formula 1 is covalently linked to a molecule comprising an Fc region via a mucin-domain polypeptide linker. SEQ ID NO: 52 is an example of unsubstituted scIL-10 fused to mucin linker which is in turn fused to the hinge of a native IgG1 Fc region.

A preferred fusion partner is a mucin domain polypeptide (not including an Fc region) as is described in WO 2013/184939.

A preferred fusion partner comprises serum albumin or a domain of serum albumin. Human serum albumin is preferred when the fusion proteins of the invention are used for treating humans. In another embodiment, fusion partners comprise human transferrin.

Uses of scIL-10 Proteins

In one aspect, the invention provides scIL-10 (including fusions of scIL-10 to an appropriate fusion partner and dimerized complexes thereof) that are useful as diagnostic or therapeutic agents. In one aspect, the invention provides proteins useful in the treatment of disorders.

The invention also provides a method for achieving a beneficial effect in a subject comprising the step of administering to the subject a therapeutically or prophylactically-effective amount of scIL-10 (including fusions of scIL-10 to an appropriate fusion partner and dimerized complexes thereof) of the invention. The effective amount can produce a beneficial effect in helping to treat a disease or disorder. In some cases, the method for achieving a beneficial effect can include administering a therapeutically effective amount of a fusion protein composition to treat a subject for diseases and disease categories wherein a therapeutic protein or peptide does not exist.

Preferably scIL-10 is not linked to any fusion partner.

Preferably, scIL-10 is covalently linked to an appropriate fusion partner such as scIL-10-L1-HINGE-Fc. Preferably, the invention provides dimer complexes of scIL-10 fused to an appropriate fusion partner.

Preferably scIL-10 (including fusions of scIL-10 to an appropriate fusion partner and dimerized complexes thereof) are used to treat patients who suffer from, for example, autoimmune disorders, fibrotic diseases, inflammatory diseases, ischemic diseases, neurodegenerative diseases, neuropathic diseases, pain disorders, auditory disorders, psychiatric disorders, cancer and trauma and injury.

Examples of autoimmune disorders include, but are not limited to: acute disseminated encephalomyelitis (ADEM), acute necrotizing hemorrhagic leukoencephalitis, Addison's disease, agammaglobulinemia, alopecia areata, amyloidosis, ankylosing spondylitis, anti-GBM/anti-TBM nephritis, antiphospholipid syndrome (APS), autoimmune angioedema, autoimmune aplastic anemia, autoimmune dysautonomia, autoimmune hepatitis, autoimmune hyperlipidemia, autoimmune immunodeficiency, autoimmune inner ear disease (AIED), autoimmune lymphoproliferative syndrome (ALPS), autoimmune myocarditis, autoimmune oophoritis, autoimmune pancreatitis, autoimmune retinopathy, autoimmune thrombocytopenic purpura (ATP), autoimmune thyroiditis, autoimmune urticaria, axonal & neuronal neuropathies, Balo disease, Behcet's disease, cardiomyopathy, Castleman disease, celiac disease, Chagas disease, chronic fatigue syndrome, chronic inflammatory demyelinating polyneuropathy (CIDP), chronic recurrent multifocal ostomyelitis (CRMO), cicatricial pemphigoid/benign mucosal pemphigoid, Cogans syndrome, cold agglutinin disease, congenital heart block, Coxsackie myocarditis, CREST disease, Crohn's disease, demyelinating neuropathies, dermatitis herpetiformis, dermatomyositis, Devic's disease (neuromyelitis optica), discoid lupus, Dressler's syndrome, endometriosis, eosinophilic esophagitis, eosinophilic fasciitis, erythema nodosum, essential mixed cryoglobulinemia, Evans syndrome, experimental allergic encephalomyelitis, fibromyalgia, fibrosing alveolitis, giant cell arteritis (temporal arteritis), giant cell myocarditis, glomerulonephritis, Goodpasture's syndrome, granulomatosis with Polyangiitis (GPA) (formerly called Wegener's Granulomatosis), Grave's disease, Guillain-Barre syndrome, Hashimoto's encephalitis, Hashimoto's thyroiditis, hemolytic anemia, Henoch-Schonlein purpura, herpes gestationis, hypogammaglobulinemia, idiopathic pulmonary fibrosis, idiopathic thrombocytopenic purpura (ITP), IgA nephropathy, IgG4-related sclerosing disease, immunoregulatory lipoproteins, inclusion body myositis, interstitial cystitis, juvenile arthritis, juvenile diabetes (Type 1 diabetes), juvenile myositis, Kawasaki disease, Lambert-Eaton syndrome, leukocytoclastic vasculitis, lichen planus, lichen sclerosus, ligneous conjunctivitis, linear IgA disease (LAD), Lupus (systemic lupus erythematosus), Lyme disease, chronic, Meniere's disease, microscopic polyangiitis, mixed connective tissue disease (MCTD), Mooren's ulcer, Mucha-Habermann disease, multiple sclerosis (MS), myasthenia gravis, myositis, narcolepsy, neuromyelitis optica (Devic's), neutropenia, ocular cicatricial pemphigoid, optic neuritis, palindromic rheumatism, PANDAS (Pediatric Autoimmune Neuropsychiatric Disorders Associated with *Streptococcus*), paroxysmal nocturnal hemoglobinuria (PNH), Parry Romberg syndrome, Pars planitis (peripheral uveitis), Parsonnage-Turner syndrome, pemphigus, peripheral neuropathy, perivenous encephalomyelitis, pernicious anemia, POEMS syndrome, polyarteritis nodosa, polymyalgia rheumatica, polymyositis, postmyocardial infarction syndrome, postpericardiotomy syndrome, primary biliary cirrhosis, primary sclerosing cholangitis, progesterone dermatitis, psoriasis, psoriatic arthritis, pure red cell aplasia, pyoderma gangrenosum, Raynauds phenomenon, reactive Arthritis, reflex sympathetic dystrophy, Reiter's syndrome, relapsing polychondritis, restless legs syndrome, retroperitoneal fibrosis, rheumatic fever, rheumatoid arthritis (RA), rheumatoid arthritis, sarcoidosis, Schmidt syndrome, scleritis, scleroderma, Sjogren's syndrome, sperm & testicular autoimmunity, stiff person syndrome, subacute bacterial endocarditis, Susac's syndrome, sympathetic ophthalmia, Takayasu's arteritis, Temporal arteritis/Giant cell arteritis, thrombocytopenic purpura, Tolosa-Hunt syndrome, transverse myelitis, type 1 diabetes, type I, II, & III autoimmune polyglandular syndromes, ulcerative colitis, undifferentiated connective tissue disease (UCTD), uveitis, vasculitis, vesiculobullous dermatosis, vitiligo, and Wegener's granulomatosis.

Examples of fibrotic diseases which may be treated by the scIL-10 and scIL-10 variant peptides (including fusions of each to an appropriate fusion partner) of the invention include, but are not limited to: adhesive capsulitis, arthrofibrosis, atrial fibrosis, chronic kidney disease, cirrhosis of the liver, cystic fibrosis (CF), Dupuytren's contracture, endomyocardial fibrosis, glial scar, idiopathic pulmonary fibrosis, keloid, macular degeneration, mediastinal fibrosis, myelofibrosis, NAFLD/NASH, nephrogenic systemic fibrosis, Peyronie's disease, progressive massive fibrosis (lungs), proliferative vitreoretinopathy, pulmonary fibrosis, retroperitoneal fibrosis, scar tissue formation resulting from strokes, scleroderma, systemic sclerosis, tissue adhesion.

Examples of inflammatory diseases include, but are not limited to: allergic enteritis, alpha-1-antitrypsin deficiency, ankylosing spondylitis, asthma, Barrett's esophagus, Behcet's disease, chronic fatigue syndrome (CFS/CFIDS/ME), chronic Lyme disease (borreliosis), cocaine-associated vasculitis, Crohn's disease, deficiency of the Interleukin-1 Receptor Antagonist (DIRA), depression, diabetes, Familial Mediterranean Fever (FMF), fibromyalgia (FM), gastroesophageal reflux disease (GERD), glomerulonephritis, graft versus host disease, granulomatous angiitis, Hashimoto's thyroiditis, hypertension, hyperthyroidism, hypothyroidism, inflammatory bowel disease (IBD), inflammatory myopathies (polymyositis, inclusion body myositis, dermatomyositis), interstitial cystitis (IC), irritable bowel syndrome (IBS), ischemic colitis, kidney stones, Lofgren's syndrome, Lupus erythematosis, methamphetamine-associated vasculitis, migraine headache, Morgellon's, multiple chemical sensitivity (MCS), multiple sclerosis (MS), neonatal onset multisystem inflammatory disease (NOMID), optic neuritis, osteoarthritis, pemphigus vulgaris, polymyalgia rheumatica, prostatitis, psoriasis, psoriatic arthritis, radiation colitis, Raynaud's syndrome/phenomenon, reactive arthritis (Reiter syndrome), reflex sympathetic dystrophy (RSD), restless leg syndrome, rheumatoid arthritis (RA), sarcoidosis, scleroderma, seasonal affective disorder (SAD), septic shock, sinusitis, Sjögren's syndrome, temporal arteritis, tumor necrosis factor (TNF) receptor-associated periodic syndrome (TRAPS), ulcerative colitis, uveitis, vasculitis, and vertigo.

Examples of ischemic diseases include, but are not limited to: acute coronary syndrome, angina pectoris, angor animi, copeptin, coronary artery disease, coronary ischemia, hibernating myocardium, ischemic stroke, management of acute coronary syndrome, meldonium, myocardial infarction, myocardial infarction complications, myocardial infarction diagnosis, myocytolysis, post-anoxic encephalopathy, Prinzmetal's angina, Sgarbossa's criteria, stroke, TIMI, transient ischemic attack (TIA) and unstable angina.

Examples of neurodegenerative diseases include, but are not limited to: ataxia telangiectasia, autosomal dominant cerebellar ataxia, Baggio-Yoshinari syndrome, Batten disease, estrogen and neurodegenerative diseases, hereditary motor and sensory neuropathy with proximal dominance, Infantile Refsum disease, JUNQ and IPOD, locomotor ataxia, Lyme disease, Machado-Joseph disease, mental retardation and microcephaly with pontine and cerebellar hypoplasia, multiple system atrophy, neuroacanthocytosis, neuronal ceroid lipofuscinosis, Niemann-Pick disease, pontocerebellar hypoplasia, protein aggregation, pyruvate dehydrogenase deficiency, radiation myelopathy, Refsum disease, retinitis pigmentosa, Sandhoff disease, Shy-Drager syndrome, spinal muscular atrophy, spinocerebellar ataxia, subacute combined degeneration of spinal cord, subacute sclerosing panencephalitis, Tabes dorsalis, Tay-Sachs disease, toxic encephalopathy, toxic leukoencephalopathy and Wobbly Hedgehog Syndrome.

Examples of neuropathic diseases include, but are not limited to: Bell's Palsy, campylobacter-associated motor axonopathies, Charcot-Marie-Tooth, chronic inflammatory demyelinating polyneuropathy, diabetic amyotrophy avulsion, diabetic neuropathies, Guillain Barre Syndrome and vasculitis.

Examples of pain disorders include, but are not limited to: Amplified musculoskeletal pain syndromes, Anterior cutaneous nerve entrapment syndrome, central pain syndrome, chronic functional abdominal pain, chronic pain, chronic prostatitis/chronic pelvic pain syndrome, chronic wound pain, degenerative disc disease, dentomandibular sensorimotor dysfunction, failed back syndrome, fibromyalgia, interstitial cystitis, irritable bowel syndrome (MS), myofascial pain syndrome, pelvic pain, post-vasectomy pain syndrome, reflex neurovascular dystrophy, sickle-cell disease, theramine, and vulvodynia.

Examples of auditory disorders include, but are not limited to: conductive hearing loss, sensorineural hearing loss (SNHL), mixed hearing loss.

Examples of psychiatric disorders include, but are not limited to: major depressive disorder, treatment-refractory depression, treatment-resistant depression.

Examples of trauma and injury include, but are not limited to: including central nervous system (CNS) injuries, traumatic brain injury, spinal cord injury, crush injuries, shock, tendon damage, wounds to the cornea, wounds to the eye, skin wounds.

Preferably, an scIL-10 proteins (including fusions of scIL-10 to an appropriate fusion partner and dimerized complexes thereof) of the invention may be used to treat patients who suffer from, for example, autoimmune disorders including autoimmune lymphoproliferative syndrome (ALPS), autoimmune thyroiditis, Crohn's disease, Grave's disease, Hashimoto's thyroiditis, Kawasaki disease, Lupus (systemic lupus erythematosus), multiple sclerosis (MS), myasthenia gravis, psoriasis, rheumatoid arthritis, Sjogren's syndrome, type 1 diabetes, ulcerative colitis; fibrotic diseases including Chronic Kidney Disease, cirrhosis of the liver, macular degeneration, NAFLD/NASH, proliferative vitreoretinopathy, pulmonary fibrosis, scar tissue formation resulting from strokes, tissue adhesion; including inflammatory diseases including allergic enteritis, alpha-1-antitrypsin deficiency, asthma, Behcet's disease, cocaine-associated vasculitis, glomerulonephritis, Graft Versus Host Disease, granulomatous angiitis, inflammatory bowel disease, inflammatory myopathies (polymyositis, inclusion body myositis, dermatomyositis), ischemic colitis, methamphetamine-associated vasculitis, optic neuritis, pemphigus vulgaris, radiation colitis, sarcoidosis, Septic Shock, temporal arteritis, vasculitis; ischemic diseases including myocardial infarction, post-anoxic encephalopathy, stroke; neurodegenerative diseases including neuronal ceroid lipofuscinosis, radiation myelopathy, retinitis pigmentosa, spinal muscular atrophy; neuropathic diseases including campylobacter-associated motor axonopathies, Charcot-Marie-Tooth, chronic inflammatory demyelinating polyneuropathy, diabetic amyotrophy avulsion, diabetic neuropathies, Guillain Barre Syndrome; auditory disorders including Conductive hearing loss, Sensorineural hearing loss (SNHL), Mixed hearing loss; psychiatric disorders including major depressive disorder, treatment-refractory depression, treatment-resistant depression; trauma and injury including central nervous system (CNS) injuries, traumatic brain injury, spinal cord injury, crush injuries, shock, tendon damage, wounds to the cornea, wounds to the eye, skin wounds.

Most preferably, scIL-10 proteins (including fusions of scIL-10 to an appropriate fusion partner and dimerized complexes thereof) in accordance with the invention may be used to treat patients who suffer from, for example, autoimmune disorders including autoimmune lymphoproliferative syndrome (ALPS), autoimmune thyroiditis, Crohn's disease, Grave's disease, Hashimoto's thyroiditis, Kawasaki disease, Lupus (systemic lupus erythematosus), multiple sclerosis (MS), myasthenia gravis, psoriasis, rheumatoid arthritis, Sjogren's syndrome, type 1 diabetes, ulcerative colitis; fibrotic diseases including Chronic Kidney Disease, cirrhosis of the liver, macular degeneration, NAFLD/NASH, proliferative vitreoretinopathy, pulmonary fibrosis, scar tissue formation resulting from strokes, tissue adhesion; inflammatory diseases including allergic enteritis, alpha-1-antitrypsin deficiency, asthma, Behcet's disease, cocaine-associated vasculitis, glomerulonephritis, Graft Versus Host Disease, granulomatous angiitis, inflammatory bowel disease, inflammatory myopathies (polymyositis, inclusion body myositis, dermatomyositis), ischemic colitis, methamphetamine-associated vasculitis, optic neuritis, pemphigus vulgaris, radiation colitis, sarcoidosis, Septic Shock, temporal arteritis, vasculitis; ischemic diseases including myocardial infarction, post-anoxic encephalopathy, stroke; neurodegenerative diseases including neuronal ceroid lipofuscinosis, radiation myelopathy, retinitis pigmentosa, spinal muscular atrophy; neuropathic diseases including campylobacter-associated motor axonopathies, Charcot-Marie-Tooth, chronic inflammatory demyelinating polyneuropathy, diabetic amyotrophy avulsion, diabetic neuropathies, Guillain Barre Syndrome; auditory disorders including Conductive hearing loss, Sensorineural hearing loss (SNHL), Mixed hearing loss; psychiatric disorders including major depressive disorder, treatment-refractory depression, treatment-resistant depression; trauma and injury including central nervous system (CNS) injuries, traumatic brain injury, spinal cord injury, crush injuries, shock, tendon damage, wounds to the cornea, wounds to the eye, skin wounds.

Preferably sell-10 proteins (including fusions of scIL-10 to an appropriate fusion partner and dimerized complexes thereof) of the invention may be used to treat patients who suffer from, for example cancer of the uterus, cervix, breast, ovaries, prostate, testes, penis, gastrointestinal tract, esophagus, oropharynx, stomach, small or large intestines, colon, or rectum, kidney, renal cell, bladder, bone, bone marrow, skin, head or neck, skin, liver, gall bladder, heart, lung, pancreas, salivary gland, adrenal gland, thyroid, brain, gliomas, ganglia, central nervous system (CNS) and peripheral nervous system (PNS), and immune system, spleen or thymus, papilloma virus-induced cancers, epithelial cell cancers, endothelial cell cancers, squamous cell carcinomas, adenocarcinomas, carcinomas, melanomas, sarcomas, teratocarcinomas, immunogenic tumors, non-immunogenic tumors, dormant tumors, lymphomas, leukemias, myelomas, chemically-induced cancers, metastasis, and angiogenesis, and Tuberous sclerosis.

Preferably, scIL-10 fusion proteins (including fusions of scIL-10 to an appropriate fusion partner and dimerized complexes thereof) in accordance with the invention may be used to treat patients who suffer from auditory disorders, renal cell carcinoma, melanoma, psoriasis, fibrosis, depression, and inflammatory bowel disease (IBD).

Preferably, scIL-10 fusion proteins (including fusions of scIL-10 to an appropriate fusion partner and dimerized complexes thereof) in accordance with the invention may also be used in the manufacture of a medicament to treat patients to diseases as set forth above, auditory disorders, auditory disorders, renal cell carcinoma, melanoma, psoriasis, fibrosis, depression, and inflammatory bowel disease (IBD).

The application further provides pharmaceutically acceptable compositions comprising scIL-10 proteins (including fusions of scIL-10 to an appropriate fusion partner and dimerized complexes thereof) described herein. Therapeutic formulations comprising scIL-10 proteins are prepared for storage by mixing the described proteins having the desired degree of purity with optional physiologically acceptable carriers, excipients or stabilizers (Remington's Pharmaceutical Sciences 16th edition, Osol, A. Ed. (1980)), in the form of aqueous solutions, lyophilized or other dried formulations. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The formulations herein may also contain more than one active compounds as necessary for the particular indication being treated, preferably those with complementary activities that do not adversely affect each other. Such molecules are suitably present in combination in amounts that are effective for the purpose intended.

The preferably, scIL-10 proteins (including fusions of scIL-10 to an appropriate fusion partner and dimerized complexes thereof) in accordance with the invention may also be entrapped in microcapsules prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nanoparticles and nanocapsules) or in macroemulsions. Such techniques are disclosed in Remington's Pharmaceutical Sciences 16th edition, Osol, A. Ed. (1980).

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the fibronectin based scaffold proteins described herein, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides, copolymers of lactide and glycolide, copolymers of L-glutamic acid and y ethyl-L-glutamate, non-degradable ethylene-vinyl acetate, degradable lactic acid-glycolic acid copolymers. While polymers such as ethylene-vinyl acetate and lactic acid-glycolic acid enable sustained release of, certain hydrogels release proteins for shorter time periods. When encapsulated proteins remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

While the skilled artisan will understand that the dosage of each scIL-10 protein (including fusions of scIL-10 to an appropriate fusion partner and dimerized complexes thereof) in accordance with the invention will be dependent on the patient's particular circumstances. The dosage ranges from about 0.0001 to 100 mg/kg, and more usually 0.01 to 5 mg/kg, of the host body weight. For example, dosages can be 0.3 mg/kg body weight, 1 mg/kg body weight, 3 mg/kg body weight, 5 mg/kg body weight or 10 mg/kg body weight or within the range of 1-30 mg/kg. An exemplary treatment regime entails administration once per week, once every two weeks, once every three weeks, once every four weeks, once a month, once every 3 months or once every three to 6 months. Dosage regimens include 1 mg/kg body weight or 3 mg/kg body weight by intravenous administration, with the protein being given using one of the following dosing schedules: every four weeks for six dosages, then every three months; every three weeks; 3 mg/kg body weight once followed by 1 mg/kg body weight every three weeks. Preferably, scIL-10 fusion proteins (including fusions of each to an appropriate fusion partner and dimerized complexes thereof in accordance with the invention is usually administered on multiple occasions. Intervals between single dosages can be, for example, weekly, monthly, every three months or yearly. Intervals can also be irregular as indicated by measuring blood levels of the soluble protein in the patient. In some methods, dosage is adjusted to achieve a plasma concentration of soluble protein of about 0.1-1000 pg/ml and in some methods about 5-300 mg/ml.

For therapeutic applications, scIL-10 proteins (including fusions of scIL-10 to an appropriate fusion partner and dimerized complexes thereof) in accordance with the invention are administered to a subject, in a pharmaceutically acceptable dosage form. They can be administered intravenously as a bolus or by continuous infusion over a period of time, by intramuscular, subcutaneous, intra-ocular, intra-articular, intrasynovial, intrathecal, oral, topical, or inhalation routes. The protein may also be administered by intratumoral, peritumoral, intralesional, or perilesional routes, to exert local as well as systemic therapeutic effects. Suitable pharmaceutically acceptable carriers, diluents, and excipients are well known and can be determined by those of skill in the art as the clinical situation warrants. Examples of suitable carriers, diluents and/or excipients include: (1) Dulbecco's phosphate buffered saline, pH about 7.4, containing about 1 mg/ml to 25 mg/ml human serum albumin, (2) 0.9% saline (0.9% w/v NaCl), and (3) 5% (w/v) dextrose. The methods of the present invention can be practiced in vitro, in vivo, or ex vivo.

Administration of scIL-10 proteins (including fusions of scIL-10 to an appropriate fusion partner and dimerized complexes thereof), and one or more additional therapeutic agents, whether co-administered or administered sequentially, may occur as described above for therapeutic applications. Suitable pharmaceutically acceptable carriers, diluents, and excipients for co-administration will be understood by the skilled artisan to depend on the identity of the particular therapeutic agent being co-administered.

When present in an aqueous dosage form, rather than being lyophilized, scIL-10 (including fusions of scIL-10 to an appropriate fusion partner and dimerized complexes thereof) typically will be formulated at a concentration of about 0.1 mg/ml to 100 mg/ml, although wide variation outside of these ranges is permitted. For the treatment of disease, the appropriate dosage of scIL-10 (including fusions of scIL-10 to an appropriate fusion partner and dimerized complexes thereof) will depend on the type of disease to be treated, the severity and course of the disease, whether the scIL-10 proteins (including fusions of scIL-10 to an appropriate fusion partner and dimerized complexes thereof) are administered for preventive or therapeutic purposes, the course of previous therapy, the patient's clinical history and response to the scIL-10 protein (including fusions of scIL-10 to an appropriate fusion partner and dimerized complexes thereof), and the discretion of the attending physician. The scIL-10 protein is suitably administered to the patient at one time or over a series of treatments.

EXAMPLES

Example 1: Unsubstituted scIL-10

Design of scIL-10:$C_L$:$C_{H}1$:Fc and scIL-10:$C_{H1}$:$C_L$:Fc

Figure 2:
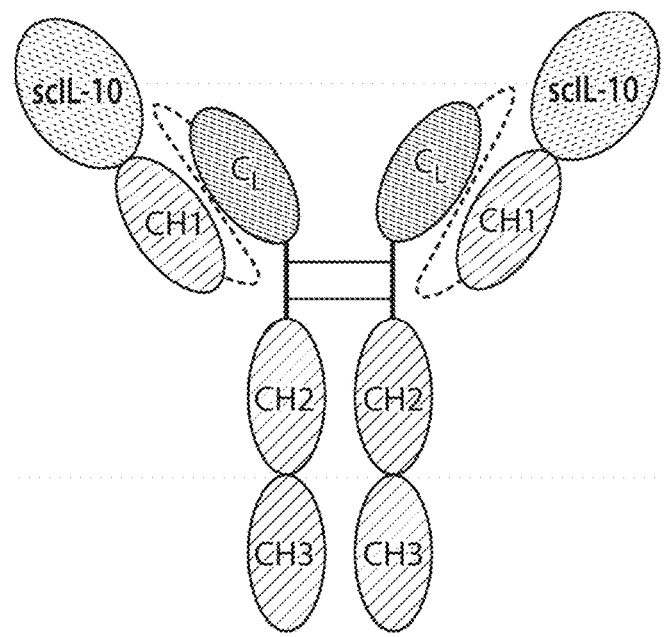
FIG. 2 is a diagram of an Fc fusion protein homodimer of two polypeptide chains, wherein in each polypeptide chain comprises scIL-10 which is then fused to the Fc region of an IgG1 antibody via the novel scCH1CL linker.

The scIL-10 single chain fusion body molecule contains a covalently linked IL-10 homodimer fusion protein linked to the CL-CH1-Fc (Formula 3) domain or the CH1-CL-Fc of the IgG1 heavy chain (FIGS. 1 and 2). The amino acid sequences of each molecule synthesized is found in Table 1. For expression in mammalian cells, the N-terminal leader sequence of SEQ ID NO: 48 was added to each of the protein sequences found in Table 1.

TABLE 1

| Protein | Sequence |
|---|---|
| Unsubstituted scIL-10 (10 aa linker): CL: CH1: Fc (SEQ ID NO: 12) | SPGQGTQSENSCTHFPGNLPNMLRDLRDAFSRVKTFFQMKDQLDNLLLKESLLEDFKGYLGCQALS EMIQFYLEEVMPQAENQDPDIKAHVNSLGENLKTLRLRLRRCHRFLPCENKSKAVEQVKNAFNKLQ EKGIYKAMSEFDIFINYIEAYMTMKIRNGGSGGGGSGGSPGQGTQSENSCTHFPGNLPNMLRDLRDA FSRVKTFFQMKDQLDNLLLKESLLEDFKGYLGCQALSEMIQFYLEEVMPQAENQDPDIKAHVNSLG ENLKTLRLRLRRCHRFLPCENKSKAVEQVKNAFNKLQEKGIYKAMSEFDIFINYIEAYMTMKIRNG GGGSGGGGSRTVAAPSVFIFPPSDEQLKSGTASVVCLLNNFYPREAKVQWKVDNALQSGNSQESVTE QDSKDSTYSLSSTLTLSKADYEKHKVYACEVTHQGLSSPVTKSFNRGECGGGGSGGGGSGGGGSGG GGSASTKGPSVFPLAPSSKSTSGGTAALGCLVKDYFPEPVTVSWNSGALTSGVHTFPAVLQSSGLYSL SSVVTVPSSSLGTQTYICNVNHKPSNTKVDKRVEPKSCDKTHTCPPCPAPELLGGPSVFLFPPKPKDT LMISRTPEVTCVVVDVSHEDPEVKFNWYVDGVEVHNAKTKPREEQYNSTYRVVSYLTVLHQDWLN GKEYKCKVSNKALPAPIEKTISKAKGQPREPQVYTLPPSREEMTKNQVSLTCLVKGFYPSDIAVEWE SNGQPENNYKTTPPVLDSDGSFFLYSKLTVDKSRWQQGNVFSCSVMHEALHNHYTQKSLSLSPGK (SEQ ID NO: 12) |
| Unsubstituted scIL-10 (10 aa linker): CH1: CL: Fc (SEQ ID NO: 53) | SPGQGTQSENSCTHFPGNLPNMLRDLRDAFSRVKTFFQMKDQLDNLLLKESLLEDFKGYLGCQALS EMIQFYLEEVMPQAENQDPDIKAHVNSLGENLKTLRLRLRRCHRFLPCENKSKAVEQVKNAFNKLQ EKGIYKAMSEFDIFINYIEAYMTMKIRNGGSGGGGSGGSPGQGTQSENSCTHFPGNLPNMLRDLRDA FSRVKTFFQMKDQLDNLLLKESLLEDFKGYLGCQALSEMIQFYLEEVMPQAENQDPDIKAHVNSLG ENLKTLRLRLRRCHRFLPCENKSKAVEQVKNAFNKLQEKGIYKAMSEFDIFINYIEAYMTMKIRNG GGGSGGGGSASTKGPSVFPLAPSSKSTSGGTAALGCLVKDYFPEPVTVSWNSGALTSGVHTFPAVLQ SSGLYSLSSVVTVPSSSLGTQTYICNVNHKPSNTKVDKRVGGGGSGGGGSGGGGSGGGGSRTVAAPS VFIFPPSDEQLKSGTASVVCLLNNFYPREAKVQWKVDNALQSGNSQESVTEQDSKDSTYSLSSTLTLS KADYEKHKVYACEVTHQGLSSPVTKSFNRGECGGSGGEPKSCDKTHTCPPCPAPELLGGPSVFLFPP KPKDTLMISRTPEVTCVVVDVSHEDPEVKFNWYVDGVEVHNAKTKPREEQYNSTYRVVSVLTVLHQ DWLNGKEYKCKVSNKALPAPIEKTISKAKGQPREPQVYTLPPSREEMTKNQVSLTCLVKGFYPSDIA VEWESNGQPENNYKTTPPVLDSDGSFFLYSKLTVDKSRWQQGNVFSCSVMHEALHNHYTQKSLSLS PGK (SEQ ID NO: 53) |

TABLE 1-continued

| Protein | Sequence |
|---|---|
| Unsubstituted scIL-10 (5 aa linker) Fc (Control) SEQ ID NO: 13 | SPGQGTQSENSCTHFPGNLPNMLRDLRDAFSRVKTFFQMKDQLDNLLLKESLLEDFKGYLGCQALS EMIQFYLEEVMPQAENQDPDIKAHVNSLGENLKTLRLRLRRCHRFLPCENKSKAVEQVKNAFNKLQ EKGIYKAMSEFDIFINYIEAYMTMKIRNGGSGGSPGQGTQSENSCTHFPGNLPNMLRDLRDAFSRVK TFFQMKDQLDNLLLKESLLEDFKGYLGCQALSEMIQFYLEEVMPQAENQDPDIKAHVNSLGENLKT LRLRLRRCHRFLPCENKSKAVEQVKNAFNKLQEKGIYKAMSEFDIFINYIEAYMTMKIRNEPKSSDK THTCPPCPAPELLGGPSVFLFPPKPKDTLMISRTPEVTCVVVDVSHEDPEVKFNWYVDGVEVHNAKT KPREEQYNSTYRVVSVLTVLHQDWLNGKEYKCICVSNKALPAPIEKTISKAKGQPREPQVYTLPPSRE EMTKNQVSLTCLVKGFYPSDIAVEWESNGQPENNYKTTPPVLDSDGSFFLYSKLTVDKSRWQQGNV FSCSVMHEALHNHYTQKSLSLSPGK (SEQ ID NO: 13) |

Expression of scIL-10:$C_L$:$C_H$1:Fc and scIL-10:$C_{H1}$:$C_L$:Fc

The genes were synthetically synthesized and supplied in pcDNA3.1 expression vector (GeneArt), and transiently expressed in HEK293 cells using the Expi293 expression system (Life Technologies). Proteins were purified using Protein A (GE Healthcare) with low pH elution and dialyzed against 2 L 1×PBS 2 times.

Figure 3:
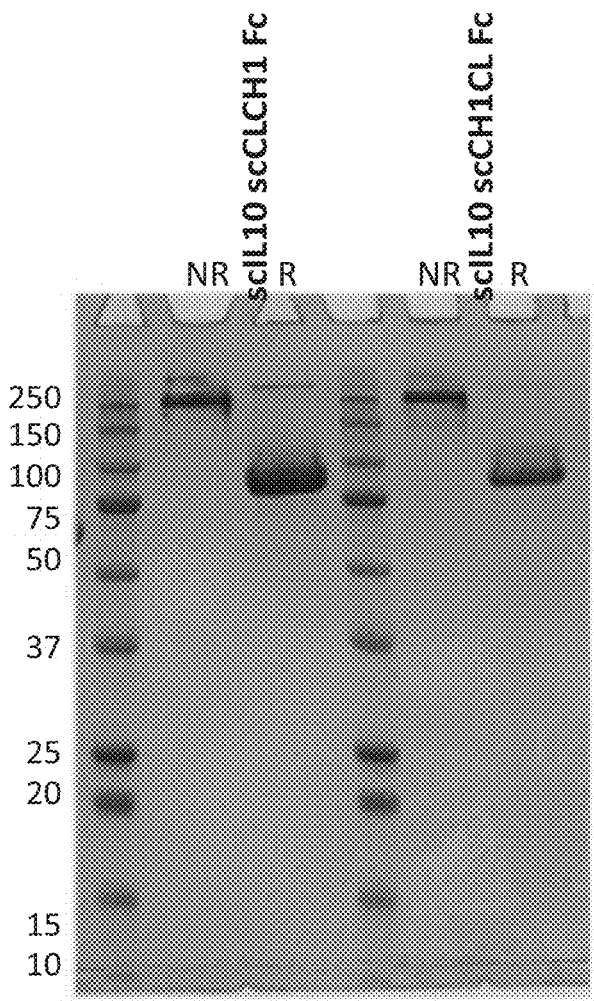
FIG. 3 is an SDS-PAGE showing expression of an Fc fusion protein comprising scIL-10 fused to the Fc region of an IgG1 antibody via the novel scCLCH1 linker (left) or via the novel scCH1CL linker (right) under reducing and non-reducing conditions.
Figure 4:
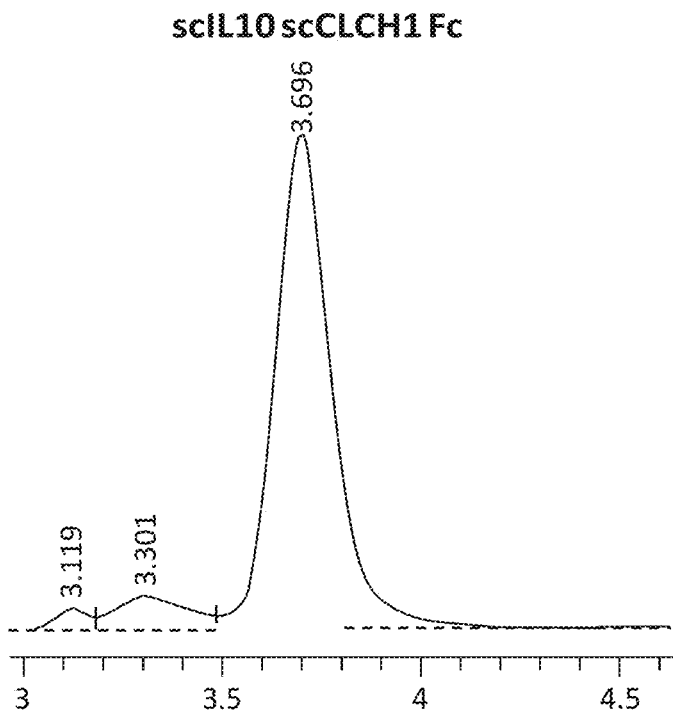
FIG. 4 is a chromatogram showing the characterization of the IL-10 fused to the Fc region of an IgG1 antibody via the novel scCLCH1 linker by analytical gel filtration.
Figure 5:
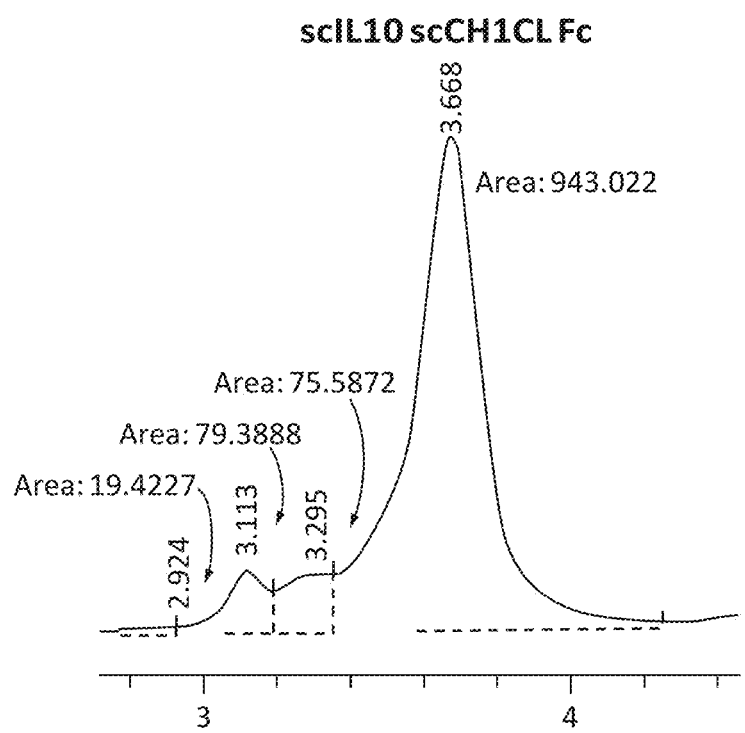
FIG. 5 is a chromatogram showing the characterization of the IL-10 fused to the Fc region of an IgG1 antibody via the novel scCH1CL linker by analytical gel filtration.

The molecules were analyzed by SDS PAGE gel under reducing and non-reducing conditions (FIG. 3). For reducing and non-reducing conditions, 2.5 ug of protein was loaded onto an Any kD gel (Invitrogen) with a Precision Plus Protein Kaleidoscope standard (Invitrogen) (MW range 10 kD-250 kD). The molecule was characterized by analytical gel filtration on an) (Bridge Protein BEH SEC column, 200 Å, 3.5 μm, 7.8 mm×150 mm (Waters). The column was equilibrated and run at 0.9 ml/min with 100 mM sodium phosphate pH 7.0 as a running buffer for all analyses. Purified samples (0.5 mg/ml) were injected (15 ul) and eluted with a run time of 15 min (FIGS. 4 and 5).

Bioactivity of scIL-10:$C_L$:$C_H$1: Fc and scIL-10:$C_{H1}$:$C_L$:Fc

Figure 6:
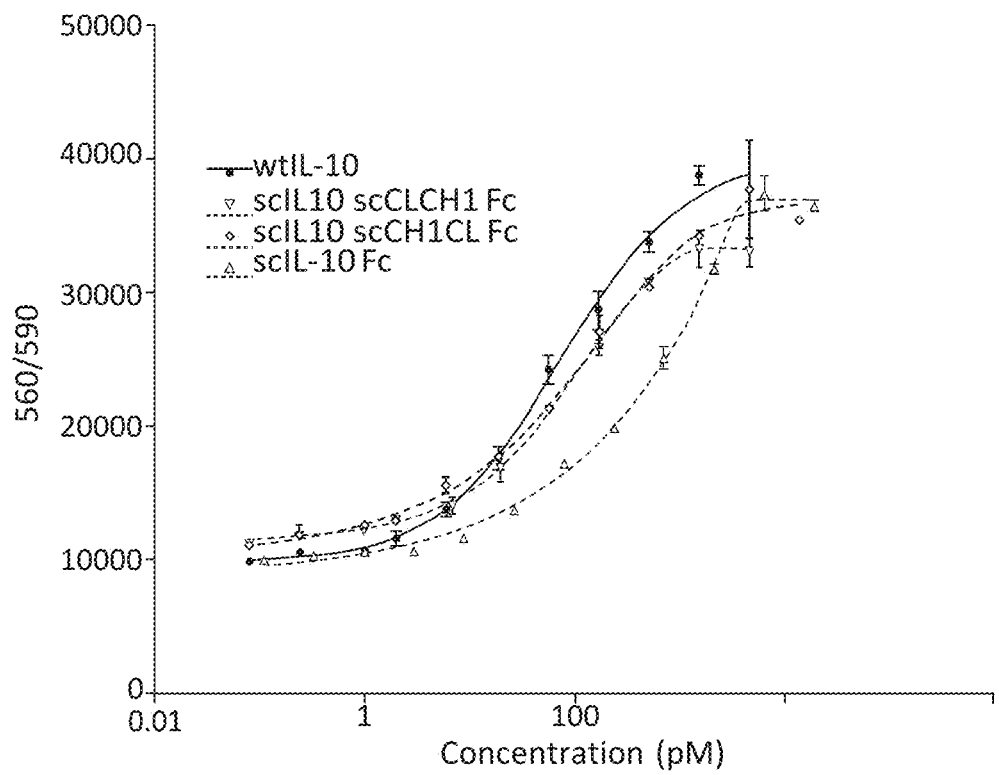
FIG. 6 is a graph showing stimulation of mouse mast cell line MC/9 by the IL-10 single chain fusion proteins of the invention as compared to the scIL-10 direct Fc fusion protein used as a control.

In vitro bioactivity was assessed by evaluating the ability of scIL-10:$C_L$:$C_H$1:Fc and scIL-10:$C_{H1}$:$C_L$:Fc to stimulate proliferation of the mouse mast cell line MC/9 (ATCC CRL-8306). The scIL-10 direct Fc fusion protein (scIL-10:Fc) was used as a control. For the assay, MC/9 cells were plated at 10,000 cells/well in DMEM media containing 10% heat inactivated fetal bovine serum, 2 mM glutamine and 0.05 mM 2-mercaptoethanol. Cells were incubated for 72 hours at 37° C., 5% $CO_2$ with varying concentrations of human IL-10 (R&D Systems), scIL-10:$C_L$:$C_H$1:Fc, scIL-10: $C_{H1}$:$C_L$:Fc or scIL-10:Fc. After 72 hours, the cells were stained with CellTiter-Blue (Promega) for 4 hours at 37° C., 5% $CO_2$ according to the manufacturer's protocol. Fluorescent measurements were taken at 560/590 nm. IL-10 ($EC_{50}$=75 pM), scIL-10:$C_L$:$C_H$1:Fc ($EC_{50}$=79 pM), scIL-10:$C_{H1}$:$C_L$:Fc ($EC_{50}$=93 pM) and scIL-10:Fc ($EC_{50}$=493 pM) were active in a dose dependent fashion (FIG. 6).

Mouse PK of scIL-10:$C_L$:$C_H$1: Fc and scIL-10:$C_{H1}$:$C_L$:Fc scIL-10:$C_L$:$C_H$1:Fc, scIL-10:$C_{H1}$:$C_L$:Fc, and scIL-10:Fc pharmacokinetics in mice were evaluated at a single intravenous doses of 0.5 mg/kg administered into tail vein and a single subcutaneous doses of 2.5 mg/kg administered into the interscapular region. Blood samples (n=3 samples/time point/fusion protein) were collected at 0.083, 0.5, 1, 4, 6, 24, 48, 96, 168, 192 and 216 hours after administration of scIL-10:$C_L$:$C_H$1:Fc, scIL-10:$C_{H1}$:$C_L$:Fc and scIL-10:Fc. For each time point/fusion protein/route of administration, serum was pooled and concentrations were measured using standard MSD techniques. Bioanalytical data was subjected to non-compartmental pharmacokinetic analysis using Phoenix WinNonlin 6.4 software. The pharmacokinetic parameter included standard pharmacokinetic parameters of maximum concentration ($C_{max}$), time to maximum concentration ($T_{max}$), area under the time versus concentration curve (AUC), mean residence time (MRT), elimination half-life (t½), clearance (CL), distribution volume at steady state ($V_{ss}$), and bioavailability (% F) were determined and reported in Tables 2 and 3.

TABLE 2

| Row ID | Compound | Dose (mg/kg) | Dose (~nMole/kg) | ROA | Cmax (nM) | Tmax (h) | Cmax/D (nM/D) | AUClast (h * nM) |
|---|---|---|---|---|---|---|---|---|
| 1 | scIL-10:Fc SEQ ID NO: 13 | 0.5 | 3.93 | IV | 94.9 | 0.083 | 24.2 | 2080 |
| 2 | scIL-10:Fc SEQ ID NO: 13 | 2.5 | 19.63 | SC | 221 | 24 | 11.3 | 12700 |
| 3 | scIL-10:$C_L$:$C_H$1:Fc SEQ ID NO: 12 | 0.5 | 2.85 | IV | 140 | 0.083 | 49.2 | 2850 |
| 4 | scIL-10:$C_L$:$C_H$1:Fc SEQ ID NO: 12 | 2.5 | 14.25 | SC | 227 | 24 | 15.9 | 19500 |
| 5 | scIL-10:$C_{H1}$:$C_L$:Fc SEQ ID NO: 53 | 0.5 | 2.84 | IV | 115 | 0.083 | 40.5 | 1300 |
| 6 | scIL40:$C_{H1}$:$C_L$:Fc SEQ ID NO: 53 | 2.5 | 14.2 | SC | 120 | 24 | 8.48 | 7570 |

TABLE 3

| Row ID | AUCinf (h * nM) | AUCinf/D (h * nM) | MRTinf (h) | t½ (h) | CL (mL/hr/kg) | Vss (mL/kg) | % F |
|---|---|---|---|---|---|---|---|
| 1 | 2170 | 552 | 33 | 21 | 1.811 | 59.57 | NA |
| 2 | 12700 | 649 | 46 | 11 | NA | NA | ~100 |
| 3 | 2850 | 999 | 30 | 7.8 | 1.001 | 29.56 | NA |
| 4 | 19500 | 1370 | 56 | 8.5 | NA | NA | ~100 |
| 5 | 1300 | 458 | 16 | 9.3 | 2.183 | 35.44 | NA |
| 6 | 7570 | 533 | 41 | 9.1 | NA | NA | ~100 |

Example 2: (scIL-10)-L1-HINGE-Fc Fusion Proteins

Design of scIL-10 Variant Fusion Proteins

The scIL-10 of Formula 1 are fused to a single chain Fc linker of Formula 2 wherein L1 is CL-CH1-Fc as per Formula 3. The amino acid sequences of each full length scIL-10-L1-HINGE-Fc fusion variant protein synthesized is found in Table 4. The description column of Table 4 indicates the scIL-10 used in the construct with the fusion partner. For example wtIL-10:linker:D41F indicates that in accordance with Formula 1, the first monomer subunit is wt IL-10 of SEQ ID NO: 1 and is therefore unsubstituted linked to a linker which is in turn linked to the second monomer subunit wherein the wtIL10 of SEQ ID NO: 1 is substituted at amino acid 41 such that the isoleucine at amino acid 41 is substituted with phenylalanine (D41F).

For expression in mammalian cells, the N-terminal leader sequence of SEQ ID NO: 48 was added to each of the protein sequences found in Table 4.

TABLE 4

| Description | Amino Acid Sequence/SEQ ID NO |
|---|---|
| scIL-10: CL: CH1: Fc | SPGQGTQSEN SCTHFPGNLP NMLRDLRDAF SRVKTFFQMK DQLDNLLLKE SLLEDFKGYL GCQALSEMIQ FYLEEVMPQA ENQDPDIKAH VNSLGENLKT LRLRLRRCHR FLPCENKSKA VEQVKNAFNK LQEKGIYKAM SEFDIFINYI EAYMTMKIRN GGSGGGGSGG SPGQGTQSEN SCTHFPGNLP NMLRDLRDAF SRVKTFFQMK DQLDNLLLKE SLLEDFKGYL GCQALSEMIQ FYLEEVMPQA ENQDPDIKAH VNSLGENLKT LRLRLRRCHR FLPCENKSKA VEQVKNAFNK LQEKGIYKAM SEFDIFINYI EAYMTMKIRN GGGGSGGGGS RTVAAPSVFI FPPSDEQLKS GTASVVCLLN NFYPREAKVQ WKVDNALQSG NSQESVTEQD SKDSTYSLSS TLTLSKADYE KHKVYACEVT HQGLSSPVTK SFNRGECGGG GSGGGGSGGG GSGGGGSAST KGPSVFPLAP SSKSTSGGTA ALGCLVKDYF PEPVTVSWNS GALTSGVHTF PAVLQSSGLY SLSSVVTVPS SSLGTQTYIC NVNHKPSNTK VDKRVEPKSC DKTHTCPPCP APELLGGPSV FLFPPKPKDT LMISRTPEVT CVVVDVSHED PEVKFNWYVD GVEVHNAKTK PREEQYNSTY RVVSVLTVLH QDWLNGKEYK CKVSNKALPA PIEKTISKAK GQPREPQVYT LPPSREEMTK NQVSLTCLVK GFYPSDIAVE WESNGQPENN YKTTPPVLDS DGSFFLYSKL TVDKSRWQQG NVFSCSVMHE ALHNHYTQKS LSLSPGK (SEQ ID NO: 12) |
| M22A: linker: D41N (R1 + R2 mutant) | SPGQGTQSEN SCTHFPGNLP NALRDLRDAF SRVKTFFQMK DQLDNLLLKE SLLEDFKGYL GCQALSEMIQ FYLEEVMPQA ENQDPDIKAH VNSLGENLKT LRLRLRRCHR FLPCENKSKA VEQVKNAFNK LQEKGIYKAM SEFDIFINYI EAYMTMKIRN GGSGGGGSGG SPGQGTQSEN SCTHFPGNLP NMLRDLRDAF SRVKTFFQMK NQLDNLLLKE SLLEDFKGYL GCQALSEMIQ FYLEEVMPQA ENQDPDIKAH VNSLGENLKT LRLRLRRCHR FLPCENKSKA VEQVKNAFNK LQEKGIYKAM SEFDIFINYI EAYMTMKIRN GGGGSGGGGS RTVAAPSVFI FPPSDEQLKS GTASVVCLLN NFYPREAKVQ WKVDNALQSG NSQESVTEQD SKDSTYSLSS TLTLSKADYE KHKVYACEVT HQGLSSPVTK SFNRGECGGG GSGGGGSGGG GSGGGGSAST KGPSVFPLAP SSKSTSGGTA ALGCLVKDYF PEPVTVSWNS GALTSGVHTF PAVLQSSGLY SLSSVVTVPS SSLGTQTYIC NVNHKPSNTK VDKRVEPKSC DKTHTCPPCP APELLGGPSV FLFPPKPKDT LMISRTPEVT CVVVDVSHED PEVKFNWYVD GVEVHNAKTK PREEQYNSTY RVVSVLTVLH QDWLNGKEYK CKVSNKALPA PIEKTISKAK GQPREPQVYT LPPSREEMTK NQVSLTCLVK GFYPSDIAVE WESNGQPENN YKTTPPVLDS DGSFFLYSKL TVDKSRWQQG NVFSCSVMHE ALHNHYTQKS LSLSPGK (SEQ ID NO: 44) |
| D41N: linker: M22A (R1 + R2 mutant) | SPGQGTQSEN SCTHFPGNLP NMLRDLRDAF SRVKTFFQMK NQLDNLLLKE SLLEDFKGYL GCQALSEMIQ FYLEEVMPQA ENQDPDIKAH VNSLGENLKT LRLRLRRCHR FLPCENKSKA VEQVKNAFNK LQEKGIYKAM SEFDIFINYI EAYMTMKIRN GGSGGGGSGG SPGQGTQSEN SCTHFPGNLP NALRDLRDAF SRVKTFFQMK DQLDNLLLKE SLLEDFKGYL GCQALSEMIQ FYLEEVMPQA ENQDPDIKAH VNSLGENLKT LRLRLRRCHR FLPCENKSKA VEQVKNAFNK LQEKGIYKAM SEFDIFINYI EAYMTMKIRN GGGGSGGGGS RTVAAPSVFI FPPSDEQLKS GTASVVCLLN NFYPREAKVQ WKVDNALQSG NSQESVTEQD SKDSTYSLSS TLTLSKADYE KHKVYACEVT HQGLSSPVTK SFNRGECGGG GSGGGGSGGG GSGGGGSAST KGPSVFPLAP SSKSTSGGTA ALGCLVKDYF PEPVTVSWNS GALTSGVHTF PAVLQSSGLY SLSSVVTVPS SSLGTQTYIC NVNHKPSNTK VDKRVEPKSC DKTHTCPPCP APELLGGPSV FLFPPKPKDT LMISRTPEVT CVVVDVSHED PEVKFNWYVD GVEVHNAKTK PREEQYNSTY RVVSVLTVLH QDWLNGKEYK CKVSNKALPA PIEKTISKAK GQPREPQVYT LPPSREEMTK NQVSLTCLVK GFYPSDIAVE WESNGQPENN YKTTPPVLDS DGSFFLYSKL TVDKSRWQQG NVFSCSVMHE ALHNHYTQKS LSLSPGK (SEQ ID NO: 43) |
| wtIL-10: linker: M22A, D41N (R1 + R2 mutant) | SPGQGTQSEN SCTHFPGNLP NMLRDLRDAF SRVKTFFQMK DQLDNLLLKE SLLEDFKGYL GCQALSEMIQ FYLEEVMPQA ENQDPDIKAH VNSLGENLKT LRLRLRRCHR FLPCENKSKA VEQVKNAFNK LQEKGIYKAM SEFDIFINYI EAYMTMKIRN GGSGGGGSGG SPGQGTQSEN SCTHFPGNLP NALRDLRDAF SRVKTFFQMK NQLDNLLLKE SLLEDFKGYL GCQALSEMIQ FYLEEVMPQA ENQDPDIKAH VNSLGENLKT LRLRLRRCHR FLPCENKSKA VEQVKNAFNK LQEKGIYKAM SEFDIFINYI EAYMTMKIRN GGGGSGGGGS RTVAAPSVFI FPPSDEQLKS GTASVVCLLN NFYPREAKVQ WKVDNALQSG NSQESVTEQD SKDSTYSLSS TLTLSKADYE KHKVYACEVT HQGLSSPVTK SFNRGECGGG GSGGGGSGGG GSGGGGSAST KGPSVFPLAP SSKSTSGGTA ALGCLVKDYF PEPVTVSWNS GALTSGVHTF PAVLQSSGLY |

TABLE 4-continued

| Description | Amino Acid Sequence/SEQ ID NO |
|---|---|
| | SLSSVVTVPS SSLGTQTYIC NVNHKPSNTK VDKRVEPKSC DKTHTCPPCP<br>APELLGGPSV FLFPPKPKDT LMISRTPEVT CVVVDVSHED PEVKFNWYVD<br>GVEVHNAKTK PREEQYNSTY RVVSVLTVLH QDWLNGKEYK CKVSNKALPA<br>PIEKTISKAK GQPREPQVYT LPPSREEMTK NQVSLTCLVK GFYPSDIAVE<br>WESNGQPENN YKTTPPVLDS DGSFFLYSKL TVDKSRWQQG NVFSCSVMHE<br>ALHNHYTQKS LSLSPGK (SEQ ID NO: 42) |
| wtIL-10: linker: D41N<br>(R1 mutant) | SPGQGTQSEN SCTHFPGNLP NMLRDLRDAF<br>SRVKTFFQMK DQLDNLLLKE SLLEDFKGYL GCQALSEMIQ FYLEEVMPQA<br>ENQDPDIKAH VNSLGENLKT LRLRLRRCHR FLPCENKSKA VEQVKNAFNK<br>LQEKGIYKAM SEFDIFINYI EAYMTMKIRN GGSGGGGSGG SPGQGTQSEN<br>SCTHFPGNLP NMLRDLRDAF SRVKTFFQMK NQLDNLLLKE SLLEDFKGYL<br>GCQALSEMIQ FYLEEVMPQA ENQDPDIKAH VNSLGENLKT LRLRLRRCHR<br>FLPCENKSKA VEQVKNAFNK LQEKGIYKAM SEFDIFINYI EAYMTMKIRN<br>GGGGSGGGGS RTVAAPSVFI FPPSDEQLKS GTASVVCLLN NFYPREAKVQ<br>WKVDNALQSG NSQESVTEQD SKDSTYSLSS TLTLSKADYE KHKVYACEVT<br>HQGLSSPVTK SFNRGECGGG GSGGGGSGGG GSGGGGSAST KGPSVFPLAP<br>SSKSTSGGTA ALGCLVKDYF PEPVTVSWNS GALTSGVHTF PAVLQSSGLY<br>SLSSVVTVPS SSLGTQTYIC NVNHKPSNTK VDKRVEPKSC DKTHTCPPCP<br>APELLGGPSV FLFPPKPKDT LMISRTPEVT CVVVDVSHED PEVKFNWYVD<br>GVEVHNAKTK PREEQYNSTY RVVSVLTVLH QDWLNGKEYK CKVSNKALPA<br>PIEKTISKAK GQPREPQVYT LPPSREEMTK NQVSLTCLVK GFYPSDIAVE<br>WESNGQPENN YKTTPPVLDS DGSFFLYSKL TVDKSRWQQG NVFSCSVMHE<br>ALHNHYTQKS LSLSPGK (SEQ ID NO: 41) |
| M22A: linker: D41A<br>(R1 + R2 mutant) | SPGQGTQSEN SCTHFPGNLP NALRDLRDAF<br>SRVKTFFQMK DQLDNLLLKE SLLEDFKGYL GCQALSEMIQ FYLEEVMPQA<br>ENQDPDIKAH VNSLGENLKT LRLRLRRCHR FLPCENKSKA VEQVKNAFNK<br>LQEKGIYKAM SEFDIFINYI EAYMTMKIRN GGSGGGGSGG SPGQGTQSEN<br>SCTHFPGNLP NMLRDLRDAF SRVKTFFQMK AQLDNLLLKE SLLEDFKGYL<br>GCQALSEMIQ FYLEEVMPQA ENQDPDIKAH VNSLGENLKT LRLRLRRCHR<br>FLPCENKSKA VEQVKNAFNK LQEKGIYKAM SEFDIFINYI EAYMTMKIRN<br>GGGGSGGGGS RTVAAPSVFI FPPSDEQLKS GTASVVCLLN NFYPREAKVQ<br>WKVDNALQSG NSQESVTEQD SKDSTYSLSS TLTLSKADYE KHKVYACEVT<br>HQGLSSPVTK SFNRGECGGG GSGGGGSGGG GSGGGGSAST KGPSVFPLAP<br>SSKSTSGGTA ALGCLVKDYF PEPVTVSWNS GALTSGVHTF PAVLQSSGLY<br>SLSSVVTVPS SSLGTQTYIC NVNHKPSNTK VDKRVEPKSC DKTHTCPPCP<br>APELLGGPSV FLFPPKPKDT LMISRTPEVT CVVVDVSHED PEVKFNWYVD<br>GVEVHNAKTK PREEQYNSTY RVVSVLTVLH QDWLNGKEYK CKVSNKALPA<br>PIEKTISKAK GQPREPQVYT LPPSREEMTK NQVSLTCLVK GFYPSDIAVE<br>WESNGQPENN YKTTPPVLDS DGSFFLYSKL TVDKSRWQQG NVFSCSVMHE<br>ALHNHYTQKS LSLSPGK (SEQ ID NO: 40) |
| D41A: linker: M22A<br>(R1 + R2 mutant) | SPGQGTQSEN SCTHFPGNLP NMLRDLRDAF<br>SRVKTFFQMK AQLDNLLLKE SLLEDFKGYL GCQALSEMIQ FYLEEVMPQA<br>ENQDPDIKAH VNSLGENLKT LRLRLRRCHR FLPCENKSKA VEQVKNAFNK<br>LQEKGIYKAM SEFDIFINYI EAYMTMKIRN GGSGGGGSGG SPGQGTQSEN<br>SCTHFPGNLP NALRDLRDAF SRVKTFFQMK DQLDNLLLKE SLLEDFKGYL<br>GCQALSEMIQ FYLEEVMPQA ENQDPDIKAH VNSLGENLKT LRLRLRRCHR<br>FLPCENKSKA VEQVKNAFNK LQEKGIYKAM SEFDIFINYI EAYMTMKIRN<br>GGGGSGGGGS RTVAAPSVFI FPPSDEQLKS GTASVVCLLN NFYPREAKVQ<br>WKVDNALQSG NSQESVTEQD SKDSTYSLSS TLTLSKADYE KHKVYACEVT<br>HQGLSSPVTK SFNRGECGGG GSGGGGSGGG GSGGGGSAST KGPSVFPLAP<br>SSKSTSGGTA ALGCLVKDYF PEPVTVSWNS GALTSGVHTF PAVLQSSGLY<br>SLSSVVTVPS SSLGTQTYIC NVNHKPSNTK VDKRVEPKSC DKTHTCPPCP<br>APELLGGPSV FLFPPKPKDT LMISRTPEVT CVVVDVSHED PEVKFNWYVD<br>GVEVHNAKTK PREEQYNSTY RVVSVLTVLH QDWLNGKEYK CKVSNKALPA<br>PIEKTISKAK GQPREPQVYT LPPSREEMTK NQVSLTCLVK GFYPSDIAVE<br>WESNGQPENN YKTTPPVLDS DGSFFLYSKL TVDKSRWQQG NVFSCSVMHE<br>ALHNHYTQKS LSLSPGK (SEQ ID NO: 39) |
| wtIL-10: linker: M22A,<br>D41A (R1 + R2 mutant) | SPGQGTQSEN SCTHFPGNLP NMLRDLRDAF<br>SRVKTFFQMK DQLDNLLLKE SLLEDFKGYL GCQALSEMIQ FYLEEVMPQA<br>ENQDPDIKAH VNSLGENLKT LRLRLRRCHR FLPCENKSKA VEQVKNAFNK<br>LQEKGIYKAM SEFDIFINYI EAYMTMKIRN GGSGGGGSGG SPGQGTQSEN<br>SCTHFPGNLP NALRDLRDAF SRVKTFFQMK AQLDNLLLKE SLLEDFKGYL<br>GCQALSEMIQ FYLEEVMPQA ENQDPDIKAH VNSLGENLKT LRLRLRRCHR<br>FLPCENKSKA VEQVKNAFNK LQEKGIYKAM SEFDIFINYI EAYMTMKIRN<br>GGGGSGGGGS RTVAAPSVFI FPPSDEQLKS GTASVVCLLN NFYPREAKVQ<br>WKVDNALQSG NSQESVTEQD SKDSTYSLSS TLTLSKADYE KHKVYACEVT<br>HQGLSSPVTK SFNRGECGGG GSGGGGSGGG GSGGGGSAST KGPSVFPLAP<br>SSKSTSGGTA ALGCLVKDYF PEPVTVSWNS GALTSGVHTF PAVLQSSGLY<br>SLSSVVTVPS SSLGTQTYIC NVNHKPSNTK VDKRVEPKSC DKTHTCPPCP<br>APELLGGPSV FLFPPKPKDT LMISRTPEVT CVVVDVSHED PEVKFNWYVD<br>GVEVHNAKTK PREEQYNSTY RVVSVLTVLH QDWLNGKEYK CKVSNKALPA<br>PIEKTISKAK GQPREPQVYT LPPSREEMTK NQVSLTCLVK GFYPSDIAVE<br>WESNGQPENN YKTTPPVLDS DGSFFLYSKL TVDKSRWQQG NVFSCSVMHE<br>ALHNHYTQKS LSLSPGK (SEQ ID NO: 38) |

TABLE 4-continued

| Description | Amino Acid Sequence/SEQ ID NO |
|---|---|
| wtIL-10: linker: D41A (R1 mutant) | SPGQGTQSEN SCTHFPGNLP NMLRDLRDAF SRVKTFFQMK DQLDNLLLKE SLLEDFKGYL GCQALSEMIQ FYLEEVMPQA ENQDPDIKAH VNSLGENLKT LRLRLRRCHR FLPCENKSKA VEQVKNAFNK LQEKGIYKAM SEFDIFINYI EAYMTMKIRN GGSGGGGSGG SPGQGTQSEN SCTHFPGNLP NMLRDLRDAF SRVKTFFQMK AQLDNLLLKE SLLEDFKGYL GCQALSEMIQ FYLEEVMPQA ENQDPDIKAH VNSLGENLKT LRLRLRRCHR FLPCENKSKA VEQVKNAFNK LQEKGIYKAM SEFDIFINYI EAYMTMKIRN GGGGSGGGGS RTVAAPSVFI FPPSDEQLKS GTASVVCLLN NFYPREAKVQ WKVDNALQSG NSQESVTEQD SKDSTYSLSS TLTLSKADYE KHKVYACEVT HQGLSSPVTK SFNRGECGGG GSGGGGSGGG GSGGGGSAST KGPSVFPLAP SSKSTSGGTA ALGCLVKDYF PEPVTVSWNS GALTSGVHTF PAVLQSSGLY SLSSVVTVPS SSLGTQTYIC NVNHKPSNTK VDKRVEPKSC DKTHTCPPCP APELLGGPSV FLFPPKPKDT LMISRTPEVT CVVVDVSHED PEVKFNWYVD GVEVHNAKTK PREEQYNSTY RVVSVLTVLH QDWLNGKEYK CKVSNKALPA PIEKTISKAK GQPREPQVYT LPPSREEMTK NQVSLTCLVK GFYPSDIAVE WESNGQPENN YKTTPPVLDS DGSFFLYSKL TVDKSRWQQG NVFSCSVMHE ALHNHYTQKS LSLSPGK (SEQ ID NO: 37) |
| M22A: linker: D41F (R1 + R2 mutant) | SPGQGTQSEN SCTHFPGNLP NALRDLRDAF SRVKTFFQMK DQLDNLLLKE SLLEDFKGYL GCQALSEMIQ FYLEEVMPQA ENQDPDIKAH VNSLGENLKT LRLRLRRCHR FLPCENKSKA VEQVKNAFNK LQEKGIYKAM SEFDIFINYI EAYMTMKIRN GGSGGGGSGG SPGQGTQSEN SCTHFPGNLP NMLRDLRDAF SRVKTFFQMK FQLDNLLLKE SLLEDFKGYL GCQALSEMIQ FYLEEVMPQA ENQDPDIKAH VNSLGENLKT LRLRLRRCHR FLPCENKSKA VEQVKNAFNK LQEKGIYKAM SEFDIFINYI EAYMTMKIRN GGGGSGGGGS RTVAAPSVFI FPPSDEQLKS GTASVVCLLN NFYPREAKVQ WKVDNALQSG NSQESVTEQD SKDSTYSLSS TLTLSKADYE KHKVYACEVT HQGLSSPVTK SFNRGECGGG GSGGGGSGGG GSGGGGSAST KGPSVFPLAP SSKSTSGGTA ALGCLVKDYF PEPVTVSWNS GALTSGVHTF PAVLQSSGLY SLSSVVTVPS SSLGTQTYIC NVNHKPSNTK VDKRVEPKSC DKTHTCPPCP APELLGGPSV FLFPPKPKDT LMISRTPEVT CVVVDVSHED PEVKFNWYVD GVEVHNAKTK PREEQYNSTY RVVSVLTVLH QDWLNGKEYK CKVSNKALPA PIEKTISKAK GQPREPQVYT LPPSREEMTK NQVSLTCLVK GFYPSDIAVE WESNGQPENN YKTTPPVLDS DGSFFLYSKL TVDKSRWQQG NVFSCSVMHE ALHNHYTQKS LSLSPGK (SEQ ID NO: 29) |
| D41F: linker: M22A (R1 + R2 mutant) | SPGQGTQSEN SCTHFPGNLP NMLRDLRDAF SRVKTFFQMK FQLDNLLLKE SLLEDFKGYL GCQALSEMIQ FYLEEVMPQA ENQDPDIKAH VNSLGENLKT LRLRLRRCHR FLPCENKSKA VEQVKNAFNK LQEKGIYKAM SEFDIFINYI EAYMTMKIRN GGSGGGGSGG SPGQGTQSEN SCTHFPGNLP NALRDLRDAF SRVKTFFQMK DQLDNLLLKE SLLEDFKGYL GCQALSEMIQ FYLEEVMPQA ENQDPDIKAH VNSLGENLKT LRLRLRRCHR FLPCENKSKA VEQVKNAFNK LQEKGIYKAM SEFDIFINYI EAYMTMKIRN GGGGSGGGGS RTVAAPSVFI FPPSDEQLKS GTASVVCLLN NFYPREAKVQ WKVDNALQSG NSQESVTEQD SKDSTYSLSS TLTLSKADYE KHKVYACEVT HQGLSSPVTK SFNRGECGGG GSGGGGSGGG GSGGGGSAST KGPSVFPLAP SSKSTSGGTA ALGCLVKDYF PEPVTVSWNS GALTSGVHTF PAVLQSSGLY SLSSVVTVPS SSLGTQTYIC NVNHKPSNTK VDKRVEPKSC DKTHTCPPCP APELLGGPSV FLFPPKPKDT LMISRTPEVT CVVVDVSHED PEVKFNWYVD GVEVHNAKTK PREEQYNSTY RVVSVLTVLH QDWLNGKEYK CKVSNKALPA PIEKTISKAK GQPREPQVYT LPPSREEMTK NQVSLTCLVK GFYPSDIAVE WESNGQPENN YKTTPPVLDS DGSFFLYSKL TVDKSRWQQG NVFSCSVMHE ALHNHYTQKS LSLSPGK (SEQ ID NO: 28) |
| wtIL-10 : linker: M22A, D41F (R1 + R2 mutant) | SPGQGTQSEN SCTHFPGNLP NMLRDLRDAF SRVKTFFQMK DQLDNLLLKE SLLEDFKGYL GCQALSEMIQ FYLEEVMPQA ENQDPDIKAH VNSLGENLKT LRLRLRRCHR FLPCENKSKA VEQVKNAFNK LQEKGIYKAM SEFDIFINYI EAYMTMKIRN GGSGGGGSGG SPGQGTQSEN SCTHFPGNLP NALRDLRDAF SRVKTFFQMK FQLDNLLLKE SLLEDFKGYL GCQALSEMIQ FYLEEVMPQA ENQDPDIKAH VNSLGENLKT LRLRLRRCHR FLPCENKSKA VEQVKNAFNK LQEKGIYKAM SEFDIFINYI EAYMTMKIRN GGGGSGGGGS RTVAAPSVFI FPPSDEQLKS GTASVVCLLN NFYPREAKVQ WKVDNALQSG NSQESVTEQD SKDSTYSLSS TLTLSKADYE KHKVYACEVT HQGLSSPVTK SFNRGECGGG GSGGGGSGGG GSGGGGSAST KGPSVFPLAP SSKSTSGGTA ALGCLVKDYF PEPVTVSWNS GALTSGVHTF PAVLQSSGLY SLSSVVTVPS SSLGTQTYIC NVNHKPSNTK VDKRVEPKSC DKTHTCPPCP APELLGGPSV FLFPPKPKDT LMISRTPEVT CVVVDVSHED PEVKFNWYVD GVEVHNAKTK PREEQYNSTY RVVSVLTVLH QDWLNGKEYK CKVSNKALPA PIEKTISKAK GQPREPQVYT LPPSREEMTK NQVSLTCLVK GFYPSDIAVE WESNGQPENN YKTTPPVLDS DGSFFLYSKL TVDKSRWQQG NVFSCSVMHE ALHNHYTQKS LSLSPGK (SEQ ID NO: 27) |
| M22A: linker: D41F (R1 + R2 mutant) | SPGQGTQSEN SCTHFPGNLP NALRDLRDAF SRVKTFFQMK FQLDNLLLKE SLLEDFKGYL GCQALSEMIQ FYLEEVMPQA ENQDPDIKAH VNSLGENLKT LRLRLRRCHR FLPCENKSKA VEQVKNAFNK LQEKGIYKAM SEFDIFINYI EAYMTMKIRN GGSGGGGSGG SPGQGTQSEN SCTHFPGNLP NMLRDLRDAF SRVKTFFQMK DQLDNLLLKE SLLEDFKGYL GCQALSEMIQ FYLEEVMPQA ENQDPDIKAH VNSLGENLKT LRLRLRRCHR |

TABLE 4-continued

| Description | Amino Acid Sequence/SEQ ID NO |
|---|---|
| | FLPCENKSKA VEQVKNAFNK LQEKGIYKAM SEFDIFINYI EAYMTMKIRN GGGGSGGGGS RTVAAPSVFI FPPSDEQLKS GTASVVCLLN NFYPREAKVQ WKVDNALQSG NSQESVTEQD SKDSTYSLSS TLTLSKADYE KHKVYACEVT HQGLSSPVTK SFNRGECGGG GSGGGGSGGG GSGGGGSAST KGPSVFPLAP SSKSTSGGTA ALGCLVKDYF PEPVTVSWNS GALTSGVHTF PAVLQSSGLY SLSSVVTVPS SSLGTQTYIC NVNHKPSNTK VDKRVEPKSC DKTHTCPPCP APELLGGPSV FLFPPKPKDT LMISRTPEVT CVVVDVSHED PEVKFNWYVD GVEVHNAKTK PREEQYNSTY RVVSVLTVLH QDWLNGKEYK CKVSNKALPA PIEKTISKAK GQPREPQVYT LPPSREEMTK NQVSLTCLVK GFYPSDIAVE WESNGQPENN YKTTPPVLDS DGSFFLYSKL TVDKSRWQQG NVFSCSVMHE ALHNHYTQKS LSLSPGK (SEQ ID NO: 26) |
| M22A: linker: M22A (R2 mutant) | SPGQGTQSEN SCTHFPGNLP NALRDLRDAF SRVKTFFQMK DQLDNLLLKE SLLEDFKGYL GCQALSEMIQ FYLEEVMPQA ENQDPDIKAH VNSLGENLKT LRLRLRRCHR FLPCENKSKA VEQVKNAFNK LQEKGIYKAM SEFDIFINYI EAYMTMKIRN GGSGGGGSGG SPGQGTQSEN SCTHFPGNLP NALRDLRDAF SRVKTFFQMK DQLDNLLLKE SLLEDFKGYL GCQALSEMIQ FYLEEVMPQA ENQDPDIKAH VNSLGENLKT LRLRLRRCHR FLPCENKSKA VEQVKNAFNK LQEKGIYKAM SEFDIFINYI EAYMTMKIRN GGGGSGGGGS RTVAAPSVFI FPPSDEQLKS GTASVVCLLN NFYPREAKVQ WKVDNALQSG NSQESVTEQD SKDSTYSLSS TLTLSKADYE KHKVYACEVT HQGLSSPVTK SFNRGECGGG GSGGGGSGGG GSGGGGSAST KGPSVFPLAP SSKSTSGGTA ALGCLVKDYF PEPVTVSWNS GALTSGVHTF PAVLQSSGLY SLSSVVTVPS SSLGTQTYIC NVNHKPSNTK VDKRVEPKSC DKTHTCPPCP APELLGGPSV FLFPPKPKDT LMISRTPEVT CVVVDVSHED PEVKFNWYVD GVEVHNAKTK PREEQYNSTY RVVSVLTVLH QDWLNGKEYK CKVSNKALPA PIEKTISKAK GQPREPQVYT LPPSREEMTK NQVSLTCLVK GFYPSDIAVE WESNGQPENN YKTTPPVLDS DGSFFLYSKL TVDKSRWQQG NVFSCSVMHE ALHNHYTQKS LSLSPGK (SEQ ID NO: 25) |
| wtIL-10: linker: M22A (R2 mutant) | SPGQGTQSEN SCTHFPGNLP NMLRDLRDAF SRVKTFFQMK DQLDNLLLKE SLLEDFKGYL GCQALSEMIQ FYLEEVMPQA ENQDPDIKAH VNSLGENLKT LRLRLRRCHR FLPCENKSKA VEQVKNAFNK LQEKGIYKAM SEFDIFINYI EAYMTMKIRN GGSGGGGSGG SPGQGTQSEN SCTHFPGNLP NALRDLRDAF SRVKTFFQMK DQLDNLLLKE SLLEDFKGYL GCQALSEMIQ FYLEEVMPQA ENQDPDIKAH VNSLGENLKT LRLRLRRCHR FLPCENKSKA VEQVKNAFNK LQEKGIYKAM SEFDIFINYI EAYMTMKIRN GGGGSGGGGS RTVAAPSVFI FPPSDEQLKS GTASVVCLLN NFYPREAKVQ WKVDNALQSG NSQESVTEQD SKDSTYSLSS TLTLSKADYE KHKVYACEVT HQGLSSPVTK SFNRGECGGG GSGGGGSGGG GSGGGGSAST KGPSVFPLAP SSKSTSGGTA ALGCLVKDYF PEPVTVSWNS GALTSGVHTF PAVLQSSGLY SLSSVVTVPS SSLGTQTYIC NVNHKPSNTK VDKRVEPKSC DKTHTCPPCP APELLGGPSV FLFPPKPKDT LMISRTPEVT CVVVDVSHED PEVKFNWYVD GVEVHNAKTK PREEQYNSTY RVVSVLTVLH QDWLNGKEYK CKVSNKALPA PIEKTISKAK GQPREPQVYT LPPSREEMTK NQVSLTCLVK GFYPSDIAVE WESNGQPENN YKTTPPVLDS DGSFFLYSKL TVDKSRWQQG NVFSCSVMHE ALHNHYTQKS LSLSPGK (SEQ ID NO: 24) |
| M22A: linker: wtIL-10 (R2 mutant) | SPGQGTQSEN SCTHFPGNLP NALRDLRDAF SRVKTFFQMK DQLDNLLLKE SLLEDFKGYL GCQALSEMIQ FYLEEVMPQA ENQDPDIKAH VNSLGENLKT LRLRLRRCHR FLPCENKSKA VEQVKNAFNK LQEKGIYKAM SEFDIFINYI EAYMTMKIRN GGSGGGGSGG SPGQGTQSEN SCTHFPGNLP NMLRDLRDAF SRVKTFFQMK DQLDNLLLKE SLLEDFKGYL GCQALSEMIQ FYLEEVMPQA ENQDPDIKAH VNSLGENLKT LRLRLRRCHR FLPCENKSKA VEQVKNAFNK LQEKGIYKAM SEFDIFINYI EAYMTMKIRN GGGGSGGGGS RTVAAPSVFI FPPSDEQLKS GTASVVCLLN NFYPREAKVQ WKVDNALQSG NSQESVTEQD SKDSTYSLSS TLTLSKADYE KHKVYACEVT HQGLSSPVTK SFNRGECGGG GSGGGGSGGG GSGGGGSAST KGPSVFPLAP SSKSTSGGTA ALGCLVKDYF PEPVTVSWNS GALTSGVHTF PAVLQSSGLY SLSSVVTVPS SSLGTQTYIC NVNHKPSNTK VDKRVEPKSC DKTHTCPPCP APELLGGPSV FLFPPKPKDT LMISRTPEVT CVVVDVSHED PEVKFNWYVD GVEVHNAKTK PREEQYNSTY RVVSVLTVLH QDWLNGKEYK CKVSNKALPA PIEKTISKAK GQPREPQVYT LPPSREEMTK NQVSLTCLVK GFYPSDIAVE WESNGQPENN YKTTPPVLDS DGSFFLYSKL TVDKSRWQQG NVFSCSVMHE ALHNHYTQKS LSLSPGK (SEQ ID NO: 23) |
| D41F: linker: D41F (R1 mutant) | SPGQGTQSEN SCTHFPGNLP NMLRDLRDAF SRVKTFFQMK FQLDNLLLKE SLLEDFKGYL GCQALSEMIQ FYLEEVMPQA ENQDPDIKAH VNSLGENLKT LRLRLRRCHR FLPCENKSKA VEQVKNAFNK LQEKGIYKAM SEFDIFINYI EAYMTMKIRN GGSGGGGSGG SPGQGTQSEN SCTHFPGNLP NMLRDLRDAF SRVKTFFQMK FQLDNLLLKE SLLEDFKGYL GCQALSEMIQ FYLEEVMPQA ENQDPDIKAH VNSLGENLKT LRLRLRRCHR FLPCENKSKA VEQVKNAFNK LQEKGIYKAM SEFDIFINYI EAYMTMKIRN GGGGSGGGGS RTVAAPSVFI FPPSDEQLKS GTASVVCLLN NFYPREAKVQ WKVDNALQSG NSQESVTEQD SKDSTYSLSS TLTLSKADYE KHKVYACEVT HQGLSSPVTK SFNRGECGGG GSGGGGSGGG GSGGGGSAST KGPSVFPLAP SSKSTSGGTA ALGCLVKDYF PEPVTVSWNS GALTSGVHTF PAVLQSSGLY SLSSVVTVPS SSLGTQTYIC NVNHKPSNTK VDKRVEPKSC DKTHTCPPCP |

TABLE 4-continued

| Description | Amino Acid Sequence/SEQ ID NO |
|---|---|
| | APELLGGPSV FLFPPKPKDT LMISRTPEVT CVVVDVSHED PEVKFNWYVD<br>GVEVHNAKTK PREEQYNSTY RVVSVLTVLH QDWLNGKEYK CKVSNKALPA<br>PIEKTISKAK GQPREPQVYT LPPSREEMTK NQVSLTCLVK GFYPSDIAVE<br>WESNGQPENN YKTTPPVLDS DGSFFLYSKL TVDKSRWQQG NVFSCSVMHE<br>ALHNHYTQKS LSLSPGK (SEQ ID NO: 22) |
| wtIL-10: linkerD41F (R1 mutant) | SPGQGTQSEN SCTHFPGNLP NMLRDLRDAF<br>SRVKTFFQMK DQLDNLLLKE SLLEDFKGYL GCQALSEMIQ FYLEEVMPQA<br>ENQDPDIKAH VNSLGENLKT LRLRLRRCHR FLPCENKSKA VEQVKNAFNK<br>LQEKGIYKAM SEFDIFINYI EAYMTMKIRN GGSGGGGSGG SPGQGTQSEN<br>SCTHFPGNLP NMLRDLRDAF SRVKTFFQMK FQLDNLLLKE SLLEDFKGYL<br>GCQALSEMIQ FYLEEVMPQA ENQDPDIKAH VNSLGENLKT LRLRLRRCHR<br>FLPCENKSKA VEQVKNAFNK LQEKGIYKAM SEFDIFINYI EAYMTMKIRN<br>GGGGSGGGGS RTVAAPSVFI FPPSDEQLKS GTASVVCLLN NFYPREAKVQ<br>WKVDNALQSG NSQESVTEQD SKDSTYSLSS TLTLSKADYE KHKVYACEVT<br>HQGLSSPVTK SFNRGECGGG GSGGGGSGGG GSGGGGSAST KGPSVFPLAP<br>SSKSTSGGTA ALGCLVKDYF PEPVTVSWNS GALTSGVHTF PAVLQSSGLY<br>SLSSVVTVPS SSLGTQTYIC NVNHKPSNTK VDKRVEPKSC DKTHTCPPCP<br>APELLGGPSV FLFPPKPKDT LMISRTPEVT CVVVDVSHED PEVKFNWYVD<br>GVEVHNAKTK PREEQYNSTY RVVSVLTVLH QDWLNGKEYK CKVSNKALPA<br>PIEKTISKAK GQPREPQVYT LPPSREEMTK NQVSLTCLVK GFYPSDIAVE<br>WESNGQPENN YKTTPPVLDS DGSFFLYSKL TVDKSRWQQG NVFSCSVMHE<br>ALHNHYTQKS LSLSPGK (SEQ ID NO: 21) |
| D41F: linker: wtIL10(R1 mutant) | SPGQGTQSEN SCTHFPGNLP NMLRDLRDAF<br>SRVKTFFQMK FQLDNLLLKE SLLEDFKGYL GCQALSEMIQ FYLEEVMPQA<br>ENQDPDIKAH VNSLGENLKT LRLRLRRCHR FLPCENKSKA VEQVKNAFNK<br>LQEKGIYKAM SEFDIFINYI EAYMTMKIRN GGSGGGGSGG SPGQGTQSEN<br>SCTHFPGNLP NMLRDLRDAF SRVKTFFQMK DQLDNLLLKE SLLEDFKGYL<br>GCQALSEMIQ FYLEEVMPQA ENQDPDIKAH VNSLGENLKT LRLRLRRCHR<br>FLPCENKSKA VEQVKNAFNK LQEKGIYKAM SEFDIFINYI EAYMTMKIRN<br>GGGGSGGGGS RTVAAPSVFI FPPSDEQLKS GTASVVCLLN NFYPREAKVQ<br>WKVDNALQSG NSQESVTEQD SKDSTYSLSS TLTLSKADYE KHKVYACEVT<br>HQGLSSPVTK SFNRGECGGG GSGGGGSGGG GSGGGGSAST KGPSVFPLAP<br>SSKSTSGGTA ALGCLVKDYF PEPVTVSWNS GALTSGVHTF PAVLQSSGLY<br>SLSSVVTVPS SSLGTQTYIC NVNHKPSNTK VDKRVEPKSC DKTHTCPPCP<br>APELLGGPSV FLFPPKPKDT LMISRTPEVT CVVVDVSHED PEVKFNWYVD<br>GVEVHNAKTK PREEQYNSTY RVVSVLTVLH QDWLNGKEYK CKVSNKALPA<br>PIEKTISKAK GQPREPQVYT LPPSREEMTK NQVSLTCLVK GFYPSDIAVE<br>WESNGQPENN YKTTPPVLDS DGSFFLYSKL TVDKSRWQQG NVFSCSVMHE<br>ALHNHYTQKS LSLSPGK (SEQ ID NO: 20) |
| wtIL-10: linker: I87A (vIL10 mutant) | SPGQGTQSEN SCTHFPGNLP NMLRDLRDAF<br>SRVKTFFQMK DQLDNLLLKE SLLEDFKGYL GCQALSEMIQ FYLEEVMPQA<br>ENQDPDIKAH VNSLGENLKT LRLRLRRCHR FLPCENKSKA VEQVKNAFNK<br>LQEKGIYKAM SEFDIFINYI EAYMTMKIRN GGSGGGGSGG SPGQGTQSEN<br>SCTHFPGNLP NMLRDLRDAF SRVKTFFQMK DQLDNLLLKE SLLEDFKGYL<br>GCQALSEMIQ FYLEEVMPQA ENQDPDAKAH VNSLGENLKT LRLRLRRCHR<br>FLPCENKSKA VEQVKNAFNK LQEKGIYKAM SEFDIFINYI EAYMTMKIRN<br>GGGGSGGGGS RTVAAPSVFI FPPSDEQLKS GTASVVCLLN NFYPREAKVQ<br>WKVDNALQSG NSQESVTEQD SKDSTYSLSS TLTLSKADYE KHKVYACEVT<br>HQGLSSPVTK SFNRGECGGG GSGGGGSGGG GSGGGGSAST KGPSVFPLAP<br>SSKSTSGGTA ALGCLVKDYF PEPVTVSWNS GALTSGVHTF PAVLQSSGLY<br>SLSSVVTVPS SSLGTQTYIC NVNHKPSNTK VDKRVEPKSC DKTHTCPPCP<br>APELLGGPSV FLFPPKPKDT LMISRTPEVT CVVVDVSHED PEVKFNWYVD<br>GVEVHNAKTK PREEQYNSTY RVVSVLTVLH QDWLNGKEYK CKVSNKALPA<br>PIEKTISKAK GQPREPQVYT LPPSREEMTK NQVSLTCLVK GFYPSDIAVE<br>WESNGQPENN YKTTPPVLDS DGSFFLYSKL TVDKSRWQQG NVFSCSVMHE<br>ALHNHYTQKS LSLSPGK (SEQ ID NO: 19) |
| I87A: linker: wtIL-10 (vIL10 mutant) | SPGQGTQSEN SCTHFPGNLP NMLRDLRDAF<br>SRVKTFFQMK DQLDNLLLKE SLLEDFKGYL GCQALSEMIQ FYLEEVMPQA<br>ENQDPDAKAH VNSLGENLKT LRLRLRRCHR FLPCENKSKA VEQVKNAFNK<br>LQEKGIYKAM SEFDIFINYI EAYMTMKIRN GGSGGGGSGG SPGQGTQSEN<br>SCTHFPGNLP NMLRDLRDAF SRVKTFFQMK DQLDNLLLKE SLLEDFKGYL<br>GCQALSEMIQ FYLEEVMPQA ENQDPDIKAH VNSLGENLKT LRLRLRRCHR<br>FLPCENKSKA VEQVKNAFNK LQEKGIYKAM SEFDIFINYI EAYMTMKIRN<br>GGGGSGGGGS RTVAAPSVFI FPPSDEQLKS GTASVVCLLN NFYPREAKVQ<br>WKVDNALQSG NSQESVTEQD SKDSTYSLSS TLTLSKADYE KHKVYACEVT<br>HQGLSSPVTK SFNRGECGGG GSGGGGSGGG GSGGGGSAST KGPSVFPLAP<br>SSKSTSGGTA ALGCLVKDYF PEPVTVSWNS GALTSGVHTF PAVLQSSGLY<br>SLSSVVTVPS SSLGTQTYIC NVNHKPSNTK VDKRVEPKSC DKTHTCPPCP<br>APELLGGPSV FLFPPKPKDT LMISRTPEVT CVVVDVSHED PEVKFNWYVD<br>GVEVHNAKTK PREEQYNSTY RVVSVLTVLH QDWLNGKEYK CKVSNKALPA<br>PIEKTISKAK GQPREPQVYT LPPSREEMTK NQVSLTCLVK GFYPSDIAVE<br>WESNGQPENN YKTTPPVLDS DGSFFLYSKL TVDKSRWQQG NVFSCSVMHE<br>ALHNHYTQKS LSLSPGK (SEQ ID NO: 18) |

TABLE 4-continued

| Description | Amino Acid Sequence/SEQ ID NO |
|---|---|
| I87A: linker: I87A (vIL10 mutant) | SPGQGTQSEN SCTHFPGNLP NMLRDLRDAF SRVKTFFQMK DQLDNLLLKE SLLEDFKGYL GCQALSEMIQ FYLEEVMPQA ENQDPDAKAH VNSLGENLKT LRLRLRRCHR FLPCENKSKA VEQVKNAFNK LQEKGIYKAM SEFDIFINYI EAYMTMKIRN GGSGGGGSGG SPGQGTQSEN SCTHFPGNLP NMLRDLRDAF SRVKTFFQMK DQLDNLLLKE SLLEDFKGYL GCQALSEMIQ FYLEEVMPQA ENQDPDAKAH VNSLGENLKT LRLRLRRCHR FLPCENKSKA VEQVKNAFNK LQEKGIYKAM SEFDIFINYI EAYMTMKIRN GGGGSGGGGS RTVAAPSVFI FPPSDEQLKS GTASVVCLLN NFYPREAKVQ WKVDNALQSG NSQESVTEQD SKDSTYSLSS TLTLSKADYE KHKVYACEVT HQGLSSPVTK SFNRGECGGG GSGGGGSGGG GSGGGGSAST KGPSVFPLAP SSKSTSGGTA ALGCLVKDYF PEPVTVSWNS GALTSGVHTF PAVLQSSGLY SLSSVVTVPS SSLGTQTYIC NVNHKPSNTK VDKRVEPKSC DKTHTCPPCP APELLGGPSV FLFPPKPKDT LMISRTPEVT CVVVDVSHED PEVKFNWYVD GVEVHNAKTK PREEQYNSTY RVVSVLTVLH QDWLNGKEYK CKVSNKALPA PIEKTISKAK GQPREPQVYT LPPSREEMTK NQVSLTCLVK GFYPSDIAVE WESNGQPENN YKTTPPVLDS DGSFFLYSKL TVDKSRWQQG NVFSCSVMHE ALHNHYTQKS LSLSPGK (SEQ ID NO: 17) |
| M22A, D41F: linker: M22A, D41F(R1 + R2pan mutant) | SPGQGTQSEN SCTHFPGNLP NALRDLRDAF SRVKTFFQMK FQLDNLLLKE SLLEDFKGYL GCQALSEMIQ FYLEEVMPQA ENQDPDIKAH VNSLGENLKT LRLRLRRCHR FLPCENKSKA VEQVKNAFNK LQEKGIYKAM SEFDIFINYI EAYMTMKIRN GGSGGGGSGG SPGQGTQSEN SCTHFPGNLP NALRDLRDAF SRVKTFFQMK FQLDNLLLKE SLLEDFKGYL GCQALSEMIQ FYLEEVMPQA ENQDPDIKAH VNSLGENLKT LRLRLRRCHR FLPCENKSKA VEQVKNAFNK LQEKGIYKAM SEFDIFINYI EAYMTMKIRN GGGGSGGGGS RTVAAPSVFI FPPSDEQLKS GTASVVCLLN NFYPREAKVQ WKVDNALQSG NSQESVTEQD SKDSTYSLSS TLTLSKADYE KHKVYACEVT HQGLSSPVTK SFNRGECGGG GSGGGGSGGG GSGGGGSAST KGPSVFPLAP SSKSTSGGTA ALGCLVKDYF PEPVTVSWNS GALTSGVHTF PAVLQSSGLY SLSSVVTVPS SSLGTQTYIC NVNHKPSNTK VDKRVEPKSC DKTHTCPPCP APELLGGPSV FLFPPKPKDT LMISRTPEVT CVVVDVSHED PEVKFNWYVD GVEVHNAKTK PREEQYNSTY RVVSVLTVLH QDWLNGKEYK CKVSNKALPA PIEKTISKAK GQPREPQVYT LPPSREEMTK NQVSLTCLVK GFYPSDIAVE WESNGQPENN YKTTPPVLDS DGSFFLYSKL TVDKSRWQQG NVFSCSVMHE ALHNHYTQKS LSLSPGK (SEQ ID NO: 30) |
| M22A, D41F: linker: M22A (R1 + R2 triple mutant) | SPGQGTQSEN SCTHFPGNLP NALRDLRDAF SRVKTFFQMK FQLDNLLLKE SLLEDFKGYL GCQALSEMIQ FYLEEVMPQA ENQDPDIKAH VNSLGENLKT LRLRLRRCHR FLPCENKSKA VEQVKNAFNK LQEKGIYKAM SEFDIFINYI EAYMTMKIRN GGSGGGGSGG SPGQGTQSEN SCTHFPGNLP NALRDLRDAF SRVKTFFQMK DQLDNLLLKE SLLEDFKGYL GCQALSEMIQ FYLEEVMPQA ENQDPDIKAH VNSLGENLKT LRLRLRRCHR FLPCENKSKA VEQVKNAFNK LQEKGIYKAM SEFDIFINYI EAYMTMKIRN GGGGSGGGGS RTVAAPSVFI FPPSDEQLKS GTASVVCLLN NFYPREAKVQ WKVDNALQSG NSQESVTEQD SKDSTYSLSS TLTLSKADYE KHKVYACEVT HQGLSSPVTK SFNRGECGGG GSGGGGSGGG GSGGGGSAST KGPSVFPLAP SSKSTSGGTA ALGCLVKDYF PEPVTVSWNS GALTSGVHTF PAVLQSSGLY SLSSVVTVPS SSLGTQTYIC NVNHKPSNTK VDKRVEPKSC DKTHTCPPCP APELLGGPSV FLFPPKPKDT LMISRTPEVT CVVVDVSHED PEVKFNWYVD GVEVHNAKTK PREEQYNSTY RVVSVLTVLH QDWLNGKEYK CKVSNKALPA PIEKTISKAK GQPREPQVYT LPPSREEMTK NQVSLTCLVK GFYPSDIAVE WESNGQPENN YKTTPPVLDS DGSFFLYSKL TVDKSRWQQG NVFSCSVMHE ALHNHYTQKS LSLSPGK (SEQ ID NO: 31) |
| M22A, D41F: linker: D41F (R1 + R2 triple mutant) | SPGQGTQSEN SCTHFPGNLP NALRDLRDAF SRVKTFFQMK FQLDNLLLKE SLLEDFKGYL GCQALSEMIQ FYLEEVMPQA ENQDPDIKAH VNSLGENLKT LRLRLRRCHR FLPCENKSKA VEQVKNAFNK LQEKGIYKAM SEFDIFINYI EAYMTMKIRN GGSGGGGSGG SPGQGTQSEN SCTHFPGNLP NMLRDLRDAF SRVKTFFQMK FQLDNLLLKE SLLEDFKGYL GCQALSEMIQ FYLEEVMPQA ENQDPDIKAH VNSLGENLKT LRLRLRRCHR FLPCENKSKA VEQVKNAFNK LQEKGIYKAM SEFDIFINYI EAYMTMKIRN GGGGSGGGGS RTVAAPSVFI FPPSDEQLKS GTASVVCLLN NFYPREAKVQ WKVDNALQSG NSQESVTEQD SKDSTYSLSS TLTLSKADYE KHKVYACEVT HQGLSSPVTK SFNRGECGGG GSGGGGSGGG GSGGGGSAST KGPSVFPLAP SSKSTSGGTA ALGCLVKDYF PEPVTVSWNS GALTSGVHTF PAVLQSSGLY SLSSVVTVPS SSLGTQTYIC NVNHKPSNTK VDKRVEPKSC DKTHTCPPCP APELLGGPSV FLFPPKPKDT LMISRTPEVT CVVVDVSHED PEVKFNWYVD GVEVHNAKTK PREEQYNSTY RVVSVLTVLH QDWLNGKEYK CKVSNKALPA PIEKTISKAK GQPREPQVYT LPPSREEMTK NQVSLTCLVK GFYPSDIAVE WESNGQPENN YKTTPPVLDS DGSFFLYSKL TVDKSRWQQG NVFSCSVMHE ALHNHYTQKS LSLSPGK (SEQ ID NO: 32) |
| M22A: linker: M22A, D41F(R1 + R2triple mutant) | SPGQGTQSEN SCTHFPGNLP NALRDLRDAF SRVKTFFQMK DQLDNLLLKE SLLEDFKGYL GCQALSEMIQ FYLEEVMPQA ENQDPDIKAH VNSLGENLKT LRLRLRRCHR FLPCENKSKA VEQVKNAFNK LQEKGIYKAM SEFDIFINYI EAYMTMKIRN GGSGGGGSGG SPGQGTQSEN SCTHFPGNLP NALRDLRDAF SRVKTFFQMK FQLDNLLLKE SLLEDFKGYL GCQALSEMIQ FYLEEVMPQA ENQDPDIKAH VNSLGENLKT LRLRLRRCHR |

TABLE 4-continued

| Description | Amino Acid Sequence/SEQ ID NO |
|---|---|
| | FLPCENKSKA VEQVKNAFNK LQEKGIYKAM SEFDIFINYI EAYMTMKIRN<br>GGGGSGGGGS RTVAAPSVFI FPPSDEQLKS GTASVVCLLN NFYPREAKVQ<br>WKVDNALQSG NSQESVTEQD SKDSTYSLSS TLTLSKADYE KHKVYACEVT<br>HQGLSSPVTK SFNRGECGGG GSGGGGSGGG GSGGGGSAST KGPSVFPLAP<br>SSKSTSGGTA ALGCLVKDYF PEPVTVSWNS GALTSGVHTF PAVLQSSGLY<br>SLSSVVTVPS SSLGTQTYIC NVNHKPSNTK VDKRVEPKSC DKTHTCPPCP<br>APELLGGPSV FLFPPKPKDT LMISRTPEVT CVVVDVSHED PEVKFNWYVD<br>GVEVHNAKTK PREEQYNSTY RVVSVLTVLH QDWLNGKEYK CKVSNKALPA<br>PIEKTISKAK GQPREPQVYT LPPSREEMTK NQVSLTCLVK GFYPSDIAVE<br>WESNGQPENN YKTTPPVLDS DGSFFLYSKL TVDKSRWQQG NVFSCSVMHE<br>ALHNHYTQKS LSLSPGK (SEQ ID NO: 33) |
| D41F: linker: M22A, D41F(R1 + R2triple mutant) | SPGQGTQSEN SCTHFPGNLP NMLRDLRDAF<br>SRVKTFFQMK FQLDNLLLKE SLLEDFKGYL GCQALSEMIQ FYLEEVMPQA<br>ENQDPDIKAH VNSLGENLKT LRLRLRRCHR FLPCENKSKA VEQVKNAFNK<br>LQEKGIYKAM SEFDIFINYI EAYMTMKIRN GGSGGGGSGG SPGQGTQSEN<br>SCTHFPGNLP NALRDLRDAF SRVKTFFQMK FQLDNLLLKE SLLEDFKGYL<br>GCQALSEMIQ FYLEEVMPQA ENQDPDIKAH VNSLGENLKT LRLRLRRCHR<br>FLPCENKSKA VEQVKNAFNK LQEKGIYKAM SEFDIFINYI EAYMTMKIRN<br>GGGGSGGGGS RTVAAPSVFI FPPSDEQLKS GTASVVCLLN NFYPREAKVQ<br>WKVDNALQSG NSQESVTEQD SKDSTYSLSS TLTLSKADYE KHKVYACEVT<br>HQGLSSPVTK SFNRGECGGG GSGGGGSGGG GSGGGGSAST KGPSVFPLAP<br>SSKSTSGGTA ALGCLVKDYF PEPVTVSWNS GALTSGVHTF PAVLQSSGLY<br>SLSSVVTVPS SSLGTQTYIC NVNHKPSNTK VDKRVEPKSC DKTHTCPPCP<br>APELLGGPSV FLFPPKPKDT LMISRTPEVT CVVVDVSHED PEVKFNWYVD<br>GVEVHNAKTK PREEQYNSTY RVVSVLTVLH QDWLNGKEYK CKVSNKALPA<br>PIEKTISKAK GQPREPQVYT LPPSREEMTK NQVSLTCLVK GFYPSDIAVE<br>WESNGQPENN YKTTPPVLDS DGSFFLYSKL TVDKSRWQQG NVFSCSVMHE<br>ALHNHYTQKS LSLSPGK (SEQ ID NO: 34) |

Expression of sc-IL-10 Variant Fusion Proteins

The genes were synthetically synthesized and supplied in pcDNA3.1 expression vector (GeneArt), and transiently expressed in HEK293 cells using the Expi293 expression system (Life Technologies). Proteins were purified using Protein A (GE Healthcare) with low pH elution and dialyzed against 2 L 1×PBS 2 times.

The molecules were analyzed by SDS PAGE gel under reducing and non-reducing conditions. For reducing and non-reducing conditions, 2.5 ug of protein was loaded onto an Any kD gel (Invitrogen) with a Precision Plus Protein Kaleidoscope standard (Invitrogen) (MW range 10 kD-250 kD). The molecule was characterized by analytical gel filtration on an XBridge Protein BEH SEC column, 200 Å, 3.5 μm, 7.8 mm×150 mm (Waters). The column was equilibrated and run at 0.9 ml/min with 100 mM sodium phosphate pH 7.0 as a running buffer for all analyses. Purified samples (0.5 mg/ml) were injected (15 ul) and eluted with a run time of 15 min.

Mouse PBMC Cytokine Release Assay

In vitro bioactivity was assessed by evaluating the ability of our scIL-10 constructs to inhibit the production of TNFα in LPS stimulated C57BL/6 mouse PBMCs (Bioreclamation). For the assay, PBMCs cells were plated at 50,000 cells/well in RPMI media containing 10% heat inactivated fetal bovine serum. Cells were incubated for 18 hours at 37° C., 5% $CO_2$ with 100 ng/mL LPS and varying concentrations of the scIL-10 constructs (R&D Systems). After 18 hours, TNFα production was measured using V-Plex mouse TNFα MSD (Mesoscale Discovery). See Tables 5 and 6 below for IC50 values.

MC/9 Assay

In vitro bioactivity was assessed by evaluating the ability of our scIL-10 constructs to stimulate proliferation of the mouse mast cell line MC/9 (ATCC CRL-8306). For the assay, MC/9 cells were plated at 10,000 cells/well in DMEM media containing 10% heat inactivated fetal bovine serum, 2 mM glutamine and 0.05 mM 2-mercaptoethanol. Cells were incubated for 72 hours at 37° C., 5% $CO_2$ with varying concentrations of human IL-10 (R&D Systems), RDB3515, RDB3516 or RDB3509. After 72 hours, the cells were stained with CellTiter-Blue (Promega) for 4 hours at 37° C., 5% $CO_2$ according to the manufacturer's protocol. Fluorescent measurements were taken at 560/590 nm. See Tables 5 and 6 below for EC50 values.

TABLE 5

| SEQ ID NO | DESCRIPTION | PBMC + LPS (pM) | MC/9 (pM) | RATIO |
|---|---|---|---|---|
| | wtIL-10 | 0.45 | 5 | 11.1 |
| 12 | scIL-10:CL:CH1:Fc | 0.06 | 60 | 1000 |
| 13 | scIL-10:Fc | 0.08 | 409 | 5112.5 |
| 14 | (scIL-10:Fc), hinge truncation mutant 1 | 0.06 | 494 | 8233.3 |
| 15 | (scIL-10:Fc), hinge truncation mutant 2 | 0.1 | 864 | 8640 |
| 16 | (scIL-10:Fc), hinge truncation mutant 3 | 1.4 | 1007 | 719.3 |
| 17 | I87A:linker:I87A (vIL10 mutant) | 0.38 | 1775 | 4671.1 |
| 18 | I87A:linker:wtIL-10 (vIL10 mutant) | 0.03 | 107 | 3566.7 |
| 19 | wtIL-10:linker:I87A (vIL10 mutant) | 0.18 | 346 | 1922.2 |
| 20 | D41F:linker:wtIL-10 (R1 mutant) | 0.12 | 264 | 2200 |
| 21 | wtIL-10:linkerD41F (R1 mutant) | 0.18 | 1368 | 7600 |
| 22 | D41F:linker:D41F (R1 mutant) | ND | ND | No activity |

TABLE 5-continued

| SEQ ID NO | DESCRIPTION | PBMC + LPS (pM) | MC/9 (pM) | RATIO |
|---|---|---|---|---|
| 23 | M22A:linker:wtIL-10 (R2 mutant) | 0.077 | 47 | 610.4 |
| 24 | wtIL-10:linker:M22A (R2 mutant) | 0.045 | 38 | 844.4 |
| 25 | M22A:linker:M22A (R2 mutant) | 0.73 | 541 | 741.1 |
| 26 | M22A:linker:D41F (R1 + R2 mutant) | 2.1 | 987 | 470 |
| 27 | wtIL-10:linker:M22A, D41F (R1 + R2 mutant) | 2.6 | 6590 | 2534.6 |
| 28 | D41F:linker:M22A (R1 + R2 mutant) | 8.9 | ND | >>10000 |
| 29 | M22A:linker:D41F (R1 + R2 mutant) | 4.4 | ND | >>10000 |
| 30 | M22A, D41F:linker:M22A, D41F (R1 + R2 pan mutant) | ND | ND | No activity |
| 31 | M22A, D41F:linker:M22A (R1 + R2 triple mutant) | 65 | ND | >>10000 |
| 32 | M22A, D41F:linker:D41F (R1 + R2 triple mutant) | ND | ND | No activity |
| 33 | M22A:linker:M22A, D41F (R1 + R2 triple mutant) | 502 | ND | >>10000 |
| 34 | D41F:linker:M22A, D41F (R1 + R2 triple mutant) | ND | ND | No activity |
| 35 | scIL-10:CL:CH1:Fc (scIL10 5aa linker) | 0.007 | 0.6 | 85.7 |
| 36 | scIL-10:CL:CH1:Fc (scIL10 3aa linker) | 0.03 | 1.5 | 50 |

TABLE 6

| SEQ ID NO | DESCRIPTION | PBMC + LPS | MC/9 | Ratio |
|---|---|---|---|---|
| 12 | scIL-10:CL:CH1:Fc | 0.5 | 133 | 266 |
| 37 | wtIL-10:linker:D41A (R1 mutant) | 0.6 | 1430 | 2383.333 |
| 38 | wtIL-10:linker:M22A, D41A (R1 + R2 mutant) | 2.4 | 3602 | 3602 |
| 39 | D41A:linker:M22A (R1 + R2 mutant) | 11.1 | ND | ND |
| 40 | M22A:linker:D41A (R1 + R2 mutant) | 6 | ND | ND |
| 41 | wtIL-10:linker:D41N (R1 mutant) | 1.4 | 747 | 533.5714 |
| 42 | wtIL-10:linker:M22A, D41N (R1 + R2 mutant) | 0.8 | 791 | 988.75 |
| 43 | D41N:linker:M22A (R1 + R2 mutant) | 4.6 | 2780 | 604.3478 |
| 44 | M22A:linker:D41N (R1 + R2 mutant) | 2.1 | ND | ND |

As shown in Table 5, the ratio for WT IL-10 was ~11. The ratio for SEQ ID NO: 12 was 1000, showing that just by building the scIL-10 sequence on the CL:CH1:Fc scaffold, the anti-inflammatory window is increased. The following experiments were conducted with various configurations of scIL-10 molecules of Formula 1 including unsubstituted scIL-10, scIL-10 variants and LINKER lengths of various sizes on the CL:CH1:Fc scaffold.

Figure 7:
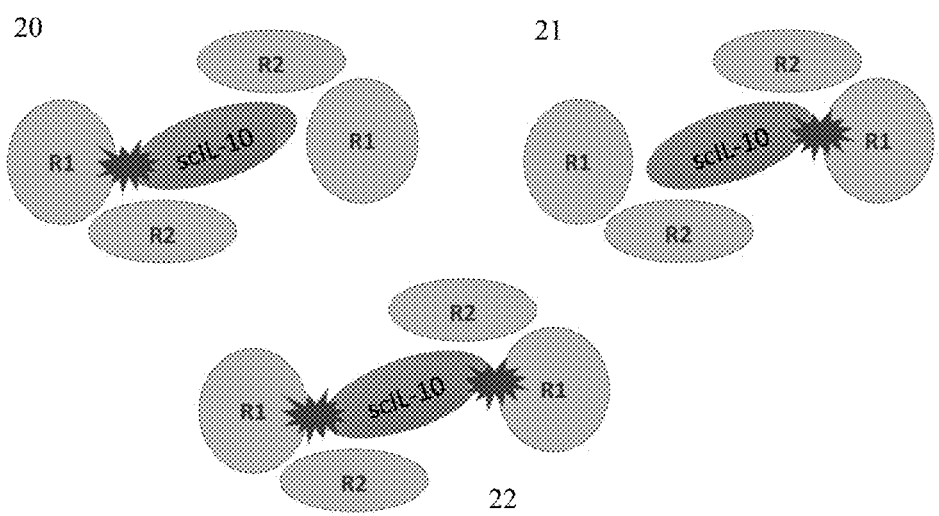
FIG. 7 is a schematic of the effects of amino acid substitutions that disrupt either one or both of the two IL-10R1 interfaces (SEQ ID NOS: 20, 21 and 22).

Experiments were conducted using the constructs of Tables 5 and 6 to explore the effects unsubstituted scIL-10 and scIL-10 variants that disrupt the scIL-10 interfaces with different combinations of the two IL-10R1 and two IL-10R2 receptor chains from the scIL-10 heteropentameric signaling complex. Mutations that disrupt either one of the two IL-10R1 interfaces SEQ ID NOS: 20, 21, 37 and 41 as illustrated in FIG. 7, slightly weaken the anti-inflammatory potency, while significantly weakening the immunostimulatory potency, resulting in an increase in the anti-inflammatory window size.

Introducing a double mutation that simultaneously disrupts both IL-10R1 interfaces (SEQ ID NO: 22) results in a construct with no measurable anti-inflammatory or immunostimulatory activities. This demonstrates that in order for scIL-10 to signal via the IL-10 receptor, it must be able to recruit at least 1 IL-10R1 receptor chain. Since the IL-10R1 receptor chain is known to be the "high affinity" receptor chain (binding more tightly to IL-10 than IL-10R2 does), it is likely that mutations that simultaneously disrupt both IL-10R1 binding interfaces would eliminate or significantly weaken the ability of scIL-10 to bind to the IL-10 receptor, resulting in no signal transduction at all.

Figure 8:
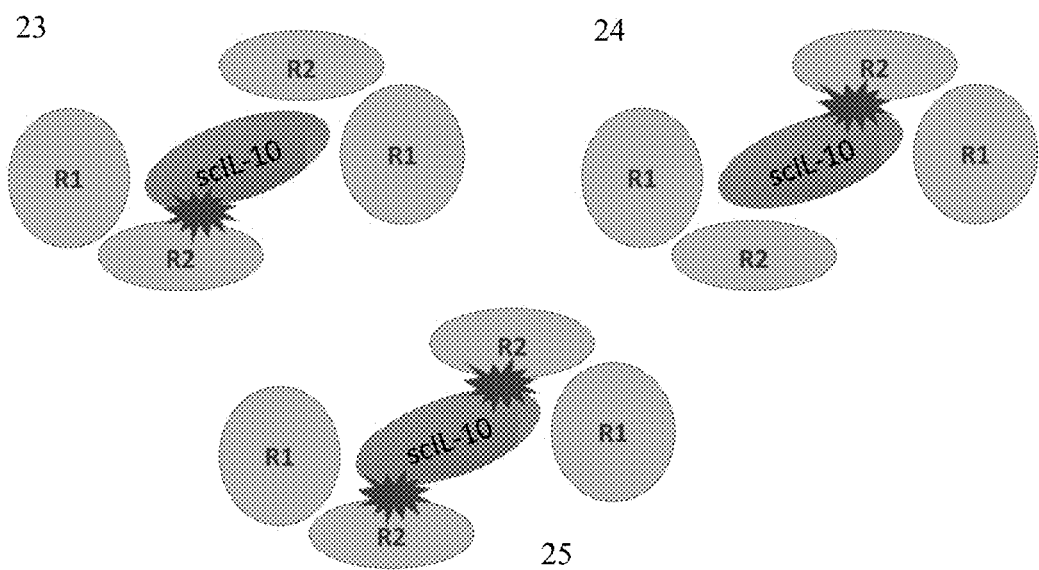
FIG. 8 is a schematic of the effects of amino acid substitutions that disrupt either one or both of the two IL-10R2 interfaces (SEQ ID NOS: 23, 24 and 25).
Figure 9:
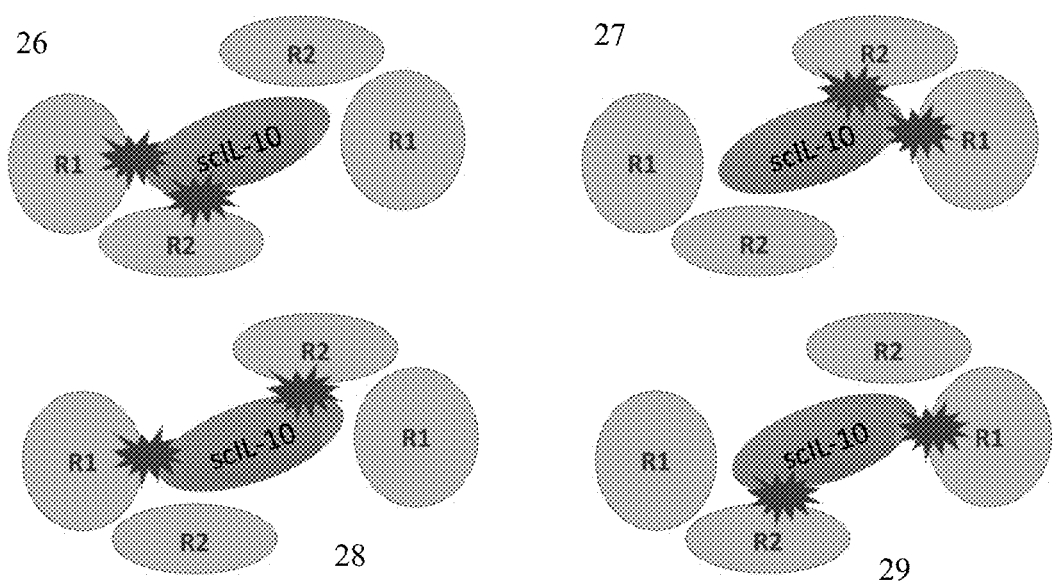
FIG. 9 is a schematic of the effects of amino acid substitutions that simultaneously disrupt one of the IL-10R1 and one of the IL-10R2 interfaces. (SEQ ID NOS: 26-29).

Mutations that disrupt either one of the two IL-10R2 interfaces (SEQ ID NOS: 23 and 24), as illustrated in FIG. 8, demonstrate no change in the anti-inflammatory potency, while showing a slight increase in the immunostimulatory potency, resulting in slightly decreased anti-inflammatory window sizes. Introducing a double-mutant that simultaneously disrupts both IL-10R2 interfaces (SEQ ID NO: 29) leads to a loss in potency for both anti-inflammatory and immunostimulatory activities, resulting in a construct with an anti-inflammatory window size similar to that of the IL-10R2 interface single mutants, which is slightly reduced relative to the native scIL-10 construct. This result demonstrates that mutations that disrupt the IL-10R2 interface do not alone have the potential to expand the anti-inflammatory window of scIL-10.

Mutations that simultaneously disrupt one of the IL-10R1 and one of the IL-10R2 interfaces were explored as illustrated in FIG. 8. Mutations located in the IL-10R1 and IL-10R2 sites from the same side of the scIL-10 fused dimer (SEQ ID NOS: 26 AND 27) demonstrate weakened potency for both anti-inflammatory and immunostimulatory activities; one of those combinations (SEQ ID NO: 27) displays a significantly increased anti-inflammatory window size. Mutations located in an IL-10R1 interface and an IL-10R2 interface from opposite sides of the scIL-10 fused dimer (SEQ ID NOS: 28 and 29) display weakened anti-inflammatory potency, and no measurable immunostimulatory activities at the concentrations tested. Therefore, they display extremely large anti-inflammatory windows. Since IL-10 receptor signal transduction requires IL-10R1 and IL-10R2 to be clustered following IL-10 binding, these data indicate that the optimal strategy for attenuating immunostimulatory activity (and thereby increasing the anti-inflammatory window) is to target both of the pairs of IL-10R1/IL-10R2 receptor chains. Since the IL-10R1 interface scan revealed that signaling requires that at least one IL-10R1 interface be competent for binding, it is necessary to target the IL-10R2 interface on the opposite side of the scIL-10 fused dimer, to effectively disrupt both pairs of IL-10R1/IL-10R2 receptor chains that cluster upon scIL-10 binding. This pattern of mutations more dramatically modulates scIL-10 bioactivity on cells that mediate immunostimulation, while the cells that mediate the anti-inflammatory effects remain quite sensitive to scIL-10 signaling.

Example 3 Varying Linker Length of scIL-10

The scIL-10 of Formula 1 wherein LINKER length is varied are fused to a single chain Fc linker of Formula 2 wherein L1 is CL-CH1-Fc as per Formula 3. The amino acid sequences of each full length scIL-10-L1-HINGE-Fc fusion variant protein synthesized is found in Table 7.

For expression in mammalian cells, the N-terminal leader sequence of SEQ ID NO: 48 was added to each of the protein sequences found in Table 7.

The amino acid sequences of each fusion protein are found in Table 7. Expression of peptides are as described in Example 2. Bioactivity of was tested in a mouse PBMC cytokine release assay and an MC/9 assay as described in Example 2. The results are found in Table 5 of Example 2. The results show that decreasing the size of the linker reduces the size of the anti-inflammatory window, implying that the linker length affects the strength of the IL-10R1 and IL-10R2 interfaces in ways that reduce the selectivity for anti-inflammatory potency over immunostimulatory potency.

TABLE 7

| Description | Amino Acid Sequence |
|---|---|
| Unsubstituted scIL-10 (5 aa linker): CL: CH1: Fc) | SPGQGTQSEN SCTHFPGNLP NMLRDLRDAF SRVKTFFQMK DQLDNLLLKE SLLEDFKGYL GCQALSEMIQ FYLEEVMPQA ENQDPDIKAH VNSLGENLKT LRLRLRRCHR FLPCENKSKA VEQVKNAFNK LQEKGIYKAM SEFDIFINYI EAYMTMKIRN GGSGGSPGQG TQSENSCTHF PGNLPNMLRD LRDAFSRVKT FFQMKDQLDN LLLKESLLED FKGYLGCQAL SEMIQFYLEE VMPQAENQDP DIKAHVNSLG ENLKTLRLRL RRCHRFLPCE NKSKAVEQVK NAFNKLQEKG IYKAMSEFDI FINYIEAYMT MKIRNGGGGS GGGGSRTVAA PSVFIFPPSD EQLKSGTASV VCLLNNFYPR EAKVQWKVDN ALQSGNSQES VTEQDSKDST YSLSSTLTLS KADYEKHKVY ACEVTHQGLS SPVTKSFNRG ECGGGGSGGG GSGGGGSGGG GSASTKGPSV FPLAPSSKST SGGTAALGCL VKDYFPEPVT VSWNSGALTS GVHTFPAVLQ SSGLYSLSSV VTVPSSSLGT QTYICNVNHK PSNTKVDKRV EPKSCDKTHT CPPCPAPELL GGPSVFLFPP KPKDTLMISR TPEVTCVVVD VSHEDPEVKF NWYVDGVEVH NAKTKPREEQ YNSTYRVVSV LTVLHQDWLN GKEYKCKVSN KALPAPIEKT ISKAKGQPRE PQVYTLPPSR EEMTKNQVSL TCLVKGFYPS DIAVEWESNG QPENNYKTTP PVLDSDGSFF LYSKLTVDKS RWQQGNVFSC SVMHEALHNH YTQKSLSLSP GK (SEQ ID NO: 35) |
| scIL-10 of Formula 1 wherein LINKER is 3 amino acid linker | SPGQGTQSEN SCTHFPGNLP NMLRDLRDAF SRVKTFFQMK DQLDNLLLKE SLLEDFKGYL GCQALSEMIQ FYLEEVMPQA ENQDPDIKAH VNSLGENLKT LRLRLRRCHR FLPCENKSKA VEQVKNAFNK LQEKGIYKAM SEFDIFINYI EAYMTMKIRN GGGSPGQGTQ SENSCTHFPG NLPNMLRDLR DAFSRVKTFF QMKDQLDNLL LKESLLEDFK GYLGCQALSE MIQFYLEEVM PQAENQDPDI KAHVNSLGEN LKTLRLRLRR CHRFLPCENK SKAVEQVKNA FNKLQEKGIY KAMSEFDIFI NYIEAYMTMK IRNGGGGSGG GGSRTVAAPS VFIFPPSDEQ LKSGTASVVC LLNNFYPREA KVQWKVDNAL QSGNSQESVT EQDSKDSTYS LSSTLTLSKA DYEKHKVYAC EVTHQGLSSP VTKSFNRGEC GGGGSGGGGS GGGGSGGGGS ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKRVEP KSCDKTHTCP PCPAPELLGG PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPSREE MTKNQVSLTC LVKGFYPSDI AVEWESNGQP ENNYKTTPPV LDSDGSFFLY SKLTVDKSRW QQGNVFSCSV MHEALHNHYT QKSLSLSPGK (SEQ ID NO: 36) |

Example 4: Modulating the Anti-Inflammatory Window of scIL-10 Via Steric Crowding The amino acid sequences of each scIL-10 fusion protein used in this experiment are found in Table 8. Expression of peptides is as described in Example 2. Bioactivity of peptides was tested in a mouse PBMC cytokine release assay and an MC/9 assay as described in Example 2. The results are found in Table 5 of Example 2. The results show that as the hinge is shortened, the anti-inflammatory window increases in size. Without being limited to any particular theory, this implies that hinge truncation increases steric crowding between two scIL-10 moieties, resulting in modulation of the IL-10R1 and IL-10R2 interfaces, which translates to altered anti-inflammatory and immunostimulatory potencies.

TABLE 8

| Description: | Amino Acid Sequence |
|---|---|
| scIL-10: Fc (5 aa linker) | SPGQGTQSEN SCTHFPGNLP NMLRDLRDAF SRVKTFFQMK DQLDNLLLKE SLLEDFKGYL GCQALSEMIQ FYLEEVMPQA ENQDPDIKAH VNSLGENLKT LRLRLRRCHR FLPCENKSKA VEQVKNAFNK LQEKGIYKAM SEFDIFINYI EAYMTMKIRN GGSGGSPGQG TQSENSCTHF PGNLPNMLRD LRDAFSRVKT FFQMKDQLDN LLLKESLLED FKGYLGCQAL SEMIQFYLEE VMPQAENQDP DIKAHVNSLG ENLKTLRLRL RRCHRFLPCE NKSKAVEQVK NAFNKLQEKG IYKAMSEFDI FINYIEAYMT MKIRNEPKSS DKTHTCPPCP APELLGGPSV FLFPPKPKDT LMISRTPEVT CVVVDVSHED PEVKFNWYVD GVEVHNAKTK PREEQYNSTY RVVSVLTVLH QDWLNGKEYK CKVSNKALPA PIEKTISKAK GQPREPQVYT LPPSREEMTK NQVSLTCLVK GFYPSDIAVE WESNGQPENN YKTTPPVLDS DGSFFLYSKL TVDKSRWQQG NVFSCSVMHE ALHNHYTQKS LSLSPGK (SEQ ID NO: 13) |
| (scIL-10: Fc), 4AA hinge truncation | SPGQGTQSEN SCTHFPGNLP NMLRDLRDAF SRVKTFFQMK DQLDNLLLKE SLLEDFKGYL GCQALSEMIQ FYLEEVMPQA ENQDPDIKAH VNSLGENLKT LRLRLRRCHR FLPCENKSKA VEQVKNAFNK LQEKGIYKAM SEFDIFINYI EAYMTMKIRN GGSGGSPGQG TQSENSCTHF PGNLPNMLRD LRDAFSRVKT FFQMKDQLDN LLLKESLLED FKGYLGCQAL SEMIQFYLEE VMPQAENQDP DIKAHVNSLG ENLKTLRLRL RRCHRFLPCE NKSKAVEQVK NAFNKLQEKG IYKAMSEFDI FINYIEAYMT MKIRNSDKTH TCPPCPAPEL LGGPSVFLFP PKPKDTLMIS RTPEVTCVVV DVSHEDPEVK FNWYVDGVEV HNAKTKPREE QYNSTYRVVS VLTVLHQDWL NGKEYKCKVS NKALPAPIEK TISKAKGQPR EPQVYTLPPS REEMTKNQVS LTCLVKGFYP SDIAVEWESN GQPENNYKTT PPVLDSDGSF FLYSKLTVDK SRWQQGNVFS CSVMHEALHN HYTQKSLSLS PGK (SEQ ID NO: 14) |
| (scIL-10: Fc), 7 aa hinge truncation | SPGQGTQSEN SCTHFPGNLP NMLRDLRDAF SRVKTFFQMK DQLDNLLLKE SLLEDFKGYL GCQALSEMIQ FYLEEVMPQA ENQDPDIKAH VNSLGENLKT LRLRLRRCHR FLPCENKSKA VEQVKNAFNK LQEKGIYKAM SEFDIFINYI EAYMTMKIRN GGSGGSPGQG TQSENSCTHF PGNLPNMLRD LRDAFSRVKT FFQMKDQLDN LLLKESLLED FKGYLGCQAL SEMIQFYLEE VMPQAENQDP DIKAHVNSLG ENLKTLRLRL RRCHRFLPCE NKSKAVEQVK NAFNKLQEKG IYKAMSEFDI FINYIEAYMT MKIRNTHTCP PCPAPELLGG PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPSREE MTKNQVSLTC LVKGFYPSDI AVEWESNGQP ENNYKTTPPV LDSDGSFFLY SKLTVDKSRW QQGNVFSCSV MHEALHNHYT QKSLSLSPGK (SEQ ID NO: 15) |
| (scIL-10: Fc), 10 aa hinge truncation. | SPGQGTQSEN SCTHFPGNLP NMLRDLRDAF SRVKTFFQMK DQLDNLLLKE SLLEDFKGYL GCQALSEMIQ FYLEEVMPQA ENQDPDIKAH VNSLGENLKT LRLRLRRCHR FLPCENKSKA VEQVKNAFNK LQEKGIYKAM SEFDIFINYI EAYMTMKIRN GGSGGSPGQG TQSENSCTHF PGNLPNMLRD LRDAFSRVKT FFQMKDQLDN LLLKESLLED FKGYLGCQAL SEMIQFYLEE VMPQAENQDP DIKAHVNSLG ENLKTLRLRL RRCHRFLPCE NKSKAVEQVK NAFNKLQEKG IYKAMSEFDI FINYIEAYMT MKIRNTHTCP PCPAPELLGG PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPSREE MTKNQVSLTC LVKGFYPSDI AVEWESNGQP ENNYKTTPPV LDSDGSFFLY SKLTVDKSRW QQGNVFSCSV MHEALHNHYT QKSLSLSPGK (SEQ ID NO: 16) |

Example 5—scIL-10

Experiments were conducted with scIL-10 of Formula 1 wherein LINKER was of varying lengths. The amino acid sequences synthesized for these experiments are shown in Table 9. Expression of SEQ ID NOS: 45 and 46 is as described in Example 2. Bioactivity of SEQ ID NOS 45 was tested in an MC/9 assay as described in Example 2. The data showed that the value for SEQ ID NO: 45 in the MC/9 was 5.6 pM.

Bioactivity of SEQ ID NOS 45 and 46 will be further tested in a mouse PBMC cytokine release assay and an MC/9 assay as described in Example 2. The results will show that the scIL-10 moiety, absent any fusion partner, demonstrates highly potent bioactivity, consistent with the trends observed for scIL-10 Fc fusion proteins.

TABLE 9

| Description | Amino Acid Sequence |
|---|---|
| scIL-10 with 5 amino acid linker | SPGQGTQSEN SCTHFPGNLP NMLRDLRDAF SRVKTFFQMK DQLDNLLLKE SLLEDFKGYL GCQALSEMIQ FYLEEVMPQA ENQDPDIKAH VNSLGENLKT LRLRLRRCHR FLPCENKSKA VEQVKNAFNK LQEKGIYKAM SEFDIFINYI EAYMTMKIRN GGSGGSPGQG TQSENSCTHF PGNLPNMLRD LRDAFSRVKT FFQMKDQLDN LLLKESLLED FKGYLGCQAL SEMIQFYLEE VMPQAENQDP DIKAHVNSLG ENLKTLRLRL RRCHRFLPCE NKSKAVEQVK NAFNKLQEKG IYKAMSEFDI FINYIEAYMT MKIRN (SEQ ID NO: 45) |
| scIL-10 with 10 amino acid linker | SPGQGTQSEN SCTHFPGNLP NMLRDLRDAF SRVKTFFQMK DQLDNLLLKE SLLEDFKGYL GCQALSEMIQ FYLEEVMPQA ENQDPDIKAH VNSLGENLKT LRLRLRRCHR FLPCENKSKA VEQVKNAFNK LQEKGIYKAM SEFDIFINYI EAYMTMKIRN GGSGGGGSGG SPGQGTQSEN SCTHFPGNLP NMLRDLRDAF SRVKTFFQMK DQLDNLLLKE SLLEDFKGYL GCQALSEMIQ FYLEEVMPQA ENQDPDIKAH VNSLGENLKT LRLRLRRCHR FLPCENKSKA VEQVKNAFNK LQEKGIYKAM SEFDIFINYI EAYMTMKIRN (SEQ ID NO: 46) |

Example 6

The scIL-10 of Formula 1 was fused to a mucin domain linker comprising a tandem repeat of MUC 20 which in turn was fused to an Fc domain. The amino acid sequence of the (scIL-10 (5aa linker))-(mucin linker)-Fc is found in Table 10. For expression in mammalian cells, the N-terminal leader sequence of SEQ ID NO: 48 was added to the protein found in Table 11.

The amino acid sequences of each fusion protein are found in Table 10. Expression of peptides are as described in Example 2. Bioactivity of was tested in a mouse PBMC cytokine release assay and an MC/9 assay as described in Example 2. The results are found in Table 11. The results show that the bioactivities of scIL-10 Fc fusion proteins are consistent regardless of the composition of the linker domain connecting the scIL-10 and Fc domains.

TABLE 10

| Description | Amino Acid Sequence |
|---|---|
| (scIL-10(5 aa linker))-(mucin linker)-Fc | MYRMQLLSCI ALSLALVTNS SPGQGTQSEN SCTHFPGNLP NMLRDLRDAF SRVKTFFQMK DQLDNLLLKE SLLEDFKGYL GCQALSEMIQ FYLEEVMPQA ENQDPDIKAH VNSLGENLKT LRLRLRRCHR FLPCENKSKA VEQVKNAFNK LQEKGIYKAM SEFDIFINYI EAYMTMKIRN GGSGGSPGQG TQSENSCTHF PGNLPNMLRD LRDAFSRVKT FFQMKDQLDN LLLKESLLED FKGYLGCQAL SEMIQFYLEE VMPQAENQDP DIKAHVNSLG ENLKTLRLRL RRCHRFLPCE NKSKAVEQVK NAFNKLQEKG IYKAMSEFDI FINYIEAYMT MKIRNSGSGG ASSESSASSD GPHPVITESR ASSESSASSD GPHPVITESR EPKSSDKTHT CPPCPAPELL GGPSVFLFPP KPKDTLMISR TPEVTCVVVD VSHEDPEVKF NWYVDGVEVH NAKTKPREEQ YNSTYRVVSV LTVLHQDWLN GKEYKCKVSN KALPAPIEKT ISKAKGQPRE PQVYTLPPSR EEMTKNQVSL TCLVKGFYPS DIAVEWESNG QPENNYKTTP PVLDSDGSFF LYSKLTVDKS RWQQGNVFSC SVMHEALHNH YTQKSLSLSP GK (SEQ ID NO: 52) |

TABLE 11

| SEQ ID NO | PMBC | MC/9 | Ratio |
|---|---|---|---|
| 52 | 0.11 pM | 21 pM | 190.9 |

Example 7 In Vitro Evaluation of IL-10 Receptor Signaling in Human PBMCs

In vitro bioactivity in a human cell system was assessed by evaluating the ability of scIL-10:$C_L$:$C_{H1}$:Fc constructs to activate STAT3, as measured by intracellular levels of phosphorylated STAT3 protein. The unmutated scIL-10:$C_L$:$C_{H1}$:Fc sequence (SEQ ID NO: 12) was used as a control, and constructs containing the receptor-engagement mutations were used to explore the anti-inflammatory window in human cells. Both the single R1 mutant (wtIL-10:linker: D41A (SEQ ID NO: 37)) and double R1+R2 mutant (wtIL-10:linker:M22 Å, D41A (SEQ ID NO: 38)) constructs were used. PBMCs were obtained from BioReclamationIVT, and plated at 4×$10^6$ cells/well in serum-free media containing (X-vivo 10). Cells were incubated for 1 hour at 37° C., 5% $CO_2$, with varying concentrations of SEQ ID NO: 12, SEQ ID NO: 37, and SEQ ID NO: 38. After 1 hour, cells were fixed, stained with antibodies for cell surface markers, permeabilized, and stained with antibodies for pSTAT3.

Cell populations were analyzed by flow cytometry. Populations of B cells, monocytes, NK cells, CD4 T cells, and CD8 T cells were identified by cell surface markers (Table 12). Within each population, the percentage of cells that were positive for pSTAT3 were counted. For each population, the percent of pSTAT3+ cells was plotted against the concentration of test article, and a sigmoidal curve fit identified an $EC_{50}$ for STAT3 activation. The ratio of the $EC_{50}$ value for monocytes to the $EC_{50}$ values for CD4 and CD8 T cells was used to estimate the anti-inflammatory window for each construct.

TABLE 12

| Cell population | RDB 3515 (Seq ID 12) | RDB 3544 (Seq ID 38) | RDB 3543 (Seq ID 37) |
|---|---|---|---|
| Monocytes | 3.36 pM | 12.5 pM | 5.09 pM |
| CD8 Central Memory | 194 pM | 2.46 nM | 1.12 nM |

TABLE 12-continued

| Cell population | RDB 3515 (Seq ID 12) | RDB 3544 (Seq ID 38) | RDB 3543 (Seq ID 37) |
|---|---|---|---|
| CD8 Effector Memory | 165 pM | 1.90 nM | 1.08 nM |
| CD8 Terminal Effector | 158 pM | 1.23 nM | 1.07 nM |
| AVERAGE RATIO | 51X | 150X | 205X |

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred features thereof, it will be understood by those skilled in the art that various changes in form and details may be made therein without departing from the scope of the invention encompassed by the appended claims. It should also be understood that the various features of the invention described herein are not mutually exclusive and that features may be combined in whole or in part in accordance with the invention.

The invention claimed is:

1. A method of increasing the anti-inflammatory window size of an IL-10 therapy in a patient suffering from an IL-10-related disease or disorder, comprising administering an effective amount to the patient a single chain IL-10 (scIL-10) polypeptide comprising an amino acid sequence arrangement from N-terminus to C-terminus in accordance with Formula 1:

(first monomer subunit)-LINKER-(second monomer subunit)    Formula 1 wherein the first monomer subunit and the second monomer subunit may be independently selected from: SEQ ID NO: 1; or SEQ ID NO: 1 comprising at least one amino acid substitution, wherein the at least one amino acid substitution is at an amino acid position of SEQ ID NO: 1 that is selected from: amino acid position 22, amino acid position 41, amino acid position 87, and any combination thereof with the proviso that at least one of the first monomer subunit or the second monomer subunit comprises at least one amino acid substitution;
wherein LINKER is an amino acid linker of between about 1 and about 100 amino acids in length; and
wherein scIL-10 is optionally covalently attached to a fusion partner,
thereby increasing the anti-inflammatory window size in the patient suffering from an IL-10-related disease or disorder.

2. The method of claim 1, wherein LINKER is 5-15 amino acids in length.

3. The method of claim 1, wherein the amino acid substitutions comprise the substitution of amino acids of scIL-10 that interface with IL-10R1, IL-10R2 or amino acids that interface with both IL-10R1 and IL-10R2.

4. The method of claim 1, wherein aspartic acid at position 41 is substituted on the first monomer subunit or on the second monomer subunit but not both monomer subunits.

5. The method of claim 4, wherein methionine at position 22 is substituted on only one monomer subunit that is not the same monomer subunit comprising the substitution of aspartic acid at position 41.

6. The method of claim 1, wherein the amino acid substitution comprises isoleucine at position 87 to alanine (I87A).

7. The method of claim 3, wherein the amino acid substitutions are selected from: methionine at position 22 to alanine (M22A); aspartic acid at position 41 to asparagine (D41N); aspartic acid at position 41 to alanine (D41A); aspartic acid at position 41 to phenylalanine (D41F).

8. The method of claim 1, comprising a fusion partner wherein scIL-10 is fused to the hinge region IgG1.

9. The method of claim 1, comprising a fusion partner wherein scIL-10 is fused to a modified hinge region if IgG1 wherein the modification to the hinge region is the deletion of between 1 and 10 amino acids from the hinge region of IgG1.

10. The method of claim 1, comprising a fusion partner wherein scIL-10 is fused to the hinge region of IgG1 via a mucin linker.

11. The method of claim 10, wherein the mucin linker comprises an amino acid sequence that is a tandem repeat of MUC20.

12. The method of claim 1, comprising a fusion partner wherein scIL-10 is fused to a single chain Fc linker wherein the fusion protein has the sequence of Formula 2

(scIL-10)-L1-HINGE-Fc            Formula 2 wherein,
- L1 is a linker having the following arrangement from amino-terminus to carboxy-terminus:

L2-CL-L3-CH1-L4 or L2-CH1-L3-CL-L4 wherein,
- L2 and L4 are independently polypeptide linkers or are independently absent;
- L3 is a polypeptide linker;
- CL is a constant region polypeptide of an immunoglobulin light chain; and
- CH1 is a constant region polypeptide from a CH1 domain of an immunoglobulin heavy chain;
- HINGE is a hinge sequence of an immunoglobulin or is absent with the proviso that if HINGE is absent, L4 is present; and
- Fc is the carboxy-terminus of an immunoglobulin or any active fragment or derivative thereof.

13. The method of claim 1, wherein the polypeptide comprises SEQ ID NOS: 12-21, 23-29, 31, 33, and 35-45 and 52.

14. The method of claim 1, wherein the IL-10-related disease or disorder is selected from the group consisting of: an autoimmune disorder, a fibrotic disease, an inflammatory disease, an ischemic disease, a neurodegenerative disease, a neuropathic disease, a pain disorder, an auditory disorder, a psychiatric disorder, and cancer.

* * * * *